US012616714B2

(12) United States Patent
Sewing et al.

(10) Patent No.: US 12,616,714 B2
(45) Date of Patent: May 5, 2026

(54) ENHANCED OLIGONUCLEOTIDES FOR MODULATING FUBP1 EXPRESSION

(71) Applicant: Hoffmann-La Roche Inc., Little Falls, NJ (US)

(72) Inventors: Sabine Sewing, Basel (CH); Søren Ottosen, Hørsholm (DK); Jacob Ravn, Hørsholm (DK); Lykke Pedersen, Horsholm (DK); Souphalone Luangsay, Basel (CH); Erich Koller, Basel (CH); Johanna Marie Walther, Basel (CH); Helene Maria Gylling, Hvidovre (DK); Natascha Hruschka, Basel (CH); Susanne Mohr, Basel (CH); Valentina D'Arienzo, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/359,196

(22) Filed: Jun. 25, 2021

(65) Prior Publication Data

US 2022/0031730 A1 Feb. 3, 2022

(30) Foreign Application Priority Data

Jun. 26, 2020 (EP) .................................... 20182437

(51) Int. Cl.
| | |
|---|---|
| *A61K 31/712* | (2006.01) |
| *A61K 31/7125* | (2006.01) |
| *C12N 15/113* | (2010.01) |

(52) U.S. Cl.
CPC ........ *A61K 31/712* (2013.01); *A61K 31/7125* (2013.01); *C12N 15/113* (2013.01); *C12N 2310/11* (2013.01); *C12N 2310/315* (2013.01); *C12N 2320/33* (2013.01)

(58) Field of Classification Search
CPC .............. A61K 31/712; A61K 31/7125; A61K 31/7088; C12N 15/113; C12N 2310/11; C12N 2310/315; C12N 2310/341; C12N 2310/3515
See application file for complete search history.

(56) References Cited

U.S. PATENT DOCUMENTS

| | | | |
|---|---|---|---|
| 5,580,760 A | 12/1996 | Levens et al. | |
| 7,745,391 B2 * | 6/2010 | Mintz ...................... | A61P 37/00 514/19.3 |
| 8,349,809 B2 | 1/2013 | Brown | |
| 8,513,207 B2 | 8/2013 | Brown | |
| 11,345,948 B2 * | 5/2022 | Feng ................... | C12Q 1/6827 |
| 2002/0155119 A1 * | 10/2002 | Sikes ................... | C12Q 1/6886 435/325 |
| 2005/0238706 A1 | 10/2005 | Ahmad et al. | |
| 2021/0024934 A1 | 1/2021 | Luangsay et al. | |

FOREIGN PATENT DOCUMENTS

| | | | |
|---|---|---|---|
| EP | 2742135 A1 | 6/2014 | |
| WO | 93/07883 A1 | 4/1993 | |
| WO | 98/39352 A1 | 9/1998 | |
| WO | 99/14226 A2 | 3/1999 | |
| WO | 2000/047599 A1 | 8/2000 | |
| WO | 00/66604 A2 | 11/2000 | |
| WO | 01/23613 A1 | 4/2001 | |
| WO | 2004/017940 A2 | 3/2004 | |
| WO | 2004/027061 A1 | 4/2004 | |
| WO | 2004/046160 A2 | 6/2004 | |
| WO | 2005/014806 A2 | 2/2005 | |
| WO | 2006/082053 A1 | 8/2006 | |
| WO | 2007/031091 A2 | 3/2007 | |
| WO | 2007/090071 A2 | 8/2007 | |
| WO | 2007/134181 A2 | 11/2007 | |
| WO | 2007/146511 A2 | 12/2007 | |
| WO | 2008/113832 A2 | 9/2008 | |
| WO | 2008/150729 A2 | 12/2008 | |
| WO | 2008/154401 A2 | 12/2008 | |
| WO | 2009/006478 A2 | 1/2009 | |

(Continued)

OTHER PUBLICATIONS

Li, Qian, et al. "Application of improved GaINAc conjugation in development of cost-effective siRNA therapies targeting cardiovascular diseases." Molecular Therapy (2024).*
Pei-Yao Fu at al. (Far upstream element-binding protein 1 facilitates hepatocellular carcinoma invasion and metastasis, Carcinogenesis, vol. 41, Issue 7, Jul. 2020, pp. 950-960).*
Debaize, L., Troadec, MB. The master regulator FUBP1: its emerging role in normal cell function and malignant development. Cell. Mol. Life Sci. 76, 259-281 (2019).*
Sciabola et al. ("PFRED: A computational platform for siRNA and antisense oligonucleotides design." PLoS One 16.1 (2021)).*
Alweiss et al., The Role of cccDNA in HBV Maintenance, 2017, Viruses, vol. 9, No. 156, pp. 1-12, 13 pages.

(Continued)

*Primary Examiner* — Kimberly Chong
(74) *Attorney, Agent, or Firm* — McDonnell Boehnen Hulbert & Berghoff LLP

(57) ABSTRACT

The present invention relates to enhanced antisense oligonucleotides that are complementary to the Far Upstream Element-Binding Protein 1 (FUBP1) and are capable of reducing a FUBP1 target nucleic acid, such as FUBP1 mRNA. The invention relates to enhanced antisense oligonucleotides targeting FUBP1 or conjugates thereof for use in treating and/or preventing a hepatitis B virus (HBV) infection, in particular a chronic HBV infection. The invention in particular relates to the use of the enhanced antisense oligonucleotides targeting FUBP1 or conjugates thereof for destabilizing cccDNA, such as HBV cccDNA. The invention further relates to enhanced antisense oligonucleotides targeting FUBP1 or conjugates thereof for use in treating cancer. A pharmaceutical composition and its use in the treatment and/or prevention of an HBV infection, or its use in the treatment of cancer is also disclosed.

19 Claims, 38 Drawing Sheets

Specification includes a Sequence Listing.

(56)                    References Cited

FOREIGN PATENT DOCUMENTS

| WO | 2010/036698 A1 | 4/2010 |
| WO | 2010/077578 A1 | 7/2010 |
| WO | 2011/017521 A2 | 2/2011 |
| WO | 2011/047312 A1 | 4/2011 |
| WO | 2011/156202 A1 | 12/2011 |
| WO | 2012/024170 A2 | 2/2012 |
| WO | 2012/055362 A1 | 5/2012 |
| WO | 2012/143379 A1 | 10/2012 |
| WO | 2012/145697 A1 | 10/2012 |
| WO | 2013/003520 A1 | 1/2013 |
| WO | 2013/022966 A1 | 2/2013 |
| WO | 2013/033230 A1 | 3/2013 |
| WO | 2013/154798 A1 | 10/2013 |
| WO | 2013/159109 A1 | 10/2013 |
| WO | 2014/076196 A1 | 5/2014 |
| WO | 2014/179620 A1 | 11/2014 |
| WO | 2014/179629 A2 | 11/2014 |
| WO | 2014/207232 A1 | 12/2014 |
| WO | 2015/173208 A2 | 11/2015 |
| WO | 2016/054421 A1 | 4/2016 |
| WO | 2016/055601 A1 | 4/2016 |
| WO | 2016/100975 A1 | 6/2016 |
| WO | 2016/127002 A1 | 8/2016 |
| WO | 2017/015175 A1 | 1/2017 |
| WO | 2017/027350 A2 | 2/2017 |
| WO | 2017/178656 A1 | 10/2017 |
| WO | 2017/216390 A1 | 12/2017 |
| WO | 2017/216391 A1 | 12/2017 |
| WO | 2019/193165 A1 | 10/2019 |

OTHER PUBLICATIONS

Hauck et al., Pyrazolo[1,5a]pyrimidines as a new class of FUSE binding protein 1 (FUBP1) inhibitors, Bioorganic & Medicinal Chemistry, 2016, vol. 24, No. 22, pp. 5717-5729, 13 pages.

Huth et al., NMR-Driven Discovery of Benzoylanthranilic Acid Inhibitors of Far Upstream Element Binding Protein Binding to the Human Oncogene c-myc Promoter, 2004, J Med. Chem., vol. 47, pp. 4851-4857, 7 pages.

International Preliminary Report on Patentability received for PCT Patent Application No. PCT/EP2019/058664 , mailed on Oct. 15, 2020, 8 pages.

International Search Report and Written Opinion received for PCT Patent Application No. PCT/EP2019/058664 , mailed on Jul. 2, 2019, 11 pages.

Khageh Hosseini Sabrina et al: Camptothecin and its analog SN-38, the active metabolite of irinotecan, inhibit binding of the transcriptional regulator and oncoprotein FUBPI to its DNA target sequence Fuse, Biochemical Pharmacology, Elsevier, US, vol. 146, Oct. 13, 2017 (Oct. 13, 2017), pp. 53-62, XP085248323.

Rabenhorst et al., Overexpression of the Far Upstream Element Binding Protein 1 in Hepatocellular Carcinoma Is Required for Tumor Growth, 2009, Hepatology, vol. 50, pp. 1121-1129, 9 pages.

Sun et al., Involvement of PUF60 in Transcriptional and Post-transcriptional Regulation of Hepatitis B Virus Pregenomic RNA Expression, 2017, Scientific Reports, vol. 7:12874, pp. 1-15, 15 pages.

Xiang et al., Fuse-binding protein 1 is a target of the EZH@ inhibitor GSK343, in osteosarcoma cells, 2016, International Journal of Oncology, vol. 49, pp. 623-628, 6 pages.

Zhang et al., Far upstream element binding protein 1: a commander of transcription, translation and beyond, 2013, Oncogene, vol. 32, pp. 2907-2916, 10 pages.

Zhang et al., Knockdown of FUSE binding protein 1 enhances the sensitivity of epithelial ovarian cancer cells to Carboplatin, 2017, Oncology Letters, vol. 14, pp. 5819-5824, 5 pages.

Zubaidah: "2-D DIGE profiling of hepatocellular carcinoma tissues identified isoforms of far upstream binding proteins (FUBP) as novel candidates in liver carcinogenesis", Proteomics, vol. 8, Aug. 2, 2008 (Aug. 2, 2008), pp. 5086-5096, XP002785461.

Ansel et al., "Pharmaceutical Dosage Forms and Drug Delivery Systems," Williams & Wilkins, 6th Edition. pp. 105-116, 194-200; 1456-1457 (1995) (41 pages).

B Hirt, "Selective extraction of polyoma DNA from infected mouse cell cultures", J Mol Biol., vol. 26(2), Jun. 1967, pp. 365-369. doi: 10.1016/0022-2836(67)90307-5.

Bastin, R.J. et al., Salt Selection and Optimisation Procedures for Pharmaceutical New Chemical Entities, Organic Process Research & Development, (2000), vol. 4, pp. 427-435.

Bergstrom DE, "Unnatural nucleosides with unusual base pairing properties", Current Protocols in Nucleic Acid Chemistry, 2009, Suppl. 37 1.4.1, 32 pgs.

Biessen et al., "Targeted delivery of oligodeoxynucleotides to parenchymal liver cells in vivo," Biochem J., 1999, vol. 340, pp. 783-792, 10 pages.

Caruthers et al., "Chemical Synthesis of Deoxyoligonucleotides by the Phosphoramidite Method," Methods Enzymol. 154: 287-313 (1987) (27 pages).

Chang, Mei-Hwei, "Hepatitis B virus infection," Elsevier, Seminars in Fetal Neonatal Medicine, 2007, vol. 12, pp. 160-167, 8 pages.

Dawei Cai, et al., "A southern blot assay for detection of hepatitis B virus covalently closed circular DNA from cell cultures", Methods Mol Biol. vol. 1030, 2013, pp. 151-161. doi: 10.1007/978-1-62703-484-5_13.

Deleavey, GF et al., "Designing Chemically Modified Oligonucleotides for Targeted Gene Silencing," Chemistry and Biology, 2012, vol. 19(8), pp. 937-954, 18 pages.

Dixit et al. J Virol 89:7905-7921, pp. 1-28 (Year: 2015).

Duff, et al., "Intrabody tissue-specific delivery of antisense conjugates in animals: ligand-linker-antisense oligomer conjugates," Methods Enzvmol, Dec. 3, 20001, 313:297-321.

Freier, S.M. et al., The ups and downs of nucleic acid duplex stability: structure-stability studies on chemically-modified DNA:RNA duplexes, Nucleic Acids Research, 1997, vol. 25(22), pp. 4429-4443.

Gennaro, AR et al., "Remington's Pharmaceutical Sciences," Mack Publishing Company, 17th ed., 1985, 9 pages.

Guo et al 2016 Sci Rep 6: 2552.

Hansen et al., "Entropy titration. A Calorimetric Method for the Determination of t..Go (K), t..H0 and t..S0 1," Chemical Communications. 36-38, (1965) (3 pages).

Hirao, I et al., "Natural versus Artificial Creation of Base Pairs in DNA: Origin of Nucleobases from the Perspectives of Unnatural Base Pair Studies," Accounts of Chemical Research, 2012, vol. 45, No. 12, pp. 2055-2065, 11 pages.

Holdgate et al., "Measurements of Binding Thermodynamics in Drug Discovery," Drug Discov Today. 10(22):1543-1550 (2005) (8 pages).

Jobst et al., "Selective sugar binding to the carbohydrate recognition domains of the rat hepatic and macrophage asialoglycoprotein receptors," J Biol Chem, Mar. 22, 1992, 271(12):6686-6693.

Ladner et al 1997 Antimicrobial Agents and Chemotherapy 41(8) 171-1720.

Langer, R, "New Methods of Drug Delivery," Science, 1990, vol. 249, issue 4976, pp. 1527-1533, 7 pages.

Malz et al., "Overexpression of far upstream element binding proteins: a mechanism regulating proliferation and migration in liver cancer cells" Hepatology, vol. 50, Issue 4, 2009, pp. 1130-1139.

Masakazu Kakuni, et al, "Chimeric Mice with Humanized Livers: A Unique Tool for in Vivo and in Vitro Enzyme Induction Studies", Int. J. Mol. Sci., vol. 15, 2014, pp. 58-74; doi:10.3390/ijms15010058.

McTigue et al., "Sequence-Dependent Thermodynamic Parameters for Locked Nucleic Acid (LNA)-DNA Duplex Formation," Biochemistry. 43(18):5388-5405 (2004) (18 pages).

Mergny, JL et al., "Analysis of Thermal Melting Curves," Oligonucleotides, 2003, vol. 13(6), pp. 515-537, 23 pages.

Mitsuoka et al., "A bridged nucleic acid, 2',4'-BNA COC: synthesis of fully modified oligonucleotides bearing thymine, 5 methylcytosine, adenine and guanine 2',4'-BNA COC monomers and RNA-selective nucleic-acid recognition," Nucleic Acids Research, Mar. 2009, 37(4):1225-1238, 14 pgs.

(56)                    References Cited

OTHER PUBLICATIONS

Morita et al., "2'-O,4'-C-Ethylene-Bridged Nucleic Acids (ENA): Highly Nuclease-Resistant and Thermodynamically Stable Oligonucleotides for Antisense Drug," Bioorg Med Chem Lett. 12(1): 73-76 (2002) (4 pages).

Ramdzan et al., 2-D DIGE profiling of hepatocellular carcinoma tissues identified isoforms of far upstream binding protein (FUBP) as novel candidates in liver carcinogenesis, 2008, Proteomics, vol. 8, pp. 5086-5096, 11 pages.

Santa Lucia, JJr., "A unified view of polymer, dumbbell, and oligonucleotide DNA nearest-neighborthermodynamics," Proc Nall Acad Sci USA, 1998, 95(4), pp. 1460-1465, 6 pages.

Scoles et al., "Antisense oligonucleotides: A primer", Neurol Genet, 5(2):e323, Apr. 1, 2019, 10 pages.

Seth et al., "Synthesis and Biophysical Evaluation of 2',4'-Constrained 2'0-Methoxyethyl and 2',4'-Constrained 2'0-Ethyl Nucleic Acid Analo !!Iles," J. Org. Chem., 2010, 75:1569-1581.

Soan and Yang, "Construction of shRNA lentiviral vector", North American Journal of Medical Sciences, vol. 2. No. 12, Dec. 2010.

Stephen Locarnini, et al., "Molecular genetics of HBV infection", Review Antivir Ther., vol. 15 Suppl 3, 2010, pp. 3-14. doi: 10.3851/IMP1619.

Sugimoto, N. et al., Thermodynamic Parameters Tto Predict Stability of RNA/DNA Hybrid Duplexes, Biochemistry, 1995, vol. 34(35), pp. 11211-11216.

Swayze et al., "Antisense oligonucleotides containing locked nucleic acid improve potency but cause significant hepatotoxicity in animals", Nucleic Acids Res, vol. 35(2), 2007, pp. 687-700.

Szabo et al. Pathology Oncology Research Vo. 10, pp. 5-11 (Year: 2004).

Tringali et al 2012 Journal of Pharmacy and Pharmacology vol. 64, p. 360-365.

Uhlmann, E., Recent advances in the medicinal chemistry of antisense oligonucleotides, Current Opinion in Drug Discovery & Development, 2000, vol. 3, No. 2, pp. 203-213.

Wan et al., "The Medicinal Chemistry of Therapeutic Oligonucleotides," J Med Chem. 59(21):9645-9667 (2016) (23 pages).

Yan, et al., "HBVcircle: A novel tool to investigate hepatitis B virus covalently closed circular Dna", J Hepatol . Jun. 2017;66(6):1149-1157. doi: 10.1016/j.jhep.2017.02.004. Epub Feb. 14, 2017.

Zhang et al. J. Virol 82:5761-5773, pp. 1-27 (Year: 2008).

* cited by examiner

Fig. 11
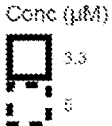
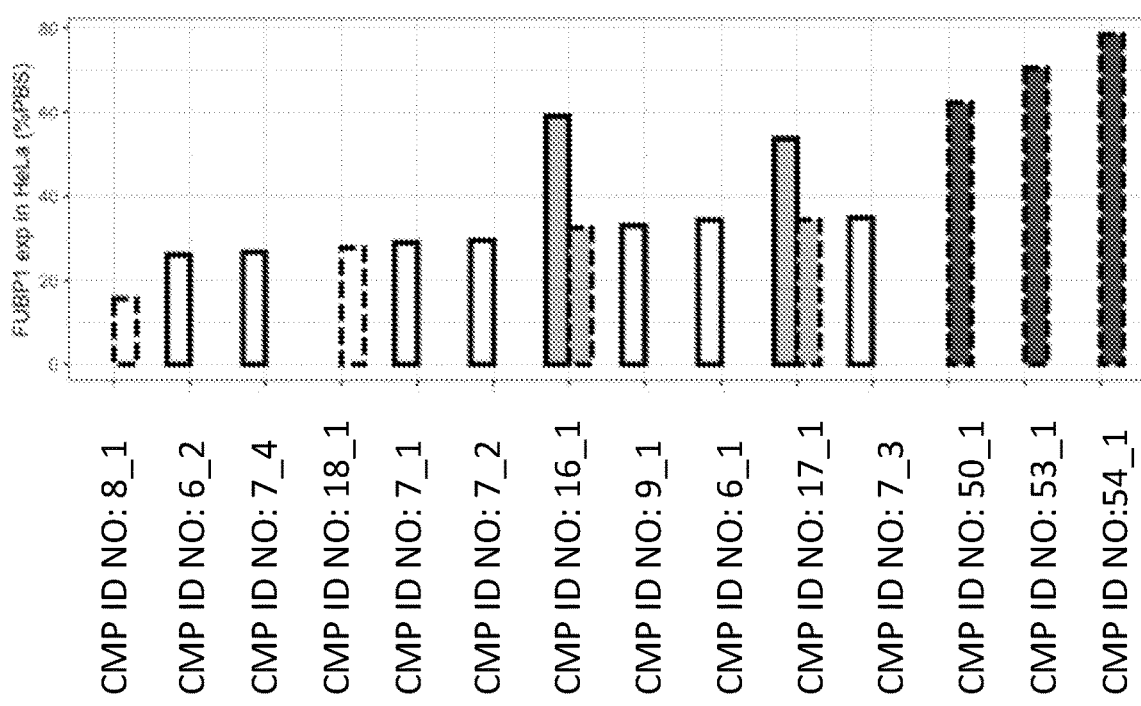

FUBP1 mRNA, ASOs @ 10uM

SEQUENCE LISTING

<160> NUMBER OF SEQ ID NOS: 22

<210> SEQ ID NO 1
<211> LENGTH: 35056
<212> TYPE: DNA
<213> ORGANISM: homo sapiens

<400> SEQUENCE: 1
gcgcaagaat gtaatagagc ttcgacggcc gccattttct ttctttctta gctgttagct      60
gagaggaagt ctctgaacag gcggcagcgg ctcttatagt gcaaccatgg cagactattc     120
aacagtgcct cccccctctt ctggctcagc tggtggcggt ggtggcggcg gtggtggtgg     180
aggagttaac gacgctttca aagatgcact gcagagagcc cggcaggtaa gtgtggaccg     240

-continued

```
cgcggcggaa tcccgaaagc tcacggtaat tggccgctga ctgagtaggc cgctaccctt      300
aagcgcatga ggaagaggaa agaggtgttc ttccgggctg aaatgtgaag agacacgttt      360
ccccatgttg gtaataacga ttagagacca gaacccagtt ttgtgttctt ggtgcctaat      420
ccacttagaa ccccgacgcg tgctacgcaa agaaggcctg aagtctttct cccgcttctg      480
cggcactcgc gtgtctccag tgagctagtt tagataaaga tcctcttcca ggggataaag      540
cgcagttagt ttcacacaat ttaatggaag gttctggtaa tgagtttggg aaagaactag      600
ggtctgtcct ggagccatag caagggaagg gatttatcat taaagtagcc tttacagctc      660
atttccgttc tctctcgcaa ttaaaaccgc tttcagtacc attcaccgtc acacctctac      720
aaggaaggga cttgaaagca gccttttttct gggcgggatt tacgtgtcag tctgttccac      780
cagtccgccc cccttatttc tcaaaatggc ctcaggccca ttataccaga ggtttcaatt      840
tgaatctgcc tctcagttca gagtcgtaaa ctgaccagac ctctttgtat tacgtagtgc      900
gtgcatttgc cctgaaggca ccactttccc agacgaaagc tgttaaaata gtgcgtgtat      960
tccaggaaaa taaaagatac cttaatttga actttacatt cttagatagt cccctaatat     1020
atttaacatt tcaaaatgta tggtgttggt atagatttgc atgtaagcaa aagaatccta     1080
ttctctgtga cactatgcat attgtactag gtgctgggca ttttttacta gtttttaagct     1140 aatgataatt agaaaccagt gttgtgctgt gttttcgttg cattaggagt tcacttagtt     1200
aactttttac cgggacagtt gaaggaacat tgagtcaaaa ttagaattca taaaatccgt     1260
tgtaacacat ctaatgtgaa cgcattataa acatgtacct gtactttttt ataaccagaa     1320
atactaggag tagtcaacaa aaggtcatca ttaatattag ttctgcggtt ttttccacgt     1380
aatttaagaa attctgaaca tgtttagcaa caagcatata actatgacaa acactcttag     1440 cgtgtttat tagattgatt tgtaaaactt aagggaacta ttttatttac tggaaccaac     1500
tattttattt taccagaacc agcacattgg attaattggt atcgcacact gtaggtagat     1560
actggagttt tgttttgttt tgtttgagac ggagtctccc tctgtcgccc agactggagt     1620
gcagtggtgc gatctcgtcc cactgcaacc tctgcctccc ggcttcaagc aattctcctg     1680
cctcagcctc ccgagtagct gggattacag gcgcccgcca ccatgcccgg ctaatttttt     1740 gtgtttttt tgtttgtttg tttgttttca gtagagacag ggtttcacca tgctggccag     1800
gctggtctcg aactcctgac ctcgtgatcc gcccgtcttg gcctcccaaa gctgggatta     1860
caggcgtgag ccgctgcgcc cggccttgtt tttttttcgtt tgtttgtttt aatgcatgaa     1920
ttgtttccta ctaagaagct atgatatagt tccttgacca aatgcagatg aacaggatta     1980
tctgattaat actttaacga gagcagacaa aatatggata tttaattcat ccacttgctt     2040
tataagtgtt tatagagttt gttaggaggg gatgcccaat ttcctaagta aaggtgatat     2100
atgagcaaga cattataaaa tgaaagagag tttggccagt gaagaaaaga agcagcatgc     2160
gcagaggtgt ggggacttga gggaatggca aggacccaga agtgaagtcg ctagaagatg     2220
ggggtgggag gacgtgaaac gaggcaagga aaggtacaag cggatccaga tactggaaga     2280
ccttgtgttg caatgcttta attaaaaatt ggatttcagg ccgggtacgg tggctcacgc     2340
ctgtagtccc agcactttgg gaggctgagg caggcagatc acttgaagtc ggagtttaag     2400
accagcctgg ccaacatggt gaaaccccat ctttacaaaa aatacaaaaa gtagccgggc     2460
ttggtggcct gtgcctgtag tcctagctac ttgggaggct gaggcacaag aaccgcttca     2520
acctgggaag tggaggttgc agtgagtgga gatcacgctg ctgcactcca gcctggtcat     2580
agagcgagac cctgtctcaa aaaaaaaaaa attggatttt attattaggc taagccataa     2640
```

```
tttctttata cttcttaaaa tatagaaatt gttggcaaat tgtgaaattt attgttgtat    2700
aatgctaata gatcagttgt cctgatgtct ttgctgtaat gatttcttta taaaaatgat    2760
cttaaatctg agctccctaa ctttagtttt tgcctggaat tacccattac atttgatgat    2820
atctctaaat gtcagttgta gctgttactc tgatgatata agtggaatat acagaagcgt    2880
acttagacaa aagttaggtt aatatctgaa ctacttcctc cttgtgtatt taagagaata    2940
ttgacttaag tttctagaat cctcaactaa tcctaagttt attttctttg tctagaatac    3000
tatgctgttt ttgttttttgg aaggaagaga tataggcata gtttcctgct ctcaaggagc    3060
ttcaaaggct gtaccagtgg ggatgccatt ggtattttta gctggatagt tgttattcag    3120
aaaagcagga caagtaatta tgattcctgg tccgtacctg gtaatgccag taatgttaac    3180
tctagctggt tgttgacatc tggtcattta gttgccaatc ttctttttttt ttttctggct    3240 tttatgtgaa attttttagat ttttataata tcctgagcta aattcaacac agggacacca    3300
gattgctgct ttagttcagg gtttccagcc tgtgcactta agaaatttat ttttgtgtat    3360
atcaagctgt aactccagag attgggattg tttgattggg tctttagcag tggtactaat    3420
agcaacttct gtctctagaa cattggaaaa ttaaaatgtg tttatctacc gttttttttcc    3480 tcgaggttat atgaaggtag aaatgaatca gactagatga ttagctaagc gagactatta    3540
accctcatcc cttcccctct agacaactat gaaattagtc attatgtatt cgatccttct    3600
tgcagtctct tctctgacag ttataaaagt gatttaggct gcataatgtt gtttgaatga    3660
aatgaaaata tagactagag ctgttttttt ttttatttcc atcagtctct tcagtgaaaa    3720
ctaacatttg agcatgattc ttttttttaaa tcattttgtg acagtttagc aaggcttgtg    3780
ataagcaagt tatggtatgg taatatttct agtgtccacg tttcttcaca tgtctggtgt    3840
atgggaacta ctaactccat caggaccttg cctatagtag gtactcaaca tttactgaat    3900
taaatcaata aacattttta atgaattaca gtacaagtca gacctctgta tctgtgggct    3960
ctgcatctgc aaattcagcc aaccatggat cagaaatatt agaaaaatgg aagaacagtc    4020
cagcaataca agtaatatga ataaaaacaa tacaacaact atgtacattg tatcaggtat    4080
tataagtaat ttagagatgc tttaagtata ctgaaggatt tgcgtaggtt atatgcagat    4140
actgtaccat tttatataag gaacttgagc atctgtggat tttggtattt gcatggttcc    4200
tggaaccaat cccccaggga tactgaggga ctatagttga tcataccacc tgatttttaga    4260 gattttctga gtctcagaag ttaattaagt aaactacaat agtctgttct taacctcgga    4320
ggatacattc caagaacctc agtgaatatc tgaaaccaca gatagtattg aatccaatat    4380
atacacggta atatttttttc ctatacatat gtatctataa agtttaaatt ctaaatcaga    4440
cacagtatta acgataataa taaattagtg caagactggg catagtggtt cacacctata    4500
atcttaacac tttaactatg acgttgtctt tgaaaagaaa tcagctagcc aaggtggctc    4560
atggctgtaa tcctagtgtt ttgagaagct aagtcaggaa gattgcttga gcccaggagt    4620
ctgagaccac cctaggcaac atggtgaaac cctgtttcta taaaaaatac caaaaaatag    4680
gctgggcgcg gtggctcacg cctgtaatct cagcactttg ggaggctgag gcgggtggat    4740
cacgaggtca ggagattgag accgtcctgg ctaacacggt gaaaccccgt ctctactaaa    4800
aatacaaaaa attagccggg agtagtgggc gcctgtagtc ccagctactc aggagactga    4860
ggcaggagaa tggcgtgaac ccgggaggtg gagcttgcag tgaaccgaga tcgcgccact    4920
gcatgccagc ctgggcaaca gagcgagact ccatctcaaa aaaaaaaaaa aaaaaaccaa    4980
```

```
aaaattagcc agacgtggtg gtgcttgcct gtagtaccag ctatccagaa ggctgaggtg      5040
ggaggattgc ttgaacttgg gaggtcaagt ctagaatgtt gacaatgttg ggtcctttat      5100
gtagttgcat aagtgagcca tgatcgtgcc actgcactac atccttgggc aacagcctga      5160
ccctgtctca aaattttaat ttaattaaaa aaataaaata gaacaattac aacaatacac      5220
tgtattactg gacaagaagg gcaaatttaa aaaaaattaa accaatatgc tataataagt      5280
tatatgaatg aggggacccct cccctacccc agaatatctg attgtactat atcataggta      5340
actgaaaccg tgaagagcaa aaactgaaga taaagagact actgtgtctt ttaagtttct      5400
tttcaactcc caaattcttg gatttctcac ctcttggctt cctcaatdga ggtgagaaat      5460
gttaaagtag tgaaaacagg aaaaataact tactcattca agaagtagat aatggtccag      5520
atggaaagct tgaattattt ttgtaaaact aaaattaaat aaagtagcca ggcatggtgg      5580
cttacgcctg taatcccagc actttgggag gctgaggcgg gtggatcact tgcggtcagg      5640
agttcaagac cagcctggcc aacaaggtga aaccctgtct atactaaaaa tacaaaaatt      5700
agctgagcat ggtggcgggc gcctgtaatc ccagctactc gagaggctga ggcaggagaa      5760
tcgcttgaac ttgggggggcg gacattgcag tgagcccaga tcacgccact gcactctagt      5820
ctgggtaaca tcttgagact ccatctcaaa taataataat aattaaataa agtaaaaagt      5880
ttcccacacc tcataaatgt ctaataaaaa ttgaatatgt tgagttcaag tactctgaaa      5940
aaggagttga atatagttgg aggttggttt ttaggaatta ctattttct taaattaact      6000 atccttgtag tcacctagga attgtgtatt ttctatagat cttagaaaat tatcaaatct      6060
acagttcatt ttgttttttc agtttttttt ttttttttaa gagatggagt cttgctgtat      6120
tagcgttgaa ctcctggcct cagccagttc tcccatctca gcttctgaag tagctggggc      6180
tgcaggtgcc actgagcctg gcttctttat tggtattttt attaaacact tttctctaat      6240
gtctttgtaa cagttctcag ttttgaaat gctgttactg tttctttagt gtgaactgtc      6300
aactttcatt ttttctttc ttttctttc ttttctttt ttcttttttg agacagagtc      6360
tcgctctgtc acccagactg gagtgcagtg gtgcgatctt ggctcactgc gacctctgcc      6420
tcccgggttc aagtgattct cctgcctgag cctcccgagt agctggaatt acaggtgcgc      6480
accactgtgc ctggctaatt tttttttttt tttttttgtat ttttagtaga ggtggtgttt      6540
caccatgtca gtcaggctgg tcttgaactc ctgaactcat gatccccccc gcctgcctc      6600 ggcctcccaa agtgctggga ttacaggcat gagccaccac gcctggcctc agctttcatt      6660
ttcatttggt tagttttga actattcagt gggtaaagtt gtataaataa gtgtcttttc      6720
tctgtataga agtgtcttgg agttcaagga gtgctgcttt gcaaactcat agagtattta      6780
taaaagctaa ctgcagaagg tattcatagg ctaaaccgtt tcctattctt ggtagcacca      6840
ttttctctgg cctgaaatac tttccttcta ctattagtgc ctgtcgatac ccagcagtgt      6900
atttactttc ctgaggaaca attcaaatgc taagtgcttt aagacctaag ggtggaaaag      6960
cagtgttttc aggcattatt aggaaaataa gatttaaatt agacacccag aaacaaaaac      7020
aggtttgtaa ttggtaaagt gaaagatggt taaagaaggt tagattgacc aaagcgagaa      7080
tttacctttt tttttttttt tttttttgaga cagagtctca tgccgttgcc caggctggag      7140
tgcagtggcg tgatcttggc tcaccgtaac ctccacttcc tgggttcaag cagttctccc      7200
acctgagcct cccgagtagc tgggtgacat gcgccaccac gctcagctaa tttctttgta      7260
tttttagtag agactgggtt tctccatgtt ggtcaggctg gtctcgaact cctgacctca      7320
gtgatctgcc cgcccttggcc tcccaaaatg ctgggattac aggcatgagc cactgtgtcc      7380
```

-continued

```
ggctgagagt gtaccttttt ttttttttat caagcaatct agtacttgat cctaataatc    7440
tttgtggtag gtgtttgcat ttttagatga ggaaaaggga aatctatgag tcctaggaaa    7500
tacagttggt atatgggaac tgatatgtaa ttagacttaa gtgatccatg ttgaatttat    7560
gacttaagca cttaactata atcttaacct ctccagttgt ctgatgaagt tagtatatgg    7620
gaactgatac atagacttaa gtgatccatg ttgaatttat gacttcagca cttaactata    7680
attttaccct ctccagttgt ctgatgataa taaaaacttg aagcagttat ccatatgggg    7740
atctctttgg ggaatcccag tcaccaaaag ttaggttttc tttaatattt tttcatggaa    7800
gatttcaaat atactcaaaa ttgaaagaat tatataataa attctcatga gcccatcaca    7860
catcaataat gaatgtacag cattgcagtg tggagcttgg cctattgctg accactcagc    7920
aatgtggcag aaccactcca tgattcccca tggaaatggg aactacttcg gttgtccttt    7980
tatagaaaaa ttcagtaagt atctgctgat tgtgccctac ttgtgacttg aagccaggtt    8040
tttttttttg tttttttattt tttttgtttt gttttgtttg taacagtctt gctctgtcat    8100
ccaagagggg catgatattg gtgcactgca acctccacct cctgggttca agtgattctc    8160
gtgcctcagc ctcccgagta gctgggacta tgggcgtgca ccaccacacc tggctaattt    8220
ttgtatttag tagagatgga gtttcatcat gttgcccagg ctgctctcga actcctgagc    8280
tcaagcaatc tacccacctc cacctcccaa agtgctaaga ttacaggcat gagccaccat    8340
gacagcaaag ctgggtattt cttaaattgg ttcagtcagg tgcaataaat tatttgccct    8400
actctaaaat ttaaaaatct tctaagaatt atggttttgc agctgaggtt tttttaagac    8460
tcgagctccc tggactccta catatatcct tagaacaaca ttgtccaata gaagtacaat    8520
gtgagccaca tgttttgttt aacccagcat atccaaaata ttaccccctt tgcatgtgct    8580
taatataaaa atttaagatg atttatattc caggttttca atattcagtg agtaatttta    8640
cacttagagc aagtatcatt tcagactagt cacattttga gtactcaata accacatatg    8700
gctagtggct accttactag atagcatagc ctttgagtcc cacaaagtgt tcacattcta    8760
tgtgtttaca cacatctttt gaagtgtcat gacagagcca gataggatcc agattttctt    8820
taaatctggt ctctcttccg gattcctagt tgattacttc tttgttgctt cttatataggga    8880 tgtatcagaa gtttaataat cttatgatta ttatgttaac tgcctgaagt attaatggta    8940
gcaataaatt gaactataat tttaattttt caagtaaatt ttcttatgtg atactaaata    9000
tttcacatat acatgtatca ggaagtaaat gggggtaatt tagtaatgaa tagtatataa    9060
tagtttatga tggtattttt cttttttttt tttagattgc agcaaaaatt ggaggtgatg    9120
cagggacatc actgaattca aatgactatg gttatggggg acaaaaaaga cctttagaag    9180
atggaggtaa gttatactct aagtatttta aattgttttt cagagtgttt agttgaagtg    9240
attctcggta ttttttctgtt attttattga gatattaact tttattataa ggttgttaaa    9300
attgtaagct gtatattggc ctaaaagggg ggaaagaaaa ctagacaagg taagtaaaat    9360
ttgaaagaaa tttttaaaa aatttttaa aaaaggaagt tttgtcttaa tagaaaacaa    9420 tttatttttcc ctcttttagg attgtgccag attgaaagtt tgcacagacg tcttgttaat    9480
aatattaaaa aacatataaa ttgcttagaa gacacttcac tggttttact catacgtgaa    9540
tggattttaa tatgctgtat tttcgtcatt tttctatttc caattgcacc ttaaaggttg    9600
aaattcctat agtttgctac tctagtgtgt tgcaggttat accatttttt ttttaatgtt    9660
ctttactttc agtactttg tgtttcacgt ttagctttaa acctgtggat taaaacagtg    9720
```

-continued

```
gatttacagt gctatgtatt tttaaaaatc gtaatcgttg aagcttctga acttagaagt    9780
ctgcatgtat tttttgtttt aggtttgata tatgagtttt gatacatttt cttttttaccc   9840 ttttttttaa agggaggatt ctcactgagg ctatagaatg tatttgtagc tttttgaccag   9900 gagaacttgg tttcctttta tttaagtgtc tttcatattt atagtgaggt ttttaatgta    9960
gaaaaaaaat gagctaatga tgcttcagat gttgtatgta atgtattctt tttatttttat   10020 gtgtagatgg ctcttggaca agtccgagca gtacaacaca ctgggaggga atgccctctc    10080
cttttaaagg caggaatttt tatttattac ctgtgttcag tatgtaaacg tgaaataaac    10140
cagtggattc ttaaatggac acaaatattt cttggattat gtgtctgcgc atattttatt    10200
tttgctgcac aacattctga tgtttaatca tttaagtttg aaggggggag gagaatgtag    10260
tactttgagc tataggttgt ctgttccaag gtatgcattg tattcatctg tgtaatggat    10320
ttaggtgaag gtagtcatgt agttgctttg agatttttatt ttttttgctaa agtttttatgc   10380 agtgaaatgt ttgtttataa ataatagaac agtttaggtt gagattgcct tgtaatgttg    10440
tggggggttt ttttgttttt tttttttttgg gcatagcttt gtggtcactg tcagatacac   10500
tttaatatgt cagatttttg tagtttgata ggcttttctc cccccagtct tcagttcctg    10560
aggtggaagc atcattagcc tttagcatgt gatattttgc tagtaatgga cctaaagtac    10620
gttgtcttgt gtcattctaa tgtgcttaac atacattaag gtcagtgatt tcttaagaat    10680
cagataacta ttttaatgtc tgtgcatctt ttgaacgtga agagaatgaa gtatcgtttc    10740
ttttttagat tactgagttg gggttgaatt ttggcagttt tggttcaaat gataaaccat    10800
accttcagat atttcaataa atgtttatat tgttatttat tcttgtttgg gaggggagaa    10860
gctttgtact taattggcaa aaaattaaaa gacacttaat tttgcagatc aaccagatgc    10920
taagaaagtt gctcctcaaa atgactgtaa gtattccttt taaactgggt caaaagctaa    10980
agtaacaatt tcaatgttaa gattttgttc atattattgg gtatctttga agttagttgg    11040
tttatgagta ttttggatca gctagcctga atttctttgt aaatatatac ctttttctcc    11100
tattttacaa tctgtcccat taattgtggc cgggtatatg taaagattgg ttgctgaatt    11160
attttacata tttaacaact ccaattcttg atctatactt gtacaacttg aaaaaggaaa    11220
ttattttgtt ctgtgccatt gctaatataa tgtcttccct ttcattggct ctcttgcccc    11280
tgtcaatgcc aatataaata ttgtgtaaaa aatttgactc tcttcaaggt gttgtctgtg    11340
cattagggag agattttttga atgtttgatg tgattgtgtt gttaaatata taagtaaatt    11400
taaattttga attttttgttt tatttttatt taatttttttg atagcttttg gaacacagtt   11460
accaccgatg catcagcagc aaaggtatag tcacaagatt ttcaaaaagt actctgcaag    11520
ttttggttga gctgtatgta aaaacacaac cacattggtg tatattgaat atgtgtctgt    11580
gtattttttg gtgtacctag ttcatatcac tccccttggg aaggtaccat aaagtgatga    11640
ttttttcttt gagtgagaaa aatttgtgat ttggagagat aggtggaatt aaccacattt    11700
tagaagaaca ggggtgaatt agagtaactg ttaagatgac attctctaaa ctccacttca    11760
acttctttac agttaatgcc ttcagactgt tccattcatc atcccttctt cacttgatgt    11820
gtcatcttaa atttcttaat ttaactactc aagtaataag atcatatttt ttgacatgag    11880
tctgagccta gaaccttagt ttaagccatt gggagacatt agacttccat ttttattaat    11940
agattatctt ttatttgtaa acaaagtatc tttcattgaa ggaaaatggt gctttctgtt    12000
atttcttagc agatctgtaa tgacagaaga atacaaagtt ccagatggaa tggttggatt    12060
cagtaagtaa cttgattttt aaagtttttga aaacatgatc aaaacatact ttagaatctt    12120
```

-continued

```
tcaaccaaaa aaaaaatttt ttttttttcta actagtaatt ggcagaggag gtgaacagat  12180
ctcacgcata caacaggaat ctggatgcaa aatacagata gctcctggta atgttacatt  12240
ctcatggtat tttcagtgtg actagaaaac tagctttttt tttttttttaa gccttctagt  12300 aacaataatg ctacttttaa tcttttgacc tgaagttatc tgtttgtttt aaattgtaga  12360
cagtggtggc cttccagaaa ggtcctgtat gttaactgga acacctgaat ctgtccagta  12420
agtttgaaaa atcttaaaaa tctacttaag taacaacagc agaactcttt gaattttgtc  12480
tcttctcttt gttactgctt tattttacac tgtggtttcg ctgccacctt ccctcaaagt  12540
cctccaactc ctttgaagtt tatgcctcat gcctttctca ggtggggttc atcatctgaa  12600
tcattaaaca cagaaaatgg ttaaaacaac tccatatcta ctccagtctc tacttgtaaa  12660
gccacgtgta gcctggagaa gaatgcacag tcaggtcgac tggtgacact taaaactcag  12720
acattaagct caagtggact gttgtgttgc ctgcatttcc ctagttccat tcacttttcc  12780
actcctctcc caggctcttt aatactgtat ttccccacct ccaaatcttc agcatctaac  12840
cccacgctct cccacttaag cttatttact gagaaaatgg aagcaaatga taagaagctt  12900 ttcttttttcc ctaccactaa acctaccagc cttcattttt cctctgttca catagtactc  12960
aggtaattgc tttccttttg tgttcgagtg cctaaagcca gccctttctt cctactgaag  13020
gttcagcttg cagttgtact ttcttctgca ttgttagttc tccctcatta ctaggttttt  13080
tcttttcttt tttttgagac gaagtctcgc tctgttgcca ggctggagtg cagggcacg  13140 atctcggctc actgcaacct ccgcctcccg agtagctggg actaccggtg catgccacca  13200
cacccagcta atttttgtat ttttttagta gagacagggt ttcaccatgt tggccgggat  13260
ggtctcaatc tcttgacctc gtgatccacc cacctcggcc tcccaaagtc ctgggattac  13320
aggcgtgagc cacttccccc agcctgattt tctttatggc actttccaaa taatgtgtta  13380
ttcatttgac atgttatttt tacttattta atgaaatgaa gccactctag caggaaccct  13440
gtttctttga gtgctattac cccattacct agaatagcac ctgcacatag ttgatattta  13500
aatatttgtt gaatgaataa ttgtagcata tgagtaagca aaatggtagt ttaaaaatgt  13560
aaataaatca tttagttctt ggaagaatca gtttaattct gagataactt tagcattaga  13620
gttctttctt ggaaattttg gactattctt aaaaataaaa attgtatatc tagaaaattt  13680
ttttgcataa tctctcaatc tttgaccctt gatggcattt tctttcagtt aaaagtaaaa  13740
gcattgttaa agttagcatc aaggcaccta atcctgaact gggataggag gagtacttgg  13800
ttatattgtt ttatatttct ctatttgaat aagcttgggt atgctacagc ttactattta  13860
aatattaatt tgttaacagg tcagcaaaac ggttactgga ccagattgtt gaaaaaggaa  13920
gaccagctcc tggcttccat catggcgatg gaccgggaaa tgcagttcaa gaaatcatga  13980
ttccagctag caaggcagga ttagtcattg gaaaaggggg agaaactatt aaacagcttc  14040
aggtattgtt attttttgtga aatggctact tttgatctgt tttgatgccc attttttgtcc  14100 acttcctttt gttaatatat attatttcta tgattgtaac aggaacgggc tggagttaaa  14160
atggttatga ttcaagacgg gccgcagaac actggtgctg acaaacctct taggattaca  14220
ggagacccat ataaagttca agtaaactta actttatact ttataaagaa agagtgggtt  14280
gaatggggtt gggcaaaata tgcatgaata attaaaatgt tttgagacat gctttctaaa  14340
ttagctaact ttttctgctt tagcaagcca aggaaatggt gttagagtta attcgtgatc  14400
aaggcggttt cagagaagtt cggaatgagt atgggtcaag aataggagga aatgaaggga  14460
```

-continued

```
tagatgtaag taaaaatacc cattcagaaa tggttgtatg ctaattcata aatataatag  14520
tgttttctgt tttgtgttaa gtagctctaa cattgttatc cttttatttc acctttatac  14580
tttagaatac agaattctat atatcttgtt accctattta ctataaatat agaattatat  14640
gtacttttat gatttgaggc agattttcag gaaatggcgc tttttaaaa tactttttt  14700 tactttaaac cctgagaagc tagctttctt aatacttagt cttttttaca taaggtcccc  14760
attccaagat ttgctgttgg cattgtaata ggaagaaatg gagagatgat caaaaaaata  14820
caaaatgatg ctggtgttcg cattcagttt aagccaggtg agtacatata ataatcttgt  14880
aagtgttggc agcagtgagt tttgacatac atttattgtt taattaattt tgtttctttg  14940
ttttgaagat gatgggacaa cacccgaaag gatagcacaa ataacaggac ctccagaccg  15000
atgtcaacat gctgcagaaa ttattacaga ccttcttcga agtgttcagg tttgatagaa  15060
agttaacatt ttcatttttt gttttatgg aaaagtattt tccttcatga aatctgaagt  15120
tacctctata tcagagtctg cttgatgatg ctttattaat ggagaaagtt taaattgctt  15180
taaggtaaag atcttggagc aggaagaact actaccttaa gtgctacctt atttactctt  15240
gtattttaaa aaatgttatt acttattagg gccagttcat ctctacattt ctgattcagg  15300
tatatgagag ctgggaaaaa taaacttaat aattttatca tgaaacaaaa gtatttctgt  15360
gctgactctt cgttcttgtc tttccctctc tataggctgg taatcctggt ggacctggac  15420
ctggtggtcg aggaagaggt agaggtcaag gcaactggaa catgggacca cctggtggac  15480
tacaggaatt taatttttatt gtgccaactg ggaaaactgg attaataata ggaaaaggca  15540 atgtattta aactcttaat gttttaacac attattcatt tttctggaca ctttctgttg  15600
ctgtcgtaaa caagtggcaa tgctttttct ctgaccgtat tttagtagaa aagaattctt  15660
atgttaatat gtaacaagta aaacataaat gagggatctc atgtatattt agagaaagag  15720
caggatttta atcttactag cttctagaga aagcgaacta agagataatt attagcataa  15780
gaaatgtctt ttgacccaaa aagtggtttg agtgtttttg tttgtgcatt ttggtttttc  15840
ccgactcata ttttaaaaat ttgaatgttt ataagtgtat tagtttatat ttacactgct  15900
tttaaaagca gttaattcaa atattttatt ataatcacat taagtttatg tttaaacata  15960
ctaagtaaat gtaaatgtat tttaagagaa gcatgaaatg cttcctaaaa tttgattttc  16020
agtgtagaat attaaatgaa aaatcttaat acaatattgt caattaggat actgaccaaa  16080 ccatatttt aatggcccat ttaattgtga ccattttctt ctaaatagct cctagtacac  16140
ccttgaaacc tttagagaaa ttactgtctt ttgattttag gaggtgaaac cataaaaagc  16200
ataagccagc agtctggtgc aagaatagaa cttcagagaa atcctccacc aaatgcagat  16260
cctaatatga agttatttac aattcgtggc actccacaac agatagacta tgctcggcaa  16320
ctcatagaag aaaagattgg tgtgagtata ctttaaactt ttaattttta gtgtagaccc  16380
ttagactgta gttaaattaa gacgtttatt caaatacatc aaaggaaaat gtatcattac  16440
tagtcagcat ttatagattt catgatatgt ataatagata caacgtgaag attttccagc  16500
aatgaaaata acctaattaa atgtgtagtt acaggttttg agaacaacct tacatttggg  16560
tgtggctaga taagaggagg gtagtgttac ctgtaggcat gatattagtg ttggtgtagg  16620
attgtggaac atacttgaag gacatagtta acgggaattc attatttatt aagattttac  16680
tctactgaac cccagcgagg caaacaagat aaatcagata catctgccac tctacagtag  16740
aaattcataa atcctaggtt ttggactggc tcacagatca tctggggggta ttaaaatgta  16800 gactatttgg gtgcttccca ctcctacaca taatatacag agacagacct gactcaaaat  16860
```

```
gtctgggata gggcccagca tctaatttta catagatgtt tgggtgattc tggtgcacag   16920
acaaatttgg aaattttttcc tccaggaaag ttttctgtta gaacaaaaaa gtatgaaacg   16980
ctttgactgc tttttttgtaa gtgaggcaga cagtgtctta ctggagtttt taacacaaag   17040
tgtgcagggg gcatcttaaa ttattagaat tgcctaggaa aaattatttt tggtgtttgc   17100
catgctgtga atggggtgcg tgcaaaacaa ggttgacact gtttctgtca acttgggaag   17160
acaaaaatag atgtacaaaa gacgcttaag gaacgtctta caaaatgtac acaaacattg   17220
tgagttctgt tgtatggata gtttaatggt tcaaaaaatg aagaggatgt ttgtagagta   17280
atgatagagg ttgatgccat ggcaaaaaaa tgaatagcac tcatcttggt tttttatttt   17340
acagtattag cctaacatgc atgcgtcagg atttctgttg gattcatgga aaaacaagat   17400
agattgtttt ggagaagcaa tttggtgtgg tgattaagag catggactct gtagtcgggt   17460
tgcctcagtt cagaattctg tgaatcattt actggttctg tgaccttgga gaagttactc   17520
aggcttttct gtgccttggt ttcctcctgt aaaatgaaga taatggtatc tacttcatag   17580
agttgtaggg attaaatgaa tgttcatgtg tgtgtcactt aaaagaatgc ctgccacata   17640
accctaaaaa atgttgctac tttttcagta ttattttttac tacttggaaa gaataggtca   17700
tggatagtaa gtgagagatg acagcaattg gagatttaaa gagacaagtt aataaaaaga   17760
actttaaagg tcatgaagtt tagtttccct attttgcagt gagaaattta caacaaaatg   17820
tagtgttagc attttgtcca acatgtcgcc tggttgtgtt aactactcag aaggagcatt   17880
ttaggacagt taagtgtaat gtctttgttg gcttaaccaa acagaaatca gttaagcgtt   17940
attaatgatg tggcatgcat gcatgataag gatataaaat atcctgattt attgaaggaa   18000
ttaaaaaggg aatttttgtg ctattaaaca tcatgataca tgaaaggcca aaaaggatat   18060
aaattattga tctgaatggg attttagtga cagaaatagg ttgtgaggtg gatttttagtt   18120 tcatagtgaa acaactagct attaacgtta tcagtgaaat gttcagaaga cgatgataca   18180
ggacccaagc ggtttgggaa tatattgtca agacggttgt ctcatgttag gcaagtagat   18240
atagagagaa gagctgaaga taaggacctg atttctgtga gtaagatgga aaaagatagt   18300
aaaagtaaga atgataaaag gaaagggaac tactgctgtc cgcaaacaag ctaaaggaaa   18360
tttaattgct aatttaaatt taatttaatt taaattgcat ttaattgcta ctgctattga   18420
ttttagtgaa ttttacatgt ctcattatta tggcagatga aatagttttt gcaaaatgaa   18480
tgaggaaagg aaggaaaacc taaaatttgt tatttgtgac tataagaggg tagaaatgga   18540
tgattatttg gccgtagagt tgtttaacca ttactgtgtt tttctgattt ttctatgtca   18600 tcctttttttt tgtagggccc agtaaatcct ttagggccac ctgtacccca tgggccccat   18660
ggtgtcccag gcccccatgg acctcctggg cctccagggc ctggaactcc aatgggacca   18720
tacaaccctg caccttataa tcctggacca ccaggcccgg ctcctcagta agtattgggt   18780
ttagttctgg gctttcccca aagattctag tttttgggact gtttttttatg ctgattttttc   18840 tttttcagtgg tcctccagcc ccatatgctc cccagggatg gggaaatgca tatccacact   18900
ggcagcagca ggctcctcct gatccaggta gaagatgctt attatttgtg tgttatctgt   18960
attattttcc actcctgtta cattattaaa ttttctagtg ttgattctac atttgtatgc   19020
atcaccttca ctcactttac tctttcaaca gtgttaggca ctgcctctac cccagtgtat   19080
aggactgaca tgaatatgag ctctgctttt atggaatttc tttctacttg cctttggctt   19140
atgagttgat acagtagaat gataaaagct aaaagctgca ggaaagagca cagtgtcata   19200
```

-continued

```
ggttttggat accagtgctg tcaaatgtgt agtatgttca ttgtgacatt atctgtggaa   19260
aaatagtttt tacttattta gaaaagtatg tgataggggc tgggcactga ggctcacgtc   19320
tgtaatccca cctattcaga agtctgaggc tgaggcttga gaccagcctg ggcaatatgg   19380
caagacccat ctctaaaaaa atttgtttta aattagccgg gcagggtggt atgtgcctgt   19440
acttgaggct gaggtgggag gattgcttga gcctagaagt tctagattgt attgagctgt   19500
gggcacacca ttgcactccc ctgggcaaca gaatgggatc ccatctctta aaaaattatg   19560
tatatatgta acagtctata taaatatata tatataacag tccaacagag tgttaagtat   19620
tggggcatta aacttccaaa ttgtcaaata agatatctgt tctagtactc ctcatatgac   19680
aacttcatgt gagtaaaaat caggcctgta tttaataact gcatgctaaa gcccaaatac   19740
gtttaattat tttctatatt cagatttatt tttatcctat tatattctgg catctttcca   19800
taccctgtag tttgctttcc atcttggtca aagagtcatt ctttgaaacc aattaacatt   19860
tatttatgat cctttttct cacctgctac ctacctttta ggcctctttc actcgtgtag    19920
tttcaaggaa aatatactca attatggaat actttctaca cataatacat ttatcccaaa   19980
aaaacttgaa gtaatttatg taaatgaaat tgcttgatta acttcatagg aagtgtgctg   20040
tttggaatat gatgacacag catgacagtt accaagcatg acttgagttg tgctaggata   20100
taggtgtgca aagttggggt tgtgttctat agcaaaagaa tgcactccca gcgtaagcaa   20160
cactgatgga aggggctcac agggtacagg atataatact cttaacaact aatttttgga   20220
gaatgaaagg gcttttcttt ccctcttgtt ggctgattgg gatggtataa ttaatgggat   20280
tgaagagttt gagtaggtta aaaggcagat tcatattggg taacttggat ctgccaggat   20340
tgtatttttg agcactactg ggtggttagc atgattgagg aaaaatgatg ggaataagaa   20400
gtggaagtgg tctttgtatc acaagttgaa tttctcactt ggagtagtag tgaagtcact   20460
actgtaagag ctggtcagtg aatgtggttg cagcatggcc tttgggcaag aagtaaccca   20520
tttaactaaa accagctggt tggccccact cagatttatc aaagggttac tgggtccctg   20580
ggggtggata ttgcttatat tagacttaga atagcatact gttttaatat tatatgaact   20640
aaaatgtttc tttaaaaaaa gagtggtctg ttaatggatt tatgtagtgg tcaagaattt   20700
agacttcaga gtcaaataaa cctatatcag tcctagtcct acagtttact aattgtgaga   20760
tgtcaagcaa gttttttgaac tcctctaagc ctctgttttc ttatctataa attaataaat   20820
gaatgaatcg ggttgagtga atatttagta aattcttagt acatactagt tatttgtaac   20880
tgtgagactg gtttttttggt atggttttca catttgggag tagaaatacc acttcctaaa   20940
gtctgtttta tctcaaattc tctatccagg catagtgtaa agtgaaatac ctagatttct   21000
tgattaatat acagataatg gccagacgcc atggctaaaa cctgtgacgc tagcacttcg   21060
gaaggctgag gcgggcggat cacttgaggt caggagttgg agaccagcct ggcaaacatg   21120
gcgaaaccct gtctctacta aaaatacaaa aattagctgg atgtggtggc aggtgtctgt   21180
aatcccagct acttaggagg ctgagacagg agaactcctt gagaattgct ccactgccct   21240
ccagcctggg caacagagtg agacacttca tctcaaaaaa aaaaaaaaaa tacagataat   21300
gacactattg agatatgtaa acatccaaca taaaaaagca gtacattggg caattgagaa   21360
aagtttggca ggtgtcctaa taacacctta caattatatt accttgcaat tttcttttttc   21420 tagaaattct tgctcatttt tctcaaactt gactaacctt tattaagcag ctgagaattg   21480
ctactgttca gaatgaaggt ataatagaaa atttaaaagt tttaattgta tggtattcct   21540
agtataaaag acaatcaagt ttttctggt ttctagaaga ttgaaaggtc tcaaactgtt    21600
```

-continued

```
cgcacttcag ttgatgtggg agatgagtga gggtcagtca agtgtagagg agacaacata   21660
gctaaaagcc gagacacggg catagtgatt tctgaaaagt acaagcactg tgttgtggct   21720
ggagcttggg tgttgaagag atacaaccaa agggagagat gaggctgaaa tggaaaggat   21780
aagccagggg cttcaggctg ttaaagatgt tgaatgatag gctgtactta agctttgaac   21840
atcctgaaga ttgcagagaa tgaagaattt caagtaggat gacatcaagt ttataacatt   21900
caatgtgaaa taggatgaaa tgtggctaat ctttttttaag attttttatat tttctcttca   21960 ttgaaaataa ggacaaagtt cattgttcta aaataatttt ctttcttata caggttagtc   22020
cctagaaatg tttttctttta gtcatcttct agatagagct gtttgtgctt gaggcgaaac   22080
caatttagaa aaaaacaagg gcacaggatg gtttgagaca gagcattgga tttggagcca   22140
aaagaccttt attcatatcc cagttatgcc actcagtagt ttttaaccta ggaaagtcac   22200
ttagtctctg agacttggtt ttctttaata aaagctgatg gtgacaacaa aaataataga   22260
aaatttaagt tttcatatac tttttttaat gttctagtta attttgggg ctgtatattt   22320 gccagagagc tgggcggggg ggtggtgtgt gtgtgtgtga gagagaatta cagacttcac   22380
atgcaaacct tgaactttca tttattttag ctaaggcagg aacggatcca aattcagcag   22440
cttgggctgc ttattacgct cactattatc aacagcaagc acagccacca ccagcagccc   22500
ctgcaggtgc accaactaca actcaaacta atggacaagg taactacaga acttattgta   22560
tgtgaaagcc aaaagttgtg cttggaatta tatatgaagt acatcactgt ataataccta   22620
aaatttctga cattatttaa ttataattta agcagacttt tccttttttta aattgttact   22680 ttgaaatagt ttcaaacttt cataaaagtt gtaagaagaa tacccggagc acccagatag   22740
cccagctgtt aatgttttat tcccttgttt actctgttac catctatatc atacatgtgt   22800
atctgtattt attttaaata tccattataa ttagttctga aggaagctaa ttatatccag   22860
cataattagt tctgaaagaa atcactgaag actaaactgt agacatgatg tcctgttggg   22920
tacttcttca aaaatacata accatcatac agccctccaa atcagtaagt caacattgat   22980
atattaagtt ctttatatca ttatggattt ctgattttttg cagtaggtta tattttttaaa   23040 gtatttttat aattttgata atcagattat cctggatttg gccagtcagg gagtatattc   23100
agggtggtgc ctatatcctt ttgaaatacc tgtcattctt ttaagcactt ccatactgtc   23160
tggcacagta agattgttat tttgtgcttt ctgggctcca gccctcgagt cagctatttc   23220
ttcaaggagc tcttattcct tttagtagag tatggtagtt agaaacgaga cttgagtatg   23280
cttgttgcta ctgaggtgta attgcttcta gcttctttca acaggcagaa ctaggaaata   23340
tatttacata catgcatacc tacatacaca caccaaaaaa cacataaaca tcgatatatg   23400
tatatatttt taaaaactat gttcatatca ccacatccgt ttcagcattt tggggttttc   23460
aagccttttc cttttttgta cttgtttaca aacgtgagaa acctggtgtc ctcagtgtat   23520
ttccttattt gacatgcatt tacttatatg ttcaacataa ccagtcttca aacaggttgg   23580
ttttcttttc tgtccaccac ctctgtaccc ccagtacctt ctatctttgg cactgttagg   23640
gatgccacca ccacatagta cttccctcct accctcactg tcacattgca ggccctgcc   23700 agctcctgca cccaaggaaa cggccaaaat tgccttttaa aaactttaat tctgttttt   23760 gttttgtttt gcttgaacaa ggagatcagc agaatccagc cccagctgga caggttgatt   23820
ataccaaggc ttgggaagag tactacaaga aaatgggtat gtttttataca tttcttgaaa   23880 atacatactt aattaaattg aaacaaatta ttctcttcag gaagagaata attgaataaa   23940
```

-continued

```
atcactggac ttgtaaacat atcaagacag ttgtaaatta tagttttttaa atttgtggtt   24000 atatggcaag gaaattttt tttctaattg catttgtcaa ccagttatta attgaaacta   24060
gaaatgtcct tactggtaca tacaatatta acattactat acttttgaca atgacagtta   24120
tatatattat cagtctaaat gacataaggt taaattttaa tgtgtcaggc gaaaattgtg   24180
tgtgatacca ttattttgc tgcaagataa gcaggtaaga agtaatctgc agtgacggaa   24240
agtaaccaag tgatggaacc agaatctggc ttccaagagg gtctgagtcc caagcttgtc   24300
tcccaaattt gtctctttag gaaccatttg gaacctgata ctatacttct ggacaaatca   24360
ctatatttca gctgctttg ctcttagtca tttaaaatta ttacatacca cagctagatg   24420
tcacaaatga aagctaaatt ggtaagcttg gttatccttc actagcagaa aaagaaccta   24480
taggtggtag agttttgtca taagagaacg gtctacttgg gattttcaat gttttctttg   24540
ccaaagaatg tttctcattc tccacagaaa gaaaaatttc cagaaaggtg atgattttaa   24600
tcttctagat gtaaaattac atatacctga tgataaagtt gttttgcaca actggtttct   24660
ttttaaagaa aaattgtttt tcctcttaga atggcttcct aggagagtca tgttccgtct   24720
ctttctgagg cttttaacaga ttatgttttt gtgacctagc ttaggcagat ctacagtagc   24780
tacaattcgg caaaaagaaa cttttaactt aaaaacagca tactctgatt aaggttggtt   24840
acataattta ttttctgaac tgggatcctt tttagaatga atagggatgc tattaataat   24900
catgccctga cagcattgtg gtcaggacct gtaatcaact taactttaat taaatagcat   24960 caccattta aaagacttga gcatgagcca cgtgcggtgg cacacacttg tagtcccagc   25020
tgcttgggag gctaaggtgg aaggattcct tgaacacagg agattgaggc cagccttggc   25080
atcatagtga gacctggtca cgtgtttggg ttaaaaatca ctaacttcaa cttctatttt   25140
ctcaatgggt aatgtcccct agatagggtc cctagttatt attaagtagg taaaaataaa   25200
ggcttgttaa tggatttagg taattatgga ggaatgagtt tggcttctgt gctttatttt   25260
accatattga ttatttgtaa tatggccatt aatacattta ctgtttagtc tttttttgttt   25320 tacttttttat gttttactca aaatgagtgg gtgggtggaa ttctaatttt tattgttaag   25380
ggaagacatt ttaccttgtc tttaattttt tatttttttt taccatttcc ctgccagtta   25440
gagatactat actatactgt cttgaatcct ctgtaggaaa acatggcata gaaataatta   25500
aataataatt agatgttaaa taataatgct gtatgactaa agaacctcct tacccccacct   25560 tttctgttgt tgttctgtag taccacaata atcacttgtt aattttattt atttatttat   25620
ttgagaggga gtctcactct cgcccaggct ggagtgcggt ggcgcaatct cagctcactg   25680
caacctccgc ctcccaggtt caagcgattc tccggcctca tactcccaag tagctgggat   25740
tacaggcgcc tgctaccaca tccggctgat ttttttgtata tttagtagat acgggctttc   25800
atcatgttgg ccaagctggt ctcaaactcc tgacctcagg tgatccacct gcctcagcct   25860
tccaaagtgt tgggattatg ggtgtgagcc actgcaccca gcctcacctg ttaattttat   25920
gagcaaaaca gattagttgg gcaagtcctt cacatgcata tctcgttgtt gttgtttttt   25980
ttaagacgga gtcttggtct tactccccaa gcaatggtgc gatttcgtct cagtgcaacc   26040
tctgcttcct gggttcaagc tattctcctg cctcaacttc ccaagtagct gggattacag   26100
gcgcccaacc acacccagct aattttttgta tttttagtag agacagagtt tcaccatgtt   26160
ggccaggctg gtctcgaact cctgacctca ggtgatccac cgcctcagc ctcgcaaagt   26220 gttgggatta caggtgtgag ccactgcgcc tggccacatg tgtatatctt aaaggaaata   26280
atgctaggta atttagtcag gtgcttgatg agcatttgtc atcatcatac ggagtcaatt   26340
```

-continued

```
tgtctttttc tataaaagtt cttttttgtaa atgattagtt gcttaactgc tttaatttct   26400
tctaggtacc ttacctgtca tcaggatctt tttaccacaa ataagaaacc ttaaagcata   26460
aaacttggtt cagtcttcac atttcttaaa tggaaggaga aagggaataa taggagata    26520 tctttatctc aaagccaact gttgttgact tttccagtgg caggggtatg atgctaggac   26580
ttcagatttc ctgattcccc atcctagtgc ccctttttgcc aaactaggca ggctttcaca  26640
gcttttggag cctaatttaa gttttttcttg ttaagaacag aaaactccat tcatagattt   26700
taatttgtca ttatttgctt atttactgaa aaaaaaaaaa aactattgaa aacaggtgtg   26760
ggttaagttt cccaaaatta ggtttatatt tcaaaacaat tctaagttcc caaggataac   26820
accaaactaa gaggataaat ttttatttta ttttttttta ttttatttttt ttgagatgga   26880 gcctttccct gtcgcccagg ctgaagtgca gtggcatgat ctcggctcac ttgcagcatc   26940
cacctcccag gttgaagcaa ttcttctgcc tcagcctccc aagtagagaa aatcttgata   27000
agatttcaga ggcttataag gaacagcagt aaagatgggt gttttttaaag ctagaataca   27060 gggatttttt taagacccctt aagagaacaa acagggtttc aaaatagaaa ggagtaattc   27120
ttgtttggag aagtgaagac atttgggaaa agtttgactt gaggaaggcc attatgataa   27180
ggactgatgt ggtagactct gaaccctgaa gaatctggta ccttaagcct aaaggagggt   27240
agagtgagga cttgtgggaa aggtacagtt atatgggaag acaactgagt gtgaaaatct   27300
attcatgcaa ggctggctct taggctctaa tagaatcttg caagctaact ctagagcaag   27360
tcttttatct ttgggatgaa agaaatttaa ggctaaactt tatacattat aattataaaa   27420
ctataataaa tattagataa tgttctactg aagtataaac tcaactatct ggcatcaaac   27480
agtaactaag ccatgatcac accactgcca ctgtgttctg gcctaggtga cagagcaaga   27540
ccctgtctca aaacaaaatc cagtaactaa agagaggaat aagggggagcg caaggtaagg   27600 cagtacatgt ctgaaggggc agggaaagag ttctttctct acttccaact gggcaaaata   27660
aatcacattt gcccttttaga ttggaagagt gaaataagct tttcttgaac atcttttaag   27720
attggagtgt caaatattac caacttattt accaagaatt tggttttttct taaagtctaa   27780 agtgtttact attagctttc cacagggata taggagtttg cagaggttgt agtttttttaa   27840 gggaacatca atgaatttttc ttgatgcata tgcctgtttc taccatttta cattgttaat   27900
ttgcctctaa aatgagtaac tcttacaatg gggtttaaaa cctgaagact attgattgct   27960
accttgatca ggtttggttt caagtgtgca ccctgtaaga gacaatgtgt ggtttttattg   28020 ctattgtcac accagtttttt tagatattga aacctgtttc agatttgctt gaattgtgtc   28080
ttgtaagagg aaaatgttaa acttacttcc tctttgagaa cagttatttta tagaagacag   28140 gaaaatatga gaatttttaa tagtatatga gagttctctg ttacccaaga aaagagggtt   28200
tttttcaggc atttttaaag aatcataaat cttaaattct ttcactcagt tgctttgagt   28260
ctgtgacctg ttttacaatg gtgatagact gctttctgaa actatgaaat tggtcttgtt   28320
ggcagcatcc tacaaacata aaaagagctt cctgtgtgtc catgctccag tatttttgtc   28380
tatggtagtt atttcacaaa gccaagcgag ttacaaacga aataaaatag tgcttaagta   28440
aagaaactga ataggagaac atatactctc tcttctcaat ttttttatttta gaaaattata   28500 taccttcaga aattggggaa ataaggcatc agacactcag cttcatcatt ttttaaaagt   28560
ttgctgtatg cgctttatat gtatgttttt tgtgtatgaa ccatttcaaa gtaagttgca   28620
gacaagacag tttgctctaa ataaactcaa tgtctgggca cagtggttga cgcctgtaat   28680
```

-continued

```
cccaggactt tgggaggcca aggcaggtgg atcacttgag tccaggagtt caggaccagc   28740
ctggacaaca tggcaaaacc ccatctctac aaaaaaagag aaaaatgtca gctaggcatg   28800
gtgggcctgt agtcccagct actctagagg ctgaggtggg aggatcacct gagccctggg   28860
aggttgaggc tgcagtgagc catgattgca ccgctgcact ccagcctggg tggcagagtg   28920
agaccctgtc tgaaaataaa taccctcaat attatcacaa acatacagac tatatttaaa   28980
tttccatagt tgtcaggaat atgtcttttg tcgtctgtgt gttttgttta attcagagta   29040
cattcaagat tcatgcgttg catttcattg ctatatttct ttaatctctt aattcagcaa   29100
agtcacctta tttggaaaaa gacctgattg tgaaagctga gttttatgtg ttttcattga   29160
tcttgttctt tattccttgt caggttactt ttaataacat tgtgttgtaa ttggaataaa   29220
ttattaatac ttttaacatc ttattatgtg tgtgtgtaca tacactttat aggttactaa   29280
tcaggaaaaa gtcttggcta ggtcttaata cagtctttaa atcattgcct ttaagtgggc   29340
ttaaagtttt tcaaaaatgt tcttttttgta attctggaat cgaattaaga ttatgcctaa   29400
atctttacct tccttagcta aagcagtgtg gatttggggt tgattctgtt tttttactaa   29460
taatgacgct ctagaactaa aagttaacga ttaattataa ggcaaaaaga aaagagcgtt   29520
cttttttttt ttctaattgc agagtagttt cctgacacta ctaaatgaat attttaaata   29580
aaacaggagt aattctgacc ctctgtgctt ttgtcttata acctgtactt acagtggatg   29640
taattttata ttaaagttta gggtttttt ttttttggtca acaagggcaa acacaagatt   29700
attcaaaggc ttgggagaaa tattacaaga agcaaggtat tgtttttatt agaaatgaga   29760
tgttgggctt ataattgtgg ttacagcaac aaagttcttt ttttttcaaag gtcaggcagt   29820 tcctgctccg actggggctc ctccaggtgg tcagccagat tatagtgcag cctgggctga   29880
gtattataga caacaagcag cctattatgc ccagacaagt ccccagggaa tgccacagca   29940
tcctccagca cctcaggtat aatgtaattg ctaatttgtt gatttctact ccagtctgtt   30000
ttctgcatgt ttactgtttg tctgtttggg agtgtttgcc ttttaaattt ttatctggca   30060
aagtataata actatttaaa tgaagtacta cggtgtattg tttgggtttt tttgtttttt   30120
ataatgcttt ccagcatctg agtggtgaat atttctgcaa tgcctttgat tttaaaaata   30180
aattttcttc ccccagggat ttgcaaatca tgcaagaagc caccaccatt tatattaacc   30240 acttttttctt tcttaaagga ttcactcctg aattagctcc atttcaagga tttttctttaa   30300 cttttttgtgt atttcttatg tatctcttct gcacagggcc aataataaga agtggacaat   30360
acagtatttg cttcattgtg tggggaaaa aaacctttgt taaatatatg gatgcagacg   30420
acttgatgaa gatcttaatt ttgttttttgg tttaaaatag tgtttcctttt ttttttttttt   30480 tttttgaaaa tgtacaaaat atctatcact actgatagga ggttaatatt tctgtgtaga   30540
aatgaaaatt ggtttgtttt tagtatttag tgtagatgta cacattccag caaatgtatt   30600
tgcaattatg tggttgatgc tttgtgatat aaatgtactt tttcaatgta tactttcact   30660
tttaaaatgc ctgtttttgtg ctttacaata aatgatatga aacctcctgt gtcggtaagt   30720
tggatatgtg ggtatttaaa ggattcataa tttcttagca atgataaatt aagatacata   30780
tacacaaata tataagcttt ccccatgaaa tattgagttt ttaaacactg gcatgttttt   30840
ccccccttgc agtatagtgg tagattggag gatcttttcc atttattgta ttggctcttt   30900
cagcacaagt aatcctgata tcttcatttt ttttccttct gtttgattaa aaactgcatg   30960
tgtgtacaat gatctttttgg catacttcca ttgcattaac agtgaaattt cctttttatac   31020 atgaccactg tttcagacct gtactgctgc tataacagtt aacctttctg ttcttaattt   31080
```

-continued

```
gataatactt gatttccaag actgtttcgg cataactaat tttaaacagt tttcagatag   31140
tgaatatgag tagtctaata agaacagttt ttttccatgt gaagcaactc tttcaatgta   31200
tataatgtta gtgtgtttct ttctaaattt aggatagaaa agtgaatagt gtgcaaaaag   31260
tatagctaca ttgcatctgc cattgaaaca taaatggggt atggaaacgt tcaagctttt   31320 ttttttttctt tatgcagtat agataagctt tgttttgtaa atgcacaagt ccaatcattg   31380
aatcaactta atttttttat gtacttgaag tcattttatt actctttaac actcatgctg   31440
aagttctgat attttgttga aatccattgt tttactcttt gcatatttgt tggctctttg   31500
catattaata tattagacta catgcaaata cagtctgtct tgccattgtc tgttgaagtg   31560
caggtttgat ccagccagta tagaactagc tctgtagggg tgaggaggac tgtgctgtgt   31620
atcatccttg attgtgttcc ttcaaggagc attgcactgt aagtacatca gaatgacaaa   31680
ttgatgaact gcaacagtat ctttttgtca atgttccaca taatgcaaat gccatacgtt   31740
gtgtgaatat tatgttggaa tacagtgctg atatcttgga aaaccataac tgcctcttaa   31800
tttaacatag aataatacat agttctgtat ttttttttaaa gtgagcttaa tgggtaagta   31860
ttttttatat gctttagcta tagctaaaga aaactgatac ttaacaaagt tgaatagtat   31920
tattcactgg tgctcctaaa atattgtttt tcagtgtaaa atatgcatat cttctatatt   31980
taatatgaaa gtcttgaaat gtatcagaca gaaggggatt tcagtttgca aataatgagc   32040
aatgtagcaa ttttaacaca tttcataaat atatattttg tcattggtgg agagcaccat   32100
ttgttgtttt gaatatactt taaaggaaga ggtacaagga cataaatgtt gagattacct   32160
acaggatgga aatagcagta cagttcattg tagatatttt gaaatgtttt tgattgtttt   32220
atataaccta gagtgacttc ccttaccctt atttagatct gcatatatag ttctagtatg   32280
aagtttaata gttaaggagt tagctatttg ttatctttaa gagtagggta ttgacgtgaa   32340
caattgcagt attttgcatg atactgtttt atagatgacc ttttaggaaa gtggtgcatt   32400
tattaattga actgaagaag tagttcagtt gaattcagta tcataattca caaattggag   32460
gctgttgatt ttgattcatt taaggtttaa aatctttatt aattgcaaac agtgcaatta   32520
tttatacttc acagtgcctt cccagacctt ccaccttagg ttctgctgca aaaagcacca   32580
ggtaagcaca acctaaggac atatataaat aaatatttca atacattaat gttgtccctg   32640
tgaggttttt gtggttgtgt attcaaaggc aatctgctac tgcttcccca aaatgtattt   32700
tgttatttta tgctaccatc ttagtggaaa gtctgtaagt tgttaaagca actgtttaca   32760
tttctgggta atgtttttta tttttactttt ttttttttat taagacaaga aaatgatgag   32820
tagattgctg cagtaattga actacatcca aatcttttg tattttttcc ccaaatatag   32880
aagtgttaat attaagaaag gacaattaca cagttttcaa gatttaggaa atcacttgtt   32940
tagaaacttc aacagccttc acaatctgtt ttatatgatg gacagaaaat ttctttgccc   33000
tccaaaatta taatttcttt attttttttct tattcttaaa ctataataat tcagtaagga   33060
tattatgggt tagaatttta ttatgatttt tttcttagac aaaagttata tgctgaagaa   33120
ggaaaaagtt ataaggcagt atgtttttgat aaaaggcatg tgcatcagtg aaatgttaac   33180
tgtatagcaa ataacctttc ataatctgta gcaatcagta tttttctgat ttaataatat   33240
tttaataact gacgctgcat ttaattttt tgccagttta aaatgtttgt gtgttttat   33300 agatgatttt aactggtaca tattttgagt taagttgaat gtatgaaagc agcatcttat   33360
cagttttgtt tattcgattt ctaaaatgtg ctgatccttt taaaactcct gcttatctct   33420
```

-continued

```
gcaacaaaga aaaatattca aaaatactgc cttcatttc acacacagtg ctgaagatgc   33480
tgcaagcacc aaatcatagc tcataaaatc aggtcctgag atagttaccc ataaagagga   33540
atcctttgag tgtatgccat tggtgagccg atgagcatgg accatagaag ggctcaatgt   33600
agaaggtaaa attggcaaat cataattgag aaatatgaaa tgtattccca tacataatat   33660
ggtatagggt gtaatgtacc tgcttttgat cactttcat tttaaagtgc tattcacttg   33720
atcttaaatg ttccatgaac tgttaaattt cttaagttac atagttacta caccacattt   33780
atgtgtatgt tatgttttaa tagtcaatga taggtatgta caattgataa tataaagggg   33840
ctcattgaaa cttgagagcc tgttgagttt tggttagttg tagattgcat ttttataaaa   33900
aaaaatacag atagattgat gataatagat attggggcat tgtttctgtc tcatgagaat   33960
tcttttattc attaccataa gccttcactg atactataag cattatttta aatgacgctg   34020
atcttaagtc tgaaataaat ggaaagcaga aaaggtgagc cagttgattt gaatgcattg   34080
gatattagtg ttagaaacaa tgtatagttt agattgaaac tgaactgact tatttagcac   34140
ttaaacaaaa atttgacaat gttttagtt tttttaaga cagcttagtg tggtgatact   34200
tagaattcta tggtttgatg tttcttttag aaatgagaag tatagtttta tttttaata   34260 taaaaaatgg ttttaatact aaaactagta atttgatact agttgtttat aaacattgta   34320 aaaatatatct tttaaacaaa ttatcttggt agttaattca taagggtggg tttgggtagg   34380
aatagcagag tactttcaga gggaaagggg agtcattcag aagtgatagc attttattg   34440 tttgaatact ctgccagtaa aatcagctgt acttagaaag ttatctgttg tgtagaataa   34500
tgatgtagag tttactaatc agtgaggatg tcttgttttt attttctgca aactctgcct   34560
cactttaaaa tgcattataa caatacctaa ttaaagataa ttttggctct gaaagttacc   34620
ttattttttg ttgagttagt gacttcattt ttcttgccac aatataagct tttgagggat   34680 tttttttaaat tggtgctttt aataagcaaa taaatcccag ggtttatttt tcttcagtga   34740 taccccctata gaaactctta aatgtatttg cgcatatata tatatatatt ttcttatgca   34800
tgctcgatgc attttcgtcc tgagaaaaat gttctctaca gaaactaccc gtgtgtaaaa   34860
agaagattgg cttaaaatgg ctactgtgat gggaacagtg tcttagggag atgcagcttg   34920
gacttgaggt aaattgaata ctttacaact gtggtttaga gtttgcttta atgacattgt   34980
atgtaaaagg tcacatgatt gctgtaattt tgtattcatt atggtttcct caataaatgt   35040
acattgatga ctatta                                                   35056
```

<210> SEQ ID NO 2
<211> LENGTH: 1968
<212> TYPE: DNA
<213> ORGANISM: homo sapiens

<400> SEQUENCE: 2

```
atggcagact attcaacagt gcctcccccc tcttctggct cagctggtgg cggtggtggc   60
ggcggtggtg gtggaggagt taacgacgct ttcaaagatg cactgcagag agcccggcag   120
attgcagcaa aaattggagg tgatgcaggg acatcactga attcaaatga ctatggttat   180
gggggacaaa aaagaccttt agaagatgga gatcaaccag atgctaagaa agttgctcct   240
caaaatgact cttttggaac acagttacca ccgatgcatc agcagcaaag cagatctgta   300
atgacagaag aatacaaagt tccagatgga atggttggat tcataattgg cagaggaggt   360
gaacagatct cacgcataca acaggaatct ggatgcaaaa tacagatagc tcctgacagt   420
ggtggccttc cagaaaggtc ctgtatgtta actggaacac tgaatctgt ccagtcagca   480
```

```
aaacggttac tggaccagat tgttgaaaaa ggaagaccag ctcctggctt ccatcatggc      540
gatggaccgg gaaatgcagt tcaagaaatc atgattccag ctagcaaggc aggattagtc      600
attggaaaag ggggagaaac tattaaacag cttcaggaac gggctggagt taaaatggtt      660
atgattcaag acgggccgca gaacactggt gctgacaaac ctcttaggat tacaggagac      720
ccatataaag ttcaacaagc caaggaaatg gtgttagagt taattcgtga tcaaggcggt      780
ttcagagaag ttcggaatga gtatgggtca agaataggag gaaatgaagg gatagatgtc      840
cccattccaa gatttgctgt tggcattgta ataggaagaa atggagagat gatcaaaaaa      900
atacaaaatg atgctggtgt tcgcattcag tttaagccag atgatgggac aacacccgaa      960
aggatagcac aaataacagg acctccagac cgatgtcaac atgctgcaga aattattaca     1020
gaccttcttc gaagtgttca ggctggtaat cctggtggac ctggacctgg tggtcgagga     1080
agaggtagag gtcaaggcaa ctggaacatg ggaccacctg gtggactaca ggaatttaat     1140
tttattgtgc caactgggaa aactggatta ataataggaa aaggaggtga aaccataaaa     1200
agcataagcc agcagtctgg tgcaagaata gaacttcaga gaaatcctcc accaaatgca     1260
gatcctaata tgaagttatt tacaattcgt ggcactccac aacagataga ctatgctcgg     1320
caactcatag aagaaaagat tggtggccca gtaaatcctt tagggccacc tgtaccccat     1380 gggcccatg gtgtcccagg cccccatgga cctcctgggc ctccagggcc tggaactcca     1440
atgggaccat acaaccctgc accttataat cctggaccac caggcccggc tcctcatggt     1500
cctccagccc catatgctcc ccagggatgg ggaaatgcat atccacactg gcagcagcag     1560
gctcctcctg atccagctaa ggcaggaacg gatccaaatt cagcagcttg ggctgcttat     1620
tacgctcact attatcaaca gcaagcacag ccaccaccag cagccctgc aggtgcacca     1680 actacaactc aaactaatgg acaaggagat cagcagaatc agccccagc tggacaggtt     1740 gattatacca aggcttggga agagtactac aagaaaatgg gtcaggcagt tcctgctccg     1800
actggggctc ctccaggtgg tcagccagat tatagtgcag cctgggctga gtattataga     1860
caacaagcag cctattatgc ccagacaagt ccccagggaa tgccacagca tcctccagca     1920
cctcagggat ttgcaaatca tgcaagaagc caccaccatt atattaa                   1968
```

```
<210> SEQ ID NO 3
<211> LENGTH: 1935
<212> TYPE: DNA
<213> ORGANISM: homo sapiens

<400> SEQUENCE: 3
```

```
atggcagact attcaacagt gcctcccccc tcttctggct cagctggtgg cggtggtggc       60
ggcggtggtg gtggaggagt taacgacgct ttcaaagatg cactgcagag agcccggcag      120
attgcagcaa aaattggagg tgatgcaggg acatcactga attcaaatga ctatggttat      180
gggggacaaa aagacctttt agaagatgga gatcaaccag atgctaagaa agttgctcct      240
caaaatgact cttttggaac acagttacca ccgatgcatc agcagcaaag cagatctgta      300
atgacagaag aatacaaagt tccagatgga atggttggat tcataattgg cagaggaggt      360
gaacagatct cacgcataca acaggaatct ggatgcaaaa tacagatagc tcctgacagt      420
ggtggccttc agaaaggtc ctgtatgtta actggaacac ctgaatctgt ccagtcagca      480
aaacggttac tggaccagat tgttgaaaaa ggaagaccag ctcctggctt ccatcatggc      540
gatggaccgg gaaatgcagt tcaagaaatc atgattccag ctagcaaggc aggattagtc      600
```

```
attggaaaag ggggagaaac tattaaacag cttcaggaac gggctggagt taaaatggtt      660
atgattcaag acgggccgca gaacactggt gctgacaaac ctcttaggat tacaggagac      720
ccatataaag ttcaacaagc caaggaaatg gtgttagagt taattcgtga tcaaggcggt      780
ttcagagaag ttcggaatga gtatgggtca agaataggag gaaatgaagg gatagatgtc      840
cccattccaa gatttgctgt tggcattgta ataggaagaa atggagagat gatcaaaaaa      900
atacaaaatg atgctggtgt tcgcattcag tttaagccag atgatgggac aacacccgaa      960
aggatagcac aaataacagg acctccagac cgatgtcaac atgctgcaga aattattaca     1020
gaccttcttc gaagtgttca ggctggtaat cctggtggac ctggacctgg tggtcgagga     1080
agaggtagag gtcaaggcaa ctggaacatg ggaccacctg gtggactaca ggaatttaat     1140
tttattgtgc caactgggaa aactggatta ataataggaa aaggaggtga aaccataaaa     1200
agcataagcc agcagtctgg tgcaagaata gaacttcaga gaaatcctcc accaaatgca     1260
gatcctaata tgaagttatt tacaattcgt ggcactccac aacagataga ctatgctcgg     1320
caactcatag aagaaaagat tggtggccca gtaaatcctt tagggccacc tgtaccccat     1380
gggccccatg gtgtcccagg cccccatgga cctcctgggc ctccagggcc tggaactcca     1440
atgggaccat acaaccctgc accttataat cctggaccac caggcccggc tcctcatggt     1500
cctccagccc catatgctcc ccagggatgg ggaaatgcat atccacactg gcagcagcag     1560
gctcctcctg atccagctaa ggcaggaacg gatccaaatt cagcagcttg ggctgcttat     1620
tacgctcact attatcaaca gcaagcacag ccaccaccag cagcccctgc aggtgcacca     1680
actacaactc aaactaatgg acaaggagat cagcagaatc cagccccagc tggacaggtt     1740
gattatacca aggcttggga agagtactac aagaaaatgg gtcaggcagt tcctgctccg     1800
actggggctc ctccaggtgg tcagccagat tatagtgcag cctgggctga gtattataga     1860
caacaagcag cctattatgc ccagacaagt ccccagggaa tgccacagca tcctccagca     1920
cctcagggcc aataa                                                       1935
```

```
<210> SEQ ID NO 4
<211> LENGTH: 39750
<212> TYPE: DNA
<213> ORGANISM: macaca fascicularis
<220> FEATURE:
<221> NAME/KEY: misc_feature
<222> LOCATION: (1246)..(1266)
<223> OTHER INFORMATION: n is a, c, g, or t
<220> FEATURE:
<221> NAME/KEY: misc_feature
<222> LOCATION: (2077)..(2131)
<223> OTHER INFORMATION: n is a, c, g, or t
<220> FEATURE:
<221> NAME/KEY: misc_feature
<222> LOCATION: (2666)..(2690)
<223> OTHER INFORMATION: n is a, c, g, or t
<220> FEATURE:
<221> NAME/KEY: misc_feature
<222> LOCATION: (3304)..(3345)
<223> OTHER INFORMATION: n is a, c, g, or t
<220> FEATURE:
<221> NAME/KEY: misc_feature
<222> LOCATION: (3869)..(3870)
<223> OTHER INFORMATION: n is a, c, g, or t
<220> FEATURE:
<221> NAME/KEY: misc_feature
<222> LOCATION: (6076)..(6076)
<223> OTHER INFORMATION: n is a, c, g, or t
<220> FEATURE:
<221> NAME/KEY: misc_feature
<222> LOCATION: (6091)..(6093)
<223> OTHER INFORMATION: n is a, c, g, or t
```

-continued

```
<220> FEATURE:
<221> NAME/KEY: misc_feature
<222> LOCATION: (6159)..(6183)
<223> OTHER INFORMATION: n is a, c, g, or t
<220> FEATURE:
<221> NAME/KEY: misc_feature
<222> LOCATION: (6259)..(6277)
<223> OTHER INFORMATION: n is a, c, g, or t
<220> FEATURE:
<221> NAME/KEY: misc_feature
<222> LOCATION: (6869)..(6906)
<223> OTHER INFORMATION: n is a, c, g, or t
<220> FEATURE:
<221> NAME/KEY: misc_feature
<222> LOCATION: (7072)..(7139)
<223> OTHER INFORMATION: n is a, c, g, or t
<220> FEATURE:
<221> NAME/KEY: misc_feature
<222> LOCATION: (7714)..(7714)
<223> OTHER INFORMATION: n is a, c, g, or t
<220> FEATURE:
<221> NAME/KEY: misc_feature
<222> LOCATION: (11374)..(11394)
<223> OTHER INFORMATION: n is a, c, g, or t
<220> FEATURE:
<221> NAME/KEY: misc_feature
<222> LOCATION: (11454)..(11491)
<223> OTHER INFORMATION: n is a, c, g, or t
<220> FEATURE:
<221> NAME/KEY: misc_feature
<222> LOCATION: (12562)..(12562)
<223> OTHER INFORMATION: n is a, c, g, or t
<220> FEATURE:
<221> NAME/KEY: misc_feature
<222> LOCATION: (12699)..(12742)
<223> OTHER INFORMATION: n is a, c, g, or t
<220> FEATURE:
<221> NAME/KEY: misc_feature
<222> LOCATION: (12793)..(12794)
<223> OTHER INFORMATION: n is a, c, g, or t
<220> FEATURE:
<221> NAME/KEY: misc_feature
<222> LOCATION: (13648)..(13656)
<223> OTHER INFORMATION: n is a, c, g, or t
<220> FEATURE:
<221> NAME/KEY: misc_feature
<222> LOCATION: (14247)..(14261)
<223> OTHER INFORMATION: n is a, c, g, or t
<220> FEATURE:
<221> NAME/KEY: misc_feature
<222> LOCATION: (14474)..(20234)
<223> OTHER INFORMATION: n is a, c, g, or t
<220> FEATURE:
<221> NAME/KEY: misc_feature
<222> LOCATION: (21758)..(21789)
<223> OTHER INFORMATION: n is a, c, g, or t
<220> FEATURE:
<221> NAME/KEY: misc_feature
<222> LOCATION: (23223)..(23225)
<223> OTHER INFORMATION: n is a, c, g, or t
<220> FEATURE:
<221> NAME/KEY: misc_feature
<222> LOCATION: (24454)..(24512)
<223> OTHER INFORMATION: n is a, c, g, or t
<220> FEATURE:
<221> NAME/KEY: misc_feature
<222> LOCATION: (24563)..(24589)
<223> OTHER INFORMATION: n is a, c, g, or t
<220> FEATURE:
<221> NAME/KEY: misc_feature
<222> LOCATION: (25270)..(25338)
<223> OTHER INFORMATION: n is a, c, g, or t
<220> FEATURE:
<221> NAME/KEY: misc_feature
<222> LOCATION: (25723)..(25734)
<223> OTHER INFORMATION: n is a, c, g, or t
<220> FEATURE:
<221> NAME/KEY: misc_feature
<222> LOCATION: (25857)..(25857)
```

```
<223> OTHER INFORMATION: n is a, c, g, or t
<220> FEATURE:
<221> NAME/KEY: misc_feature
<222> LOCATION: (26517)..(26523)
<223> OTHER INFORMATION: n is a, c, g, or t
<220> FEATURE:
<221> NAME/KEY: misc_feature
<222> LOCATION: (27589)..(27590)
<223> OTHER INFORMATION: n is a, c, g, or t
<220> FEATURE:
<221> NAME/KEY: misc_feature
<222> LOCATION: (27660)..(27688)
<223> OTHER INFORMATION: n is a, c, g, or t
<220> FEATURE:
<221> NAME/KEY: misc_feature
<222> LOCATION: (28733)..(28733)
<223> OTHER INFORMATION: n is a, c, g, or t
<220> FEATURE:
<221> NAME/KEY: misc_feature
<222> LOCATION: (30266)..(30266)
<223> OTHER INFORMATION: n is a, c, g, or t
<220> FEATURE:
<221> NAME/KEY: misc_feature
<222> LOCATION: (30317)..(30371)
<223> OTHER INFORMATION: n is a, c, g, or t
<220> FEATURE:
<221> NAME/KEY: misc_feature
<222> LOCATION: (30453)..(30768)
<223> OTHER INFORMATION: n is a, c, g, or t
<220> FEATURE:
<221> NAME/KEY: misc_feature
<222> LOCATION: (30833)..(30837)
<223> OTHER INFORMATION: n is a, c, g, or t
<220> FEATURE:
<221> NAME/KEY: misc_feature
<222> LOCATION: (30906)..(30912)
<223> OTHER INFORMATION: n is a, c, g, or t
<220> FEATURE:
<221> NAME/KEY: misc_feature
<222> LOCATION: (30997)..(30998)
<223> OTHER INFORMATION: n is a, c, g, or t
<220> FEATURE:
<221> NAME/KEY: misc_feature
<222> LOCATION: (31271)..(31562)
<223> OTHER INFORMATION: n is a, c, g, or t
<220> FEATURE:
<221> NAME/KEY: misc_feature
<222> LOCATION: (31697)..(31697)
<223> OTHER INFORMATION: n is a, c, g, or t
<220> FEATURE:
<221> NAME/KEY: misc_feature
<222> LOCATION: (31707)..(31782)
<223> OTHER INFORMATION: n is a, c, g, or t
<220> FEATURE:
<221> NAME/KEY: misc_feature
<222> LOCATION: (32257)..(32257)
<223> OTHER INFORMATION: n is a, c, g, or t
<220> FEATURE:
<221> NAME/KEY: misc_feature
<222> LOCATION: (33477)..(33478)
<223> OTHER INFORMATION: n is a, c, g, or t
<220> FEATURE:
<221> NAME/KEY: misc_feature
<222> LOCATION: (37353)..(37427)
<223> OTHER INFORMATION: n is a, c, g, or t

<400> SEQUENCE: 4
gagatttcgt tccttcagtc tccacccctt tacggcacga tggtcgcgca agaatgtgat        60
acagcttcga cggccgccat tttctttctt tcttagctgt tagctgagag gaagtctctg       120
aacgggcggc agcggctagc gtagtgtaac catggcagac tattcaacag tgcctccacc       180
gtcttctggc tcagctggtg gcggcggtgg cggcggtggt ggtggaggag ttaacgacgc       240
tttcaaagat gcactacaga gagcccggca ggtaagtgtg gaccgcgcgg cggaatcccg       300
aaagctcacg gtaattggcc gctgactgag taggccgcta ccctttagcg catgaggaag       360
```

-continued

```
aggaaagagg tgtccttccg ggctgaaatg tgaggagaca cgtttcccct tgttggtaat      420
aaagattaga gaccagaact cagttttgtg ttcttggtgt gtaatccact tagaaccccg      480
acgcgtgcta cgcaaaggcc tgaagtcttt ctcccgcttc tgcggcactc gtgtgtcgcc      540
agcgagctag cttagcctcc ccttttcctc gagatgaaga tcctcttcca ggggataaag      600
cgcaggtagt ttcacacaat ttaatggaag gttctggtaa tcagtttggg aaagaactag      660
ggtcggtctc ctggagccat agcaagggaa gggatttgtc gttaaagtag cctttacagc      720
tcatttccgt tccctctcgc aattaaaacc gctttccgta cctttcacct tctcacctct      780
acaaggaagg gacttgaaag ccgtcttttt ctgggcggga tttacgcgtc agtctgttct      840
aacagtcagt cccccttatt tctcaaaatg gcctcaggcc cattatacca gaggtttcaa      900
tttgaatctg cctctctgtt aagagtcgta aactgaccag acctctttgt attacgtagt      960
gcgtacattt gccctgaaga caccactttc ccagacgaaa gctgttaaaa tagtgcgagt     1020
attccaggaa aatagaagat ttcttaattt gaactttaca tttttagata gtcccctaat     1080
atatttaaaa tttcaaaatg tatggtgttg gtatggattt gcatgtaagc aaaagaattc     1140
tattctctat gacactatgc atgttgtact aggtgctgga cattttttact agtgttaagc     1200 taatggtagg tagaaaccag tgttgtgctg tgttttcatt gcattnnnnn nnnnnnnnnn     1260
nnnnnncggt acagttaaag gaacattgag tcaaaatcag aattcataaa atccgttgta     1320
acatacctaa tgtgaacaca ttatcaacat gtacctgtac ttgtttataa ccagagatat     1380
tagaggtagt caacaaaagg ttatcattaa tattagttct gcggtttttt cacataattt     1440
aagaaattct gaacatgttt agcagcaagc atttgtataa ctatgacaaa cactgttagc     1500
gcgttttatt agattgattt gtaaaactta actattgtat ttattggaac caactatttt     1560
attttactag aaccagcaca ttggattact tagtatcaaa cactgtaggt agatactgga     1620
gttttgtttt gttttgtttg agacggagtc tccctctgtc gcccaggctg gattggagta     1680
gcgtggtgcg atctcgtccc actgcaacct ccgcctccgg cttcaagcaa ttctcctgcc     1740
tcagcctccc gagtggctgg aattacaggc gcccgccacc gtgcccggct aatttttttgt     1800 tttgtttttg tttttttaagt agagacaggg tttcaccatg ctggccaggc tggtctcgaa     1860
ctcctgacct cgtgatccgc ccgccttgac ctcccaaagt gctgcgatta cagcagtgag     1920
cccggccttt tttgttgttg ttgtttaaat gcatgaattg tttcctacta agaagctatg     1980
atatagttcc ttgaccaaat gcagatgaac aggattatct gataaattga ttaacgagag     2040
cagacaaaat acgggtattt aattcatctg ctcattnnnn nnnnnnnnnn nnnnnnnnnn     2100
nnnnnnnnnn nnnnnnnnnn nnnnnnnnnn ngttgggagg ggatacccag cttcctaagt     2160
aaaggagtga tatttgagca aggcattata gaataaatga gagtttggcc agtagggaaa     2220
agaagcagca tgcggagagg tatgggacgt gggggaatga caagaaccca gaattgaagt     2280
cactagaaga tggtggtggg aggacgtgaa acaaggcaag gaaaggtaca agcggatcca     2340
gatactggaa gactttgtgt tgcaatgctt taatgaaaaa ttggatttcg ggccgggttc     2400
ggtggctcat gcctgtaatc ccagcacttt gggaggctga ggcagacaga tcacttgaag     2460
tcggggttta agaccagcct ggccaacatg gtgaaacccc atctctacaa aaaatacaaa     2520
aggtagccgg gcttggtggc ctgtgcctgt agttccagct acttgggagg ctgaggcaca     2580
agaattgcct gaacctggaa agtggaggta gcagtgagtg gagatcatgc tgctgcactc     2640
cagcctgggc atagagcgag accctnnnnn nnnnnnnnnn nnnnnnnnnn ggttttatta     2700
```

```
ttaggctaag ccataatttc tttctacttt ttaaaataca gaaattgcca tcaaactgaa      2760
atttattgtc ttatatgcta ataggtcagt tgttctgtct ttactgtaat gatttcttta      2820
tgaaaatgat cttaaatctg agattcctaa ctttggcttt taactagaat tacccattac      2880
atttgatgat gtctttaaat gtcagttgta gctattagtc tgataatatg tgtggaatat      2940
acagaagggt atttagacag aagttaggtt aacatctgaa ctacttcctc cttgcgtatt      3000
taagagaata ttgagttagg tttctagaat cctcaactaa ctctaagttt attttctttg      3060
tctagaatac tatgctgttt ttgttttttgg aaggaagaga tataagaaca gtttgctgct      3120
ctcaaggagc ttcaaaggct gtaccagtgg ggatgccatt ggtatattta gctggatagt      3180
tgttattcag aaaagcagga caagtaattt tgattcctgg tccgtacttg gtaatgtcag      3240
taatgttaac tctagctggt tgttgacatc tggtcattta gttgccaatt ccttttttttt      3300 tttnnnnnnn nnnnnnnnnn nnnnnnnnnn nnnnnnnnnn nnnnntattc tgagctcaat      3360
tcaacacagg gacaccaggt tgctgctttt gttcatggtt tccagcctgt gcacttaaga      3420
aatttatttt tatgtatttc aagctgtaac tccagagatt gggattgttt gattgcgtcc      3480
ttagcagtga tactaatagc aacttctgtc tctagaacat tggaaaatta aaatgtattt      3540
atctaccgtt ttttcccttg aggttatatg aaggtagaaa tgaatcagac tagatgatta      3600
gctaagcaaa actgttaacc ctcatccctt cccctctaga caactatgaa attagtcagt      3660
atgtattcga tccttcttgc aatctcttct ctgacaatta taaaagtgat tcaggctgca      3720
taatgttgtt tgaatgaaat gaaaatacag actagagctg ttttttggttt tgttttttttt      3780 tttatttacc atcagtctgt tcagtgaaaa ctaacattta agcatgattc ttttttaaaaa      3840 tcattttgtg acagtttagc agggcttgnn tgataagcaa actatggtat ggtaatattt      3900
ctagtgtgca cgtttcttca catgtctggt atatgggaac tctaactcca tcaggacttt      3960
gcctatagta ggtactcagc atttactgaa ttaaatcaat aaacattttt gatgaattaa      4020
agtacaagtc agacctctgt gtctgtgggc tctgcatctg caaattcagc caactgtgga      4080
tcaaaaatat tagaaaaatg gaatgacggt ccaacaatac aagtaatacg aatgaaaaca      4140
atacaactat gtacattgta tcaggtatta taagtaattt agagatgctt taagtatacc      4200
aaaggatttg cataggttgt atgcagatac tgtaccattt tgtgtaagga acttgagcat      4260
ctgtggattt tggtatttgc atggttcctg gaaccaatcc ctcagggaca ctgagggact      4320
atagttggtc ataccacctg attttagaga ttttctgatc ctcagaagtt aattaagtaa      4380
actacagtag tctgttctta acctcggagg atacattcca agaacctcag tgaatatctg      4440
aaaccacata tagtattgaa tccgatatat acacggtaat attttttcct atacatgtgt      4500
atctataaag tttaaattct aaattagaca tagtattaac aataataata aattagaaaa      4560
agactgggca tagtggttca cgcctataat cttaacactt taacttttaa ctatgacgtt      4620
gtcttgaaaa agaaatcagc cagccaaggt ggctcatgtc tgtaatccta gtgttttgag      4680
aagctcagtc aggaagtttg tttgaaccca ggaatccgag accaccctag gcaacatggt      4740
gaaaccttgt ttctataaaa aaaaaccaaa aaattagcca gacctggtgg tgcatgcctg      4800
tagtaccagc tacccaggag gctgaggtgg gaggagtgct tgaacttggg aggtcaagtt      4860
tacaatgttg acaatgttgg gtcctttacg tagttgtgta agtgagccat gatcatgcca      4920
ctgcactaca gccttgggca acagcctgac cctgtctcaa aatttttaatt taattttaaa      4980 aatgaaatag aacaattaca acaatacgct gtattactga caagaagggc aaatttttaa      5040
aaaaccaata tgctgtaata agttatatga ataagggat cctcccctac cccagaatat      5100
```

-continued

```
ctgattgtac tataccgtag gtaactgcaa ccgtggagag caaaaactga agatactgtg    5160
tcttaagttt cttttttcaac tcccaaattc ttggatttct cacgtcttgg cttcctcagt   5220
agaggtgaga aatgctaaaa cagtgaaaac aggaaaaata acttactcat tcaagaagtc    5280
gattatggtc cagatggaaa atttgaatta ttttttgtaaa actaaactaa agtagccagg   5340
caccgtggct cacgcctgta atctcagcac tttgggaggc tgaggcgggt ggatcacttg    5400
aggtcaggaa ttcaagacca gcctggccaa caaggtgaaa ccctgtctct actaaaaata    5460
caaaaattag tcaggcatgg tggcgggcac ctgtagtccc ggctacttgg gaggctgagg    5520
tgggagaatc gcttgaacct gggggtgtgga cattgcagtg agcccagatc acgccactgc    5580
actccagcct gggcaacatt gtgagactac aaaaaatata atagtaagta aagtaaaaag    5640
tttcccatac ttgataaatg tctaataaaa attgaatatg ttctaggact ctgaaaaagg    5700
agttgaatat agttggaggt tggtttttag gaattatttt tcttaaatta attatccttg    5760
tagtcaccta ggaattgtat attttctgtt gatcttagaa aattgatcaa atctatagtt    5820
cattttgttt tttcaatttt tttttaaaga gatggggtct tactgtatta atgttgaact    5880
cctggcctca accaggtctc ccacctcagc ttctgaagta actgggattg caggtgccac    5940
tgagccaggc tcctttattg gtattttttat taaaagcttt tctctaatgt ctttgtaaca   6000
gttctcaatt tttgaaatgg tgttactcat tctttagagt aaactgtcaa ctttcatttt    6060
cttttttttt ttttntttt ttctttcttt nnnttgagac ggaatctcgc tctgtcaccc     6120
aggctggagt gtagtggtgg gatctcggct cactgtgann nnnnnnnnnn nnnnnnnnnn    6180
nnntctcctg cctcagcctc cagagtagct ggaattaacg ggcacgtgac accgtgccca    6240 gctactttt tttttttnn nnnnnnnnnn nnnnnngat gggggtttca ccatgttggt      6300
caggctggtc tcgaactcca gacgtcaggt gatccaccca cctcagcctc ccaaagtgct    6360
ggtattacag gcatgagcaa cagcgcccag cctcaacttt cattttcatt tggttagttt   6420
ttgaactatt cagtgggtaa ggttgtataa atgtctttttc tctgtataga agtttcttgg   6480
agttcaagga gtgctacttt gcaaactcat agagtattta taaaagctaa ctgcagaagg    6540
tgttcatagg ctaaaccgtt tcctattctt ggtagcacca ttttctctgg cctgaaatac    6600
tttccctcta ctattagtgt ctgtcagtgc ccagcagtgt atttactttc ctgaggaaca    6660
attcaaatgc taagtgcttt aagacctaag ggtggaaaag cagtgttttc aggcattatt    6720
aggaaaataa gattttaatt agacacccag aaacaaaaac aggtttgtaa ttggtaaagt    6780
gaaagatggt taaagaaggt tagattgacc aaagctagag tttttctttt tttcttttttt  6840 tttttttttt ttttttgagac agtgtctcnn nnnnnnnnnn nnnnnnnnnn nnnnnnnnnn   6900
nnnnnnggct agctgcaacc tccacttcct gggttcaaac agttctccca cctgagcctc    6960
ctgagtagct gcgaggcatg tgtcaccatg ctcagccatt ttttgtgtgt ttttagtaga    7020
gactgagttt ctccatgttg gtcaggctgg tctcgaactc ttgagctcag gnnnnnnnnn    7080
nnnnnnnnnn nnnnnnnnnn nnnnnnnnnn nnnnnnnnnn nnnnnnnnnn nnnnnnnnnt    7140
gtaccttttt ttaatcgagc aatctagttc ttgatcctaa tagtctttgt ggtgggtgtt    7200 tgcatttttta gatgaggaaa agggaaatct aggagtccta ggaaatacag ttggtatatg    7260
ggaactgata cgtaattaga cttaagcaat ccatgttgaa tttgtgactt aagcacttaa    7320
ctataaattt accctctcca gttgtctgat gataatcaaa acttgaagca gttatccata    7380
ttgggatctc tttgggggaat cccagtcacc aaaagttagg ttttctttaa tatttttttca  7440
```

-continued

```
tggaagtttt caaatatact caaaattgaa agaattatgt aataaattct catgagccca    7500
tcacacatct tcaataatga atgtacagca ttgcagtgtg gagcttggcc tattgctgac    7560
cactcatcaa tgtggcagaa ccactccatg gttccccatg gaaatgggag ctacttcagt    7620
tctcttttta cagaaaaatt caataaatat ctactgattg tgccctactt gtgacttgaa    7680
gccaggtttg tttgttgttg tttttctttt tttntttttt tttttttttt actagtcttg    7740
ctctgtcacc cgagctacag tgcaatggca tgatatcagt gcactgcaac ctccagctcc    7800
tgggttcaag tgattctctt gcctcagcct cccgagtagc tgggactatg ggcgtgcacc    7860
acaataccta gctaattttt gtatatagta gagatagagc ttcatcatgt tgcccaggct    7920
gctctcgaac tcctgagctc aagcagtcta cccacctcca cctcccaaag tactaagatt    7980
acaggcatga gccaccatgc cagcaaagct gggtatttct taaatttgtt cagtcaggtg    8040
caagaaatta tttgccctac tctgaaagtt aaaaatattc taagagaatt atggtttcgc    8100 agctgggggtt tttttaagact tgagctcctg gggctcctgc atatatcctt agaacaacat    8160
tgtccagtag aagtacaatg taagccatgt tttgtttaac ccagcatatc caaaatatta    8220 cccctttttgc atgtgcttaa tataaaaaat taagatgatt tctattccag gttttcaata    8280
ttcagtgagt aattttacac ttagagcaag tgtcatttca gactagtcac attttgagta    8340
ctcagtaacc acatatgggc tagtgctacc ttgctagata gcatagcctt tgggtcccac    8400
aaagtgttca cattctctgt ttacacacat ctttttgaagt gtcatgagag agagccagat    8460
aggatccaga ttttctttat atctgtttgg tctgtcttac ggattcctag ttgattattt    8520
ctttgttgct tcttataggg atgtatcaga agcttaataa actcatgatt attatgttaa    8580
ctgcctgaag tattaatttt agcaacaaat tgaactataa ttttaatttt tcaagtaaat    8640
tttcttatgt gatactaagt atttcatata tacatgtatt agaagtaaat gggagtttag    8700
taatgaatag tatatagtag tttgtgatta tattttttctg tttttttttttt ttagattgca    8760 gcaaaaattg gaggtgatgc tgggacatca ctgaattcaa atgactatgg ttacggggga    8820
caaaaaagac ctttagaaga tggaggtaag ttatactcat acgtattttta aattgttttt    8880 cagagtgttt agttgaagtg gttctcagta ttttttgtta ttctattgag acattacttt    8940
tattataaga ttgttaaaac tgtaaggtgt atattggcct aaagggggg aagagaccta    9000 gagaaggtaa gtaaaatttc agtcaaccag aaagttttgt cttactagaa aacagtttat    9060
tttccctctt ttaggattgt gccagattga aagtttgcac agacgtcttg ttaataatat    9120
taaaaaaaca aaaatataaa ttgcttagaa gacacttcac tggtttttact catacatgaa    9180 tggattttaa tatgctgtgt tttcgtcatt tttctatttg caattacact ttaaaggtcg    9240
aaattcgtat tgtttgctac tctagtgtgt tgcaggttat accgtttttt ttaatgttct    9300 ttgctttttag tactttttgtg tttcacgttt agctgtaaac ctatagatta aaacagtggg    9360
ttcacagtgc tttgtagttt taaaaatcat aatcattgaa gcttctgaac ttagaagtct    9420
gcatgtattt tttgtttttag gtttgatgta tgagtttga tacattttct ttttaccctt    9480
ttttttaaag gaaggattct cactgaggct atagaatgta tttgtagctt ttgaccagga    9540
gaactttgtt tcctttatt aagtgtcttt catatttata gtgaggtttt taatataaaa    9600
aaaaaaaatg agctaatgat gcttcagatg ttgtatgtaa tgtattcttt ttattttatg    9660
tgtagatggc tcttggacaa gtccgagcag tacaacacac tgggagggaa tgccctctcc    9720
ttttaaaggc aggaattttt atttattacc tgtgttcagt atgtaaacgt gaaataaacc    9780
agtggattct taaatggaca caaatatttc ttggattatg tgtctgaatt tttgctgcac    9840
```

-continued

```
aacattctga tggttaatca tttaagtttg aagggggag gagaatgtag tactttgagc    9900
tataggttgt ctgttccaag gtatgcattg tattcatctg tgtaatggat ttagatgaag    9960
gtagtcatgt agttgccttg agttttttttg ttttttgtgt tttttttgct aaagttttat   10020
acagtgaaat gtttgtttat aaataataga acagtttaag ttgagattgc cttgtaatgt   10080
tgtggggttt gtttttttt ttaatttttt ggggcatagc tttgtggtca ctgtccgata    10140
tactcaactt ttaatatgtc agattttgt agtttgatac gcttttttcc ccccagtctt    10200
cagttcctga ggtggaagca tcattagcct ttagcatgtg atattttgct agtaatggac   10260
ctaaagtact ttgtcttgta tcattctaat gtgcataaca tacattaagg tcagtgattt   10320
gttaagaatc agataactat tttaatgtct gtgcatcttt tgaatgtgaa gagaatgaag   10380
tatagtttct tttttagatt actgagtttg tgttgaattt tggcagtttt ggttcaaatg   10440
ataaaccgta ccttcagata tttcaataaa tgtttatatt tattcttgtt tgggagggga   10500
gaagctttgt acttaattgg taaaaaatta aaagacactt aattttgcag atcaaccaga   10560
tgctaagaaa gttgctcctc aaaatgactg taagtattcc ttttaaactg ggtcaaaagc   10620
tatattaaga ttttgttcat attattgggt atctttgaag ttagttggtt tatgagtatt   10680
ttggatcagc tagcctgaac ttctttgtaa atatgtacct ttttctccta ttttacaatc   10740
tgtcccatta attgtggcca ggtatatgta aggattggtt gccgaattat tttacatatt   10800
taacaactcc aattcttgat ctacgcttgt acaacttgaa aaaggaaatt atattgttct   10860
gtgccattgc taatataatg tcttcccttt cattggctct cttaccccctg tcagtgccaa   10920 tataaatatt ctgtataaaa tttgactctc ttcaaggtgt tgtctgtgca ttagggaaag   10980 gttttttgaat gtttgatgtg attttgttgt taaatacata agtaacttta aatttgaat    11040 tttcgtttta ttttattta attttttgat agcttttgga acacagttac caccgatgca    11100
tcagcagcaa aggtatagtc acaaacttt caaaaagtac tctgcaagtt ttggttgagc    11160
tgcatgtaaa aacacaacca cattggtata tattgaatat gtgtctgtat tttttggtgt   11220
acctagttca tatcactccc cttgggaagg taccataaag tgatgatttt tcttttgagt   11280
gagaaaaatt tgtgatttgg agagagagag ggaattagcc acagtttaga agaacagggg   11340
tgaattagag taactgttaa gatgacattc tctnnnnnnn nnnnnnnnnn nnnnacagtt   11400
catgccttca gactgttcca ttgatcatcc cttcttcact tgatgtatca tctnnnnnnn   11460
nnnnnnnnnn nnnnnnnnnn nnnnnnnnnn nattttttga catgagtctg agcatagaac   11520
cttagtttaa gccattggga gacattagac ttccattttt attaatagat tatctttttat   11580 ttgtaaacaa agtatctttc actgaaggaa aaatggtact ttctgttact ttttagcaga   11640
tctgtaatga cagaagaata caaagttcca gatggaatgg ttggatttag taagtaactt   11700 gattttaaa gttttgaaaa catgatcaaa acatacttta gaatctttca accaaaaaaa    11760 ctttttttt ctaactagta attggcagag gaggtgaaca gatctcacgc atacaacagg    11820
aatctggatg caaaatacag atagctcctg gtaatgttac attctcttgg tattttcaga   11880
gtgactagaa aagtagcttt tttttttct tttaggtttc tagtactaat aatgctgcct   11940
ttaatctttt gacctgaagt tctatttttg tttaaattg tagacagtgg tggccttcca    12000
gaaaggtcct gtatgttaac tggaacacct gaatctgtcc agtaagtttg aaaatcttta   12060
aaatggactt aaagtaacaa cgggagaact cttttgaattt tctctctgct ctttgttact   12120
gctttatttt acactactct ttcgttgcct ccttccctcc caagtcctct gactcctttg   12180
```

```
aagtttatgc ctcatgcctt tctcaattag ggtttatcat taaacacaga aaatggttaa   12240
aacaacttca tatctactcc agtctctact tacaaagcga agtgtagcct ggaggagaat   12300
gcgcagtaat gttgactggt gacacctaaa actcagacat taagctcaag tggactgttg   12360
tgttgtctgc atttccctag ttccattcac ttttccattc ctctccaagg ctctttaata   12420
ctatatttcc ccatctccaa atcttcagca tctaaccccca cctctctcct tcttaagctt   12480
atttacggag aaaatggaaa cgaatgataa gaagcttttc ttttcccta ccgctaaacc   12540 taccagcctt cattttttt cnctgttcac atagtactca ggtaattgct ttcctttgtg   12600
ttcatgtgcc taaagccagc cctttcttcc tattgaaggt tcagcctgca gttgtacttt   12660
cttctgcgtt attagttccc cccctttact agatttttnn nnnnnnnnnn nnnnnnnnnn   12720
nnnnnnnnnn nnnnnnnnnn nntgcaggtg catgccacca cacccagcta atttttgtat   12780
ttttttagta ganncagggt ttcaccatgt tggccaggat ggtgtcaatg tcttgacctc   12840
gttatccacc cgcctcggcc tccccaagtc ctgggattat aggcgtgagc cactgccccc   12900
agcctgattt tctttgtagc actttccaaa taatacgtta ttcatttgac atgttatttt   12960
tacttatttt aatgaaacga agccactcca gcaggaaccc tgtctctttg agtgttacca   13020
ccccattacc taaaatggca cttgcacatg gttgatattt aagtatttgt tgaatgaata   13080
attgtagcat atgagtaagt aaaatggtag tttaaaaatg taaataaata aatctttttag   13140 ttcttggaag aatcagttta attctgagat aactttagca ttagagttct tggaaattgt   13200
ggactattct taaaaataaa aattgtatat ctagaaaatt tattgcctaa tctctcaatc   13260 tttgacccctt gatggcattt tctttcagtt aaaagtaaaa acattgttaa agttagcatt   13320
aaggcaccta atcctgaatt ggggtaggag gagtacttgg ttacattgtt ttgtatttct   13380
ctatttgaat aaacttgggt atgctgcaac ttactattta aatattaatt tgttaacagg   13440
tcagcaaaac ggttactgga ccagattgtt gaaaaaggaa gaccagctcc tggcttccat   13500
catggcgatg gaccgggaaa tgcagttcaa gaaatcatga ttcctgctag caaggcagga   13560
ttagtcattg gaaaggggggg agaaactatt aaacagcttc aggtattgtt atgtttgtga   13620
aatggctact tttggtctgt tttgatgnnn nnnnnngtct gctccctttt gttaatatgt   13680
attattttct atgattataa caggaacggg cgggagttaa aatggttatg attcaagacg   13740
ggccgcaaaa cactggtgct gacaaacctc ttaggattac aggagaccca tataaagttc   13800
aagtaaactt aactttatac tttataaaga aagagtttgg gttgaatggg gttgggcaaa   13860
atatgcatga ataattaaaa tgttttgaga cgtgctttct aaattagcta acttttctta   13920
ctttagcaag ccaaggaaat ggtgttagag ttaattcgtg atcaaggtgg tttcagagaa   13980
gttcggaatg agtatgggtc aagaatagga ggaaatgaag ggatagatgt aagtaaaaat   14040
acccattcag aaatggttgt atgctaattc gtaaatatag tagtgttttc tgttttgtgt   14100
taaatagctc taacattgtt atcctttat ttcacctttta tactttagaa tacagaatta   14160
agtattttat atcttgtcac cctatttgct ataaatataa aattatatgt actattatga   14220
tttgaggcag attttcagga aatggtnnnn nnnnnnnnnn ncttttttttt actttaaacc   14280 ctgagaagct agtttctta atactcagtc ttttttacat aaggtcccca ttccaagatt   14340
tgctgttggc attgtaatag gaagaaacgg agagatgatc aaaaaaaatac aaaatgatgc   14400 tggtgttcga attcagttta agccaggtga gtgcatataa taatcttgta agtgttggca   14460
gcaatgagtt ttgnnnnnnn nnnnnnnnnn nnnnnnnnnn nnnnnnnnnn nnnnnnnnnn   14520
nnnnnnnnnn nnnnnnnnnn nnnnnnnnnn nnnnnnnnnn nnnnnnnnnn nnnnnnnnnn   14580
```

-continued

```
nnnnnnnnnn nnnnnnnnnn nnnnnnnnnn nnnnnnnnnn nnnnnnnnnn nnnnnnnnnn   14640
nnnnnnnnnn nnnnnnnnnn nnnnnnnnnn nnnnnnnnnn nnnnnnnnnn nnnnnnnnnn   14700
nnnnnnnnnn nnnnnnnnnn nnnnnnnnnn nnnnnnnnnn nnnnnnnnnn nnnnnnnnnn   14760
nnnnnnnnnn nnnnnnnnnn nnnnnnnnnn nnnnnnnnnn nnnnnnnnnn nnnnnnnnnn   14820
nnnnnnnnnn nnnnnnnnnn nnnnnnnnnn nnnnnnnnnn nnnnnnnnnn nnnnnnnnnn   14880
nnnnnnnnnn nnnnnnnnnn nnnnnnnnnn nnnnnnnnnn nnnnnnnnnn nnnnnnnnnn   14940
nnnnnnnnnn nnnnnnnnnn nnnnnnnnnn nnnnnnnnnn nnnnnnnnnn nnnnnnnnnn   15000
nnnnnnnnnn nnnnnnnnnn nnnnnnnnnn nnnnnnnnnn nnnnnnnnnn nnnnnnnnnn   15060
nnnnnnnnnn nnnnnnnnnn nnnnnnnnnn nnnnnnnnnn nnnnnnnnnn nnnnnnnnnn   15120
nnnnnnnnnn nnnnnnnnnn nnnnnnnnnn nnnnnnnnnn nnnnnnnnnn nnnnnnnnnn   15180
nnnnnnnnnn nnnnnnnnnn nnnnnnnnnn nnnnnnnnnn nnnnnnnnnn nnnnnnnnnn   15240
nnnnnnnnnn nnnnnnnnnn nnnnnnnnnn nnnnnnnnnn nnnnnnnnnn nnnnnnnnnn   15300
nnnnnnnnnn nnnnnnnnnn nnnnnnnnnn nnnnnnnnnn nnnnnnnnnn nnnnnnnnnn   15360
nnnnnnnnnn nnnnnnnnnn nnnnnnnnnn nnnnnnnnnn nnnnnnnnnn nnnnnnnnnn   15420
nnnnnnnnnn nnnnnnnnnn nnnnnnnnnn nnnnnnnnnn nnnnnnnnnn nnnnnnnnnn   15480
nnnnnnnnnn nnnnnnnnnn nnnnnnnnnn nnnnnnnnnn nnnnnnnnnn nnnnnnnnnn   15540
nnnnnnnnnn nnnnnnnnnn nnnnnnnnnn nnnnnnnnnn nnnnnnnnnn nnnnnnnnnn   15600
nnnnnnnnnn nnnnnnnnnn nnnnnnnnnn nnnnnnnnnn nnnnnnnnnn nnnnnnnnnn   15660
nnnnnnnnnn nnnnnnnnnn nnnnnnnnnn nnnnnnnnnn nnnnnnnnnn nnnnnnnnnn   15720
nnnnnnnnnn nnnnnnnnnn nnnnnnnnnn nnnnnnnnnn nnnnnnnnnn nnnnnnnnnn   15780
nnnnnnnnnn nnnnnnnnnn nnnnnnnnnn nnnnnnnnnn nnnnnnnnnn nnnnnnnnnn   15840
nnnnnnnnnn nnnnnnnnnn nnnnnnnnnn nnnnnnnnnn nnnnnnnnnn nnnnnnnnnn   15900
nnnnnnnnnn nnnnnnnnnn nnnnnnnnnn nnnnnnnnnn nnnnnnnnnn nnnnnnnnnn   15960
nnnnnnnnnn nnnnnnnnnn nnnnnnnnnn nnnnnnnnnn nnnnnnnnnn nnnnnnnnnn   16020
nnnnnnnnnn nnnnnnnnnn nnnnnnnnnn nnnnnnnnnn nnnnnnnnnn nnnnnnnnnn   16080
nnnnnnnnnn nnnnnnnnnn nnnnnnnnnn nnnnnnnnnn nnnnnnnnnn nnnnnnnnnn   16140
nnnnnnnnnn nnnnnnnnnn nnnnnnnnnn nnnnnnnnnn nnnnnnnnnn nnnnnnnnnn   16200
nnnnnnnnnn nnnnnnnnnn nnnnnnnnnn nnnnnnnnnn nnnnnnnnnn nnnnnnnnnn   16260
nnnnnnnnnn nnnnnnnnnn nnnnnnnnnn nnnnnnnnnn nnnnnnnnnn nnnnnnnnnn   16320
nnnnnnnnnn nnnnnnnnnn nnnnnnnnnn nnnnnnnnnn nnnnnnnnnn nnnnnnnnnn   16380
nnnnnnnnnn nnnnnnnnnn nnnnnnnnnn nnnnnnnnnn nnnnnnnnnn nnnnnnnnnn   16440
nnnnnnnnnn nnnnnnnnnn nnnnnnnnnn nnnnnnnnnn nnnnnnnnnn nnnnnnnnnn   16500
nnnnnnnnnn nnnnnnnnnn nnnnnnnnnn nnnnnnnnnn nnnnnnnnnn nnnnnnnnnn   16560
nnnnnnnnnn nnnnnnnnnn nnnnnnnnnn nnnnnnnnnn nnnnnnnnnn nnnnnnnnnn   16620
nnnnnnnnnn nnnnnnnnnn nnnnnnnnnn nnnnnnnnnn nnnnnnnnnn nnnnnnnnnn   16680
nnnnnnnnnn nnnnnnnnnn nnnnnnnnnn nnnnnnnnnn nnnnnnnnnn nnnnnnnnnn   16740
nnnnnnnnnn nnnnnnnnnn nnnnnnnnnn nnnnnnnnnn nnnnnnnnnn nnnnnnnnnn   16800
nnnnnnnnnn nnnnnnnnnn nnnnnnnnnn nnnnnnnnnn nnnnnnnnnn nnnnnnnnnn   16860
nnnnnnnnnn nnnnnnnnnn nnnnnnnnnn nnnnnnnnnn nnnnnnnnnn nnnnnnnnnn   16920
```

-continued

```
nnnnnnnnnn nnnnnnnnnn nnnnnnnnnn nnnnnnnnnn nnnnnnnnnn nnnnnnnnnn      16980
nnnnnnnnnn nnnnnnnnnn nnnnnnnnnn nnnnnnnnnn nnnnnnnnnn nnnnnnnnnn      17040
nnnnnnnnnn nnnnnnnnnn nnnnnnnnnn nnnnnnnnnn nnnnnnnnnn nnnnnnnnnn      17100
nnnnnnnnnn nnnnnnnnnn nnnnnnnnnn nnnnnnnnnn nnnnnnnnnn nnnnnnnnnn      17160
nnnnnnnnnn nnnnnnnnnn nnnnnnnnnn nnnnnnnnnn nnnnnnnnnn nnnnnnnnnn      17220
nnnnnnnnnn nnnnnnnnnn nnnnnnnnnn nnnnnnnnnn nnnnnnnnnn nnnnnnnnnn      17280
nnnnnnnnnn nnnnnnnnnn nnnnnnnnnn nnnnnnnnnn nnnnnnnnnn nnnnnnnnnn      17340
nnnnnnnnnn nnnnnnnnnn nnnnnnnnnn nnnnnnnnnn nnnnnnnnnn nnnnnnnnnn      17400
nnnnnnnnnn nnnnnnnnnn nnnnnnnnnn nnnnnnnnnn nnnnnnnnnn nnnnnnnnnn      17460
nnnnnnnnnn nnnnnnnnnn nnnnnnnnnn nnnnnnnnnn nnnnnnnnnn nnnnnnnnnn      17520
nnnnnnnnnn nnnnnnnnnn nnnnnnnnnn nnnnnnnnnn nnnnnnnnnn nnnnnnnnnn      17580
nnnnnnnnnn nnnnnnnnnn nnnnnnnnnn nnnnnnnnnn nnnnnnnnnn nnnnnnnnnn      17640
nnnnnnnnnn nnnnnnnnnn nnnnnnnnnn nnnnnnnnnn nnnnnnnnnn nnnnnnnnnn      17700
nnnnnnnnnn nnnnnnnnnn nnnnnnnnnn nnnnnnnnnn nnnnnnnnnn nnnnnnnnnn      17760
nnnnnnnnnn nnnnnnnnnn nnnnnnnnnn nnnnnnnnnn nnnnnnnnnn nnnnnnnnnn      17820
nnnnnnnnnn nnnnnnnnnn nnnnnnnnnn nnnnnnnnnn nnnnnnnnnn nnnnnnnnnn      17880
nnnnnnnnnn nnnnnnnnnn nnnnnnnnnn nnnnnnnnnn nnnnnnnnnn nnnnnnnnnn      17940
nnnnnnnnnn nnnnnnnnnn nnnnnnnnnn nnnnnnnnnn nnnnnnnnnn nnnnnnnnnn      18000
nnnnnnnnnn nnnnnnnnnn nnnnnnnnnn nnnnnnnnnn nnnnnnnnnn nnnnnnnnnn      18060
nnnnnnnnnn nnnnnnnnnn nnnnnnnnnn nnnnnnnnnn nnnnnnnnnn nnnnnnnnnn      18120
nnnnnnnnnn nnnnnnnnnn nnnnnnnnnn nnnnnnnnnn nnnnnnnnnn nnnnnnnnnn      18180
nnnnnnnnnn nnnnnnnnnn nnnnnnnnnn nnnnnnnnnn nnnnnnnnnn nnnnnnnnnn      18240
nnnnnnnnnn nnnnnnnnnn nnnnnnnnnn nnnnnnnnnn nnnnnnnnnn nnnnnnnnnn      18300
nnnnnnnnnn nnnnnnnnnn nnnnnnnnnn nnnnnnnnnn nnnnnnnnnn nnnnnnnnnn      18360
nnnnnnnnnn nnnnnnnnnn nnnnnnnnnn nnnnnnnnnn nnnnnnnnnn nnnnnnnnnn      18420
nnnnnnnnnn nnnnnnnnnn nnnnnnnnnn nnnnnnnnnn nnnnnnnnnn nnnnnnnnnn      18480
nnnnnnnnnn nnnnnnnnnn nnnnnnnnnn nnnnnnnnnn nnnnnnnnnn nnnnnnnnnn      18540
nnnnnnnnnn nnnnnnnnnn nnnnnnnnnn nnnnnnnnnn nnnnnnnnnn nnnnnnnnnn      18600
nnnnnnnnnn nnnnnnnnnn nnnnnnnnnn nnnnnnnnnn nnnnnnnnnn nnnnnnnnnn      18660
nnnnnnnnnn nnnnnnnnnn nnnnnnnnnn nnnnnnnnnn nnnnnnnnnn nnnnnnnnnn      18720
nnnnnnnnnn nnnnnnnnnn nnnnnnnnnn nnnnnnnnnn nnnnnnnnnn nnnnnnnnnn      18780
nnnnnnnnnn nnnnnnnnnn nnnnnnnnnn nnnnnnnnnn nnnnnnnnnn nnnnnnnnnn      18840
nnnnnnnnnn nnnnnnnnnn nnnnnnnnnn nnnnnnnnnn nnnnnnnnnn nnnnnnnnnn      18900
nnnnnnnnnn nnnnnnnnnn nnnnnnnnnn nnnnnnnnnn nnnnnnnnnn nnnnnnnnnn      18960
nnnnnnnnnn nnnnnnnnnn nnnnnnnnnn nnnnnnnnnn nnnnnnnnnn nnnnnnnnnn      19020
nnnnnnnnnn nnnnnnnnnn nnnnnnnnnn nnnnnnnnnn nnnnnnnnnn nnnnnnnnnn      19080
nnnnnnnnnn nnnnnnnnnn nnnnnnnnnn nnnnnnnnnn nnnnnnnnnn nnnnnnnnnn      19140
nnnnnnnnnn nnnnnnnnnn nnnnnnnnnn nnnnnnnnnn nnnnnnnnnn nnnnnnnnnn      19200
nnnnnnnnnn nnnnnnnnnn nnnnnnnnnn nnnnnnnnnn nnnnnnnnnn nnnnnnnnnn      19260
nnnnnnnnnn nnnnnnnnnn nnnnnnnnnn nnnnnnnnnn nnnnnnnnnn nnnnnnnnnn      19320
```

```
nnnnnnnnnn nnnnnnnnnn nnnnnnnnnn nnnnnnnnnn nnnnnnnnnn nnnnnnnnnn  19380
nnnnnnnnnn nnnnnnnnnn nnnnnnnnnn nnnnnnnnnn nnnnnnnnnn nnnnnnnnnn  19440
nnnnnnnnnn nnnnnnnnnn nnnnnnnnnn nnnnnnnnnn nnnnnnnnnn nnnnnnnnnn  19500
nnnnnnnnnn nnnnnnnnnn nnnnnnnnnn nnnnnnnnnn nnnnnnnnnn nnnnnnnnnn  19560
nnnnnnnnnn nnnnnnnnnn nnnnnnnnnn nnnnnnnnnn nnnnnnnnnn nnnnnnnnnn  19620
nnnnnnnnnn nnnnnnnnnn nnnnnnnnnn nnnnnnnnnn nnnnnnnnnn nnnnnnnnnn  19680
nnnnnnnnnn nnnnnnnnnn nnnnnnnnnn nnnnnnnnnn nnnnnnnnnn nnnnnnnnnn  19740
nnnnnnnnnn nnnnnnnnnn nnnnnnnnnn nnnnnnnnnn nnnnnnnnnn nnnnnnnnnn  19800
nnnnnnnnnn nnnnnnnnnn nnnnnnnnnn nnnnnnnnnn nnnnnnnnnn nnnnnnnnnn  19860
nnnnnnnnnn nnnnnnnnnn nnnnnnnnnn nnnnnnnnnn nnnnnnnnnn nnnnnnnnnn  19920
nnnnnnnnnn nnnnnnnnnn nnnnnnnnnn nnnnnnnnnn nnnnnnnnnn nnnnnnnnnn  19980
nnnnnnnnnn nnnnnnnnnn nnnnnnnnnn nnnnnnnnnn nnnnnnnnnn nnnnnnnnnn  20040
nnnnnnnnnn nnnnnnnnnn nnnnnnnnnn nnnnnnnnnn nnnnnnnnnn nnnnnnnnnn  20100
nnnnnnnnnn nnnnnnnnnn nnnnnnnnnn nnnnnnnnnn nnnnnnnnnn nnnnnnnnnn  20160
nnnnnnnnnn nnnnnnnnnn nnnnnnnnnn nnnnnnnnnn nnnnnnnnnn nnnnnnnnnn  20220
nnnnnnnnnn nnnnacaccc atttactgtt taattaattt tgtttctttg ttttgaagat  20280
gatgggacaa cacctgagag gatagcacaa ataacaggac ctccagaccg atgtcaacat  20340
gctgcagaaa ttattacaga ccttcttcga agtgttcagg tttgatagaa agttaacatt  20400
ttcatttttt gttttatgg  aaaaatactt tccttcatga aatctgaagt ttcctctata  20460
tcagagtctg cttgatgatg ctttattaat ggagaaagtt taaattgttt taaggtaaag  20520
atcttggagc aggaagaact actaccttaa gtgctacctt atttactctt taatttaaaa  20580
aaatgttatt acttatgatt atttgggccg gttcatctct acatttatgg ttcaggtatt  20640
tgagagctgg gaaaaataga cataattaat tttatcatga aaaaaagtat ttctgtgctg  20700 atttttttcct tcttgtctat tcctctctat aggctggtaa tcctggtgga cctggacctg  20760
gtggtcgagg aagaggtaga ggtcaaggca actggaacat gggaccacct ggtggactac  20820
aggaatttaa ttttattgtg ccaactggga aaactggatt aataatagga aaaggcaatg  20880
tattttaaac tcttaatgtt taacacatta ttcatttttc tggacactat ttctgttgct  20940
gttgtaaaca agtggcaatg cttttttctct ggctgtgttt tagtagaaaa gcattcttat  21000
gttaatacgt aacaagtaaa acataaatga aggatctaat gtatatttat aaaaagagca  21060
ggattttaat cttactagct tctagagaaa gtgaactaag ataattatta gcataagaaa  21120
ggtcttttga cccaaaaagt tgtttgagtg tttttgtttg tgcattttgg ttttttcccga  21180 ctcatatttt aaaaatttga atgtttataa gtgtattagt ttatatttat ctgctttttaa  21240 aagcagttta ttcaaatatt ttattataat cacattaagg ttaagtttaa acataccaag  21300
taaatgtaaa tgtattttaa gagaagcatg aaatgcttcc taaaatttag atttaaagtg  21360
tagaatatta aatgaaaaat cttaatacaa tactgtcaag tagaatactg actgaccaaa  21420
ccatgttttt aatggcctat ttaattgtga ccattttctt ctaaatagct tctagtatac  21480
ccttgaaacc tttagagaaa ttactgtctt ttattttagg aggtgaaacc ataaaaagca  21540
taagccaaca gtctggtgca agaatagagc ttcagagaaa tcctccacca aatgcagatc  21600
ctaatatgaa gttatttaca attcgtggca ctccacaaca gatagattat gctcggcaac  21660
```

-continued

```
tcatagaaga aaagattggt gtgagtatac tttaaacttt taatttatag tgtagaccct   21720
tagattgtag ttaaattaag acgtttattc gaatacannn nnnnnnnnnn nnnnnnnnnn   21780
nnnnnnnnnt tatagatttc atgataccta taatagatac aatgtgaaga ttttccagca   21840
atgaaaataa cctaattaaa tgtgcagtta caggttttga gaacaacctt acgtttgagt   21900
gtggatagat aggagggtgc aggcatcata ttagtgttat tgtaggattg tggaacatac   21960
ttgaaggaca cagttaatgg gaattcatta tttattaaga ttttactata ctgaacccca   22020
gcaaggcaaa caagataaat cagatgcatc ttccgctctg cagtagaaat tcgtaaatcc   22080
tagcttttgg actggctcac aaatcatctg ggtttttaaaa tgtagactat ttgggtgctt   22140
ccaactccta cacataatat acagagacag acctgactca aaatgtctgg gatagggccc   22200
agcatctgat tttacacaga tgtttgggtt tttttcttcc agaaaagttt tctgttagaa   22260
caaaaagtat aaaaagcttt gactgctttt ttgtaaatga ggcagatggt gtcttactgg   22320
agtttttaac acaaagtgtg cagggagcat cttaaattat taatcagaat ttcctaggaa   22380
aaattagttt tggtgtttgc catgctgtga atggagtgca tgcaaaacaa ggttgacgct   22440
gttttctgtg tacttgggaa gacaaaaata gatgtactaa agatgcttaa ggaacatctt   22500
ataaaatgta cacaaacatt gtaagttctg ttgtatggat agtttaattg ttcaaaaaat   22560
gaagatgttt gtggagtaat gataggaggt tgatgccata gcaaaaaaaa atgaatagca   22620
catcttggtt tttgatttta cagtattagc cttacatgca tggatcagga tttctgttgg   22680
attcatggta aaacaagata gattgtttta gagaagcaat ttggtgtggt gattaagagc   22740
acggactctt ttctctgaat catttactgg gtctgtgacc ttggagaagt tgctcaggct   22800
tttctgtgcc ttggtttcct cctataaaat gaggataatt gtatctattt catagagttg   22860
tagggattaa atgaacgttc acctgtgtgt cacttaaaag aatgcctggc acatagccct   22920
aaaaaatgtt gctacttttt cagtattatt tttactattt ggaaagaata gataatggat   22980
aataaagtga gagatgacag caattggaga cttaaagaga caagttaata aaaataactt   23040
taaaggtcat gaagtttagt ttccctattt tgcagtgaga aatttacaac aaaatatagt   23100
gttaccattt tgtccagcat gtcgcctggt tgtgttaact actcagaagg agcattttag   23160
gacagttaag tgtaatgtct ttgttggctt aacaaaacag aaatcagtta agcattatta   23220
atnnngatgt ggcatgcatg catgataagg atataaaata tcctgattta ttgaaggact   23280
taaaaaggga atgtttgtgc tgtttagaat tatgatacat gaaaggccaa aaaggatata   23340
aattattgat ctgaatgggg tttcagtgac agaaataggt tgtgaggtgg agtttggttt   23400
aatagtgaac caactagctg ttaacattat caatgaagtg ttcagaagac aattgatgat   23460
ataggaccca agcagtttgg gaatatattg tcaagatggt tgtcttatgt taggcaagta   23520
gatgtagaga gaagagctga agataaagac ctgatttctg tgattaagat gaaaaaagat   23580
agtaaaagaa agaattataa aaggaaaggg atctactgct gtcgcagaca agctaaagaa   23640
aatttaattg ctaattttaa tttaatttaa attgcattta attgctaccg ctattgattt   23700
tagtaaattt cacatgtctc cttattatgg cagataaaat agtttttgca aaatgaatga   23760
ggaaaggaag gaaaacctaa aatttgttgt ttgtgactat aagagggtag aaatggaaga   23820
ttatttgtcc atagagttgg tttgctgatt tttctatgtc ttccttttt tttttgtagg   23880 gcccagtaaa tcctttaggg ccacctgtac cccatgggcc ccatggcgtc ccaggccccc   23940
atggacctcc tgggcctcca gggcctggaa ctccaatggg accatataac cctgcacctt   24000
ataatcctgg accaccaggc ccagctcctc agtaagtatt gggtttagtt ctgggctttc   24060
```

```
ccccaaagat tctagttttt ggactacatt tttatactga attttcttct cagtggtcct   24120
ccagccccat acgctcccca gggatgggga aatgcatatc cacactggca gcagcaggct   24180
cctcctgatc caggtaaaaa gatgcttatc atttgtgtgt tagctgtatt gttttttcact  24240 cgtgttacat tattaaattt tctagtgttg attctacatt tgtatgcctc accttcactc   24300
actctactct ttcaacagcg ttaggcactg cctctacccc agtgtatata gaactgacat   24360
gaatatgatc tctgctttta tgaaattcct ttcagcttgc atttggcttt cttatgagtc   24420
gatatagcag aatgataaaa actaaaagct gcannnnnnn nnnnnnnnnn nnnnnnnnnn    24480
nnnnnnnnnn nnnnnnnnnn nnnnnnnnnn nnaatatgta gtgtgttaat tgtgacatta    24540
tctatgaaaa aatagttttt acnnnnnnnn nnnnnnnnnn nnnnnnnnng ggcactgagg   24600
ctcacgtctg taatcccacc tgttcagaag tcgaggctga ggcttgagac cagcctaggc   24660
aacatggcaa gacccatctc taaaaaaatt tgttttaaat tagccagcca gggtggtatg   24720
tgtctgtatt tctagctgct cagaaggctg gaggggggc ggggattgct tgaggctaga   24780
agttctagat tgtattgagc tgtgggcgca ccactgcact cccctgggca acagaatggg   24840
accccatctc ttaaaaaata tatatatatg tatatataaa acagtcttac agagtgttaa   24900
gtatttgggc attaaactcc caaattgtca aataagatac cggttctagt actcctcata   24960
atgacaactt catgtgagta aaaatcaggc ctgtatttaa taactgcatg ctaaaaccca   25020
aatacattta attattttct atattcagat ctgtattttc gatatgtatc tattatatcc   25080
tgtactattc tggcgtcttt ccatacctg tagtttgctt tccatcttgg tcaaagagtc    25140
attctttgaa accagttaac atttatttat gatctttttt tttcacctgc tacctacctt   25200
ttaggcctct ttcaccagag tagtttcaag gaaaatatac tcaattatgg attactttct   25260
acacataatn nnnnnnnnn nnnnnnnnnn nnnnnnnnnn nnnnnnnnnn nnnnnnnnnn      25320
nnnnnnnnnn nnnnnnnntg ctgtttggaa tatgatgaca cagcatgata gttaccaaat    25380
aatcacaact tccattaatt caaggaatga cttgagttgt gctaggatat aggtatgcaa   25440 agttgggggtt gtattctata gcaaaagaat gcactcccag cataccaaca ctgatagaag  25500
ggctcacaag gtacagaata taatactgta aacacgaatt tttggagaat gaaagggctt   25560 tgctttttcct cttgttggct aattgggatg gtataattaa gtaatgagat tgaagagttt  25620
gagtaggtta agagacagat tcatactggg taacttggat ctgccaggat tgtatttttg   25680
agcactactg ggtggttagc atgattgaga aaaaatgatg ggnnnnnnnn nnnnaagtgg   25740
tctttgtatc acatgttgag tttcccactt ggagtagtag tgaagtcact actataaaag  25800
ctggtcagtg aatgtggttg cagcatggcc tttgggcaag aagtaaccca tttaaancca   25860
gctggttggc cccactcaga tttatcaaag ggttactggg tctctggggt ggatattgct  25920
tatattagac ttagaatgac gtaacgtttt aatgtatgaa ctaaaatatt tctttaaaaa   25980
aagagtggtc tgttacggat ttatgtagtg gtcaagaatt tagacttcag agtcaaatag   26040
acctagatca gtcctagtcc tacagtttac taatggtgag atgtcaggca agttttttgaa 26100 ctcctctaag cctgtttttct tatctctaaa ttgatcaatg aatgaatctt gggttgagtg   26160
aatatttagt aaattcttag tacatactag ttatttgtga gactggtact tcagtatggt  26220
ttacacgttt gggtgtagaa ataacacttc ctaaagtctg ttttatctca aattctctgt  26280
ccaggcatag tgtaaagtga aatacctaga tttcttgatt aatatacaga taatagccgg  26340
gcgccatggc taacacctgt aatcctagta ctttgggaga ctgaggcggg cggttcactt   26400
```

-continued

```
gaggtcagga gttggagacc agcctagcca acatggcgaa aacctgtctc tactaaaaat   26460
acaaaaatta gctgggtgtg gtggcgggtg cctgtaatgc cagctacttg ggaggcnnnn   26520
nnnggagaat tgcttgagaa tcgctccact gcattccagc ctgggcaaca gagtgagaca   26580
cttcatctca aaaaataata ataaataccg ataatgacac tattgagata tgtaaacatc   26640
caggatacaa aagcagtaca ttgggcaatt gagaaaagct tggagggtgt cctaaaaaca   26700
ccttacaatt atattccttt gtagttttct ttttctacaa attctcactc cttttttctca   26760 aacttgacta accttttgtta agcagctgag aattgctact gttcagaatg aaagcataat   26820
agaaaattta aaagttttaa ttgtatgata ttcctagtat aaaggacaga atcaagtttt   26880
tttgtggttt ctagaagatt gagaggtctc aaactgtttg cacttcagtt gatgtgggag   26940
atgagtgagg gtcagtcaag tgtagaggaa acatagctaa aagctgagac atgggcatag   27000
tgatttctga aaagtacaag cactgtgttg tggctggagc ttgggtgtta aagagataca   27060
aatgaaggga gaggtgaggc tgaaatggaa aggataagcc aggggattca gactgttaaa   27120
gatgttgaat gataggctgt acttaagctt tgaccatcct gaagattcta gagaatgaag   27180
aatttcaagt aggatgacat caagtttata acattcaatg tgaaatagga tgaaatgtgg   27240
ctaatctttt ttttaagatt tttatatttt ctcttcattg aaaataagga caaagttcat   27300
tgttctaaaa taattgtttc tttcttatgc aggttagccc ctagaaatgt ttttcttaag   27360
tcatcttcca gatagagctg tttgtgcttg aggcgaaacc aatttagaaa aaaacaaggg   27420
cacaggatgg tttgagacag agcattggat ttggagccaa aagacctttta ttcatatccc   27480 agttatgcaa ctcagtagtt tttaacctgg gaaagtcact tggtctctga gccttgtttt   27540
ctttaataaa agctgatggt aacaacaaaa ataatagaaa atataaaann tttcatgtac   27600
ttttttttaa tgttctagtt aattttggga gctgtatatt tgccagagag ctgggggggn   27660 nnnnnnnnn nnnnnnnnnn nnnnnnnngt gagaattaca gacttcaaca tgcaaacctt   27720
gaactttcat ttattctagc taaggcagga acggatccaa attcagcagc ttgggctgct   27780
tattatgctc actattatca acagcaagca cagccaccac cagcagcccc tgcaggtgca   27840
ccaactacaa ctcaaactaa tggacaaggt aactaaagaa cttatatgtg aaagtcaaaa   27900
cttgtgcttg gaattatata tgaagtacat cactgtataa tacctaaaat ttctaacatt   27960
atttaattat aatttaagca gacttttcct tttttaaatt gttacctgga aatagtttca   28020
aactttcata aaagttataa gaataccagg agccacccat ataaccagct gttaatgttt   28080
tatcccttgt ttactctaat accgtctata tcatacaagt gtatgggtgt gtatttattt   28140
taaatatcca ttataattag ttctgaagga aactaattat atccagtata attagttctg   28200
aaagaaatca tttaagacta aactatagac acaatgtcct gttgggtact tcttcaaaaa   28260
tatataacca tcatacagcc ctccaaatca gtaagtcaac attaatatat taagctcttt   28320
atatcattat ggatttctga tttttgcagt gggttatatt ttttgaatat ttttataatt   28380
ttgataatca gactatccta gatttggcca gtcaggagt atattcaggg tggtgcctat   28440
atccttttga aatatctgtc gttattttaa gcacttccat actgtctggc acagtgagat   28500
tgttattttg tgttttatgg gctccaaccc ttaagtcagc tatttcttca aggagctctg   28560 attccttttta gtagagtatg gtagttagaa acgaggcttg actatgcttg ttgctactga   28620
ggtgtaattg cttctaactt ctttcagcag acagaactag gaaatatatt tacatacatg   28680
catacctaca tacacatgcc aaaaaacaca taaacattga tatgtgtata tanttttttaa   28740 aactatgttc atattacgac attcatttca gcattttggg gttttcaagc cttttccttt   28800
```

-continued

```
tctgtacttg tttacaaatg gtgagaaacc tggtatcctc agtgtatctc cttattttac   28860
atacatttac ttatatgttc gacataacca gtcttccaaa caggttggtt ttcttttctg   28920
tccaccacct ctgtaccccc agtaccttct atctttggca ccagtaggga tgccaccacc   28980
acatagtacc ttcctcctac ccctcactgt cacattgcag gcccctgcca gctcctgcac   29040
ccaaggaaac agctaaaatt gccttttaaa aactttaatt ctgttttttct gttttgtttt   29100 gttttgtttt gcttgatcaa ggagatcagc agaatccagc cccagctgga caggttgatt   29160
ataccaaggc ttgggaagag tactacaaga aaatgggtat gttttataca tttcttgaaa   29220
atacatactt aattaaattg aaacacaagg tattctcttc agaaagagaa taattgaata   29280
aaatcactgg actcgtaaac ataccaagac agttgcaaat tatagttttt aaatttgtgg   29340
ttatatagca aggaaatatt tttctttcta attgcatttg tcaaccagtt attaattgaa   29400
actagaaatt tcctcactgg cacatacagt attaacatta ctatacttt gacaatgaca    29460 gttatatata ttagtctgag tgacataagg ttaaatttta atgtgtcagg tgaaaatgga   29520
ttgtgtgtga taccattatt tttgctgcaa gataagcagg taagaagtaa tctgtagtga   29580
gggaaagtaa ctaagtgatg gaaccagaat ctggcttcca agagggtctg agtcccaagc   29640
ttgtctccca aatttgtctc tttagggacc atttggaacc tggtactata cttctggaca   29700
aatcactatg tttcaactgc ttttgctctt taaaaattat tacataccac agctagatgt   29760
cacaaacgaa aactaaattg gtaagcttgg ttatccttca ctagcagaaa aagaatctat   29820
aggtggtagt tttgtcataa gagatcggtc tacttgggat tctcagtgta agtttcaatg   29880
ttttctttgc caaagaatgt ttctcattct ccgcagaaag aaaaatttcc agaagggtga   29940
tgattttaat cttctaggtg taaaattata tatacttgat gataaagatg ttctgcacaa   30000
ctggtttctt tttaaagaaa gaaaaaattg ttttttcctca tagagtggct tcctaggaga   30060
gtcatattcc atctatttct gagactataa cagattaata tatgtttttg tgacgtagct   30120
taggcagatc tacagtagct gaaattccgc aaaaagaaac ttttaactta aaaacagcat   30180
actctgatta aggttggtta cataatatat tttctgaaca gggatctttt ttagaatgaa   30240
tagggatgct attaatcatg tcctgncggg cgcggtggct cacgcctgta atcccagcac   30300
tttgggaggc cgaggcnnnn nnnnnnnnnn nnnnnnnnnn nnnnnnnnnn nnnnnnnnnn   30360
nnnnnnnnnn ncgtctctac taaaaataca aaaaattaac cgggcgcgat ggcgggcgcc   30420
tgtagtccca gctactcagg agcctgaggc agnnnnnnnn nnnnnnnnnn nnnnnnnnnn   30480
nnnnnnnnnn nnnnnnnnnn nnnnnnnnnn nnnnnnnnnn nnnnnnnnnn nnnnnnnnnn   30540
nnnnnnnnnn nnnnnnnnnn nnnnnnnnnn nnnnnnnnnn nnnnnnnnnn nnnnnnnnnn   30600
nnnnnnnnnn nnnnnnnnnn nnnnnnnnnn nnnnnnnnnn nnnnnnnnnn nnnnnnnnnn   30660
nnnnnnnnnn nnnnnnnnnn nnnnnnnnnn nnnnnnnnnn nnnnnnnnnn nnnnnnnnnn   30720
nnnnnnnnnn nnnnnnnnnn nnnnnnnnnn nnnnnnnnnn nnnnnnnnta aaaatcttca   30780
acttctattt tctcaatggg taatgttccc tagatatggt ccctagttat tannnnntta   30840
agtagataaa aataaaggct tgttaatgga tttagctaat tactgaggaa tgagtttgac   30900
ttctgnnnnn nnttttacct tattgattat ttgtaatatg gccgttaata catttactgt   30960
ttagtctttt atgtttttact tttttatgtt ttactcnntg agtgggtggg ttgaattctg   31020
atttttattg ttaagggaag aaattctaat tttcattgtt aagggaagaa attgtcttta   31080
ttgtctttaa tttttttttt caccatttcc ctgccagtta gagatactgt gctatactgt   31140
```

```
cttaaatcct ctgtaggaaa acatggcata gaaataatta aataataata ctgcatgact   31200
aaagaacctc cttaccccac cttttctatc atttttctgt agtaccacaa taatcacctg   31260
ttaattttat nnnnnnnnnn nnnnnnnnnn nnnnnnnnnn nnnnnnnnnn nnnnnnnnnn   31320
nnnnnnnnnn nnnnnnnnnn nnnnnnnnnn nnnnnnnnnn nnnnnnnnnn nnnnnnnnnn   31380
nnnnnnnnnn nnnnnnnnnn nnnnnnnnnn nnnnnnnnnn nnnnnnnnnn nnnnnnnnnn   31440
nnnnnnnnnn nnnnnnnnnn nnnnnnnnnn nnnnnnnnnn nnnnnnnnnn nnnnnnnnnn   31500
nnnnnnnnnn nnnnnnnnnn nnnnnnnnnn nnnnnnnnnn nnnnnnnnnn nnnnnnnnnn   31560
nntcacctgt taattttatg agcaaaatag attagttgaa aacagatgta ggttaagttt   31620
tccaaaattg gctttatatt ttaaagacaa ttctaaattc cccaggataa caccaaacta   31680
agttattttt tttttttnttt tttttttnnnn nnnnnnnnnn nnnnnnnnnn nnnnnnnnnn   31740
nnnnnnnnnn nnnnnnnnnn nnnnnnnnnn nnnnnnnnnn nnggttcaag caattcttct   31800
gcctcagcct cccaagtaga gaaaatcttg atgagatttc agagagttat aaggaatggc   31860
agcaatctaa agatgggtat ttttaaagct agaatagaag gattttttat aagagactct   31920
taagagaaca agcagggttt caaagtagaa aggagtaatt cttttttgga gaagtgaaga   31980
catttgagaa aagtttgact taaggaaggc ccttacaata aggactgatg tagtagactc   32040
tgaaccctta agaatctggt accttaagcc taaaggaggg tagagtgaga cttgtaggaa   32100
aggtacaagt atataggaag acaactgagt gtgaaaatct attcaagcaa ggctgactct   32160
taggctataa taaaatctta caggctaact gtagagcaag tcttttatct tttggatgaa   32220
agaaatgtaa ggctaaactt tatagattat aattatnaaa ctataataaa tattagataa   32280
tgttctactg aagtgtaaac tcaactgtct tgaatcaaac agtaactaag ccatgatcac   32340
accactacca ctgtgttcca gcctaggtga cagagcaaga ccctgtctca aaacaaaatc   32400
caataactaa agagaataat aaggggagca aggtaaggca gtacatgtct gaaagggcaa   32460
ggaaagagtt ctttaaagtc taaagtgttt actattagct ttccacaggg atataggagt   32520
ttgcagacgt tgtagttttt taagggaaca ttgatggaat tttcttgatg aatatgcctg   32580
tttctaccat cttacatcta aaatgagtaa ctctcacagt gggtttaaaa cctgaagaat   32640
attgattgct accttgatca ggtttggttt caagtgtgca gcttgtaaga gaaaacgtgt   32700
ggttttattg ctgttgttac acgagagtat ttggcagttt tttaaatatt gaaacctgtt   32760
tcagatttgc ttgaattgtg tcttgtaaga ggcaaatgtt cctgtttgat taacagttct   32820
ttatagaaga caggaaaata tgagaatttt taatagtcta tgagagttct ctgttaccca   32880
agaaaagagg gtttgtttca tgcattttta aagaatcata aatcttaaat tctttcactc   32940
agttgctttg attctgtcac ctattttaca atggtgatgg acaggtttct gaaactagga   33000
aattggcctt gttggcaaca tcatacaaac ataaaaacag cttcctatac gtccatgctc   33060
cagtactttt gtctgtggta attatttcac aaagccaagt gagttacaaa cgaaataaaa   33120
tagtgcttaa gtaaagcaac tgaataggaa aacacatctc tcttctcaat tttttattta   33180
gaaaattata taccttcaga aattggggaa attaggtacc actcagcttc attcatcatt   33240
tttttaaagt ttgctgtatg tgctttatat gtacgttttt ctgtatgaac catttcaatg   33300
taagttgcag acaagacagt tggctctaaa gaaactcaat gtctggacac agtgattcac   33360
gcctgtaatc ccaggacttt tgggagacca aggcaggtgg atcactttag cccaggagtt   33420
aaagaccagc ctggacaacg ctgcaaaacc ccatctctgc aaaaaaagag aaaaatnnca   33480
gctaggcatg gtgggcttgt agtcccagct actctagagg cagaagtggg aggatcatct   33540
```

-continued

```
gagccgtggg aggtcgaggc tgcagcgagc catgaatgca ccgctgcact ccagcctggg   33600
tggcatagtg agaccctgtc tgaaaataaa taccttcaat agtatcacaa aaatacagac   33660
tatatttaaa tttccatagt tgtcaggaat atgtctttcg tcgtctgtgt gtttgttaaa   33720
ttcagagtgc attcaaagat tcgtgcattg catttcattg ttatatttct ttagtctctt   33780
aattcagcaa agtcatctca tttggagaaa gacctgatcg tgaaagctga gttatgtgtt   33840
tcattgatct tgttctttat tccttgtcac gttactttta ataccattgt gttgtaattg   33900
gaataaatta ttgatacttt taacatctta ctactaatct ctgtgtgtgt gtacatgtac   33960
atgtacatac actttatagg ttactaatca ggaaaaagtc ttggctaggt cttaaaataa   34020
taaaatcttt aaatcattgc aattaagtgg gttttttgtt tttaattctg gaatccaatc   34080
aagattatgc ctaaatcttt accttcctta gctaaagcag tgtggatttg gggttgattt   34140 tgtttttta ctaataatga cgctctagaa ctaaacatta tgattaatta taaggcaaaa   34200
agaaaataaa gagcgttttt tttttatttt agagtagttt cctgacacta ctaatgaata   34260
ttttaaataa aacaggagta attctgaccc tctgtgcttt tgtcttatga ttgtaattta   34320
atattaaatt taggggggttt ttttaggtca acaagggcag acacaagatt attcaaaggc   34380
ttgggaggaa tattacaaga agcaaggtat tgttttttact ggaaatgagg tgttggactt   34440
ttaattgtgg ttacagcaac aaaattcttt ttttttcaaag gtcaagcagt tcctgctccg   34500
actggggctc ctccaggtgg tcagccagat tatagtgcag cctgggctga gtattataga   34560
caacaagcag cctattatgc ccagacaagt ccccagggaa tgccacagca tcctccagca   34620
cctcaggtat aatgtaattg ctaatttgtt gatttctact ccagtctgtt ttctgcatgt   34680
ttactgtttg tctgtttggg agtgtttgcc ttttaaattt ttatctggca aagtataact   34740
tatttaaatg aagtactacg gtgtattgtt tgggttttttt tgtttgttttt ttataatgtt   34800 ttccggcatc tgagtgctga atatttctgc aatgcctttg attttaaaaa taaattttct   34860
tcccccaggg atttgcaaat catgcaagaa gctaccacca tttatattaa ccagttttttc   34920 tttcttaaag gattcactcc tgaattagct ccatttcaag gattttcttt aacttttttgt   34980 gtatttctta tgtatctctt ctgcacaggg ccaataataa gaagtggaca atacagtatt   35040
tgcttcattg tgtgggggaa aaaaacctttt gttaaatata tggatgcaga cgacttgatg   35100
aagatcttaa ttttgttttt ggtttaaaat agtgttttttt tttgttttttt tttgtttttt   35160 tttttgcaa atgtacaaaa tatctatcac tactgatagg aggttaatat ttctgtgtag   35220
aaatgaaaat tggtttgttt ttagtattta gtgtagatgt acacattcca gcaaatgtat   35280
ttgcaattat gtggttgatg ctttgtgata taaatgtact ttttcaatgt atactttcac   35340
ttttaaaatg cctgttttgt gctttacaat aaatgatatg aaacctcctg tgtcggtaag   35400
ttggatatgt gggtatttaa aggattcata atttcttagc aatgataaat taagatacat   35460
atacacaaat atataagctt tccccatgaa atattgagtt tttaaacact ggcatgtttt   35520 tcccccccttg cagtatagtg gtagattgga ggatctttttc catttattgt atttggctct   35580
ttcagcacaa gtaatcctgg tatcttcatt ttttttccttc tgtttgatta aaaactgcat   35640
gtgtgtacaa tgatcttctg gcatacttcc attgcattaa cagtgaaatt tccttttttat   35700 acatgaccac tgtttcagac ctgtactgct gctataacag ttaaccttttc tgttcttaat   35760 ttgataaatac ttgatttcca agactgtttc ggcataacta attttaaaca gttttcagat   35820
agtgaatatg agtagtctaa taagaacagt tttttttccat gtaaagcaac tctttcaatg   35880
```

-continued

```
tatataatag tgtgtttctt tctaaattta ggatagaaaa gtgaatagtg tgcaaaaagt   35940
atagctacat tgcatctgcc attgaaacat aaatggggta tggaaacgtt caagcttttt   36000
ttttttcttt aagcagtata gataagcttt gttttgtaaa tgcacaagtc caatcattga   36060
atcaacttaa tttttttatg tacttgaagt cattttatta ctctttaaca ctcatgctga   36120
agttctgata ttttgttgaa atccattgtt ttactctttg catatttgtt ggctctttgc   36180
atattaatat attagactac atgcaaatac agtctgtctt gccattgtct gttgaagtgc   36240
aggtttgatc cagccagtat agaactagct ctgtaggggt gaggaggact gtgctgtgta   36300
tcatccttga ttgtgttcct tcaaggagca ttgcactgta agtacatcag aatgacaaat   36360
tgatgaactg caacagtatc tttttgtcaa tgttccacat aatgcaaatg ccatactttg   36420
tgtgaatatt atgttggaat acagtgctga tatcttggaa aaccataact gcttcttaat   36480
ttaacataga ataatacata gttctgtatt tttttaaag tgagcttaat gggtaagtat   36540
tttttatatg ctttagctat agctaaagaa aactgatact taacaaagtt gaatagtatt   36600
attcactggt gctcctgaaa tattgttttt cagtgtaaaa tatgcatata ttctatattt   36660
aatatgaaag tcttgaaatg tatcagaagg gatttcagtt tgcaaataat gagcaatgta   36720
gcaatttaaa cacatttcat aaatatatat tttgtcattt gtggggagca ccatttgttg   36780
ttttgaatat actttaaagg aagaggtaca aggacataaa tgttgagatt acctacagga   36840
tggaaatagc agtacagttc attatagata ttttgaaatg tttttgattg ttttatataa   36900
cctagagtga cttcccttac ccttatttag atctggatat atagttctag tttgaagttt   36960
aatagttaag gagttagcta tttgttatct ttaagagtag ggtattgacg tgagcaattg   37020
cagtattttg catgatactg ttttatagat gacctttag gaaagtggtg catttattaa   37080
ttgaactgaa gaagtagttc agttgaattc agtatcataa ctcacaaatt ggaggctgtt   37140
gattttgatt catttaaggt ttaaaatctt tattaattgc aaacagtgca attatttata   37200
cttcacagtg ccttcccaga ccttccacct taggttctgc tgcaaaaagc accaggtaag   37260
cacaacctaa ggacatatat aaataaatat ttcagtacat taatgttgtc cctgtgaggt   37320
ttttgtggtt gtgtattcaa aggcaatctg ctnnnnnnnn nnnnnnnnnn nnnnnnnnnn   37380
nnnnnnnnnn nnnnnnnnnn nnnnnnnnnn nnnnnnnnnn nnnnnnccca tcttagtgga   37440
aagtctgtaa gttgttaaag caactgttta catttctggg taatgttttt atttacgttt   37500
ttttttttta tttaagacaa gaaaatgatg agtagattgc tgcagtaatt gatctacatc   37560
caaatctttt tgtattttttt ccccaaatat agaagtgtta agattaagaa aggacaatta   37620
cacagttttc aagatttagg aaatcacttg ttcagaaact tcaacagcct tcacaatctg   37680
ttttatatga tggacagaaa atttctttgc cctccaaaac tataatttct ttatttttttt   37740 cttaaactat aataattcag taaggatatt atgggttaca atttttattat gttttttctg   37800 agacaaaagt tatatgctag aaaaggaaaa agttaataag gcagtatgtt ttgataaaag   37860
gcatgtgcat cagtgaaatg ttaactgtac agcaaataac ctttcataat ctgtagcaat   37920
cagtattttt ctgatttaat atttttaataa ctgacgctgc atttatataa tttttttgcc   37980
agtttaaaat gtttgtgtgt ttttatagat gattttaact ggtacatatt ttgagttaag   38040
atgaatgtat gaaagcagca tcttaccagt tttgtttatt caatttctaa aatgtgctga   38100
tccttttaaa actcctgctt atctctgcaa caaagaaaaa tattcaaaaa tactgccttc   38160
attttcacac acagtgctga agatgctgca agcaccaaat catagctcaa taaaatcagg   38220
tcctgagata gttacccata aagaggaatc ctttgagtgt atgccattgg tgagccgatg   38280
```

```
agcatggacc atagaagggc tcaatgtaga aggtaaaatt ggcaaatcat aattgagaaa   38340
tatgaaatgt attcccatac ataatatggt atagggtgta atgtacctgc ttttgatcac   38400
ttttcatttt aaagtgctat tcacttgatc ttaaatgttc catgaactgt taaatttctt   38460
aagttacata gttattacac cacatttatg tgtatgttat gttttaatag tcaatgatag   38520
gtatgtaaat ataaagggac tcattgaaac ttgagagcct gtcgagtttt ggttagttgt   38580
agattgcatt tttattaaaa aaatatagat agatgaatga taatagatat tggggcactg   38640
tttctgtctc atgagaattc ttttattcat taccataagc cttcactgat aatataagca   38700
ttattttaaa tgacgctggt cttaaatctg aaataaatgg aaagcagaaa aggtgagcca   38760
gttgatttga atgcattgga tattagtgtt agaaacaatg tatagtttag attgaaattg   38820
aactgacttt atttagcact taaacaaaaa tttgacaatg ttttttggttt tttttttaaga   38880 cagcttagtg tggtgatact tagaattcta tggtttgatg tttctttttag aaatgagaag   38940 tatagtttta ttttttaata tcaaaaatgg ttttaatact aaaactagta atttaatact   39000
agttgtttat aaacattgta aaatatatct tttaaacaaa ttatcttagt agttaattca   39060
taagggtggt tttgggtagg aatagcagag taccttcaga gggaaagggg agtaattcag   39120
aagtgatagc atttttatttg tttgaatact ctgccagtaa aatcagctct acttagaaag   39180
ttatctgttg tgtagaataa tgatgtagag tttactaatc agtgaggatg tcttgttttt   39240
attttctgca aactctgcct cactttaaaa tgcattttaa caatacctaa ttaaaaataa   39300
ttttggttct gaaaataacc ttattttttg ttgagttagt gacttcattt ttcttgtcac   39360
aatataagct tttgagggat ttttttaaat tggtgctttt aataagcaaa tcccagggtt   39420
ttattttctt cagtgatacc cctcttaaat gtatttgcac atatatatat attttttctt   39480
atgcatgctc gatgcatttt cgtcctgaga aaaatgttct ctacagaaac tacccgtgtg   39540
taaaaagaag attggcttaa aatggctact gtgatgggaa cagtgtctta gggagatgca   39600
gcttggactt gaggtaaatt gaatacttta caaactgtgg tttagagttt gctttaatga   39660
cattgtatgt aaaaggtcac atgatagctg taattttgta ttcattatgg tttcctcaat   39720
aaataaatgt acattgatga atattataag                                     39750
```

```
<210> SEQ ID NO 5
<211> LENGTH: 26405
<212> TYPE: DNA
<213> ORGANISM: Mus musculus

<400> SEQUENCE: 5
```

```
gctgaaacat cgcgggattt ccgtctgcca gtctccgccc ctttacggca cgatggtcgt     60
gcaagaatgt gatagagcct cgacggccgc catcttcttc ctttcttagc agttaaccga    120
gagcggcgcc tccctccgcg aggaaacggc agcgtgtgct gtagcgtggg tatggccgac    180
tactccacag tgcctccgcc gtcgtctggc tcggctggcg cgggcggcgg cggagtcgtt    240
aacgacgctt tcaaagatgc cctgcagaga gcgcggcagg taagcgtgga ccgaccgcgc    300
ggcggcttcc cctccccgac ccccgagagc cgccggcggg gcaggtccgg ccctgctcgc    360
actcgcggct gccgcccgag gagatggcgt cttctcacga ggggtcccag cggctcgagg    420
ccgagcccgt tgtcgtggtc tgaagcgccc ccccctccca cgcgctctcc ccgagcgtgg    480
cctccacttc cgccccgcgc gcgcggcctc gccgcccgt gcgccctgcc tgccccggct    540
ccctcggctc cggttccgcc cgacccaggc gcgtggaagg ttctgggcgc tcaggtcacg    600
```

-continued

```
gcgagggcaa gccagggagg gccggctgcc tggctagcgg tccccgccgc ttcccgcgcc      660
gccgagctct ccaccctcgc cgtaattagc ctaacgttcc ccgcggcgtt caccagcgag      720
gctctccccg gggcgggatc tgcgtgcgat ccaccaatcc tttccccagc tccaaatggc      780
cccgggccct ttcttcccca gccttgagtt tgaatctgcc tctctcttcc caagtcgaag      840
cctccaacct ctttgtgcta cgtagggacg tactgttgcc tcgaatggca accattttcc      900
cagatgaaaa gggttggata gataagagtc cttgcatttg acaccccccc cccaataacc      960
tgaacgtcaa tgtcttcaag tagcccccgc ccccgacttc tttgtagctt aaaaatgtat     1020
aatgttgcct tgccgggtgg ggtggtgctc gactttagtc ccagcactcg agagacagag     1080
cctggcaggt ctcttgagtt tgaggccagt caaaacggcc aagagggacc tgtctcaaaa     1140
aaaaaagtat gttatggaat ttgcctgtaa ggtaaaataa acccttatgg ctctgttgta     1200
gttgctagac atgagcaggt ttttaaagcc agctttgact atactggaaa cttccttcag     1260
gaccgaaaga ttaccgactc aatcaaggtt tatcaagtct accataatac agcaagcaca     1320
cttatctagt gcatagatac tgaaaaaata tatttattca tacagaggga ttccatgagc     1380
aatgtggttg gtgtacatag aagtcagagg acaacttgtg ggagttgatt ctccttccat     1440
gtaggaccct ttggtcaggt gtaagttgtt aggctcaggg acaagtgtgt ctgcctgggc     1500
atctgaggaa acttttttgat gcagggcctc taccgaaagc ctaggcaggc ctgaggttta     1560
aggcttcctg ctgaattgtc tctagtgtag gtgtactcca cctctcggct ttggaagctt     1620
tttaagtgtg tgatttctag tcttgtgaga taaaaatcga acacgagtga gcagacagct     1680
ttgatgataa agtaaaccac agcggttaca taaatagtca cactgtgagg caggcgctgt     1740
acaggacgct gctggaaagg gatgcctcac tgaaagatgg gtgacattca tatagtgcag     1800
tgaggagtgg gagtctggcc agcatagaca agaagctgct gcttgctcta caaagatcga     1860
gggtttctgg aaggacagct ctaagaggta gtcagctaat ataggataac ataggaggag     1920
gaaaaaggtg ggaatgtgag aaaaactatg gatagattcc attgttagca agcattggct     1980
gtgataatac aagtgtttat tatagatgat agtatctgtt acacctttgg acattctggg     2040
tatgtagaaa ttccatcagg accttgcctg tgtaagtaag ggactaaggt ctcactatgt     2100
agttctggct gtcctggaac tcactgccta cctctgcctt taggactaaa ggtgtgtgcc     2160
acccatgccc agatgagatt ttgtttcaa aatgagagtc tttctgcctc accctcctga     2220
atgctggagt gacaggtctg cctacactga tcctggcaca cttactttt ctaaaaatta     2280 ttttctttat ttacattcct gcccactcac ccccagttcc tcacaccatt ccttcttcat     2340
ctccccacct cccttccctg gggcctcaag tctcaagggt taggtggatc ttctcccact     2400
gagaccagac caggcagtcc tctgctgtta cacacacaca cacacacaca cacacacaca     2460
cacatataca cacataagcc agggaacttg gaccagcccg agtgtgctgc taggcacact     2520
ttttataagt ttggtgcaac tgtgtctttg aggatgaatg tgcgcattgt taaattttcc     2580
aaaaggaaaa tttgaaagtt gctgtggacc ctgcctagga agcactagaa gtagatttgc     2640
acttccacct ttaaaactac taaagaaagt gtgggctaaa gtgtaggaga tagatgtttt     2700
cacgtcatta ccttcttaga attatcttta actccaaaat tggtgagggt gggtcagtga     2760
agaaagtggt aaatgctggt ttggtttgat ttttgtctga agtaaaaaag cacagaaata     2820
cagtagagca aaaatcaagt ggaaagcttg aattatttct gtgggttaaa ataaaaacat     2880
tacttacact taatgtgtgt ttaatagaaa cattgggttc ataattgtag catgtgagaa     2940
gttaggatta gactagctgg ggctataatc agaccatgtt cccatccacc caccacccac     3000
```

-continued

```
ccccaatgag gggagagttg aaagttttgc ttggtctttt gaatgaactg tgtaccaatt    3060 tttctttttgg atgcttgtag acctattaca tgaatggagt gtgaataagc atgctttctt   3120
atggatattc cttggtcttc aagtaaactc agaagtgttc ataaaagcta attgtagaac    3180
atagccatag tctaagccgt tttcctctcg ttcaattgta cgtaacactt cccttttaac    3240
atcagttcct gtcagtccca tacagtgcac ttaaatacct aagatatagt ttacaaatgc    3300
tatgatttga aatcaaaggg tggaaaagat tttgtttcca aatgtgtggg ttgtttttaaa   3360 tggggatata acataagttt aatagatcat taactatttg ttagctccct gaagtattag    3420
tggtagtttt aattattctt aataagtgaa tctttctagt gttttttaaaa gtatatcttt   3480 tattgtagga aatttagtgc tgagtagtac ataaagtatt aataccctga ttagtattcc    3540
gatttttctt ttaagattgc agcaaaaatt gggggtgatg ctggtacatc attgaattca    3600
aatgactatg gttatggggg acaaaaaaga cccttagaag atggaggtaa gttatagcca    3660
acaagaataa ttatcttcca tggtattcat ttgataagat tttcagtatt gtttatcaag    3720
atgatttatc aaaatactac tatctattgg tctcagaaga ataggatttt gaaaaagaca    3780
gacctagaaa aggtaggtat aatttgaatc tattgggaag tattattgta atagaaaaca    3840
ggttttgtta ttttttttttt tttttgtcct gttataggat tatgcttgct ttgagttgca   3900
cagactgtta atgatataaa taaagttatg ttatttggga aacactttac tgaatttttct   3960 catttattga atgagtcttt gatactccct ttcattcagt cagaatccac gtctaggtta    4020
aggttggttg gttgcaggca tcccattttt atattgtttt agtgttttgt gtgtttcata    4080
tttatcttta aacattgatt aaaactgtgg attcatagtg ttttctcttt ttaaaaatca    4140
tcacttctgc acttagaagt gtgtactttt ttattttagt tttgatgtat gtataaattt    4200
tgatattgat atatttgccc ttttgtaaaa gattctgata gcatatagga ctgactgtat    4260
ttgtggccct ttctggtaat acttggtttc cttttgttta agtatgttta tatttgcaag    4320
tgaggttttt aatatgcaag aaaaaatgag ctaatgatgc ttcagatgtt gtgtgtaatg    4380
tactcttttt attttatgtg tagatggctc ttggacaaat ccgagcagta ccacacactg    4440
ggagggaatg ccctctcctt ttaaaggcag gaatttttat ttattacctg tgtttagtat    4500
gtaaatgtga aataagccag tggattctta aatggacaca atggtctctt ggtttatgtg    4560 tctgaattt tgctatacaa aagccttgaa gttgggagaa taataatagt gttttgagct     4620
ataggctgtc tattcatatg ttgtatgcat tttgtttatt tgagaaaggc aatcgtgtgg    4680
ttgctttgag gttttggtgt tctgtagtga aatgcttcat ttgagaataa tagaacagtt    4740
tagattgaaa ttgtcttgta acgtgagctt tcttttttgg tatagtttta tgatcactgt    4800
cagattcact catcttttga tatgtctggt ttttatgtag tgctctctaa ttgtcagttc    4860
tagagtggat gaagcatcat taaccattag cataaggtat tcaccagcat tgaagctaaa    4920
cagtttgtgc tgtattattc caaactaaag tgtctgtgca ttgtttaaac acaagagaat    4980
gaaagaattt aggttttgtg ggttttttttt ttttttttag atttttgagt ctaggttgaa    5040
ttgtgtcagt tttgattcaa ttggtaaacc aatatatcat gtattttaat aaatatcatt    5100
attcttgctt ggtgggggtg gggagctttg tttttaattg acaaaaagta aaagacactt    5160
aattttgcag atcagccaga tgctaagaaa gtacctcccc aaaatgactg taagtacttt    5220
aagctgaggt tttgttgctt ctttaaaaat tacgtgtgtg tgtgtgtgtg tgtgtatgtg    5280
tgtgtgtatg tatgtatgta tgtatgtatg tcaagatggc ataggaattc cctgaaagtg    5340
```

-continued

```
gactacatgt gggtgctgag aacttggttc tctacaagag catgtgtcct ctttatcatc   5400
taagtcttct ctccagactg ttgtttctac tttgggtggg ttgtgagttt ggggtttggg   5460
gaatttgctt ttgagccaaa gtctcaaata tgtaattctg actgcccttg acttcacaga   5520
gatctacctg tgtaaaagta ttttttattt tgcctgatgt aattgtcatc tctgagcctt   5580
actgcctcaa accttctagt tcttttctgaa ctctggtgca aactcctctc caagctgatt   5640
caatatagct tctctcttga cctctgccgg aattgctctg cttggcctca aactatcctt   5700
ctcattttct ggcttattct gttttttacat gtgtctagct tgttccctct ctgcaaccta   5760
tatatctcta caactgttcc aataagactg tcctcccacc ccctgggcta tttatttatc   5820
tcttaagtcc tcctctctat tctcctgaga gctagacata attaatccca ttcttttttgg   5880 ggtttttttt tggggggggg gggttagaca gggtttctct gtgtagccct ggctgtcctg   5940
gaactcactc tgtagaccag gctggcctcg aactcagaaa tccacctgcc tttgcctccc   6000
aagtgctggg attaaaggtg tgcgccacca acgcccggct gtttgttttt caaaacaggg   6060
tttctctgta gctctggctg tctagaactc accctggacc aggctgacct ctgcctccca   6120
agtgctggga ttaaaaggcg tgacccacca ctgcccggct tttttttcctt ttcttttcct   6180 caaagatttg ttactttata tatgagtgca ctgtagctgc cttcaggcac actagaatcg   6240
gatcctatcc cattacagat ggttgtgagc caccctgtgg ttgctgggaa ttgatctcag   6300
gacctctgga agaacagtca gtgctcttaa ccactgagcc attttcccag ccctaatttt   6360
attcttttga ctccttctct gattgatcac tttgtctgct actctaaatt aaacatcact   6420
ttcaaacatg agtgcttcct tctacaaact aacttcatct ttactgtttg ggattaaagg   6480
tcattaaagg attaaagagc aaagccacac cacaactata agcacataca cccccacccc   6540
cgtaaataac acaatcttgg ggctcaccct ataatctaag tgatcaaata gcctacaaca   6600
gacttgcttt tgttttctcc tgtgcttgga ctaaggatgt gtgtgccttg ccatactcaa   6660
cagggttggt attacaaatg tctagctgga atttccttac aaatgtatat aggttttttac   6720 tatattttta aaaagaatg attctctttt acttgggagc cacgtatata caaacactga   6780
tggctgagct gtgactataa gttaactact ctagttgtta atctgtgtgt ccctttcctg   6840
actttcttgc tactctcagt gatgattcaa atatgaatgg tccgaatttt tttcctatgt   6900
atacatcagg gaaagagttt ggagtacgtg gtatgtttgt ctcaaataaa ctcgaactta   6960
agcttgtttt tgttcatttt ttcgtagctt ttggagcaca gttacctcca atgcatcagc   7020
agcaaaggta tagtcaaaac ttttaaagct acttttgcaag tcttagttgg attgtatgta   7080
cagccaagtt agtctataat gcaaatgtct gcataccatt ttgtatgtgt ggtttacttc   7140
tgtaaaccac attgggaaaa tggtatagaa acattgttaa tttgggaaaa caggttgaaa   7200
ttgacgcatt tcagaagagg taaaataaat gttaaagtgg cattcgcttt gacaggtgtt   7260
cagtttcctg ccctgctcac acatgctgcc tcatttaaga acctggctgg gctactggga   7320
gactttaaga ttgggtttat tagactgctt ttatgtgtat atgtacatta ttttttctgtg   7380 aggaaaatgt tagtttctgt tctttcttag cagatctgta atgacagaag aatacaaagt   7440
cccagatggg atggtcggat ttagtaagta ccattaatac taaggtttta agacaaagca   7500
tactttcaaa aatagtatga atgataactt ctccccctttc tctaccttaa ctagtaattg   7560
gcagaggagg tgaacagatc tcacgaatac agcaggaatc tggatgcaag atacagatag   7620
cacctggtaa cattccgtgt gtgtgtgtgt gtgtgtacga attacttgtt gttttgtcca   7680
gttcttacag ttttttgaga gtggctagga aactcaagta ttttaagttt ctaaatatct   7740
```

-continued

```
gatattttta ttgtattttt tacttaaact tttctttta tttaattgta gatagtggtg    7800
gcctaccaga aaggtcttgt atgctaactg gaacacctga atctgtccag taagtttgaa    7860
aatgttaagt ctacttacag ttaagactga agactataag cttcgttttc ataccatttc    7920
gctttaaaag tttacatatt atgcctttct taaaataggg ttcatcatct gaacctaaga    7980
cagagaaatt gttaaagcca gagactaagc cgtaactcag gcatttaggt gcttgccttc    8040
catgtaggaa gaactgagtt tgatcctaaa actaaaaaaa aaaaactgg cgtggtaata    8100 tcatggctca ggagttggac acaggcagat tttgggact tggtaaccaa ccagctaaca    8160
ctatttgatg ggttcaaagt cattgagaga ccttgcctca aggtacttat cacaaaaaag    8220
gtactgatgg ttgtaatttg acctatacac cttccatacg tgtctataca gactcagaaa    8280
ttattaaaac ctgccttgca caaatatgtt aataacgtca cctaaaactc atgaccaatc    8340
tagtcatgaa aattttatat tcctgttttt ctcttccact caattctaag gctctgataa    8400
aactacccaa tctttacctc taattgtctt ctccccactg ccatctcccc tccagacagg    8460
gtttcattgt atatccatag ctgactgtct ctgaactcac tcgctctgta gtccaggctg    8520
gcctaaaact taaaagatct gcctgccgaa ggcatgtacc accattgccc accacactca    8580
ctgtcttgac tgacttgtgt tgctgtgacc aagaaagtgt tatcatccta cactgaaatc    8640
ttaacaccgt tccttgcata cttttttttt tttgtctagt attgagatac tgttttacgt    8700
tcatttgcct gactttctac ttcaagaaat tcctgactaa actgattttt tacttcattc    8760
ctaaaatttt aggagtaatt tctaagagtt tatagacaga tttggaaatt acatatcata    8820
aaaatatctt tgaacctcat gttgtatttt gttaacacag tgctttaaaa ggtttgtacc    8880
attgaagttt ccccttaaa agtttatcta gtgtgtgtgc ctctcagttt ccttcaagct    8940
ctgcttctaa cagctgcatc gacagttctc tttccaaggc agaggctgag tcgtgcacta    9000
gttaaccccg ttgctgtgtg acaggatgga tggaagatgt ttaatgactg tgttcacttg    9060
gagcatacag acttcagtac ttactgccca tttgacttga cactcactcc tttggtttag    9120
gttcttgcct ccgaccatga aatgccatat gaccaattta gagtatgttt gaaacctgac    9180
taagataaaa ctgctgactt ttattatttt gggataagtt gggttatgct acgtattttt    9240
atcaagatta atttgttaac agatcagcaa aaagattatt ggaccagatt gttgaaaagg    9300
gaagaccagc ccctggcttt catcatggtg atggacctgg aaatgcagtt caggaaatca    9360
tgattccagc cagcaaagca ggactagtta ttggaaaggg gggcgagact attaaacaac    9420
ttcaggtatt attatattgt aaagaatatt attaagtctt ttgaggccac tttttattgt    9480
ttttactaac atattttcat gatattaata ggaacgggct ggtgttaaaa tggtaatgat    9540
tcaagatggg cctcaaaaca ctggtgctga taaacctctt aggattacgg gtgacccata    9600
caaagttcag gtaagcttca ctttgtctct tatatataaa ggctgagggg gtggacaaaa    9660
tacgtattaa attttttga caaatattct gaattggata actttctatt atagcaagcc    9720
aaggaaatgg tattagagtt aattcgtgat caaggtggtt tcagagaagt gcggaatgag    9780
tatggctcaa gaataggagg caatgaaggg atagatgtaa gtaagaattc tgagtcagca    9840
gtggttgtat cctaatccat gggcactagt gtttcctgc tttgaattaa atggacttgg    9900
cttaacatca tgtccctttt cttgttttct tccttggggt ttttttatct tgttattttt    9960
atgatcattt agtatattta ctttattgat taagtgggga tgagtttttg agaaatgtct   10020
tttaaaatat acttttactt aaggtcccaa ttccaagatt tgctgttggc attgtaatag   10080
```

-continued

```
gaagaaatgg agaaatgatt aaaaaaatac aaaatgatgc tggtgttcga attcagttta  10140
agccaggtaa gtttaaggta tatttaatgt tctaagaatt gatagctttt aatcttgaca  10200
tttataattg gtttgtcaca acttactctg ttttttttttg ttgttgttgt tgttattgtt  10260
ttagatgatg gaacaacacc tgataggata gcacagataa caggacctcc agacaggtgt  10320
cagcacgctg cagaaataat cacagacctt ctacgaagtg ttcaggtgtg ataggaaatt  10380
aacattttca gtttgctttc tttggaaaag tttttatcat acctgaatga aaaaaatgcc  10440
cctccaggtt atattagaat ctgttggcag tgttaaaatg actaacgtta aattgcttta  10500
aggtaaacat tttagggtag atttgcataa atgttctgcc ttatttcccc cagtgcatgt  10560
gaacttttat ttctatgggt atatgtgcct tggcaattgt gcctatggaa gccaaaggaa  10620 attttttctga agttggttct ctattatgtg ggtcctagaa attaaaccca ggtcattttg  10680
catgtatggg tagtctccca atatatttta aaagtggaag ttattactta gttgactatt  10740
tttgtttgac gtcatctctt aatttcattg tttagaaata cgagagttgg ggataataag  10800
ctaatagttt tattacagag tttatttttgt tctctccttt cttaggctgg caatcctggt  10860
ggaccgggac ctggtggtcg aggacgaggt agaggtcaag gaaactggaa tatgggccc   10920 ccgggtggac tccaggagtt taatttcatt gtgccaactg ggaaaactgg actgatcatt  10980
ggaaaaggca atgtatttta aactctttgt tttgatatac tggatatttg taaacaaaag  11040
atgctattta tattttttta ggaaaggggg cttaacatgg cagctaaaat aagaatactc  11100
tttaatgtat gctaaaaatg ggattgtgtc tcaactgctt ctagggaaag gggaccaaaa  11160
gtctgtcagt tacaaaactt gatcctaatt caaatgggtt ttgttggtgt tttttgtttt  11220
gttttgcatt taacttcttt gttacttaca aaacctgttg attgaaatat ttttctgttc  11280
tgacccatat caggGtgtat gtttagtaag gtgtgtataa aatagacttt agtgtgtttt  11340
gcattagttc tagatggaag aacaggctaa atagaaaatc ctaacattat tgtccagtgg  11400
aatgctacaa aactgtttaa tgggcaaagt aataggtgtt tggggttttt tttggttttt  11460
tttaaatagt atttctgcca gacatggtga cagacacctt taatcccagc acttagtagg  11520
cagatgcagt gtttctctt gtgagtttga agccagcatg gtctacaggg tgagttatag  11580
dacaaccagg gccacacaga gacccttgtc ttaggaaaga gtattgcttg cattctgtga  11640
acttagtgtc ttgcggtttt aggaggtgaa accataaaaa gcataagcca acagtctggt  11700
gcaagaatag aactgcagag aagccctcca cctaatgcag atcccaatat gaagttattt  11760
acaattcggg gcactccaca gcaaatagac tatgctcgac aactcataga agagaagatt  11820
ggggtaagtg tactctcatt tatagcatag ttcctggtaa cttttaaaatg tactgtggga  11880 aaatacatcg tttctaatat gaaattgcag gtattgtgat atagtgtata tacatatatt  11940
gacataggaa agatatccaa aatacaagaa ccatgaactc agaaatccgc ctgcctctgc  12000
ctgtcaagtg ctgggattaa aggcgtgcgc caccacaccc ggctgagaat accatgtgtt  12060 aagtttttccc ttgatgtgca atttgcagaa tatactctca gcagttgtca cattagggaa  12120
gtaaagggaa ctaggcagtc ttgttttttaa aagaaaatca taaaaagagt aagaaacaca  12180
gaagactaag ctgaaagaac tctgctggag ctgaggattt cagtgaattt tacatggcag  12240
atgatgacat tttatttttt gcaccaaaat tcaaagaggg taaatttaaa tttgttattt  12300
aagcgtagaa atggaagagt agttggactt tgaattactc aaccattaca ttgtttgagt  12360
gtctagttat tgtttatgtt ttcttttcct ttttttttttt ataatagggc ccagtaaatc  12420
ctttagggcc acctgtaccc catgggcccc atggggttcc aggtcctcat gggcctcctg  12480
```

-continued

```
gacctccagg gccgggaact ccaatgggac catacaaccc tgcaccttac aatccaggac   12540
cacctggccc agctcctcag taagtaccac atttgcttgg ttctgggctt tccctaaaga   12600
cctaggaatt gggggctgga gagatgacga tggctcagca gtgcagagca cttgttcctg   12660
ttgcagaggg acctgagctc acttcccagc accacacggg ggttcgcaac cattcgtgac   12720
aggttccagg gtatctttac agcgacacta ggcatacata gctgcatata catacatgca   12780
atacatgcag aggcaaaacc tacacataaa ataaataaag ctggctttta ttaatggtat   12840
ttgtgttttg ttccccaccc ctagcggtcc tccagcccca tatgctcccc agggatgggg   12900
aaatgcgtat ccacattggc agcaacaggc tcctcctgac ccaggtaaag ggtaatctac   12960
tattaatatg ttagcttcat tgtatactgc tggtcacagt cctaaactac ctactgcatg   13020
tgcgatcttt taaggcactt cccctgcagt ataggatgac actgctgtct agtatgttgt   13080
gactttattc atagtagttc atatttataa aataatgtgt ttaacactac tatgttctca   13140
aataataagt ataaattatt ttgttgctga taaaattaag gtcccttaat taccaaaaca   13200
ggagagtaca tttatttttc tctcttataa tctggatttt ctatagcatg gtgttctcat   13260
tatatcttcc catactggtt ttgtttctac tccatcatga tcaggaatca acttggaaat   13320
aggacttttt tctttgtttt tcttttgttt tttcactttg cagcccctgt agtttgattc   13380
atttgaaaag tttgagagaa cgtgttctga gttatagatt tctacatagt gtatttttta   13440
caaatcaaag ttgatttaga tgtaattgct ttgttggatt tgttaaatgt tttaatattt   13500
taatgtatgt taaattcata ggaacttttc tcagtcacca aataaccaca acttctattc   13560
atttaagaaa caacttgagc cgggcggcag tggtgaacgc cattagtccc agcacacagg   13620
agacagaagc aggcagatct ctgagttcga ggacagcctg atctacagag catgttcaag   13680
gatagccagg gacacacagg aaaaatccta tctcaaaaaa gagagagaga gaaaaaaaaa   13740
gaaaaagaaa taacttgaat tgtgatggca tctgaatatg aaagatgagt gtcgattagc   13800
aaaagagtgc attcccaggg cagacaagaa gcatcagtta tgacttcctt tgtaagggtt   13860
ttaaaagtga atcttctcct tctaacaagc atttagacgt ggcatgatca aatagagttg   13920
gaacaggtta tattgaaggt tttatatggc taattcaatt tcataggatt gctcaaatga   13980
gtgatgtttg atattagcac tgtaaggtct ggtcagtgaa tatgacttcc agcattacct   14040
ggaagactga ctcggcaata tgttgcttaa atttgacttg gaagtataca gtattttatt   14100
gtctgcattt tcaagaaact gctgctgtga ggttgagatt tatatagatg tcaagaattt   14160
aatcttcaat cttaaatgga taatatgcga attcatccta tgtaaaagaa tagtgagctc   14220
ttagtacctg ctagttgcaa gtcacaaaaa aaaagtttgg gttttggttt ggtttttgag   14280
ttacaaaggt gagcttagtg cagaggatgc tggttgtggt gacttgggaa tagggcagca   14340
gctaaaactt gagtattggg ggatgctaaa agaattaata gaaaggataa gccacagtgc   14400
tggggataag cattagaacc tgagttctat ccctcccacc tgttgtaaag aaaaataaat   14460
aaagcgcttt aataaagttc gtaaaaagga tccgtaaagt ttcctggcct gctcttgtaa   14520
ccaaatctag gagctctggg ttcagagaga aatcctatct caaaaaaaat taggaaggaa   14580
ggctggagag agggctcagt ggataagaaa agcaataact gctcttccag aggtctgagt   14640
tcaattccca gcaaccacat ggtagttcac aaccatctgc aatgggatct gatgccctct   14700
gctggtgttt ctgaagagag cttcaagtgt actcatatac aaaataataa taattctttt   14760
aaaaaatgag gaagggtgtc agagaggtag cttagtgatt attataaagg tcttcctgct   14820
```

-continued

```
ctttgagagg atgcaagttg agatccagtt actctcacac cttctggttc tctttagtaa    14880
cccacatttg tgtagataca cacaggttca cagatacaca taactagaag tgggacttta    14940
aagtctagat aaaacaaggt gagcatgtct agggagatca cccagaatca gtacacacaa    15000
acagacacgc cacgcacga tggctaagct ggggagggcg gccagaccac agcatgtagc     15060
ccggaaacag gaaaagtgga ggaagaaaag gtaacggctt ggaaatccaa cggcctgtgt     15120
taaatggggc atggtcttaa aactgtacag gagctttcaa atgataagct atgcttgaag    15180
tatcctaaag gtgttagaaa aggatagagc aggactttca ggattgtgac tgaaataaat    15240
ataaactgca tgtatctaac ctttgtttct ttcttgtaca aattagtcca taactgcctg    15300
ctatacagaa ctgttgcact tggcagctta acttgttggg ggaaaaaaag caaagacacg    15360
ggattgagct gagacaaacc attggattgg aagccaaaag atcatccatt tatataccag    15420
ttccaccgat cactagtaaa ttacttaata cctgtaacct aggaaattac ttaattcccg    15480
aggctgaagt ttctgaacta aaagccaagt gatgatgata atactagaac attttgaaag    15540
tttccattcg ctattggtaa cttttgagcc tatttgtcag gaatcaccaa aaaggtaagg    15600
gttggtttct agagtttaca tattaacctt gaaaccgctc tttgttttta cattgtagcc    15660
aaggcaggag cagatccaaa ctcggcagct tgggctgctt attatgctca ctattaccag    15720
cagcaggcac aacccccacc tgcagctcct gccggtgcac cagctacaac ccaaacgaac    15780
ggacaaggta actacggtaa tgaaagattt tatttcctat tttaaagcta tagtttgtgt    15840
ttggattcat gtatgaagtc ataacaaaac tctctttcag tcctgagaat tgttgggcct    15900
tgtgcatgat ggtatcatta ggttagatcc tcgggcctaa ggttttgaag actcagttgt    15960
gactttgtgt aagcaaacta agtcaaataa tagttggaag aataatgcct taagtagtga    16020
gactgttaac tgtcctcccc ccacccccat ttacttcact accctgattt atgtctgtta    16080
taatagttct gaagagagct actgaaaact gtacttagag acataaaatc atatcacctt    16140
tctacagacc cttattcatt ccaaaataaa tgaccaccat ggactttaaa gtcagttact    16200
catcattgat ataccactgt tatacacagc ccttgcttag atcaccaact gaccccgtgt    16260
tttcattagg ttcattaagt ctcatcaagc tagagcactt tcttggtctt cttttatgcc    16320
tctaataaga ggataactca acagttagat agctgccaag ctatagagtt actaaccatg    16380
gttgtttaaa tggtcttgct actaccagcc tggttttttgc actatactac aactatgtac    16440
tgtaaagaat tacctagggg ctggtgagat ggctcagtgg ataagagcac ccgactgctc    16500
ttccaaaggt ccggagttca aatcccagca accacatggt ggctcacaac catctgtaat    16560
gggatacgat ccgattctag tgtgcctgaa ggcagctaca gtgtacttac atataataaa    16620
taaataaatc ttttaaaaaa aaaaagaatt acctagtatt ttctgctact ttttactgga    16680
gtaatgtcac tatcctatac attgaacttc tgcctcagcc ttagtctgta ttattaataa    16740
accttgcctt ggtaccctac tattacagca gctgttaact gttagtttct gtcattgtat    16800
attagttgct attttactac aaggaataga ttgccctttt ttaactactt tcattatatt    16860
gtcctagatt tggggtggtt ggggttatct tcaaggtggc tctggtgcct ctgacgttcg    16920
ttcttcaggt gcttccttag tacctgacac agtaagataa ctttgtcttc tgagctccaa    16980
tcggtgattc atttcctttt ctctctctct ttctctctct ctctctctct ctctctctcc    17040
ctctctctct ctctctctct ctctctctct ctcaggatag aatttagaga tcagtctaag    17100
tatactaatt gctatctaaa tgtcactaat tataatcctg tccaaattag aactaaaaag    17160
tatgtttggg gctggcattc agtcaatagt acttgttcct gcagaaaacc caggtttgat    17220
```

-continued

```
tgctagtacc cacatggtaa ctcacactga aactgattcc aggggaccca gtgccctctt   17280
ctgatctgtg gagcaccaga tacccagggt gcacagatta tacatgtgga caaaatgctc   17340
acacataaaa ttaaacagta tctttaaaaa catgcaggac aacacgtgtc tactaaaaat   17400
cacatgatta tatactactt tttcatttaa tctttaaaat tagtgcttca aagctatttg   17460
tggcttttct aaaaatgtgt gcaggagata tcaagggatg aaccatgctt gaactgtcct   17520
taaaaatgga tagaaaccat gttctatatt tcttttgtgt gcatttactt actattccca   17580
gtttctgtgt ccacccctc tatacccact tgtcatgtat tcccaacaaa cacttgcaca   17640
actccgtggt gtagacagtg ctaattacag tactgatggt gtagaagcaa aagtgcataa   17700
caaccttcag aaacttaaat cttgttttgt ttgtttgttt tttaaaaagg agatcagcag   17760
gctccagctc cagctggaca ggttgattat acaaaggctt gggaagaata ctacaagaaa   17820
atgggtatgc tctacagttt acgtcttatc ctttatctta gtaactaaac ggaagtaaat   17880
acacattaca aagctagaga tgagtaacaa aacatttgct tgttttttaaa aaagaatact   17940 tgaggtaact catccgtatg ttttttataat gttaaagttt atattaaaca agctaggcag   18000
tggtgatacc tgcctttaat cccagtactt ggaaggtaga ggaaggtaga tctccgagtt   18060
tgaggccagc cttgtctaca aagcaagttc caggacactt gggactctta gacagagaaa   18120
ccccatcttg aaaaacaaaa ataataataa acaggaaagg tgacatcctg aaaattgactg   18180 gaagttaaga catattaaga gcaattcaag aaattcttat aattgtgctt atggcagaga   18240
aatacaattg tcagcaagtt aataattaaa acctggcatt tccttactag gtaataatat   18300
atggctttat tactgtactt ttgtgtagtg gtctaaatgg aatgagatta aattttaggc   18360
cagcaaagta gttgtatcac tggctttact gcaaaataag cataaaatta gcccacagtg   18420
acattgcttt acatttctaa acatttgcat gcattgaaaa ggaaaaaagg gtgacctttt   18480
aaaaagattt tgacaactat tgaacgtaat tcttaacata accatagtga ttgtgttaat   18540
gtatttcttg tcggtgatac agctttcgac aaagttcctt tcagaacaac tgtttgggga   18600
aatgtgataa caaacttctg cagtgaacag atgggctgat aacttttctt aacctcactg   18660
atcgcaggca ggttctaaca gatggacctt agcactagaa acttgaaacc tgccgggcgt   18720
ggtggcacac acctttaatc ccagcacttg gtgggcagag gcaggcagat ttctgagttc   18780
gaggacagcc tggtctacag agtgagttcc atccaggaca gccagggcta cacagagaaa   18840
ccctgtttgg ggcctggggg gaagaaactt gaaaccttaa aacaatattg tgtgtaatta   18900
gaatgcttac ataatttctt ctctgaactg tgatattttt gagagtagat ggaaatgtat   18960
taatcattcc gtggtagccg tgctgaaata gtgctacttg tttataagaa gctgagcatg   19020
ccaaggtgaa agtgcgctaa ctccattgtt tgttttttact gtgtgagtgt tgattgggta   19080
gaaacctggt aactggacta cgtaattaag acagagtaag gtatttgtct gtgctcgatt   19140
atgtcatgtt atttgtttac atgacttcaa ataagtttta tagatatttt gcattctgta   19200 ttcttaaaaaa gtatattgac taggactttt gagagtaggt attttaactc aattaggttt   19260 tagttttaa tattctagca ctttccagca cacagttctg tgaattcctc ttcttctaat   19320
tattattatt attattagag atttatttat tttatgtata tgaatgcact gtagctgtac   19380
agatggttgt gagccttcat atggttgttg gaaattgaat tttaagaact ctgctcaatc   19440
cgacccaaag atttatttac tgtcataaat aagtacaccg ttgctgactt cagacatacc   19500
agaagagggc atcatatctc actatgggtg gttgtgagct accatgtggt tgctaggatt   19560
```

-continued

```
tgaactcagg accttgagaa gagtagtact cttactcgct gagccgtctc ccagcccgaa    19620
ttcctgttct tggttgttat gtctaccgat caatcagttg gcatacatag agacagacac    19680
acacagacag cagcatcgtg caggataact atttggagac tcattttctt catttgtgct    19740 ttttgtaat tatgttgaag atcttaatcc tgtgagcaaa aaaagactaa ctgaacaatt    19800
ccctgtcata tagatcttga aagatactgt tttaggtaat ttaattaatc attgaattag    19860
tatttttaat tatatgatag ttataaaaat cattttttccc tgtaaaacat ttaactacaa    19920
tttttttctg aaagtatggt ccttgatata tttttttagta taatcatgaa ttaagagacc    19980
ttaaagcaaa aggttcagaa tagaagctca ggagatagat gggtaagagt gcttaatgac    20040
ctgggttcaa atcccactac ctatcttaaa agccaatcat gactgttgca tgttgggaag    20100
cagttgcagg agcttgctag ccaactgtgg attcagtaaa aggagcaggg gaataaggta    20160
cagagggata gaagaaggca aaggcaggca gatttctgag ttcgaggcca gcctggtctg    20220
caaagtgagt tccaggacag ccagggctat acagagaaac cctgtctcga aaaaaaagaa    20280
aaagaaactc atttgcagtt aacttgcttg tttacaaat tcattaagta tttctagaat    20340
tcgattttta tcatttgata actcagaatg gtcacttaaa acaaaattac taataaacgc    20400
tgagttttgg gctggtgaga tcgctcagtg ggtaagagca ccctactgct cgtccgaagg    20460
tccggagttc aaatcccagc aaccacatgg tggctcacaa caaccatctg taacaagatc    20520
tgacaccctc ttctggagtg tctgaagaca gctacagtgt acttacatat aataaataaa    20580 taaatctttta aaaaaaaaaa gctgagtttt acatctttca ttgaacttta tttcagctgc    20640
caggttattt ttagtaaagc tgtgatataa actcagtatg tcttttgctt cattgtgtgt    20700
gtcataaata tctttcagta cttctctgta gtttaagact agtaatatag tgacccaaat    20760
ggatagaaga gtggtgagct aggtatggtg gcacatatac gcatttagtc ctagtgctca    20820
ggaggcagaa gcaggtagat ctccaaggat gaggtcagcc ctggatagtg agaccctttc    20880
tcagttagca aaaaaaaaaa acaaagcgtt tcttctttcc ttgtcaaaga ttatatctga    20940
attttcccct ttgtttaaag gtatgtgagt ttgggtcatt ttgtctttta ctaatcaagc    21000
tgaactaaga gactgaaact tgtgattgaa gtgaaaagag tatctttgcc gtttcttgtg    21060
tgctgcactt tcccccctca tcctccctcc cttgtctaag gcatatttaa gataaacaga    21120
aactgaaggg gcaatgaggc acagataatc ctagcacgtg ggaagttgcc aagaggataa    21180
caagttttga gccacctgtg ctacataagt gaaaccctgt gttgagataa aaacaagagc    21240
tattgcccct ctgtgccttg cattataagc tgtacttaat ggtacataca ttttttgtatt    21300 aaagttgagg gggtgtttta ggtcacaagg gcagacacga ggttattaaa aggcttggaa    21360
gaagtattaa aaaggcaaga tgctgtgttt actagagaag agttactgtg agatttgtaa    21420
ttatagcagc aataaagttc tctgtttttcc tgaaggtcaa gcagttcctg ctcctgctgg    21480
ggccccacca ggtggtcagc cggattatag tgcagcctgg gctgagtact atagacagca    21540
agcagcgtat tatgcccaga caagtcccca ggggatgccg cagcatcctc cagcacctca    21600
ggtagaaaac atttgctatt tttttttgttt tgttttttgtt tttgtttttcc actccaacca    21660 tgttttctgc atgtttgtct gtttgggaat gaatatgttt tacttggtaa agtataacta    21720
catgaaatat cgtgttgtgt ttggggactc agttttttcta ataatgtttt ctggcatctg    21780
agtgctattt ttgtaatgcc tttgatttta aaaataaatt ttcttcccccc cagggatttg    21840 caaatcatgc aagaagccac catcatttat attaaccagt ttttctttct taaaggattc    21900
actcctgaat tagctccatt taaaggattt tctttaactt tttgtgtatc tcttatgtat    21960
```

```
ctcttctgca cagggccaat aataagaagt ggacaataca gtatttgctt cattgtgtgg   22020
gggaaaaaac ctttgttaaa tatatggatg cagacgactt gatgaagatc ttaattttgt   22080
ttttggttta aagtagtgtt ttttttccccc cctttttttt tattttgaaa atgtacaaaa   22140
taactatcac tactgatagg aggttaatat ttctgtgtag aaatgaaaat tggtttgttt   22200
ttagtcttta gtgtagatgt acacattcca gcaaatgtat ttgcaactat tatgtggtcg   22260
atgctttgtg atataaatgt actttttcaa tgtatacttt cacttttaaa atgcctgttt   22320
tgtgctttac aataaatgat atgaaacctc ctgtgtcggt aagttggata tgtgggtaaa   22380
ggattcatag tttcttagca gtgataaatt aagatacatg tacacgaata tataagcttt   22440
ccccatgaat tactgagttt ttaaacactg gcatgttttt tcccctgttg gagtatagtg   22500
gtagattgga ggttctttttc tgttgtattt ggctatttca gcacaagtaa tcctgatatt   22560
ttcatgtttt tccttctatt tgattaaaaa ctgcatgtgt atacaatgat ctttagtata   22620
cttccattgc attaacagtg acatttcctt ttatacatga gcactatttc agacctgtac   22680
cgctgctaca acagttaacc ttcctgttct tcacttattt ccgagactgt ttcagcataa   22740
ctaattttga acagtttgca gacagtgatt tgaggagttt ataagaaaca ttgttttttt   22800
catgtaaagc aactctttcc atgtatatat atatattata atagtgtgtt tctctctaaa   22860
ttcaggatag aaaagtaata gaatgtgaaa gtatagctac attgcatctg ccattgaaac   22920
atttggggta tgaaaatgtt caagcttttt ttttcttttt gcagtataga taagctttgt   22980
cttgtaattg cacaagtcca gtcattgaat caaattaatt ttttttatgta ctgaatcatt   23040 ttattaatct ttaacattca tgctgaagtt ctgatatttt gttgaaaacc attgtttttac   23100 tctgcatatt tgttggctct ttgcatatta atatattaga ctacatgcaa atacagtctg   23160
tcttgccatt gtctgttgaa gtgcaggttt gatccagcca gtatagaact agctctgtag   23220
gggtgaggag gactgtgctg tgtatcatcc ttgattgtgt tccttcaagg agcattgcac   23280
tgtaagtaca tcagagtgac aaattgatga actgcaacag tgtctttttg tcgatgttcc   23340
acataatgca attgctatat tttgtgtgac tattatgttg gaatacagtg ctgtcatggg   23400
aaaccataac tgcttcttaa catagaataa tacatagttc tgtatttttt ttaagtgagc   23460
ttaatgggta agtatttttg atatgcttta gctaatagct aaagaaaatt gatcagtaac   23520
aaagttgaat agtattatca gtgctcctaa aatgctgttt ttcagtgtaa aatatgccta   23580 tctttttatag tgatatgaaa aacttgaaat gtttaagaca gaagtgcttt tcagtttgca   23640
aagtttaagg acttaacgcc ttttcattaa atgttagttc tatcatctgt ggggagcacc   23700
atttgtatga ggacaaaaat gttgaggtta tagggcagaa aatagtacag ctcattgtgg   23760
atgttttgaa atgttttttg attgtttttat gtaacttagt gacttccctt ccccttattt   23820
agatctggat gcatagctct agtatgaagt ttaatagtaa tagttaaggc cttacctgtt   23880
aagatcttaa gtgtagggta ttgacatgaa cagtttcagt attttgcatg atattgttgc   23940
atagatgacc taggaaagtg ttgtggtgca tttagtaatt aaactgaagg aaatagttgg   24000
attcagtatc ataattcaca aattggaggc tgttgatttt gattcgttta aaatttaaaa   24060
tctttattaa ttgcaaacag tgcaattatt tatacttcac agtgccttcc cagaccttcc   24120
accttaggtt ctgctgcaaa aagcaacagg taagcacaac ctaaggccat ctctatataa   24180
atatatcagt acatacatgt tgtccctgtg aggtttgtgg ttgtgtactc actcaagcaa   24240
tctgctgctg ccgctgcccc aaatgtactt tgttatttat ggtaccattc tagtggaaag   24300
```

```
tctgttaagt tgttcaagca actgtttaca attttgggtg atgttttgtt tttggttttt    24360
ttgggttttt ttttttcccca ttaaaatgag tagattgctg caataactga aaaacatcca    24420 aatcttttg  tgcacccctc ctctcccaga gttatagaaa tgtttaagaa cacttcagta    24480
gttgagacat aggaaatcat ttggtcagaa atttcaacag ccttcacagc ccgtttgtat    24540
gagtaacagg aaattctctt tgccctccaa atctgatctt tttatagttt tatttttatt    24600 attttttcccc tgtattagta ctgctttaaa gtacagtaat tcagtgagat cgttttggtt    24660
cagtttcata gacagttcta ttttcatgac ttgtatttgc tgacaaggaa gaataaagaa    24720
tactggcagt aagttttggg aaaggcatgt gcatcagtga aatgttactt gtataacaaa    24780
taacctttca taatctgcat aaccagtagt ttctgattta taatatttta ataactgact    24840
gcatttattt ttgccagttt aaaatgtttt gtgttcttag gattgatgtt tagtgcatat    24900
tttgagttaa atgactatct taaagcagca ccatatcagt tgttttttatt cattttctaa    24960 aatgtgctga tcctattaaa aactcctgct tatcttttac aacaaagaaa aatattcaaa    25020
aatactgcct tcattttcac acacagtgct gaagatgctg caagcaccaa atcatagctc    25080
ataaaatcag gtcctgagat agttacccat aaagaggaat cctttgagtg tatgccattg    25140
gtgagccgat gagcatggac catagaaggg ctcaatgtag aaggtaaaat tggcaaatca    25200
taattgagaa atatgactgt gttcccatac ataatatggt atagggtgta atgtacctgc    25260
tcttgatcac tttcattta  aagtgctatt cacttaaatg ttccatgaat tgtttattgc    25320
accacagttt gtgtgtgtgt gtgtgtgtga gagagagaga gagagagaga gaaataggtc    25380
agatcagtat gttgcaagca gatctttaga gcctgtcaag ttttggttag ttgtagtttc    25440
catttggaaa tgtagatgaa tgcttgtaga tattggagat tgtttctatc ttgtaagaac    25500
ttttcactgg tgctgtaagc atttcaaata gcaccagtct taacctttaa atgggaagta    25560
gaaaaggtga gcccaaagtt tacagatgat tttaatgcta tacatgttag tgtagtgata    25620
cttagaatgc tttgtttgat gtttatttca gaaatgcgta tactagaaaa tcattttaat    25680
attaaaactg gtgacttaat actagttgta aagtgttttc ttaaagaagg atcttggtac    25740
ttaattgata aagtgggttt agataggagt agcaagtgct ctcgatagag aaagttttg    25800 ttcacttcaa tactttgtca ttacaaccag ttcttcctga aaatagttac atgtctagta    25860
aattgatgta gaattaactc gctggagata atctcatttt agttctgcaa attctgcctg    25920
gctttaaaat gcattttcat aatacttaga aataatttga ctgaaaataa ctgctttttt    25980
atttaatcag tcaatcaact tttactacaa atttaattga gggatttttt aatttaattg    26040
gtgctttaaa gaagcaaata aatccctggg ttttgttttc ttcagtaaat atcctaaaga    26100
aactctttaa tgtatttgcg agtatatata tattttctta tgcatgctcg atgcattttc    26160
gtcctgagaa aagtgttctc tacagaaact acccgtgtgt taaaagaaga ttggcttaaa    26220
atggctactg tgatgggaac agtgtcttag ggagatgcag cttggacttg aggtaaattg    26280
aatactttac aaactggctt agagttttgc tttaatgtca ttatatgtaa aagggcacat    26340
gattattgta attttgtatt ctttatggtt tccttaatta aaataataaa tgtacagtga    26400
ttact                                                                26405
```

<210> SEQ ID NO 6
<211> LENGTH: 17
<212> TYPE: DNA
<213> ORGANISM: artificial
<220> FEATURE:
<223> OTHER INFORMATION: Oligonucleotide targeting FUBP1

-continued

<400> SEQUENCE: 6
cttatgcttt ttatggt                                                      17

<210> SEQ ID NO 7
<211> LENGTH: 18
<212> TYPE: DNA
<213> ORGANISM: artificial
<220> FEATURE:
<223> OTHER INFORMATION: Oligonucleotide targeting FUBP1

<400> SEQUENCE: 7
cttatgcttt ttatggtt                                                     18

<210> SEQ ID NO 8
<211> LENGTH: 17
<212> TYPE: DNA
<213> ORGANISM: artificial
<220> FEATURE:
<223> OTHER INFORMATION: Oligonucleotide targeting FUBP1

<400> SEQUENCE: 8
gctttttatg gtttcac                                                      17

<210> SEQ ID NO 9
<211> LENGTH: 18
<212> TYPE: DNA
<213> ORGANISM: artificial
<220> FEATURE:
<223> OTHER INFORMATION: Oligonucleotide targeting FUBP1

<400> SEQUENCE: 9
tatgcttttt atggtttc                                                     18

<210> SEQ ID NO 10
<211> LENGTH: 22
<212> TYPE: DNA
<213> ORGANISM: artificial
<220> FEATURE:
<223> OTHER INFORMATION: Target region within FUBP1

<400> SEQUENCE: 10
gtgaaaccat aaaaagcata ag                                                22

<210> SEQ ID NO 11
<211> LENGTH: 18
<212> TYPE: DNA
<213> ORGANISM: artificial
<220> FEATURE:
<223> OTHER INFORMATION: Target region within FUBP1

<400> SEQUENCE: 11
aaccataaaa agcataag                                                     18

<210> SEQ ID NO 12
<211> LENGTH: 19
<212> TYPE: DNA
<213> ORGANISM: artificial
<220> FEATURE:
<223> OTHER INFORMATION: Sequence of Compound ID No 50_1 of WO
     2019/193165

<400> SEQUENCE: 12
ccatttcttc ctattacaa                                                    19

```
<210> SEQ ID NO 13
<211> LENGTH: 18
<212> TYPE: DNA
<213> ORGANISM: artificial
<220> FEATURE:
<223> OTHER INFORMATION: Sequence of Compound ID No 53_1 of WO
      2019/193165

<400> SEQUENCE: 13
gctttttatg gtttcacc                                                        18

<210> SEQ ID NO 14
<211> LENGTH: 20
<212> TYPE: DNA
<213> ORGANISM: artificial
<220> FEATURE:
<223> OTHER INFORMATION: Sequence of Compound ID No 54_1 of WO
      2019/193165

<400> SEQUENCE: 14 atgctttta tggtttcacc                                                       20

<210> SEQ ID NO 15
<211> LENGTH: 20
<212> TYPE: DNA
<213> ORGANISM: artificial
<220> FEATURE:
<223> OTHER INFORMATION: Target region within FUBP1

<400> SEQUENCE: 15
gtgaaaccat aaaaagcata                                                      20

<210> SEQ ID NO 16
<211> LENGTH: 18
<212> TYPE: DNA
<213> ORGANISM: artificial
<220> FEATURE:
<223> OTHER INFORMATION: Oligonucleotide targeting FUBP1

<400> SEQUENCE: 16
ttatgctttt tatggttt                                                        18

<210> SEQ ID NO 17
<211> LENGTH: 18
<212> TYPE: DNA
<213> ORGANISM: artificial
<220> FEATURE:
<223> OTHER INFORMATION: Oligonucleotide targeting FUBP1

<400> SEQUENCE: 17 atgctttta tggtttca                                                         18
```

```
<210> SEQ ID NO 18
<211> LENGTH: 18
<212> TYPE: DNA
<213> ORGANISM: artificial
<220> FEATURE:
<223> OTHER INFORMATION: Oligonucleotide targeting FUBP1

<400> SEQUENCE: 18
accaattttc atttctac                                                     18

<210> SEQ ID NO 19
<211> LENGTH: 18
<212> TYPE: DNA
<213> ORGANISM: Artificial Sequence
<220> FEATURE:
<223> OTHER INFORMATION: Target region within FUBP1

<400> SEQUENCE: 19
gtagaaatga aaattggt                                                     18

<210> SEQ ID NO 20
<211> LENGTH: 19
<212> TYPE: DNA
<213> ORGANISM: artificial
<220> FEATURE:
<223> OTHER INFORMATION: Oligonucleotide targeting FUBP1

<400> SEQUENCE: 20
atattaacct cctatcagt                                                    19

<210> SEQ ID NO 21
<211> LENGTH: 19
<212> TYPE: DNA
<213> ORGANISM: Artificial Sequence
<220> FEATURE:
<223> OTHER INFORMATION: Oligonucleotide targeting FUBP1

<400> SEQUENCE: 21
aatattaacc tcctatcag                                                    19

<210> SEQ ID NO 22
<211> LENGTH: 17
<212> TYPE: DNA
<213> ORGANISM: Artificial Sequence
<220> FEATURE:
<223> OTHER INFORMATION: Oligonucleotide targeting FUBP1

<400> SEQUENCE: 22
cccataacca tagtcat                                                      17
```

ENHANCED OLIGONUCLEOTIDES FOR MODULATING FUBP1 EXPRESSION

CROSS-REFERENCE TO RELATED APPLICATION

This application is a continuation of and claims the benefit of European Patent Application No. 20182437.2, filed 26 Jun. 2020, the disclosure of which is incorporated, in its entirety, by this reference.

FIELD OF INVENTION

The present invention relates to enhanced antisense oligonucleotides that are complementary to the Far Upstream Element-Binding Protein 1 (FUBP1) and are capable of reducing a FUBP1 target nucleic acid, such as FUBP1 mRNA. The invention relates to enhanced antisense oligonucleotides targeting FUBP1 or conjugates thereof for use in treating and/or preventing a hepatitis B virus (HBV) infection, in particular a chronic HBV infection. The invention in particular relates to the use of the enhanced antisense oligonucleotides targeting FUBP1 or conjugates thereof for destabilizing cccDNA, such as HBV cccDNA. The invention further relates to enhanced antisense oligonucleotides targeting FUBP1 or conjugates thereof for use in treating cancer. Also comprised in the present invention is a pharmaceutical composition and its use in the treatment and/or prevention of a HBV infection, or its use in the treatment of cancer.

BACKGROUND

Far Upstream Element-Binding Protein 1 (FUBP1 or FBP1) is a single stranded DNA-binding protein that binds to multiple DNA elements. This protein is also thought to bind RNA and contains 3'-5' helicase activity with in vitro activity on both DNA-DNA and RNA-RNA duplexes. FUBP1 is known to activate the transcription of the proto-oncogene c-myc by binding to far upstream element (FUSE) located upstream of c-myc in undifferentiated cells. The protein is primarily present in the nucleus of the cell. Upregulation of FUBP1 has been observed in many types of cancers. Furthermore, FUBP1 can bind to and mediate replication of RNA from Hepatitis C virus and Enterovirus (Zhang and Chen 2013 Oncogene vol 32 p. 2907-2916).

FUBP1 has also been identified in Hepatocellular carcinoma (HCC) where it has been suggested to be involved in HCC tumorigenesis (Ramdzan et al 2008 Proteomics Vol 8 p. 5086-5096) and that FUBP1 is required for HCC tumour growth as illustrated using lentivirus-expressed shRNA targeting FUBP1 (Rabenhorst et al 2009 Hepatology vol 50 p 1121-1129).

It has been demonstrated that knock-down of FUBP1 with lentivirus-expressed shRNA's enhances treatment response in ovarian cancer (Zhang et al 2017 Oncology Letters Vol 14 p. 5819-5824).

WO 2004/027061 disclose a screening method, which involves the step of analyzing whether or not a test substance inhibits FBP (FBP is now referred to as FUBP) and a medicinal composition for treating a proliferative disease, which contains as the active ingredient(s) a substance inhibiting FBP.

Poly(U) Binding Splicing Factor 60 (PUF60) is a potentially regulator of both transcriptional and post-transcriptional steps of HBV pregenome expression. PUF60 is known to form a complex with FUBP1 in relation to c-myc repression. However, FUBP1 does not participate in the PUF60 dependent regulation of HBV pregenome expression (Sun et al 2017 Scientific Reports 7:12874).

HBV infection remains a major health problem worldwide affecting an estimated 350 million chronically infected carriers. Approximately 25% of carriers ultimately die from chronic hepatitis, cirrhosis, or liver cancer. Hepatitis B virus is the second most significant carcinogen behind tobacco, causing from 60% to 80% of all primary liver cancer. HBV is 100 times more contagious than HIV.

The hepatitis B virus (HBV) is an enveloped, partially double-stranded DNA virus. The compact 3.2 kb HBV genome consists of four overlapping open reading frames (ORF), which encode for the core, polymerase (Pol), envelope and X-proteins respectively. The Pol ORF is the longest and the envelope ORF is located within it, while the X and core ORFs overlap with the Pol ORF. The replicative cycle of the HBV genome has two main events: 1) generation of closed circular DNA (cccDNA) from relaxed circular (RC DNA), and 2) reverse transcription of pregenomic RNA (pgRNA) to produce RC DNA. The RC DNA may stem from an infecting viral particle, or as an intracellular replication intermediate.

HBsAg quantification is a significant biomarker for prognosis and treatment response in chronic hepatitis B with the loss of circulating HBsAg in the chronically infected patient seen as a key event in achieving cure. However, the achievement of HBsAg loss and seroconversion (functional cure) is rarely observed in chronically infected patients. Hepatitis B e-antigen (also called HBV envelope antigen or HBeAg) is a viral protein that is secreted by hepatitis B infected cells. HBeAg is associated with chronic hepatitis B infections and is used as a marker of active viral disease and a patient's degree of infectiousness.

Accordingly, reducing secretion of HBeAg in addition to secretion of HBsAg would lead to an improved inhibition of development of a chronic HBV infection as compared to the inhibition of secretion of HBsAg alone.

Current therapy such as nucleos(t)ide analogues are molecules that inhibit HBV DNA synthesis but are not directed at reducing HBsAg level. Most therapies currently under development aim to reach a functional cure, defined as a durable HBsAg loss with or without anti-HBs seroconversion, with undetectable serum DNA, and with cccDNA in a transcriptionally inactive state, but do not address cccDNA persistence. In contrast, complete cure of HBV infection is defined as cccDNA loss in combination with durable HBV DNA and HBsAg loss. The persistence of cccDNA in infected hepatocytes is the main barrier for eradicating the virus in chronic hepatitis B virus (CHB) patients, and there is an urgent need to develop new therapies for the HBV complete cure that eliminates cccDNA.

In WO 2019/193165, it was shown that inhibition of FUBP1 functionality, either using a small molecule, a siRNA or a LNA antisense oligonucleotide, resulted in reduction of HBV cccDNA. In the Examples section of WO 2019/193165, single stranded LNA gapmer oligonucleotides were analyzed, which were able to inhibit FUBP1 expression.

There is a need for therapeutic agents, which can inhibit FUBP1 specifically. We have screened more than 2000 antisense oligonucleotides targeting human FUBP1 and identified sequences and compounds, which are particularly potent and effective to specifically target human FUBP1. Specifically, nine alternating flank gapmers were identified, which conferred a strong down-regulation of human FUBP1 in vitro. Eight compounds target a region within exon 14 of human FUBP1, one compound targets a region within exon 20 (CMP ID 18_1).

OBJECTIVE OF THE INVENTION

The present invention provides antisense oligonucleotides and conjugates thereof, which modulate FUBP1 expression. We identified a specific target sequence present in exon 14 or exon 20 of the human FUBP1 pre-mRNA, which may be targeted by antisense oligonucleotides, or conjugates thereof, to give effective FUBP1 inhibition. In particular, targeting position 16184-16205 of SEQ ID NO: 1 is advantageous in terms of reducing FUBP1.

Furthermore, we identified a specific target sequence present in exon 20 of the human FUBP1 pre-mRNA, which may be targeted by antisense oligonucleotides, or conjugates thereof, to give effective FUBP1 inhibition. In particular, targeting position 30536-30553 of SEQ ID NO: 1 is advantageous in terms of reducing FUBP1.

Accordingly, an objective of the present invention is to provide enhanced antisense oligonucleotides targeting FUBP1 or conjugates thereof, wherein the antisense oligonucleotides or conjugates thereof are capable of inhibiting the expression of FUBP1 in vitro and in vivo, thereby reducing cccDNA in an HBV infected cell. The enhanced antisense oligonucleotides targeting FUBP1 or the conjugate thereof can be used in the treatment and/or prevention of an HBV infection, or in the treatment of cancer.

SUMMARY OF INVENTION

The invention relates to antisense oligonucleotides, or conjugates thereof, which target a FUBP1 (Far upstream element-binding protein 1) nucleic acid, such as a mammalian FUBP1 nucleic acid, and which are capable of inhibiting the expression of said nucleic acid in a cell expressing said nucleic acid, and their use in medicine. Said antisense oligonucleotides are complementary to a mammalian FUBP1 nucleic acid, such as human FUBP1.

The invention provides for an antisense oligonucleotide, which comprises a contiguous nucleotide sequence, which is complementary to, such as fully complementary to a region from nucleotides 16184 to 16205 of the human FUBP1 pre-mRNA (as illustrated in SEQ ID NO: 1).

Also, the invention provides for an antisense oligonucleotide, which comprises a contiguous nucleotide sequence, which is complementary to, such as fully complementary to a region from nucleotides 30536-30553 of the human FUBP1 pre-mRNA (as illustrated in SEQ ID NO: 1).

In some embodiments, the antisense oligonucleotide or the contiguous nucleotide sequence is complementary to, such as fully complementary to a region from nucleotides 16184 to 16200 of SEQ ID NO: 1.

In some embodiments, the antisense oligonucleotide or the contiguous nucleotide sequence is complementary to, such as fully complementary to a region from nucleotides 16186 to 16203 of SEQ ID NO: 1.

In some embodiments, the antisense oligonucleotide or the contiguous nucleotide sequence is complementary to, such as fully complementary to a region from nucleotides 30536-30553 of SEQ ID NO: 1.

In some embodiments, the antisense oligonucleotide or the contiguous nucleotide sequence is complementary to, such as fully complementary to a region from nucleotides 16188 to 16205 of SEQ ID NO: 1. In some embodiments, the antisense oligonucleotide or the contiguous nucleotide sequence is complementary to, such as fully complementary to a region from nucleotides 16189 to 16205 of SEQ ID NO: 1.

The antisense oligonucleotide of the invention is typically 12-30, such as 12 to 22, such as 16 to 20 nucleotides in length, and comprises a contiguous nucleotide sequence of at least 12 nucleotides, such as of 13, 14, 15, 16, 17 or 18 nucleotides, which is complementary to, such as fully complementary to a region of the human FUBP1 pre-mRNA (as illustrated in SEQ ID NO: 1), selected from a region from nucleotides 16184-16205, 16184-16200, 16186-16203, 16188-16205, 16189-16205 and 30536-30553 of SEQ ID NO: 1.

The invention provides for an antisense oligonucleotide, 12-22 nucleotides in length, wherein said antisense oligonucleotide comprises a contiguous nucleotide sequence 12-22 nucleotides in length, wherein the contiguous nucleotide sequence is complementary, such as fully complementary, to SEQ ID NO 10.

The invention provides for an antisense oligonucleotide, 12-20 nucleotides in length (such as 15, 16, 17, or 18 nucleotides in length), wherein said antisense oligonucleotide comprises a contiguous nucleotide sequence 12-18 nucleotides in length (such as 15, 16, 17, or 18 nucleotides in length), wherein the contiguous nucleotide sequence is complementary, such as fully complementary, to SEQ ID NO 11.

The invention provides for an antisense oligonucleotide, 12-20 nucleotides in length (such as 15, 16, 17, or 18 nucleotides in length), wherein said antisense oligonucleotide comprises a contiguous nucleotide sequence 12-18 nucleotides in length (such as 15, 16, 17, or 18 nucleotides in length), wherein the contiguous nucleotide sequence is complementary, such as fully complementary, to SEQ ID NO 19.

The invention provides for an antisense oligonucleotide 10 to 30 nucleotides in length, which comprises a contiguous nucleotide sequence of 10 to 30 nucleotides in length, wherein the contiguous nucleotide sequence is 100% identical to a sequence selected from the group consisting of SEQ ID NOs: 6, 7, 8, 9 and 18; or at least 14 contiguous nucleotides thereof.

The invention provides for an antisense oligonucleotide 10 to 30 nucleotides in length, which comprises a contiguous nucleotide sequence of 10 to 30 nucleotides in length, wherein the contiguous nucleotide sequence is 100% identical to a sequence selected from the group consisting of SEQ ID NOs: 6, 7, 8, 9 and 18, or at least 15 contiguous nucleotides thereof.

The invention provides for an antisense oligonucleotide 10 to 30 nucleotides in length, which comprises a contiguous nucleotide sequence of 10 to 30 nucleotides in length, wherein the contiguous nucleotide sequence is 100% identical to a sequence selected from the group consisting of SEQ ID NOs: 6, 7, 8, 9 and 18, or at least 16 contiguous nucleotides thereof.

The invention provides for an antisense oligonucleotide which comprises a contiguous nucleotide sequence, which is 100% identical to a sequence selected from the group consisting of SEQ ID NOs: 6, 7, 8, 9 and 18, or 14, 15, 16, or 17 contiguous nucleotides thereof.

The invention provides for an antisense oligonucleotide, which comprises (or consists of) a contiguous nucleotide sequence selected from the group consisting of SEQ ID NOs: 6, 7, 8, 9 and 18.

The invention provides for an antisense oligonucleotide, which comprises a contiguous nucleotide sequence, which is 100% identical to SEQ ID NO: 6 (CTTATGCTTTT-TATGGT), or 14, 15 or 16 contiguous nucleotides thereof.

The invention provides for an antisense oligonucleotide, which comprises a contiguous nucleotide sequence, which is 100% identical to SEQ ID NO: 7 (CTTATGCTTTT-TATGGTT), or 14, 15, 16 or 17 contiguous nucleotides thereof.

The invention provides for an antisense oligonucleotide, which comprises a contiguous nucleotide sequence, which is 100% identical to SEQ ID NO: 8 (GCTTTTTATGGTTT-CAC), or 14, 15 or 16 contiguous nucleotides thereof.

The invention provides for an antisense oligonucleotide, which comprises a contiguous nucleotide sequence, which is 100% identical to SEQ ID NO: 9 (TATGCTTTT-TATGGTTTC), or 14, 15, 16 or 17 contiguous nucleotides thereof.

The invention provides for an antisense oligonucleotide, which comprises a contiguous nucleotide sequence, which is 100% identical to SEQ ID NO: 18 (ACCAATTTTCATTTC-TAC), or 14, 15, 16 or 17 contiguous nucleotides thereof.

The invention provides for an antisense oligonucleotide selected from

```
                     (SEQ ID NO: 6, Compound ID No 6_1)
CTTatGcttttttatgGT, (SEQ ID NO: 6, Compound ID No 6_2)
CTTaTgcttttttatgGT,
```

-continued

```
                     (SEQ ID NO: 7, Compound ID No 7_1)
CTtATgcttttttatgGTT, (SEQ ID NO: 7, Compound ID No 7_2)
CTtAtgcttttttatgGTT, (SEQ ID NO: 7, Compound ID No 7_3)
CTtAtgctttttatGgTT, (SEQ ID NO: 7, Compound ID No 7_4)
CTtAtgctttttatGGTT, (SEQ ID NO: 8, Compound ID No 8_1)
GcttTttatggtTtCAC, (SEQ ID NO: 9, Compound ID No 9_1)
TATgcTtttttatggtTTC, and (SEQ ID NO: 18, Compound ID No 18_1)
AcCAAttttcatttCtAC
``` wherein capital letters are beta-D-oxy LNA nucleosides, lowercase letters are DNA nucleosides, all LNA Cs are LNA 5-methyl cytosine, and all internucleoside linkages are phosphorothioate internucleoside linkages.

The present invention also provides for a pharmaceutically acceptable salt of the antisense oligonucleotide of the present invention.

The invention provides for an antisense oligonucleotide selected from the group listed in Table 1, or a pharmaceutically acceptable salt thereof.

TABLE 1

| | | Compound Table (Exemplary antisense oligonucleotides of the present invention) - HELM Annotation Format | |
| --- | --- | --- | --- |
| SEQ ID Number | Compound ID Number | HELM Annotation #Written 5' - 3'. | Comprised by conjugate shown in FIG. |
| 6 | 6_1 | {[LR]([5meC])[sP].[LR](T)[sP].[LR](T)[sP].[dR](A)[sP].[dR](T)[sP].[LR](G)[sP].[dR](T)[sP].[dR](T)[sP].[dR](T)[sP].[dR](T)[sP].[dR](T)[sP].[dR](A)[sP].[dR](T)[sP].[dR](G)[sP].[LR](G)[sP].[LR](T)} | 1 |
| 6 | 6_2 | {[LR]([5meC])[sP].[LR](T)[sP].[LR](T)[sP].[dR](A)[sP].[LR](T)[sP].[dR](T)[sP].[dR](T)[sP].[dR](T)[sP].[dR](T)[sP].[dR](T)[sP].[dR](T)[sP].[dR](T)[sP].[dR](A)[sP].[dR](T)[sP].[dR](G)[sP].[LR](G)[sP].[LR](T)} | 2 |
| 7 | 7_1 | {[LR]([5meC])[sP].[LR](T)[sP].[dR](T)[sP].[LR](A)[sP].[LR](T)[sP].[dR](T)[sP].[dR](T)[sP].[dR](T)[sP].[dR](T)[sP].[dR](T)[sP].[dR](T)[sP].[dR](T)[sP].[dR](A)[sP].[dR](T)[sP].[dR](G)[sP].[LR](G)[sP].[LR](T)[sP].[LR](T)} | 3 |
| 7 | 7_2 | {[LR]([5meC])[sP].[LR](T)[sP].[dR](T)[sP].[LR](A)[sP].[dR](T)[sP].[dR](T)[sP].[dR](T)[sP].[dR](T)[sP].[dR](T)[sP].[dR](T)[sP].d[dR](T)[sP].[dR](T)[sP].[dR](A)[sP].[dR](T)[sP].[dR](G)[sP].[LR](G)[sP].[LR](T)[sP].[LR](T)} | 4 |
| 7 | 7_3 | {[LR]([5meC])[sP].[LR](T)[sP].[dR](T)[sP].[LR](A)[sP].[dR](T)[sP].[dR](T)[sP].[dR](T)[sP].[dR](T)[sP].[dR](T)[sP].[dR](T)[sP].[dR](T)[sP].[dR](T)[sP].[dR](A)[sP].[dR](T)[sP].[LR](G)[sP].[dR](G)[sP].[LR](T)[sP].[LR](T)} | 5 |
| 7 | 7_4 | {[LR]([5meC])[sP].[LR](T)[sP].[dR](T)[sP].[LR](A)[sP].[dR](T)[sP].[dR](T)[sP].[dR](T)[sP].[dR](T)[sP].[dR](T)[sP].[dR](T)[sP].[dR](T)[sP].[dR](T)[sP].[dR](A)[sP].[dR](T)[sP].[LR](G)[sP].[LR](G)[sP].[LR](T)[sP].[LR](T)} | 6 |
| 8 | 8_1 | {[LR](G)[sP].[dR](C)[sP].[dR](T)[sP].[dR](T)[sP].[LR](T)[sP].[dR](T)[sP].[dR](T)[sP].[dR](A)[sP].[dR](T)[sP].[dR](G)[sP].[dR](G)[sP].[dR](T)[sP].[LR](T)[sP].[dR](T)[sP].[LR]([5meC])[sP].[LR](A)[sP].[LR]([5meC])} | 7 |

TABLE 1-continued

Compound Table (Exemplary antisense oligonucleotides of the present invention) - HELM
Annotation Format

| SEQ ID Number | Compound ID Number # | HELM Annotation Written 5' - 3'. | Comprised by conjugate shown in FIG. |
|---|---|---|---|
| 9 | 9_1 | {[LR](T)[sP].[LR](A)[sP].[LR](T)[sP].[dR](G)[sP].[dR](C)[sP].[LR](T)[sP].[dR](T)[sP].[dR](T)[sP].[dR](T)[sP].[dR](T)[sP].[dR](A)[sP].[dR](T)[sP].[dR](G)[sP].[dR](G)[sP].[dR](T)[sP].[LR](T)[sP].[LR](T)[sP].[LR]([5meC])} | 8 |
| 18 | 18_1 | {[LR](A)[sP].[dR](C)[sP].[LR]([5meC])[sP].[LR](A)[sP].[LR](A)[sP].[dR](T)[sP].[dR](T)[sP].[dR](T)[sP].[dR](T)[sP].(C)[sP].[dR](A)[sP].[dR](T)[sP].[dR](T)[sP].[dR](T)[sP].[LR]([5meC])[sP].[dR](T)[sP].[LR](A)[sP].[LR]([5meC])} | 8.1 |

Helm Annotation Key:
[LR](G) is a beta-D-oxy-LNA guanine nucleoside,
[LR](T) is a beta-D-oxy-LNA thymine nucleoside,
[LR](A) is a beta-D-oxy-LNA adenine nucleoside,
[LR]([5meC] is a beta-D-oxy-LNA 5-methyl cytosine nucleoside,
[dR](G) is a DNA guanine nucleoside,
[dR](T) is a DNA thymine nucleoside,
[dR](A) is a DNA adenine nucleoside,
[dR]([C] is a DNA cytosine nucleoside,
[sP]. is a phosphorothioate internucleoside linkage,
P. is a phosphodiester internucleoside linkage.

The invention thus provides for an antisense oligonucleotide selected fro the group consisting of compound ID Nos #6_1, 6_2, 7_1, 7_2, 7_3, 7_4; 8_1 and 9_1.

The invention further provides for an antisense oligonucleotide with compound ID No: 18_1.

In an embodiment, the antisense oligonucleotide is not an antisense oligonucleotide compound ID Nos 53_1 or 54_1 as disclosed in WO 2019/193165 (see also Table 7 in the Examples section).

In an embodiment, the antisense oligonucleotide is not an antisense oligonucleotide compound ID Nos 78_1 and 79_1 as disclosed in WO 2019/193165 (see also Table 7 in the Examples section).

The present invention further provides a conjugate comprising the antisense oligonucleotide of the present invention and at least one conjugate moiety covalently attached to said antisense oligonucleotide.

In some embodiments, the conjugate moiety is capable of binding to the asialoglycoprotein receptor, such as the human asialoglycoprotein receptor. For example, the conjugate moiety may comprise at least one asialoglycoprotein receptor-targeting moiety selected from group consisting of galactose, galactosamine, N-formyl-galactosamine, N-acetylgalactosamine, N-propionyl-galactosamine, N-n-butanoyl-galactosamine and N-isobutanoylgalactosamine.

In some embodiments, the asialoglycoprotein receptor-targeting moiety is N-acetylgalactosamine (GalNAc). Thus, the antisense oligonucleotide of the present invention may be conjugated to at least one conjugate moiety comprising at least one N-Acetylgalactosamine (GalNAc) moiety, such as at least one conjugate moiety comprising at least one N-Acetylgalactosamine (GalNAc) moiety as described below. According to one aspect of the invention, the conjugate moiety is a GalNAc residue R as described hereinunder.

In some embodiments, the conjugate moiety is an at least trivalent, such as a divalent, trivalent or tetravalent GalNAc residue residue R. Preferably the conjugate moiety is a trivalent GalNAc residue R.

The term "trivalent GalNAc residue" as used herein refers to a residue comprising three N-Acetylgalactosamine moieties, i.e. preferably three moieties of formula The conjugate moiety or the GalNAc residue R, respectively, and the antisense oligonucleotide may be linked together via a linker L, such as a biocleavable linker L. Thus, the conjugate compound may comprise a linker L, which is positioned between the antisense oligonucleotide and the conjugate moiety or GalNAc residue R, respectively.

In some embodiments, the linker L comprises between 1 and 10 linked nucleosides, such as 1, 2, 3, 4, 5, 6, 7, 8·9 or 10 linked nucleosides, such as between 2 and 6 linked nucleosides, such as between 2 and 5 linked nucleosides, such as between 2 and 4 linked nucleosides. In some embodiments, the linker comprises two linked nucleotides. Thus, the nucleosides may be DNA nucleosides. Typically, the nucleosides are linked via phosphodiester internucleoside linkages. Moreover, the linker L may be linked to the antisense compound via a phosphodiester internucleoside linkage.

Exemplary conjugates are provided in Table 2 (in HELM Annotation format) as well as in FIGS. 1 to 8, FIG. 8.1 and FIG. 10.

The invention provides for a conjugate selected from the group of conjugates listed in Table 2, or a pharmaceutically acceptable salt thereof.

TABLE 2

Compound Table (Exemplary conjugates of the present invention) - HELM Annotation
Format (for the annotation on the HELM annotation, see explanations for Table 1).

| SEQ ID Number | Oligo Compound ID Number # (acc. to Table 1 above) | HELM Annotation Written 5' - 3'. | Exemplary compound - see FIG. |
|---|---|---|---|
| 6 | 6_1 | {[5gn2c6]P.[dR](C)P.[dR](A)P.[LR]([5meC])[sP].[LR](T)[sP].[LR](T)[sP].[dR](A)[sP].[dR](T)[sP].[LR](G)[sP].[dR](C)[sP].[dR](T)[sP].[dR](T)[sP].[dR](T)[sP].[dR](T)[sP].[dR](T)[sP].[dR](A)[sP].[dR](T)[sP].[dR](G)[sP].[LR](G)[sP].[LR](T)} | 1 |
| 6 | 6_2 | {[5gn2c6]P.[dR](C)P.[dR](A)P.[LR]([5meC])[sP].[LR](T)[sP].[LR](T)[sP].[dR](A)[sP].[LR](T)[sP].[dR](G)[sP].[dR](C)[sP].[dR](T)[sP].[dR](T)[sP].[dR](T)[sP].[dR](T)[sP].[dR](T)[sP].[dR](A)[sP].[dR](T)[sP].[dR](G)[sP].[LR](G)[sP].[LR](T)} | 2 |
| 7 | 7_1 | {[5gn2c6]P.[dR](C)P.[dR](A)P.[LR]([5meC])[sP].[LR](T)[sP].[dR](T)[sP].[LR](A)[sP].[LR](T)[sP].[dR](G)[sP].[dR](C)[sP].[dR](T)[sP].[dR](T)[sP].[dR](T)[sP].[dR](T)[sP].[dR](T)[sP].[dR](A)[sP].[dR](T)[sP].[dR](G)[sP].[LR](G)[sP].[LR](T)[sP].[LR](T)} | 3 |
| 7 | 7_2 | {[5gn2c6]P.[dR](C)P.[dR](A)P.[LR]([5meC])[sP].[LR](T)[sP].[dR](T)[sP].[LR](A)[sP].[dR](T)[sP].[dR](G)[sP].[dR](C)[sP].[dR](T)[sP].[dR](T)[sP].[dR](T)[sP].[dR](T)[sP].[dR](T)[sP].[dR](A)[sP].[dR](T)[sP].[dR](G)[sP].[LR](G)[sP].[LR](T)[sP].[LR](T)} | 4 |
| 7 | 7_3 | {[5gn2c6]P.[dR](C)P.[dR](A)P.[LR]([5meC])[sP].[LR](T)[sP].[dR](T)[sP].[LR](A)[sP].[dR](T)[sP].[dR](G)[sP].[dR](C)[sP].[dR](T)[sP].[dR](T)[sP].[dR](T)[sP].[dR](T)[sP].[dR](T)[sP].[dR](A)[sP].[dR](T)[sP].[LR](G)[sP].[dR](G)[sP].[LR](T)[sP].[LR](T)} | 5 |
| 7 | 7_4 | {[5gn2c6]P.[dR](C)P.[dR](A)P.[LR]([5meC])[sP].[LR](T)[sP].[dR](T)[sP].[LR](A)[sP].[dR](T)[sP].[dR](G)[sP].[dR](C)[sP].[dR](T)[sP].[dR](T)[sP].[dR](T)[sP].[dR](T)[sP].[dR](T)[sP].[dR](A)[sP].[dR](T)[sP].[LR](G)[sP].[LR](G)[sP].[LR](T)[sP].[LR](T)} | 6 |
| 8 | 8_1 | {[5gn2c6]P.[dR](C)P.[dR](A)P.[LR](G)[sP].[dR](C)[sP].[dR](T)[sP].[dR](T)[sP].[LR](T)[sP].[dR](T)[sP].[dR](T)[sP].[dR](A)[sP].[dR](T)[sP].[dR](G)[sP].[dR](G)[sP].[dR](T)[sP].[LR](T)[sP].[dR](T)[sP].[LR]([5meC])[sP].[LR](A)[sP].[LR]([5meC])} | 7 |
| 9 | 9_1 | {[5gn2c6]P.[dR](C)P.[dR](A)P.[LR](T)[sP].[LR](A)[sP].[LR](T)[sP].[dR](G)[sP].[dR](C)[sP].[LR](T)[sP].[dR](T)[sP].[dR](T)[sP].[dR](T)[sP].[dR](1)[sP].[dR](A)[sP].[dR](T)[sP],[dR](G)[sP].[dR](G)[sP].[dR](T)[sP].[LR](T)[sP].[LR](T)[sP].[LR]([5meC])} | 8 |
| 18 | 18_1 | {[5gn2c6]}P.[dR](C)P.[dR](A)P.[LR](A)[sP].[dR](C)[sP].[LR]([5meC])[sP].[LR](A)[sP].[LR](A)[sP].[dR](T)[sP].[dR](T)[sP].[dR](T)[sP].[dR](T)[sP].[dR](C)[sP].[dR](A)[sP].[dR](T)[sP].[dR](T)[sP].[dR](T)[sP].[LR]([5meC])[sP].[dR](T)[sP].[LR](A)[sP].[LR]([5meC])} | 8.1 |

In the above Table, [5gn2c6] is a GalNAc residue R having the formula:

It is to be understood that R as shown in the figure above and as used in the above table is a mixture of the two stereoisomers shown in FIGS. 9D1 and 9D2.

According to a further aspect of the invention, R as shown in the figure above and as used in the above table is the stereoisomer as shown in to FIG. 9D1.

According to a further aspect of the invention R as shown in the figure above and as used in the above table is the stereoisomer as shown in FIG. 9D1. The structures of the conjugates provided in Table 2 are shown in FIGS. 1 to 8, and 8.1.

The invention provides for the conjugate of FIG. 1, or a pharmaceutically acceptable salt thereof.

The invention provides for the antisense oligonucleotide of Compound ID Number 61, or a pharmaceutically acceptable salt thereof.

The invention provides for the conjugate of FIG. 2, or a pharmaceutically acceptable salt thereof.

The invention provides for the antisense oligonucleotide of Compound ID Number 6_2, or a pharmaceutically acceptable salt thereof.

The invention provides for the conjugate of FIG. 3, or a pharmaceutically acceptable salt thereof.

The invention provides for the antisense oligonucleotide of Compound ID Number 7_1, or a pharmaceutically acceptable salt thereof.

The invention provides for the conjugate of FIG. 4, or a pharmaceutically acceptable salt thereof.

The invention provides for the antisense oligonucleotide of Compound ID Number 7_2, or a pharmaceutically acceptable salt thereof.

The invention provides for the conjugate of FIG. 5, or a pharmaceutically acceptable salt thereof.

The invention provides for the antisense oligonucleotide of Compound ID Number 7_3, or a pharmaceutically acceptable salt thereof.

The invention provides for the conjugate of FIG. 6, or a pharmaceutically acceptable salt thereof.

The invention provides for the antisense oligonucleotide of Compound ID Number 7_4, or a pharmaceutically acceptable salt thereof.

The invention provides for the conjugate of FIG. 7, or a pharmaceutically acceptable salt thereof.

The invention provides for the antisense oligonucleotide of Compound ID Number 8_1, or a pharmaceutically acceptable salt thereof.

The invention provides for the conjugate of FIG. 8, or a pharmaceutically acceptable salt thereof.

The invention provides for the antisense oligonucleotide of Compound ID Number 9_1, or a pharmaceutically acceptable salt thereof.

The invention provides for the antisense oligonucleotide of Compound ID Number or a pharmaceutically acceptable salt thereof.

The invention provides for the conjugate of FIG. 8.1, or a pharmaceutically acceptable salt thereof.

The Compound of Formula (I)

The present invention also provides for compounds of the following formula (I)

(I)

wherein n is 0 or 1 p is 0 or 1 with the proviso that in case n is 1, p is preferably 1, and with the proviso that in case n is 0 and p is 0, R is preferably H, L is a linker, preferably L is a linker comprising or consisting of 2-10 nucleosides, such as 2-5 nucleosides, R is a GalNAc residue, preferably a trivalent GalNAc residue, and A is an antisense oligonucleotide residue according to the present invention.

The term "antisense oligonucleotide residue" refers to an antisense oligonucleotide according to the present invention which is attached via its 5' end to residue R via -(L)$_n$-(O—P(=O)(—OH)—)$_p$—, such as an antisense oligonucleotide as shown in Table 6. Preferred antisense oligonucleotide residues are depicted in FIGS. 1A, 2A, 3A, 4A, 5A, 6A, 7A and 8A. A further preferred antisense oligonucleotide residue is depicted in FIG. 8.1A.

The GalNAc Residue R

R is a GalNAc residue, preferably a trivalent GalNAc residue. The term "GalNAc residue" as used herein refers to a residue comprising at least one N-Acetylgalactosamine (GalNAc) moiety, i.e. at least one moiety of formula The term "trivalent GalNAc residue" as used herein refers to a residue comprising three N-acetylgalactosamine (GalNAc) moieties, i.e. preferably three moieties of formula Preferably, the GalNAc residue comprises at least one, preferably three GalNAc building blocks (L$^a$) having the following structure, (L$^a$)

wherein Linker$^a$ is selected from alkyl groups, alkyl-oxy-alkyl groups, alkyl groups comprising at least one phosphodiester linkage, alkyl groups comprising at least one amide linkage, alkyl-oxy-alkyl groups groups comprising at least one phosphodiester linkage and alkyl-oxy-alkyl groups comprising at least one amide linkage.

The term "alkyl" refers to substituted or unsubstituted, linear or branched, alkyl groups, such as C1 to C20 alkyl groups, preferably, C2 to C8, such as C2, C3, C4, C5, C6, C7 or C8, alkyl groups. Preferably the alkyl groups are unsubstituted, more preferably linear and unsubstituted, alkyl groups.

The term "alkyl-oxy-alkyl" groups refers to at least two alkyl groups linked via an oxygen, preferably to ethyl-oxy-ethyl groups, such as —(CH$_2$—O)$_x$— groups with integer x preferably being in the range of from 2 to 20, more preferably in the range of from 2 to 6, such as 2, 3, 4, 5 or 6, more preferably x is 3 or 5.

According to an aspect of the invention, the GalNAc building block (L$^a$) is selected from the group of the following structures (L$^a$).

If more than one residue (L$^a$) is present in a GalNAc residue, such as the three residues in the trivalent GalNAc residue, then all residues are preferably the same.

Most preferably, L$^a$ has the structure

In case, the conjugate moiety R comprises multiple, such as preferably three, GalNAc moieties, R comprises besides the GalNAc building blocks (L$^a$), a multivalent, preferably a tetravalent, building block (L$^b$), to which the building blocks (L$^a$) are preferably being attached, to the antisense oligonucleotide residue A via -(L)$_n$-(O—P(=O)(—OH)—)$_p$—.

L$^b$ is preferably selected from one of the following structures:

15

16 with X being O or S, and with Z being O or NH, and wherein n is of rom 1 to 4, preferably 2 or 3, more preferably 2.

More preferably, $L^b$ has the structure

It is to be understood that, $L^b$ has either the structure $L^{b*}$ or the structure $L^{b**}$ or is a mixture thereof. According to a preferred aspect $L^b$ is a mixture of $L^{b*}$ and $L^{b**}$:

($L^{b*}$)

($L^{b**}$)

Thus, the conjugate moiety R preferably comprises a structure $(L^a)_3$-$L^b$-, more preferably R comprises one of the following structures

17

-continued

18 more preferably, the structure wherein $L^b$ is preferably a mixture of $L^{b*}$ and $L^{b**}$, and wherein X is O or S, and with Z being O or NH, and wherein n is of from to 3, preferably 2, and with $L^a$ being as described above, preferably with $L^a$ being selected from the group consisting of and mixtures thereof, wherein preferably all residues ($L^a$) within the GalNAc residue are the same.

In case $(L^a)_3$-$L^b$ is

L$^a$ is more preferably selected from the group consisting of

In case $(L^a)_3$-$L^b$ is or preferably $L^a$ is preferably

Optionally, the conjugate moiety R additionally comprises a linker $L^c$. Thus, R preferably has the structure $(L^a)_3$-$L^b$-$(L^c)_c$- with integer c being 1 or 0.

Such linker compounds are known those skilled in the art and are suitably chosen to attach $(L^a)_3$-$L_b$ to the remaining part of the compound, i.e. to the antisense oligonucleotide residue via -(L)$_n$-(O—P(=O)(—OH)—)$_p$—.

Depending on the structure of $L^b$, $L^c$ is selected from the group consisting of alkyl, alkyl-oxy-alkyl, amino-alkyl (—NH-alkyl-), amino-alkyl-oxy-alkyl, unnatural amino acid residues, and natural amino acid residues. According to one aspect of the invention, $L^c$ is a substituted or unsubstituted lysine group.

According to one aspect of the invention, R is $(L^a)_3$-$L^b$-$(L^c)_c$ with c=1 and $(L^a)_3$-$L_b$ is $L^c$ is preferably an amino-alkyl group or an amino acid, such as a substituted or un substitute lysine group, in particular $L^c$ is e.g. selected from the group consisting of with the amino group being attached to the carbonyl group of $L^b$ thereby forming an amide bond. Preferred residues R according to this aspect are depicted in FIG. 9A1, 9A2; 9C1, 9C2, 9D1, 9D2. Thus, according to one aspect of the invention, R is selected from the group consisting of the residues depicted in FIGS. 9A1, 9A2; 9C1, 9C2, 9D1 and 9D2.

According to a further aspect of the invention, R has the structure $(L^a)_3\text{-}L^b\text{-}(L^c)$, with c being 0, and wherein $(L^a)_3\text{-}L_b$ is Preferred residues R according to this aspect of the invention are depicted in FIGS. 9B1 and 9B2.

According to a further aspect of the invention, R has the structure $(L^a)_3\text{-}L^b\text{-}(L^c)_c$ with $(L^a)_3\text{-}L_b$ being and with Z being O. In this case, c is preferably 1 and $L^c$ is preferably an alkyl group, more preferably a C3 to C6 alkyl group, more preferably a propyl group, most preferably a n-propyl group. Preferred residues R according to this aspect are depicted in FIGS. 9E1, 9F1, 9G1 and 9H1. Thus, according to one aspect of the invention, R is selected from the group consisting of the residues depicted in FIGS. 9E1, 9F1, 9G1 and 9H1

According to a further aspect of the invention, R has the structure $(L^a)_3\text{-}L^b\text{-}(L^c)_c$ with $(L^a)_3\text{-}L^b$ being and with Z being NH. In this case cis preferably 1 and $L^c$ is preferably an alkyl group, a namino acid comprising group or a group having the following structure:

In particular, in this case $L^c$ is

A preferred residue R according to this aspect of the invention is depicted in FIG. 9J1.

According to a further aspect of the invention, R has the structure $(L^a)_3\text{-}L^b\text{-}(L^c)_c$ with $(L^a)_3\text{-}L^b$ being and with Z being NH and c being 0. A preferred residue R according to this aspect of the invention is depicted in FIG. 9I1.

According to one aspect of the invention, R is $(L^a)_3$-$L^b$-$(L^c)_c$ with c=0 and wherein $(L^a)_3$-$L_b$ is Preferred residues R according to this aspect of the invention are depicted in FIGS. 9L1 and 9L2.

Thus, R is preferably selected from the residues depicted in FIG. 9A1, 9A2; 9C1, 9D2, 9D1, 9D2, 9E1, 9F1, 9G1, 9H1, 9I1, 9J1, 9L1 9L2, and mixtures thereof, such as stereoismeric mixtures of 9A1 and 9A2; of 9C1 and 9C2 or of 9D1 and 9D2, more preferably R is selected from the residues depicted in 9D1, 9D2 and a mixture thereof, more preferably R is a mixture of the residues depicted in 9D1 and 9D2, such as a mixture having a molar ratio of 9D1 to 9D2 in the range of from 10:90 to 90:10, such as in the range of from 30:70 to 70:30, such as in the range of from 45:55 to 55:45.

Thus, compound (I) is preferably selected from the compounds depicted in FIG. 10A1, 10A2; 10C1, 10C2, 10D1, 10D2, 10E1, 10F1, 10G1, 10H1, 10I1, 10J1, 10L1, 10L2 and mixtures thereof, such as stereoismeric mixtures of 10A1 and 10A2; of 10C1 and 10C2 or of 10D1 and 10D2, depicted in 10D1, 10D2, and mixtures thereof, more preferably compound (1) is a mixture of the compounds depicted in 10D1 and 10D2, such as a mixture having a molar ratio of 10D1 to 10D2 in the range of from 10:90 to 90:10, such as in the range of from 30:70 to 70:30, such as in the range of from 45:55 to 55:45.

The Linker L

In the above formula, L is a linker as defined herein, preferably L is a linker comprising or consisting of 2-10 nucleosides, such as 2-5 nucleosides, such as 2 nucleosides, wherein optionally the nucleosides are phosphodiester linked nucleosides.

As the linker L comprises between 1 and 10 linked nucleosides, such as 1, 2, 3, 4, 5, 6, 7, 8, 9 or 10 linked nucleosides, such as between 2 and 6 linked nucleosides, such as between 2 and 5 linked nucleosides, such as between 2 and 4 linked nucleosides. In some embodiments, the linker comprises two linked nucleotides. Thus, the nucleosides may be DNA nucleosides. Typically, the nucleosides are linked via phosphodiester internucleoside linkages. Moreover, the linker L may be linked to the antisense compound via a phosphodiester internucleoside linkage. Further, the linker L is linked to conjugate moiety R via a suitable function group, such as eg, via an amide, an amine, an ether, an ester, a phosphodiester (—O—P(=O)(—OH)—O—) or thiophosphodiester (—O—P(=S)(—OH)—O—) linkage. It is to be understood that L may optionally additionally comprise alkyl groups or alkyl-oxy-alkyl groups between the nucleosides and the functional group linking L to R. In this case, the nucleosides are preferably linked via a phosphodiester bond to the alkyl groups or alkyl-oxy-alkyl group which in turn is linked to R via a suitable function group, such as eg, via an amide, an amine, an ether, an ester, a phosphodiester (—O—P(=O)(—OH)—O—) or thiophosphodiester (—O—P(=S)(—OH)—O—) bond

According to a preferred embodiment L is

The Antisense (A) Oligonucleotide Residue

A is an antisense oligonucleotide residue according to the present invention, such an antisense oligonucleotide shown in Table 6, being attached via its 5'prime end to R via -$(L)_n$-(O—P(=O)(—OH)—)$_p$. Preferably, A is an antisense oligonucleotide residue selected from the residues depicted in FIGS. 1A, 2A, 3A, 4A, 5A, 6A, 7A and 8A or depicted in FIGS. 1A, 2A 3A, 4A, 5A, 6A, 7A, 8A and 8.1A.

According to a further aspect of the invention, A is the antisense oligonucleotide residue depicted in FIG. 8.1A.

Thus, compound (1) is preferably selected from the compounds depicted in FIG. 10A1, 10A2; 10C1, 10C2, 10D1, 10D2, 10E1, 10F1, 10G1, 10H1, 10I1, 10J1, 10L1 10L2, and mixtures thereof, such as stereoismeric mixtures of 10A1 and 10A2; of 10C1 and 10C2 or of 10D1 and 10D2, more preferably compound (1) is selected from the compounds depicted in 10D1 and 10D2, and a mixture thereof, more preferably compound (1) is a mixture of compound 10D1 and 10D2, preferably with A being selected from the antisense oligonucleotide shown in Table 6, preferably with A being an antisense oligonucleotide residue selected from the residues depicted in FIGS. 1A, 2A 3A, 4A, 5A, 6A, 7A and 8A, and with L is a linker comprising or consisting of 2-10 nucleosides, such as 2-5 nucleosides, such as 2 nucleosides, wherein optionally the nucleosides are phosphodiester linked nucleosides, more preferably wherein L is In a further aspect, R is a residue having the structure (I)

L is a linker as defined herein, preferably L is a linker comprising or consisting of 2-10 nucleosides, such as 2-5 nucleosides, such as 2 nucleosides, wherein optionally the nucleosides are phosphodiester linked nucleosides, more preferably L is and A is an antisense oligonucleotide according to the present invention, such an as antisense oligonucleotide shown in Table 6.

According to one aspect of the invention, A is an antisense oligonucleotide residue selected from the residues depicted in FIGS. 1A, 2A 3A, 4A, 5A, 6A, 7A and 8A or depicted in FIGS. 1A, 2A 3A, 4A, 5A, 6A, 7A 8A, and 8.1A.

According to a further aspect of the invention, A is the antisense oligonucleotide residue depicted in FIG. 8.1A.

The invention provides pharmaceutical compositions comprising the antisense oligonucleotide of the invention or the conjugate of the present invention, and a pharmaceutically acceptable diluents, carriers, salts and/or adjuvants.

The invention provides for a pharmaceutically acceptable salt of the antisense oligonucleotide of the invention or the conjugate thereof. In some embodiments, the pharmaceutically acceptable salt is selected from the group consisting of a sodium salt, a potassium salt and an ammonium salt.

The invention provides for a pharmaceutical solution of the antisense oligonucleotide of the invention or the conjugate thereof, wherein the pharmaceutical solution comprises the antisense oligonucleotide of the invention or the conjugate thereof and a pharmaceutically acceptable solvent, such as phosphate buffered saline. Alternative, the solvent is water or a sodium chloride solution.

The invention provides for the antisense oligonucleotide of the invention or the conjugate thereof in solid powdered form, such as in the form of a lyophilized powder.

The invention provides for a pharmaceutically acceptable salt of the antisense oligonucleotide of the invention or the conjugate thereof.

The invention provides for a pharmaceutically acceptable salt of the antisense oligonucleotide according to the invention, or the conjugate of the invention, wherein the pharmaceutically acceptable salt is a sodium salt. Alternatively, the salt is a potassium salt.

The invention provides for a pharmaceutical composition comprising the antisense oligonucleotide of the invention, or the conjugate of the invention, or the salt of the invention and a pharmaceutically acceptable diluent, solvent, carrier, salt and/or adjuvant.

The invention provides for a method for inhibiting FUBP1 expression in a target cell, which is expressing FUBP1, said method comprising administering an antisense oligonucleotide of the invention, or the conjugate of the invention, or the salt of the invention, or the composition of the invention in an effective amount to said cell. The method may be an in vivo method or an in vitro method.

The invention provides for a method for treating and/or preventing an HBV infection in a subject such as a human, comprising administering a therapeutically or prophylactically effective amount of an antisense oligonucleotide of the invention, or the conjugate of the invention, or the salt of the invention, or the composition of the invention, such as to treat and/or prevent a disease selected from the group consisting of HBV infection, such as chronic HBV infection and proliferative diseases such as cancer, in particular hepatocellular carcinoma.

In some embodiments, the antisense oligonucleotide of the invention, or the conjugate of the invention, or the salt of the invention, or the pharmaceutical composition of the invention, is for the use in the treatment and/or prevention of an HBV infection, such as a chronic HBV infection.

The invention provides the antisense oligonucleotide of the invention, or the conjugate of the invention, or the pharmaceutical composition, or the salt of the invention for use in medicine. In a further aspect, the invention provides methods for inhibition of FUBP1 expression in a target cell, which is expressing FUBP1, by administering an antisense oligonucleotide of the invention, or conjugate of the invention in an effective amount to said cell. In a further aspect, the invention provides methods for in vivo or in vitro method for inhibition of FUBP1 expression in a target cell, which is expressing FUBP1, by administering an antisense oligonucleotide, or the conjugate of the invention in an effective amount to said cell. The cell may for example be a human cell, such as a liver cell, such as a hepatocyte. In one embodiment, the cell is a hepatocellular carcinoma cell.

In a further aspect, the invention provides methods for reducing cccDNA in an HBV infected cell, by administering an antisense oligonucleotide of the invention, or conjugate of the invention in an effective amount to said cell.

In a further aspect, the invention provides methods for in vivo or in vitro method for reducing cccDNA in an HBV infected cell, by administering an antisense oligonucleotide of the invention, or the conjugate of the invention in an effective amount to said cell.

In a further aspect, the invention provides methods for treating and/or preventing a disease selected from the group consisting of HBV infection, such as chronic HBV infection and proliferative diseases such as cancer, in particular hepatocellular carcinoma.

In a further aspect, the invention provides the antisense oligonucleotide, or the conjugate of the invention, or the pharmaceutical composition of the invention, for use in the manufacture of a medicament for the treatment and/or prevention of a disease selected from the group consisting of HBV infection, such as chronic HBV infection and proliferative diseases such as cancer, in particular hepatocellular carcinoma.

in a further aspect, the invention provides the antisense oligonucleotide, or the conjugate of the invention, or the pharmaceutical composition of the invention, for use in the manufacture of an anti drug.

In a further aspect, the invention provides the antisense oligonucleotide, or the conjugate of the invention, or the pharmaceutical composition of the invention, for use in the manufacture of an antitumor drug.

The invention provides for the antisense oligonucleotide of the invention, or the conjugate of the invention, or the pharmaceutical composition of the invention, for use in the treatment and/or prevention of a disease selected from the group consisting of HBV infection, such as chronic HBV infection and proliferative diseases such as cancer, in particular hepatocellular carcinoma.

SEQUENCE LISTING

The content of the sequence listing submitted electronically herewith (Name: P36078-WO-FUBP1-sequence-listing-ST25.txt: Size: 144.377 bytes; and Date of Creation: Jun. 25, 2021) is hereby incorporated by reference. In the event of a discrepancy between the sequence listing and the specification or figures, the information disclosed in the specification (including the figures) shall be deemed to be correct.

BRIEF DESCRIPTION OF FIGURES

Figure 1:
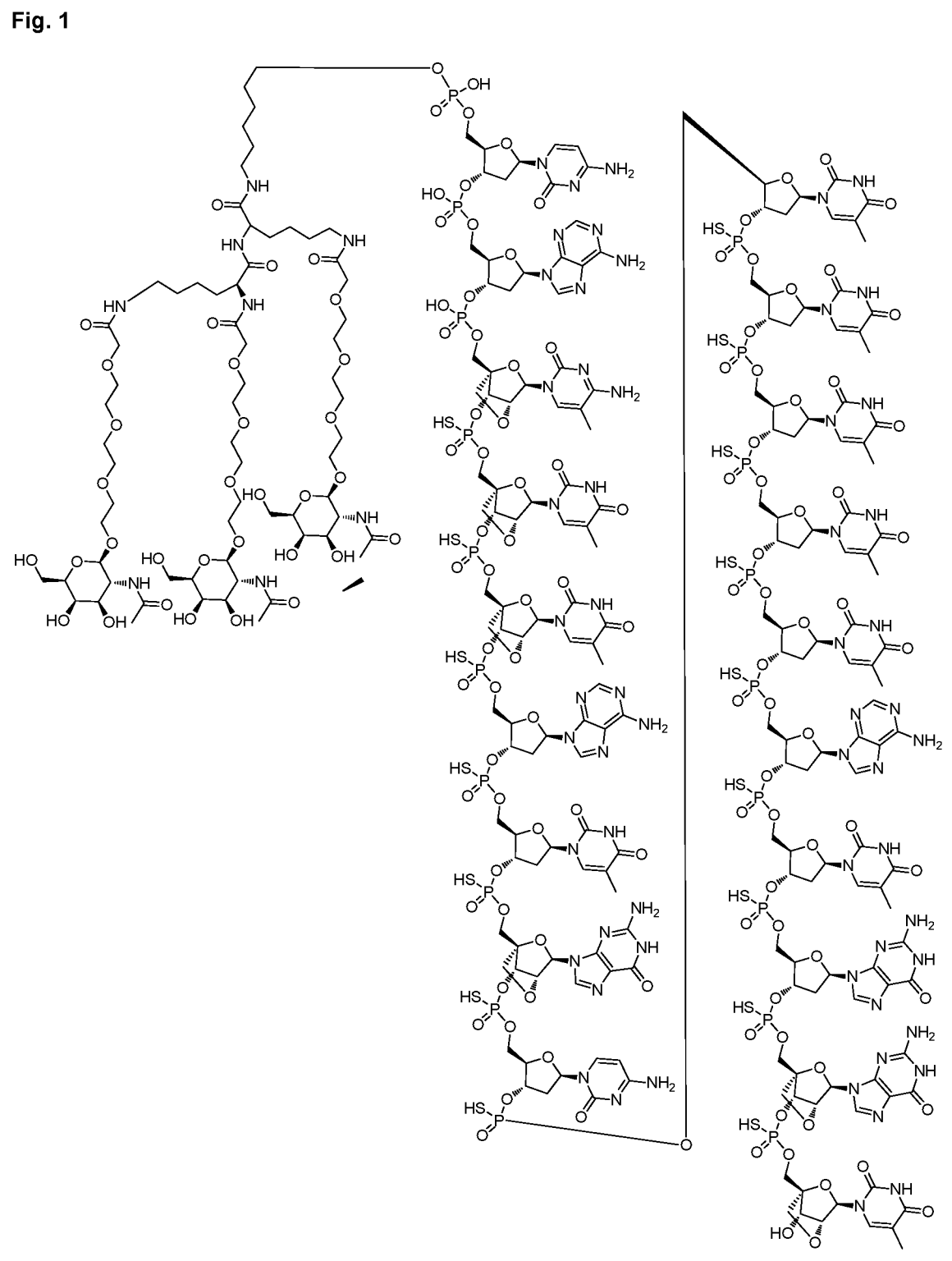
Figure 1A:
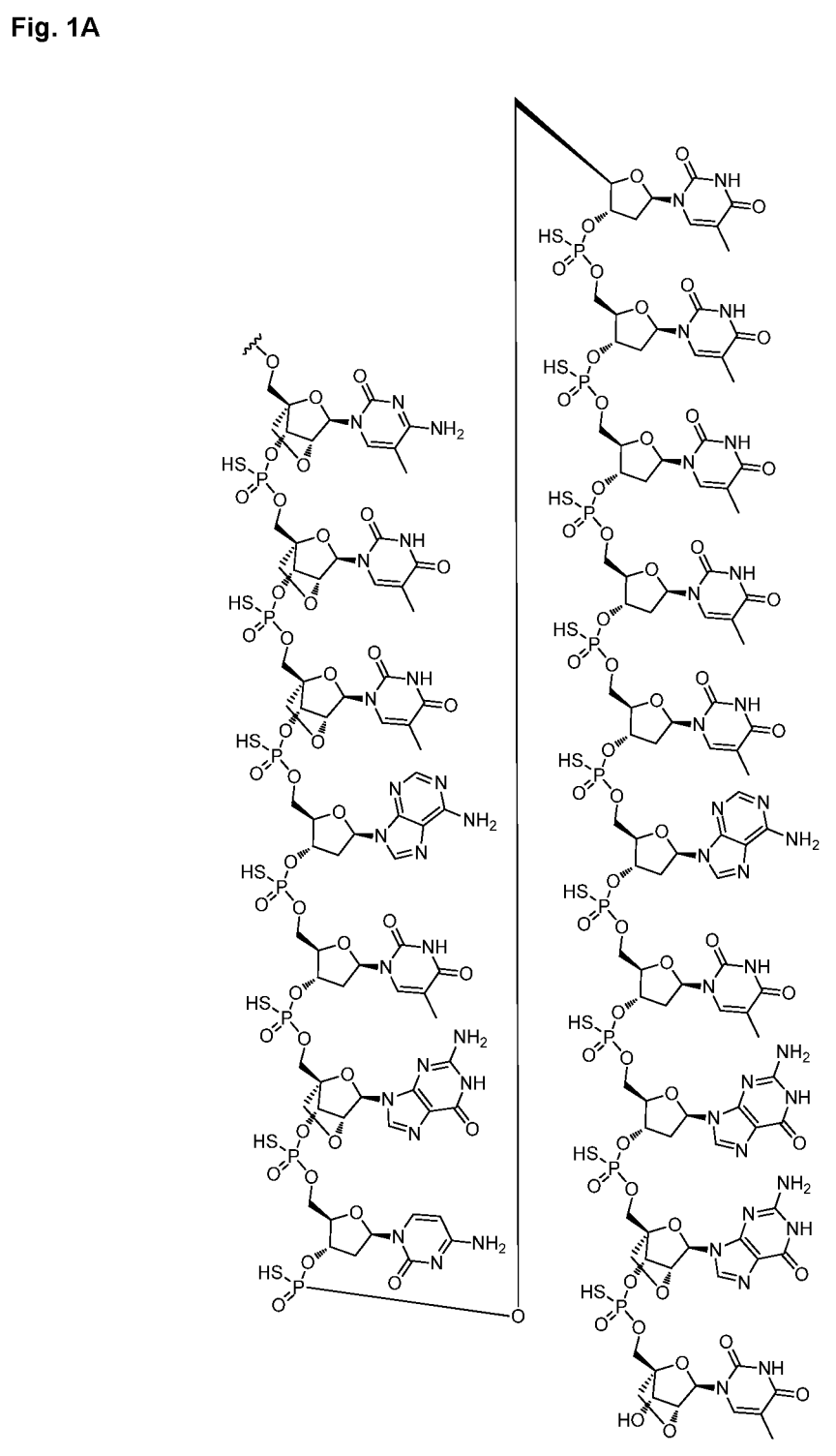

FIG. 1 Compound 6_1 (SEQ ID NO: 6) conjugated to a GalNAc moiety via a phosphodiester linked DNA dinucleotide FIG. 1A Residue A of Compound 6_1 (SEQ ID NO: 6)

FIG. 2 Compound 6_2 (SEQ ID NO: 6) conjugated to a GalNAc moiety via a phosphodiester linked DNA dinucleotide FIG. 2A Residue A of Compound 6_2 (SEQ ID NO: 6)

FIG. 3 Compound 7_1 (SEQ ID NO: 7) conjugated to a GalNAc moiety via a phosphodiester linked DNA dinucleotide FIG. 3A Residue A of Compound 7_1 (SEQ ID NO: 7)

Figure 4:
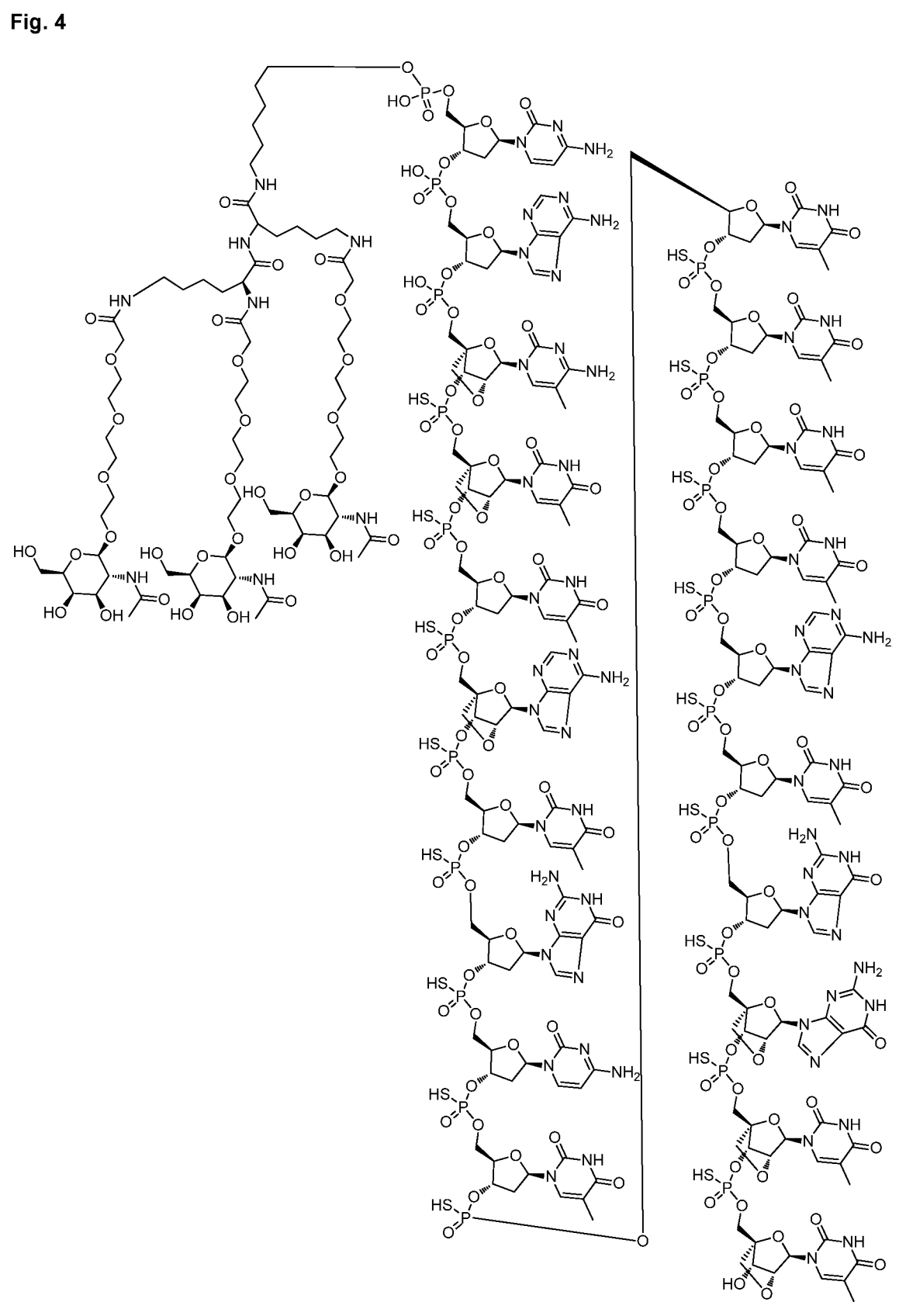
Figure 4A:
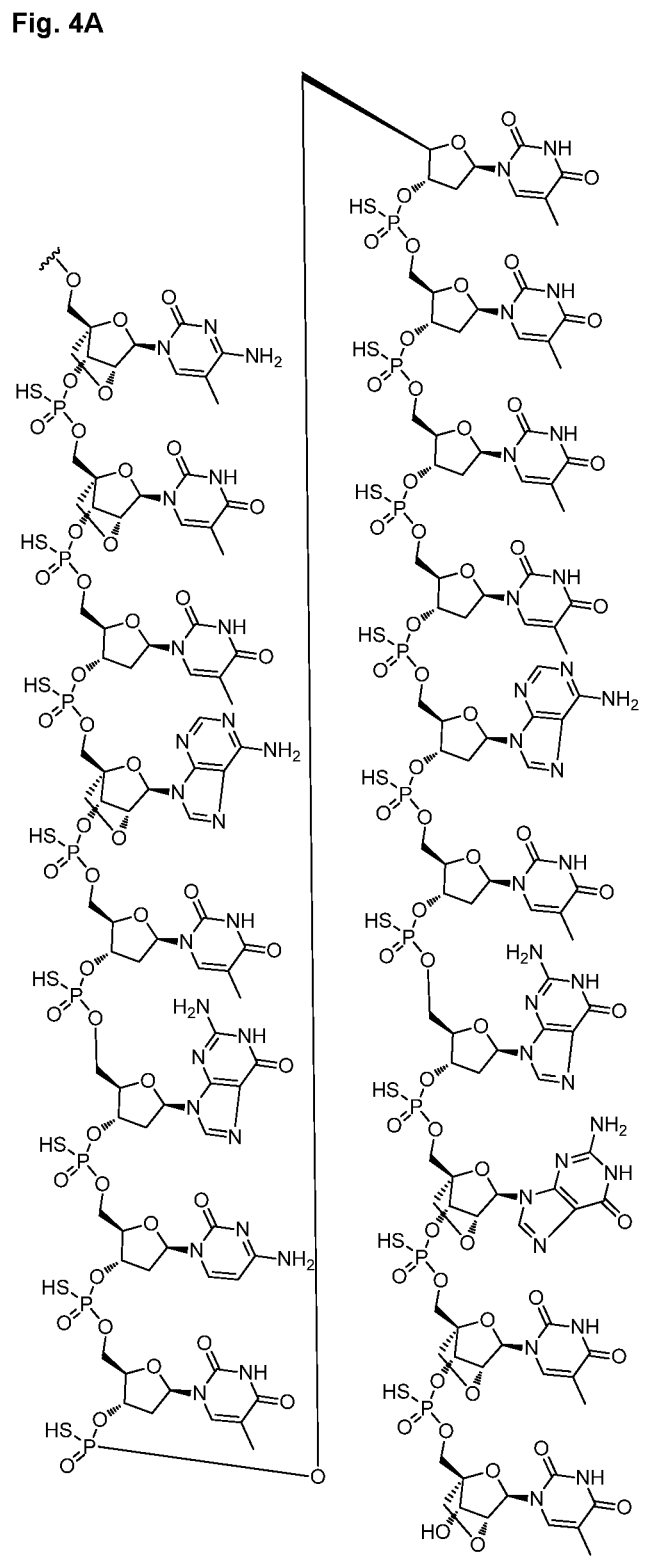

FIG. 4 Compound 7_2 (SEQ ID NO: 7) conjugated to a GalNAc moiety via a phosphodiester linked DNA dinucleotide FIG. 4A Residue A of Compound 7_2 (SEQ ID NO: 7)

FIG. 5 Compound 7_3 (SEQ ID NO: 7) conjugated to a GalNAc moiety via a phosphodiester linked DNA dinucleotide FIG. 5A Residue of Compound 7_3 (SEQ ID NO: 7)

FIG. 6 Compound 7_4 (SEQ ID NO: 7) conjugated to a GalNAc moiety via a phosphodiester linked DNA dinucleotide FIG. 6A Residue A of Compound 7_4 (SEQ ID NO:

FIG. 7 Compound 8_1 (SEQ ID NO: 8) conjugated to a GalNAc moiety via a phosphodiester linked DNA dinucleotide FIG. 7A Residue A of Compound (SEQ ID NO: 8)

FIG. 8 Compound 9_1 (SEQ ID NO: 9) conjugated to a GalNAc moiety via a phosphodiester linked DNA dinucleotide FIG. 8A Residue A of Compound 9_1 (SEQ ID NO: 9)

FIG. 8.1 Compound 18_1 (SEQ ID NO: 18) conjugated to a GalNAc moiety via a phosphodiester linked DNA dinucleotide FIG. 8.1A Residue A of Compound 18_1 (SEQ ID NO: 18)

FIGS. 9A1-L2 FIG. 9 illustrates exemplary GalNAc moieties. The compound in FIG. 9L is composed of monomeric GalNAc phosphoramidites added to the oligonucleotide while still on the solid support as part of the synthesis, X is S or O. Y is S or O, and n=1-3 (see WO 2017/178656). FIG. 9B and FIG. 9D are also termed GalNAc2 or GN2 herein, without and with C8 linker respectively.

Figure 10:
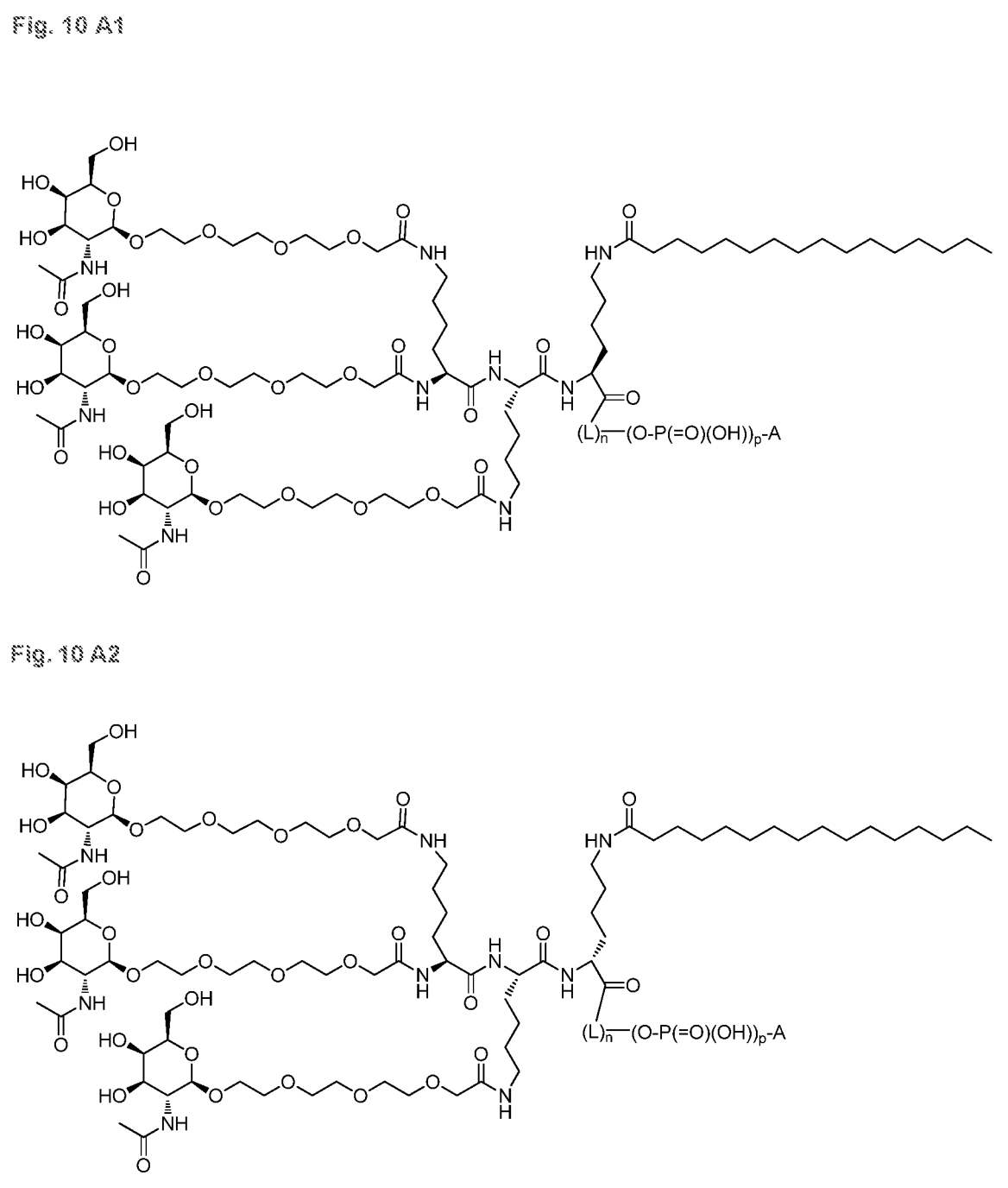
Figure 10:
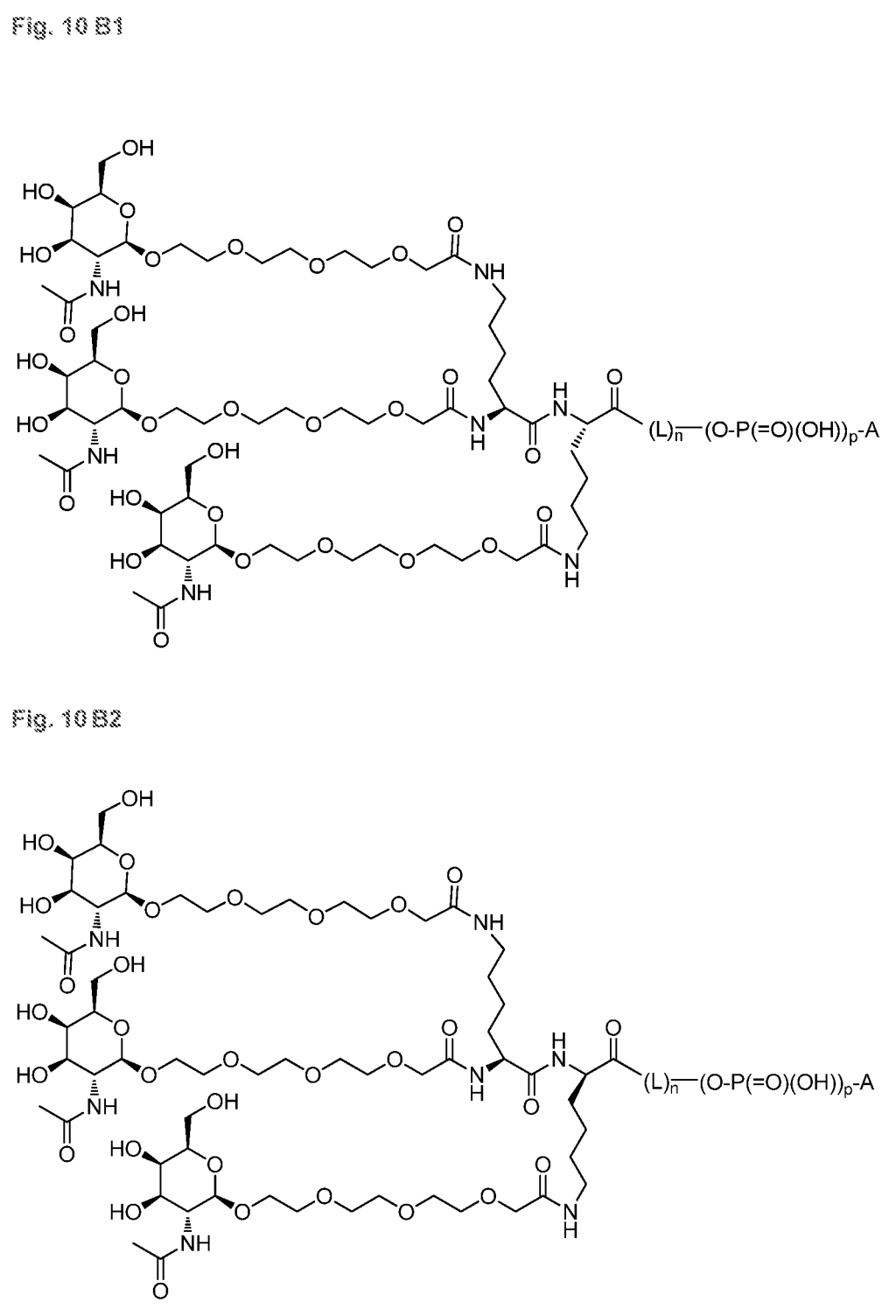
Figure 10:
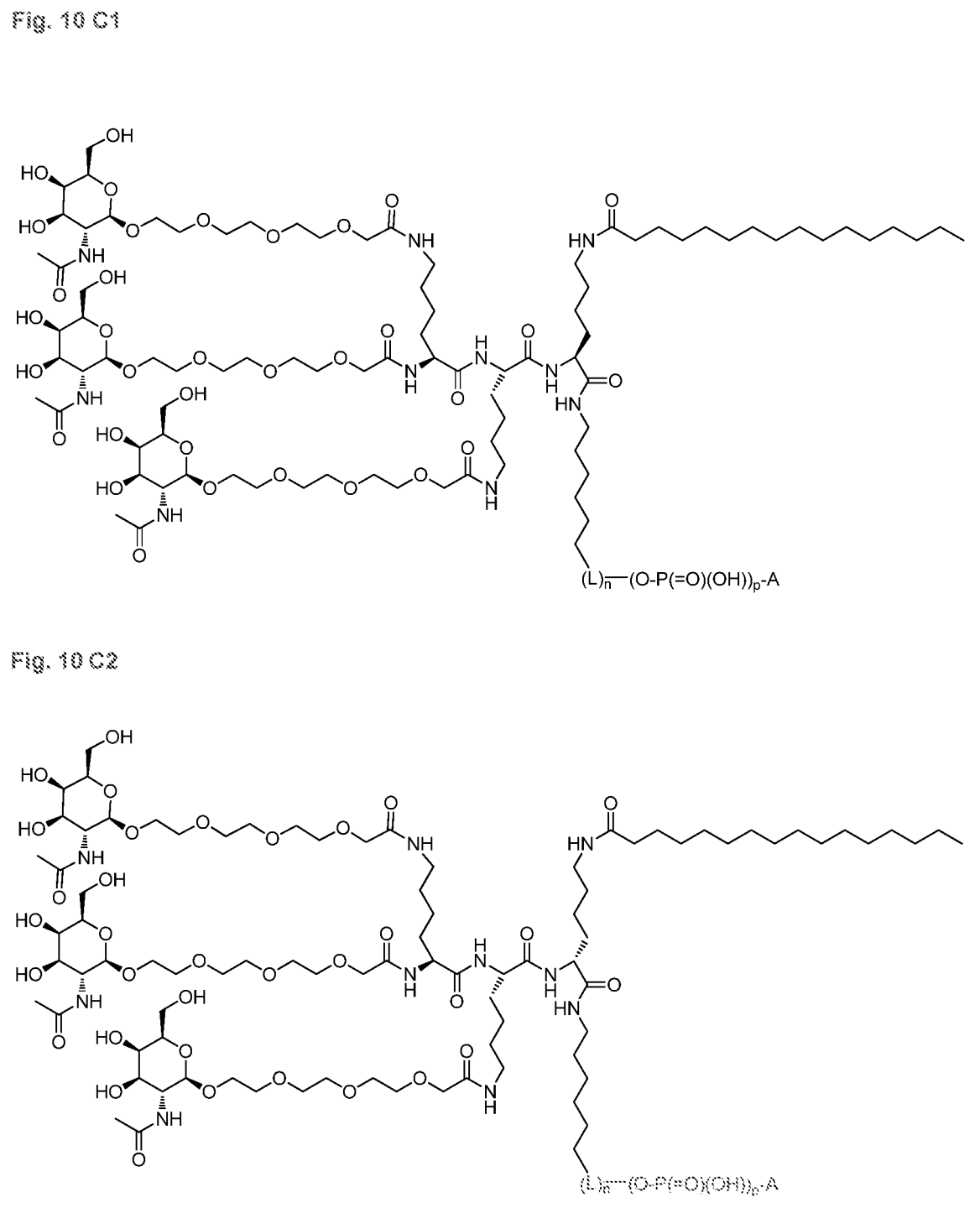
Figure 10:
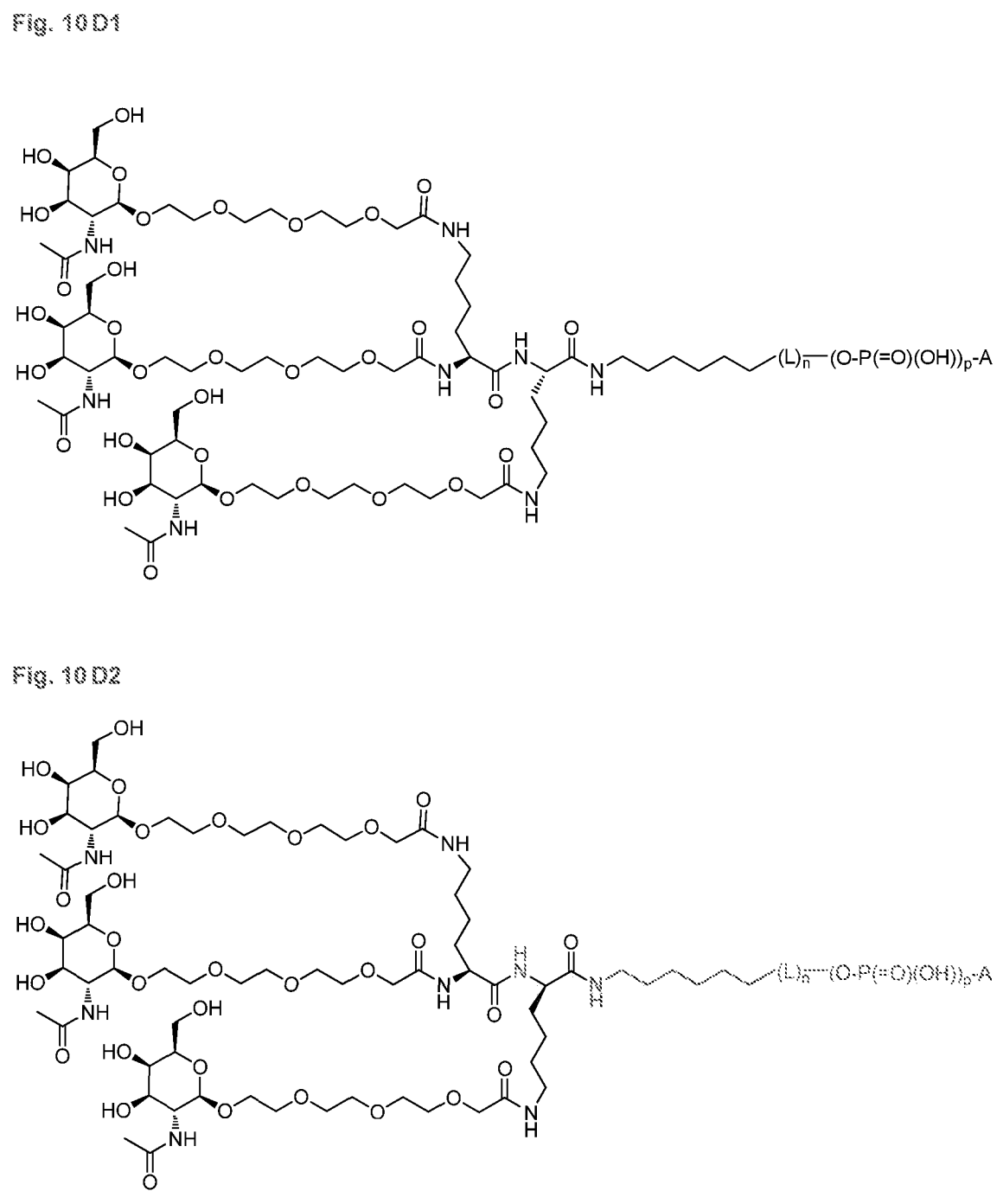
Figures 10E1, 10F1:
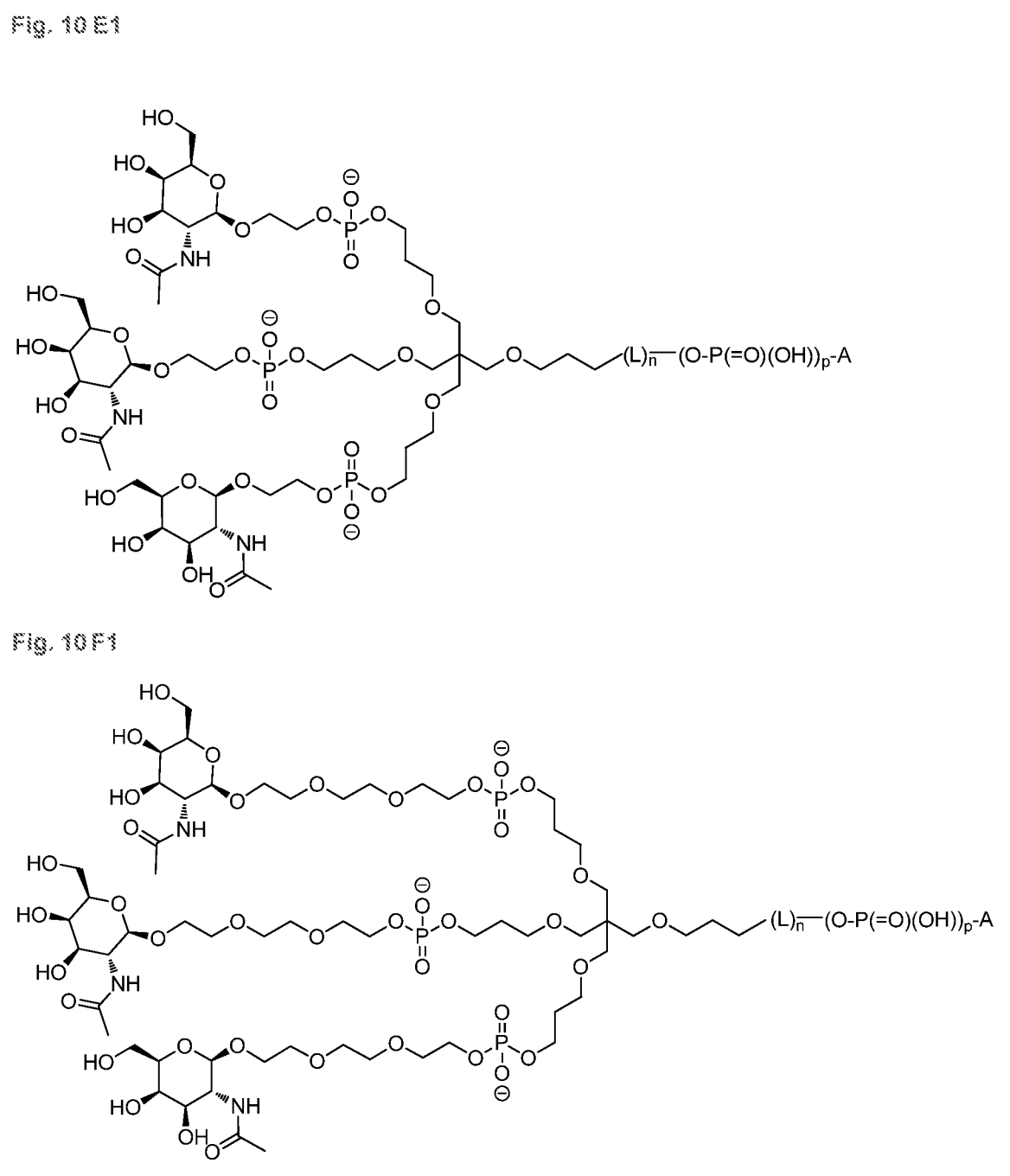
Figure 10:
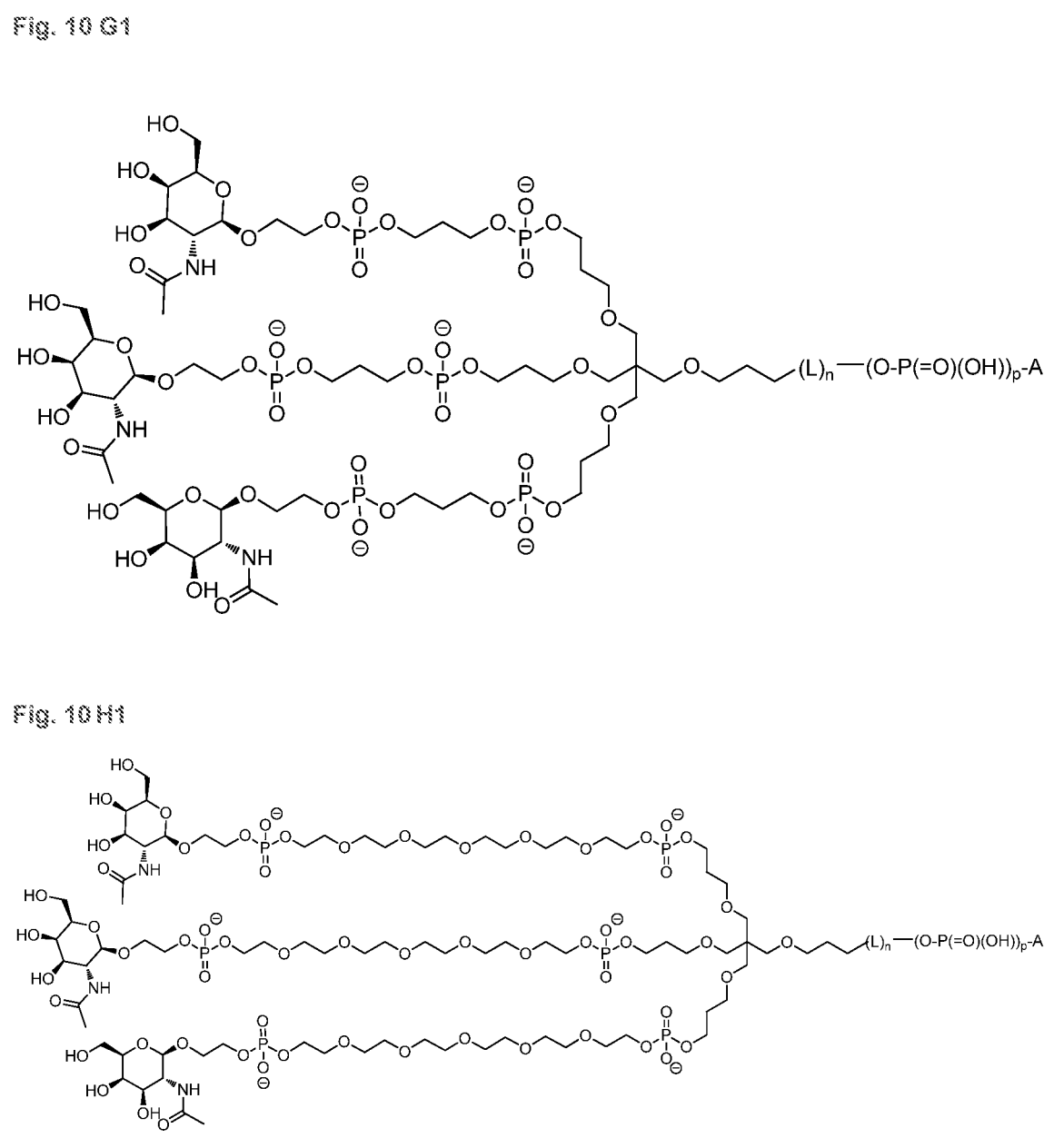
Figure 10:
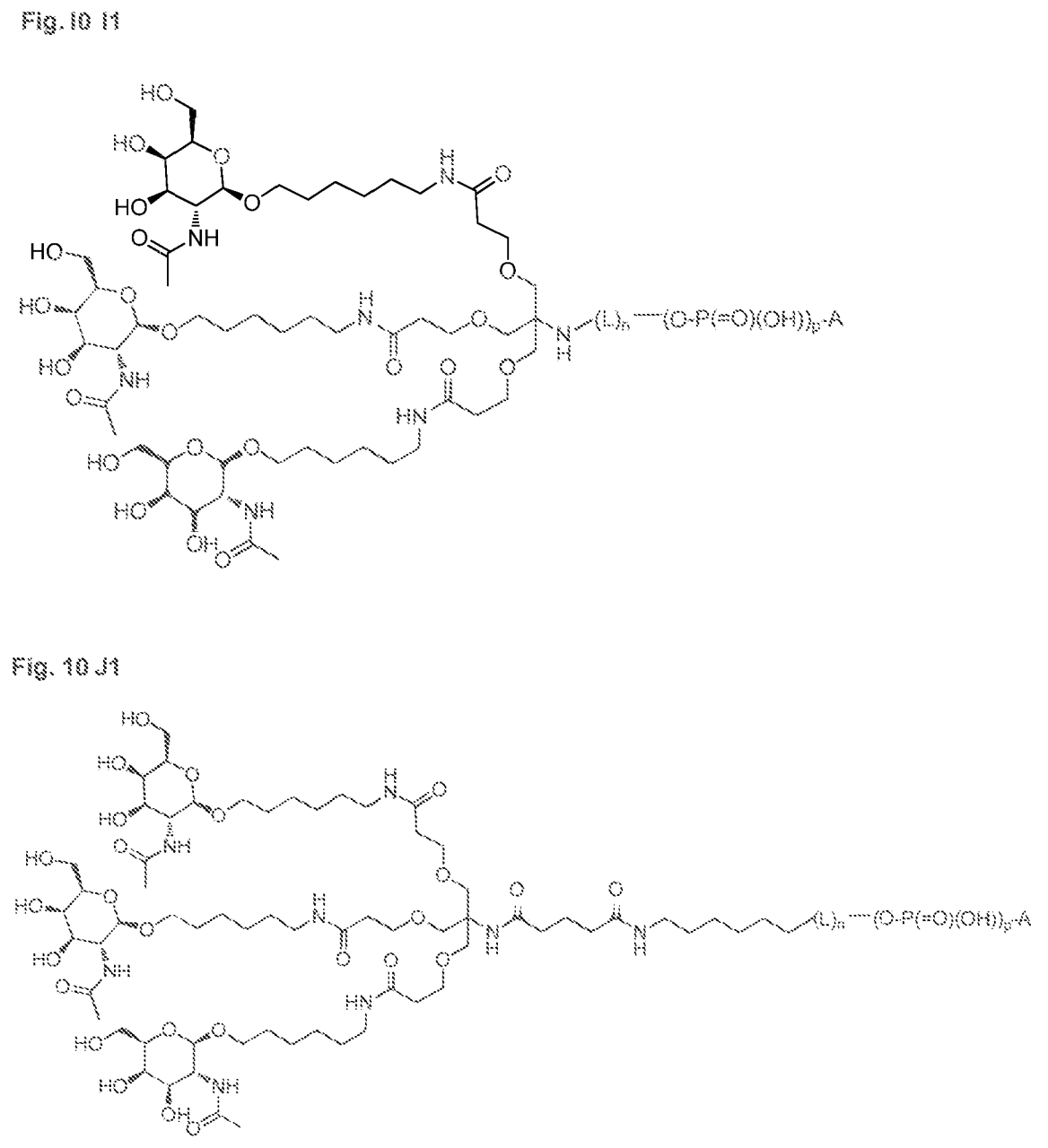
Figure 10:
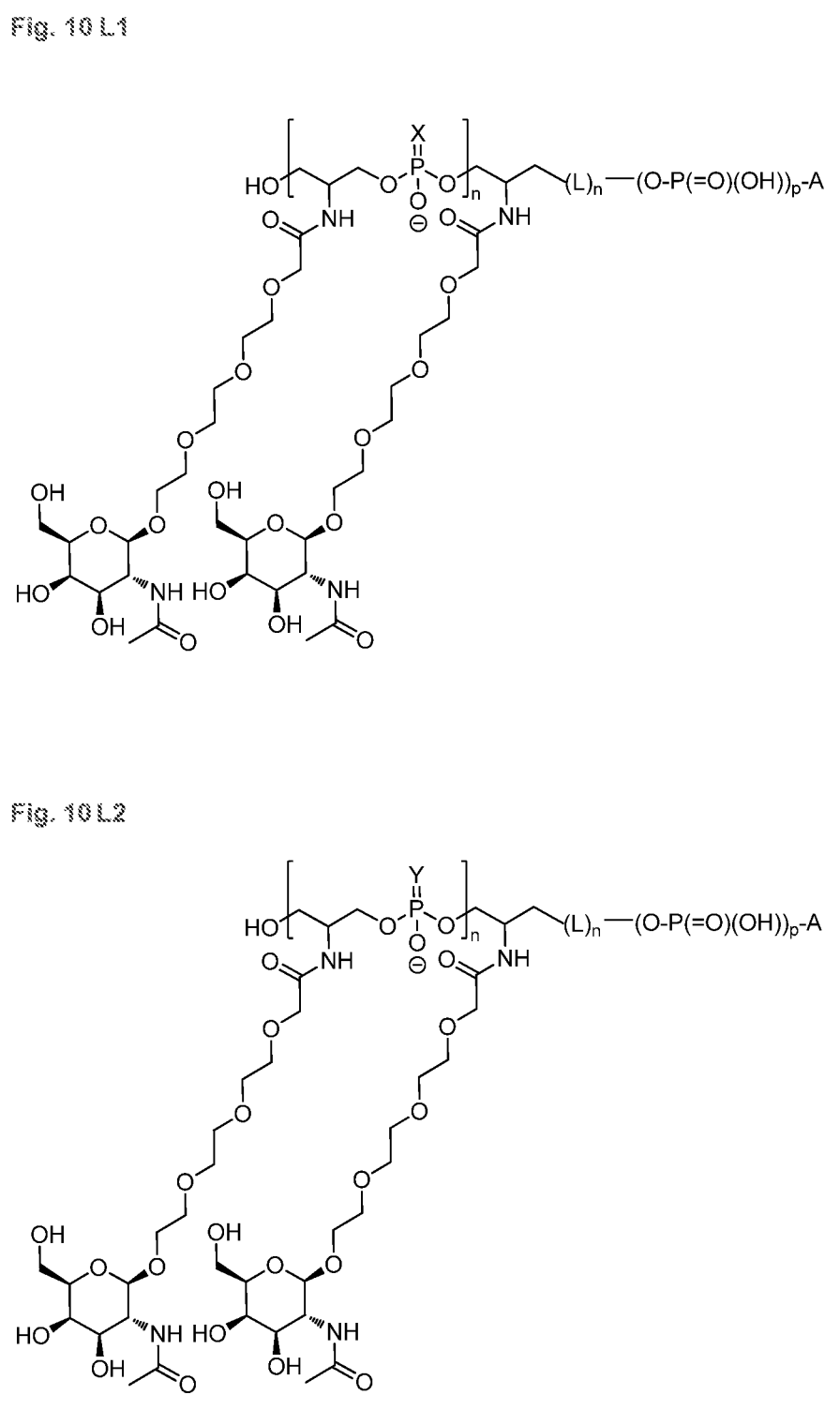

FIGS. 10A1-L2 FIG. 10 illustrates exemplary antisense oligonucleotide conjugates. Compounds in FIG. 10A-D comprise a di-lysine brancher molecule, a PEG3 spacer and three terminal GalNAc carbohydrate moieties. In the compounds in FIG. 10A and FIG. 10B the oligonucleotide is typically attached directly to the asialoglycoprotein receptor-targeting conjugate moiety without a linker. In the compounds in FIG. 10C and FIG. 10D the oligonucleotide is attached to the asialoglycoprotein receptor-targeting conjugate moiety via a C6 linker. The compounds in FIG. 10E-J comprise a commercially available trebler brancher molecule and spacers of varying length and structure and three terminal GalNAc carbohydrate moieties. The compound in FIG. 10L is composed of monomeric GalNAc phosphoramidites added to the oligonucleotide while still on the solid support as part of the synthesis. X=S or O. Y is S or O. and n=1-3 (see WO 2017/178656).

FIG. 11 FIG. 11 illustrates the results of an analysis of the in vitro efficacy of anti-FUBP1 compounds in Hela cells. FUBP1 mRNA levels are normalized and shown as % of control.

DEFINITIONS

HBV Infection

Figure 12:
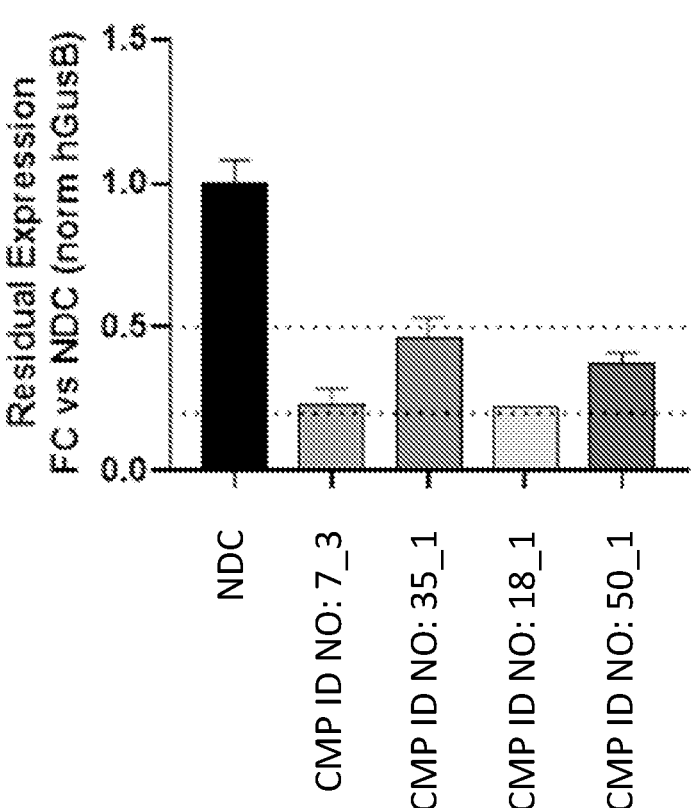
FIG. 12 Target engagement: FUBP1 mRNA. As described in Example 3, four antisense oligonucleotide compounds have been tested in HBV infected PHH cells. Each compound has been delivered to cells at a concentration of 10 μM once per week for three weeks. FUBP1 mRNA target KD has been evaluated one week after the last treatment. Total RNA has been extracted from cells using a MagNA Pure robot and the MagNA Pure 96 Cellular RNA Large Volume Kit according to the manufacturer's protocol and FUBP1 mRNA quantified by TaqMan qPCR. The figure shows the residual expression of the Target mRNA compared to negative control (NDC=1) with oligos tested at 10 μM. Data are normalized to the human GUS B reference gene and the mean+SD from two biological replicates are reported for each oligo tested. FC of 50% and 20% are highlighted on the graph. CMP ID NO: 7_3 shows the best FUBP1 mRNA KD with 80% reduction mRNA expression respectively at 10 μM. CMP ID NO: 18_1 shows the strongest effect in reducing FUBP1 mRNA compared to the prior art oligos (CMP ID Nos: 35_1 and 50_1), equally to the oligonucleotide with CMP ID NO: 7_3. They both reduce target mRNA expression at 10 µM by about 80% compared to the NDC (see Example 3 in more detail).

The term "hepatitis B virus infection" or "HBV infection" is commonly known in the art and refers to an infectious disease that is caused by the hepatitis B virus (HBV) and affects the liver. A HBV infection can be an acute or a chronic infection. Chronic hepatitis B virus (CHB) infection is a global disease burden affecting 248 million individuals worldwide. Approximately 686,000 deaths annually are attributed to HBV-related end-stage liver diseases and hepatocellular carcinoma (HCC) (GBD 2013; Schweitzer et al., 2015). WHO projected that without expanded intervention, the number of people living with CHB infection will remain at the current high levels for the next 40-50 years, with a cumulative 20 million deaths occurring between 2015 and 2030 (WHO 2016). CHB infection is not a homogenous disease with singular clinical presentation. Infected individuals have progressed through several phases of CHB-associated liver disease in their life; these phases of disease are also the basis for treatment with standard of care (SOC). Current guidelines recommend treating only selected CHB-infected individuals based on three criteria—serum ALT level, HBV DNA level, and severity of fiver disease (EASL, 2017). This recommendation was due to the fact that SOC i.e. nucleos(t)ide analogs (NAs) and pegylated interferon-alpha (PEG-IFN), are not curative and must be administered for long periods of time thereby increasing their safety risks. NAs effectively suppress HBV DNA replication; however, they have very limited/no effect on other viral markers. Two hallmarks of HBV infection, hepatitis B surface antigen (HBsAg) and covalently closed circular DNA (cccDNA), are the main targets of novel drugs aiming for HBV cure. In the plasma of CHB individuals, HBsAg subviral (empty) particles outnumber HBV virions by a factor of 103 to 105 (Ganem & Prince, 2014); its excess is believed to contribute to immunopathogenesis of the disease, including inability of individuals to develop neutralizing anti-HBs antibody, the serological marker observed following resolution of acute HBV infection.

In some embodiments, the term "HBV infection" refers to "chronic HBV infection".

Further, the term encompasses infection with any HBV genotype.

In some embodiments, the patient to be treated is infected with HBV genotype A.

In some embodiments, the patient to be treated is infected with HBV genotype B.

In some embodiments, the patient to be treated is infected with HBV genotype C (which was tested in the Examples section, Example 3)

In some embodiments, the patient to be treated is infected with HBV genotype D.

In some embodiments; the patient to be treated is infected with HBV genotype E.

In some embodiments, the patient to be treated is infected with HBV genotype F.

In some embodiments, the patient to be treated is infected with HBV genotype G.

In some embodiments, the patient to be treated is infected with HBV genotype H.

In some embodiments, the patient to be treated is infected with HBV genotype I.

In some embodiments, the patient to be treated is infected with HBV genotype J.

cccDNA (Covalently Closed Circular DNA)

cccDNA is the viral genetic template that resides in the nucleus of infected hepatocytes, where it gives rise to all HBV RNA transcripts needed for productive infection and is responsible for viral persistence during natural course of chronic HBV infection (Locarnini & Zoulim, 2010 Antivir Ther. 15 Supp 3:3-14. doi: 10.3851/IMP1619). Acting as a viral reservoir, cccDNA is the source of viral rebound after cessation of treatment, necessitating long term, often, life-time treatment. PEG-IFN can only be administered to a small subset of CHB due to its various side effects.

Consequently, novel therapies that can deliver a complete cure, defined by degradation or elimination of HBV cccDNA, to the majority of CHB patients are highly needed.

Compound

Herein, the term "compound" means any molecule capable of inhibition FUBP1 expression or activity. Particular compounds of the invention are nucleic acid molecules, such as antisense oligonucleotides according to the invention or any conjugate comprising such a nucleic acid molecule. For example, herein the compound may be a nucleic acid molecule targeting FUBP1, in particular an antisense oligonucleotide.

Oligonucleotide

The term "oligonucleotide" as used herein is defined as it is generally understood by the skilled person as a molecule comprising two or more covalently linked nucleosides. Such covalently bound nucleosides may also be referred to as nucleic acid molecules or oligomers. Oligonucleotides are commonly made in the laboratory by solid-phase chemical synthesis followed by purification and isolation. When referring to a sequence of the oligonucleotide, reference is made to the sequence or order of nucleobase moieties, or modifications thereof, of the covalently linked nucleotides or nucleosides. The oligonucleotide of the invention is man-made, and is chemically synthesized, and is typically purified or isolated. The oligonucleotide of the invention may comprise one or more modified nucleosides such as 2' sugar modified nucleosides. The oligonucleotide of the invention may comprise one or more modified internucleoside linkages, such as one or more phosphorothioate internucleoside linkages.

Antisense Oligonucleotides

The term "antisense oligonucleotide" or "ASO" as used herein is defined as oligonucleotides capable of modulating expression of a target gene by hybridizing to a target nucleic acid, in particular to a contiguous sequence on a target nucleic acid. Antisense oligonucleotides are not essentially double stranded and are therefore not siRNAs or shRNAs. Preferably, the antisense oligonucleotides of the present invention are single stranded. It is understood that single stranded oligonucleotides of the present invention can form hairpins or intermolecular duplex structures (duplex between two molecules of the same oligonucleotide), as long as the degree of intra or inter self-complementarity is less than 50% across of the full length of the oligonucleotide.

In some embodiments, the single stranded antisense oligonucleotide of the invention may not contain RNA nucleosides.

Advantageously, the antisense oligonucleotide of the invention comprises one or more modified nucleosides or nucleotides, such as 2' sugar modified nucleosides. Furthermore, it is advantageous that the nucleosides which are not modified are DNA nucleosides.

Contiguous Nucleotide Sequence

The term "contiguous nucleotide sequence" refers to the region of the oligonucleotide, which is complementary to the target nucleic acid. The term is used interchangeably herein with the term "contiguous nucleobase sequence" and the term "oligonucleotide motif sequence". In some embodiments, all the nucleosides of the oligonucleotide constitute the contiguous nucleotide sequence. In some embodiments the oligonucleotide comprises the contiguous nucleotide sequence, such as a F-G-F' gapmer region, and may optionally comprise further nucleotide(s), for example a nucleotide linker region which may be used to attach a functional group (e.g. a conjugate group) to the contiguous nucleotide sequence. The nucleotide linker region may or may not be complementary to the target nucleic acid. In some embodiments, the nucleobase sequence of the antisense oligonucleotide is the contiguous nucleotide sequence.

Nucleotides and Nucleosides

Nucleotides and nucleosides are the building blocks of oligonucleotides and polynucleotides, and for the purposes of the present invention include both naturally occurring and non-naturally occurring nucleotides and nucleosides. In nature, nucleotides, such as DNA and RNA nucleotides comprise a ribose sugar moiety, a nucleobase moiety and one or more phosphate groups (which is absent in nucleosides). Nucleosides and nucleotides may also interchangeably be referred to as "units" or "monomers".

Modified Nucleoside

The term "modified nucleoside" or "nucleoside modification" as used herein refers to nucleosides modified as compared to the equivalent DNA or RNA nucleoside by the introduction of one or more modifications of the sugar moiety or the (nucleo)base moiety. Advantageously, one or more of the modified nucleosides of the antisense oligonucleotide of the invention comprise a modified sugar moiety. The term "modified nucleoside" may also be used herein interchangeably with the term "nucleoside analogue" or modified "units" or modified "monomers". Nucleosides with an unmodified DNA or RNA sugar moiety are termed DNA or RNA nucleosides herein. Nucleosides with modifications in the base region of the DNA or RNA nucleoside are still generally termed DNA or RNA if they allow Watson Crick base pairing.

Modified Internucleoside Linkage

The term "modified internucleoside linkage" is defined as generally understood by the skilled person as linkages other than phosphodiester (PO) linkages, that covalently couples two nucleosides together. The oligonucleotides of the invention may therefore comprise one or more modified internucleoside linkages such as a one or more phosphorothioate internucleoside linkages, or one or more phosphorodithioate internucleoside linkages.

In some embodiments at least 50% of the internucleoside linkages in the oligonucleotide, or contiguous nucleotide sequence thereof, are phosphorothioate, such as at least 60%, such as at least 70%, such as at least 75%, such as at least 80% or such as at least 90% of the internucleoside linkages in the oligonucleotide, or contiguous nucleotide sequence thereof, are phosphorothioate. In some embodiments all of the internucleoside linkages of the oligonucleotide, or contiguous nucleotide sequence thereof, are phosphorothioate.

In some advantageous embodiments, all the internucleoside linkages of the contiguous nucleotide sequence of the oligonucleotide are phosphorothioate, or all the internucleoside linkages of the oligonucleotide are phosphorothioate linkages.

Phosphorothioate linkages may exist in different tautomeric forms, for example as illustrated below:

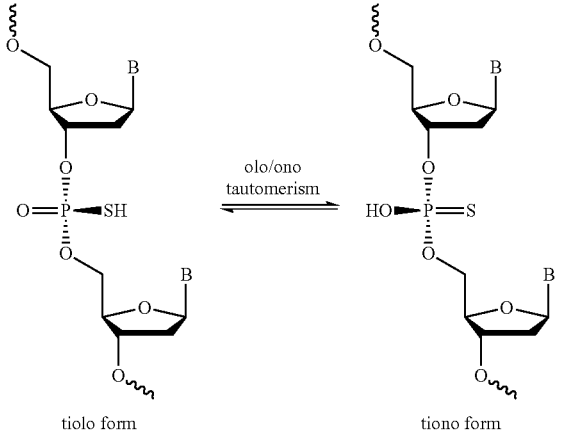

olo/ono tautomerism tiolo form                              tiono form

It is recognized that, as disclosed in EP 2742135, antisense oligonucleotides may comprise other internucleoside linkages (other than phosphodiester, phosphorothioate and phosphorodithioate), for example alkyl phosphonate/methyl phosphonate internucleoside, which according to EP 2742135 may for example be tolerated in an otherwise DNA phosphorothioate the gap region.

Nucleobase

The term nucleobase includes the purine (e.g. adenine and adenine) and pyrimidine (e.g. urea, thymine and cytosine) moiety present in nucleosides and nucleotides, which form hydrogen bonds in nucleic acid hybridization. In the context of the present invention the term nucleobase also encompasses modified nucleobases which may differ from naturally occurring nucleobases, but are functional during nucleic acid hybridization. In this context "nucleobase" refers to both naturally occurring nucleobases such as adenine, guanine, cytosine, thymidine, uracil, xanthine and hypoxanthine, as well as non-naturally occurring variants. Such variants are for example described in Hirao et al (2012) Accounts of Chemical Research vol 45 page 2055 and Bergstrom (2009) Current Protocols in Nucleic Acid Chemistry Suppl. 371.4.1.

In some embodiments, the nucleobase moiety is modified by changing the purine or pyrimidine into a modified purine or pyrimidine, such as substituted purine or substituted pyrimidine, such as a nucleobased selected from isocytosine, pseudoisocytosine, 5-methyl cytosine, 5-thiozolo-cytosine, 5-propynyl-cytosine, 5-propynyl-uracil, 5-bromouracil 5-thiazolo-uracil, 2-thio-uracil, 2'thio-thymine, inosine, diaminopurine, 6-aminopurine, 2-aminopurine, 2,6-diaminopurine and 2-chloro-6-aminopurine.

The nucleobase moieties may be indicated by the letter code for each corresponding nucleobase, e.g. A, T, G, C or U, wherein each letter may optionally include modified nucleobases of equivalent function. For example, in the exemplified oligonucleotides, the nucleobase moieties are selected from A, T, G, C, and 5-methyl cytosine. Optionally, for LNA gapmers, 5-methyl cytosine LNA nucleosides may be used.

Modified Oligonucleotide

The term "modified oligonucleotide" describes an oligonucleotide comprising one or more sugar-modified nucleosides and/or modified internucleoside linkages. The term "chimeric oligonucleotide" is a term that has been used in the literature to describe oligonucleotides comprising sugar modified nucleosides and DNA nucleosides. The antisense oligonucleotide of the invention is advantageously a chimeric oligonucleotide.

Complementarity

The term "complementarity" describes the capacity for Watson-Crick base-pairing of nucleosides/nucleotides. Watson-Crick base pairs are guanine (G)-cytosine (C) and adenine (A) thymine (T)/uracil (U). It will be understood that oligonucleotides may comprise nucleosides with modified nucleobases, for example 5-methyl cytosine is often used in place of cytosine, and as such the term complementarity encompasses Watson Crick base-paring between non-modified and modified nucleobases (see for example Hirao et al (2012) Accounts of Chemical Research vol 45 page 2055 and Bergstrom (2009) Current Protocols in Nucleic Acid Chemistry Suppl. 371.4.1).

The term "% complementary" as used herein, refers to the proportion of nucleotides (in percent) of a contiguous nucleotide sequence in a nucleic acid molecule (e.g. oligonucleotide) which across the contiguous nucleotide sequence, are complementary to a reference sequence (e.g. a target sequence or sequence motif). The percentage of complementarity is thus calculated by counting the number of aligned nucleobases that are complementary (from Watson Crick base pair) between the two sequences (when aligned with the target sequence 5'-3' and the oligonucleotide sequence from 3'-5'), dividing that number by the total number of nucleotides in the oligonucleotide and multiplying by 100. In such a comparison a nucleobase/nucleotide which does not align (form a base pair) is termed a mismatch. Insertions and deletions are not allowed in the calculation of % complementarity of a contiguous nucleotide sequence. It will be understood that in determining complementarity, chemical modifications of the nucleobases are disregarded as long as the functional capacity of the nucleobase to form Watson Crick base pairing is retained (e.g. 5'-methyl cytosine is considered identical to a cytosine for the purpose of calculating % identity).

The term "fully complementary", refers to 100% complementarity,

Identity

The term "Identity" as used herein, refers to the proportion of nucleotides (expressed in percent) of a contiguous nucleotide sequence in a nucleic acid molecule (e.g. oligonucleotide) which across the contiguous nucleotide sequence, are identical to a reference sequence (e.g. a sequence motif). The percentage of identity is thus calculated by counting the number of aligned nucleobases that are identical (a Match) between two sequences (in the contiguous nucleotide sequence of the compound of the invention and in the reference sequence), dividing that number by the total number of nucleotides in the oligonucleotide and multiplying by 100. Therefore, Percentage of Identity= (Matches×100)/Length of aligned region (e.g. the contiguous nucleotide sequence). Insertions and deletions are not allowed in the calculation the percentage of identity of a contiguous nucleotide sequence. It will be understood that in determining identity, chemical modifications of the nucleobases are disregarded as long as the functional capacity of the nucleobase to form Watson Crick base pairing is retained (e.g. 5-methyl cytosine is considered identical to a cytosine for the purpose of calculating % identity).

Hybridization

The term "hybridization", "hybridizing" or "hybridizes" as used herein is to be understood as two nucleic acid strands (e.g. an oligonucleotide and a target nucleic acid) forming hydrogen bonds between base pairs on opposite strands thereby forming a duplex. The affinity of the binding between two nucleic acid strands is the strength of the hybridization. It is often described in terms of the melting temperature ($T_m$) defined as the temperature at which half of the oligonucleotides are duplexed with the target nucleic acid. At physiological conditions $T_m$ is not strictly proportional to the affinity (Mergny and Lacroix, 2003, Oligonucleotides 13:515-537). The standard state Gibbs free energy $\Delta G^\circ$ is a more accurate representation of binding affinity and is related to the dissociation constant ($K_d$) of the reaction by $\Delta G^\circ=-RT\ln(K_d)$, where R is the gas constant and T is the absolute temperature. Therefore, a very low $\Delta G^\circ$ of the reaction between an oligonucleotide and the target nucleic acid reflects a strong hybridization between the oligonucleotide and target nucleic acid. $\Delta G^\circ$ is the energy associated with a reaction where aqueous concentrations are 1M, the pH is 7, and the temperature is 37° C. The hybridization of oligonucleotides to a target nucleic acid is a spontaneous reaction and for spontaneous reactions $\Delta G^\circ$ is less than zero. $\Delta G^\circ$ can be measured experimentally, for example, by use of the isothermal titration calorimetry (ITC) method as described in Hansen et al., 1965, Chem. Comm. 36-38 and Holdgate et al., 2005, Drug Discov Today. The skilled person will know that commercial equipment is available for $\Delta G^\circ$ measurements. $\Delta G^\circ$ can also be estimated numerically by using the nearest neighbor model as described by SantaLucia, 1998, Proc Natl Acad Sci USA. 95: 1460-1465 using appropriately derived thermodynamic parameters described by Sugimoto et al., 1995, Biochemistry 34:11211-11216 and McTigue et al., 2004, Biochemistry 43:5388-5405. In order to have the possibility of modulating its intended nucleic acid target by hybridization, oligonucleotides of the present invention hybridize to a target nucleic acid with estimated $\Delta G^\circ$ values below −10 kcal for oligonucleotides that are 10-30 nucleotides in length. In some embodiments the degree or strength of hybridization is measured by the standard state Gibbs free energy $\Delta G^\circ$. The oligonucleotides may hybridize to a target nucleic acid with estimated $\Delta G^\circ$ values below the range of −10 kcal, such as below −15 kcal, such as below −20 kcal and such as below −25 kcal for oligonucleotides that are 8-30 nucleotides in length. In some embodiments the oligonucleotides hybridize to a target nucleic acid with an estimated $\Delta G^\circ$ value of −10 to −60 kcal, such as −12 to −40, such as from −15 to −30 kcal or −16 to −27 kcal such as −18 to −25 kcal.

The Target

The term "target" as used herein refers to the mammalian protein "Far Upstream Element-Binding Protein 1", alternatively known as "FUBP1" or "FBP" or "FUBP" or "hDH V". The *Homo sapiens* FUBP1 gene is located at chromosome 1,77944055 . . . 77979435, complement (NC_000001.11, Gene ID 1462). The FUBP1 gene encodes a ssDNA binding protein that activates the far upstream element of c-myc and stimulates expression of c-myc in undifferentiated cells. Regulation of FUSE by FUBP occurs through single-strand binding of FUBP to the non-coding strand. The FUBP1 protein has ATP-dependent DNA helicase activity. The amino acid sequence of human FUBP1 is known in the art and can be assessed via UniProt, see e.g. UniProt entry Q96AE4 for human FUBP1, hereby incorporated by reference.

Target Nucleic Acid

According to the present invention, the target nucleic add is a nucleic add, which encodes mammalian FUBP1 and may for example be a gene, a RNA, an mRNA, and pre-mRNA, a mature mRNA or a cDNA sequence. The target may therefore be referred to as a FUBP1 target nucleic acid.

Suitably, the target nucleic acid encodes a FUBP1 protein, in particular mammalian FUBP1, such as the human FUBP1 gene encoding pre-mRNA or mRNA sequences provided herein as SEQ ID NO: 1, 2 and/or 3. SEQ ID NO: 1 is sequence of the human FUBP1 pre-mRNA. SEQ ID NO: 2 and 3 are sequences of human FUBP1 mRNAs.

Table 3 lists predicted exon and intron regions of SEQ ID NO. 1.

Table 4 provides an overview on the genomic sequences of human, cyno monkey and mouse FUBP1. Table 5 provides an overview on pre-mRNA sequences for human, monkey and mouse FUBP1 and for on mature mRNAs for human FUBP1.

In some embodiments, the target nucleic acid is selected from the group consisting of SEQ ID NO: 1, 2, 3, 4, and/or 5, or naturally occurring variants thereof (e.g. sequences encoding a mammalian FUBP1).

In some embodiments, the target nucleic acid is selected from the group consisting of SEQ ID NO: 1, 2 and/or 3, or naturally occurring variants thereof (e.g. sequences encoding a mammalian FUBP1).

In some embodiments, the target nucleic acid is selected from the group consisting of SEQ ID NO: 1 and 4 and 5, or naturally occurring variants thereof (e.g. sequences encoding a mammalian FUBP1).

TABLE 4

Genome and assembly information for FUBP1 across species.

| Species | Chr. | Strand | Genomic coordinates | | Assembly | ensembl gene_id |
| | | | Start | End | | |
|---|---|---|---|---|---|---|
| Human | 1 | Rv | 77944055 | 77979110 | GRCh38.p10 | ENSG 00000162613 |
| Cyno monkey | 1 | Fwd | 149243675 | 149283374 | Macaca_fascicularis_5.0 | ENSMFAG 00000031825 |
| Mouse | 3 | Fwd | 152210422 | 152236826 | GRCm38.p5 | ENSMUSG 00000028034 |

Fwd = forward strand.
Rv = reverse strand.
The genome coordinates provide the pre-mRNA sequence (genomic sequence)

TABLE 3

Exon and intron regions in the human FUBP1 pre-mRNA.

| Exonic regions in the human FUBP1 premRNA (SEQ ID NO 1) | | | Intronic regions in the human FUBP1 premRNA (SEQ ID NO 1) | | |
| ID | start | end | ID | start | end |
|---|---|---|---|---|---|
| E1 | 19 | 226 | I1 | 227 | 9095 |
| E2 | 9096 | 9186 | I2 | 9187 | 10907 |
| E3 | 10908 | 10946 | I3 | 10947 | 11444 |
| E4 | 11445 | 11484 | I4 | 11485 | 12009 |
| E5 | 12010 | 12062 | I5 | 12063 | 12155 |
| E6 | 12156 | 12227 | I6 | 12228 | 12359 |
| E7 | 12360 | 12417 | I7 | 12418 | 13879 |
| E8 | 13880 | 14042 | I8 | 14043 | 14142 |
| E9 | 14143 | 14241 | I9 | 14242 | 14363 |
| E10 | 14364 | 14465 | I10 | 14466 | 14754 |
| E11 | 14755 | 14857 | I11 | 14858 | 14948 |
| E12 | 14949 | 15049 | I12 | 15050 | 15395 |
| E13 | 15396 | 15537 | I13 | 15538 | 16180 |
| E14 | 16181 | 16341 | I14 | 16342 | 18615 |
| E15 | 18616 | 18767 | I15 | 18768 | 18847 |
| E16 | 18848 | 18927 | I16 | 18928 | 22410 |
| E17 | 22411 | 22539 | I17 | 22540 | 23781 |
| E18 | 23782 | 23856 | I18 | 23857 | 29810 |
| E19 | 29811 | 29956 | I19 | 29957 | 30196 |
| E20 | 30197 | 30706 | | | |

In some embodiments, the target nucleic acid may be a cynomolgus monkey FUBP1 nucleic acid, such as an mRNA or pre-mRNA.

In some embodiments, the target nucleic acid may be a mouse FUBP1 nucleic acid, such as a mRNA or pre-mRNA.

If employing the antisense oligonucleotide of the invention in research or diagnostics the target nucleic acid may be a cDNA or a synthetic nucleic acid derived from DNA or RNA.

For in vivo or in vitro application, the therapeutic antisense oligonucleotide of the invention is typically capable of inhibiting the expression of the FUBP1 target nucleic acid in a cell, which is expressing the FUBP1 target nucleic acid. The contiguous sequence of nucleobases of the antisense oligonucleotide of the invention is typically complementary to a conserved region of the FUBP1 target nucleic acid, as measured across the length of the antisense oligonucleotide, optionally with the exception of one or two mismatches, and optionally excluding nucleotide based linker regions which may link the antisense oligonucleotide to an optional functional group such as a conjugate, or other non-complementary terminal nucleotides.

The target nucleic acid may be a messenger RNA, such as a pre-mRNA which encodes mammalian FUBP1 protein, such as human FUBP1, e.g. the human FUBP1 pre-mRNA sequence, such as that disclosed as SEQ ID NO: 1, the cynomolgus monkey FUBP1 pre-mRNA sequence, such as that disclosed as SEQ ID NO: 4, or the mouse FUBP1 pre-mRNA sequence, such as that disclosed as SEQ ID NO: 5, or a mature FUBP1 mRNA, such as a human mature mRNA disclosed as SEQ ID NO: 2 and 3. SEQ ID NOs: 1-5, 10, 11, 15 and 19 are DNA sequences—it will be understood that target RNA sequences have uracil (U) bases in place of the thymidine bases (T).

Further information on exemplary target nucleic acids is provided in Table 5.

41

TABLE 5

| Sequence details for FUBP1 across species. | | | |
|---|---|---|---|
| Species | RNA type | Length (nt) | SEQ ID NO |
| Human | Pre-mRNA | 35056 | 1 |
| Human | Mature mRNA, variant 1 | 1968 | 2 |
| Human | Mature mRNA, variant t | 1935 | 3 |
| Cyno monkey | Pre-mRNA | 39750 | 4 |
| Mouse | Pre-mRNA | 26405 | 5 |

Note:
SEQ ID NO: 4 comprises regions of multiple NNNNs, where the sequencing has been unable to accurately refine the sequence, and a degenerate sequence is therefore included. For the avoidance of doubt, the compounds of the invention are complementary to the actual target sequence and are not therefore degenerate compounds.

In some embodiments, the target nucleic acid is SEQ ID NO: 1.

In some embodiments, the target nucleic acid is SEQ ID NO: 2.

In some embodiments, the target nucleic acid is SEQ ID NO: 3.

In some embodiments, the target nucleic acid is SEQ ID NO: 4.

In some embodiments, the target nucleic acid is SEQ ID NO: 5.

In some embodiments, the target nucleic acid is SEQ ID NO: 1, 2 and 3.

In some embodiments, the target nucleic acid is SEQ ID NO: and 4. Thus, the antsense oligonucleotide may target both human and cyno monkey FUBP1.

In some embodiments, the target nucleic acid is SEQ ID NO: 1 and 5. Thus, the antisense oligonucleotide targets both human and mouse FUBP1.

In some embodiments, the target nucleic acid is SEQ ID NO: 1, 4 and 5. Thus, the antisense oligonucleotide may target human, cyno monkey and mouse FUBP1

Target Sequence

The term "target sequence" as used herein refers to a sequence of nucleotides present in the target nucleic acid, which comprises the nucleobase sequence, which is complementary to the oligonucleotide or nucleic acid molecule of the invention. In some embodiments, the target sequence consists of a region on the target nucleic acid with a nucleobase sequence that is complementary to the contiguous nucleotide sequence of the antisense oligonucleotide of the invention (i.e. a sub-sequence). This region of the target nucleic acid may interchangeably be referred to as the target nucleotide sequence, target sequence or target region. In some embodiments, the target sequence is longer than the complementary sequence of a single antisense oligonucleotide, and may, for example represent a preferred region of the target nucleic add, which may be targeted by several antisense oligonucleotides of the invention.

In one embodiment, the target sequence is a region within exon 14 of human FUBP1 mRNA (see Table 3 above).

In another embodiment, the target sequence is a region within exon 20 of human FUEP1 mRNA (see Table 3 above).

The antisense oligonucleotide of the invention comprises a contiguous nucleotide sequence, which is complementary to or hybridizes to a region on the target nucleic acid, such as a target sequence described herein.

Provided herein below are target sequence regions, as defined by regions of the human FUBP1 pre-mRNA (using SEQ ID NO 1 as a reference) which may be targeted by the oligonucleotides of the invention.

The oligonucleotide of the invention comprises a contiguous nucleotide sequence, which is complementary to or hybridizes to the target nucleic acid, such as a sub-sequence of the target nucleic acid, such as a target sequence described herein.

The oligonucleotide comprises a contiguous nucleotide sequence, which is complementary to a target sequence present in the target nucleic acid molecule. The contiguous nucleotide sequence (and therefore the target sequence) comprises at least 12 contiguous nucleotides, such as 12, 13, 14, 15, 16, 17, 18, 19, 20, 21, 22, 23, 24 nucleotides, such as from 14-20, such as from 14-18 contiguous nucleotides.

Target Sequence Regions

The inventors have identified particularly effective sequences of the FUSP1 target nucleic acid, which may be targeted by the oligonucleotide of the invention.

In some embodiments, the target sequence is SEQ ID NO 10

In some embodiments, the target sequence is SEQ ID NO 11.

In some embodiments, the target sequence is SEQ ID NO 15.

In some embodiments, the target sequence is SEQ ID NO 19.

```
SEQ ID NO 10:  GTGAAACCATAAAAAGCATAAG

SEQ ID NO 11:  AACCATAAAAAGCATAAG

SEQ ID NO 15:  GTGAAACCATAAAAAGCATA

SEQ ID NO 19:  GTAGAAATGAAAATTGGT
```

SEQ ID NO: 10, 11, 15 and 19 are DNA sequences—it will be understood that target RNA sequences have uracil (U) bases in place of the thymidine bases (T).

In some embodiments, the target sequence is the region from nucleotides 16184 to 16200 of SEQ ID NO: 1.

In some embodiments, the target sequence is the region from nucleotides 16186 to 6203 of SEQ ID NO: 1.

In some embodiments, the target sequence is the region from nucleotides 16188 to 6205 of SEQ ID NO: 1.

In some embodiments, the target sequence is the region from nucleotides 16189 to 16205 of SEQ ID NO: 1.

In some embodiments, the target sequence is the region from nucleotides 30536-30553 of SEQ ID NO: 1.

Target Cell

The term a "target cell" as used herein refers to a cell, which is expressing the target nucleic acid. In some embodiments, the target cell may be in vivo or in vitro. In some embodiments, the target cell is a mammalian cell such as a rodent cell, such as a mouse cell or a rat cell, or a primate cell such as a monkey cell or a human cell.

Typically, the target cell expresses the FUBP1 mRNA, such as the FUBP1 pre-mRNA or FUBP1 mature mRNA. For example, the target cell expresses the human FUBP1 pre-mRNA, e.g. SEQ ID NO 1, or human FUBP1 mature mRNA comprising exon 14 (or exon 20), such as SEQ ID NO: 2 or 3). For experimental evaluation a target cell may be used which expresses a nucleic acid which comprises a target sequence. The poly A tail of FUBP1 mRNA is typically disregarded for antisense oligonucleotide targeting.

The antisense oligonucleotide of the invention is typically capable of inhibiting the expression of the FUBP1 target nucleic acid in a target cell which is expressing the FUBP1 target nucleic acid, for example either in vivo or in vitro.

Further, the target cell may be a hepatocyte. In one embodiment, the target cell is HBV infected primary human hepatocytes, either derived from HBV infected individuals or from a HBV infected mouse with a humanized liver (PhoenixBio, PXB-mouse).

In one embodiment, the target cell may be infected with HBV. Further, the target cell may comprise HBV cccDNA. Thus, the target cell preferably comprises FUBP1 mRNA, such as the FUBP1 pre-mRNA or FUBP1 mature mRNA, and HBV cccDNA.

Further, the target cell may be a cancer cell, such as a hepatocellular carcinoma cell.

Naturally Occurring Variant

The term "naturally occurring variant" refers to variants of FUBP1 gene or transcripts which originate from the same genetic loci as the target nucleic acid, but may differ for example, by virtue of degeneracy of the genetic code causing a multiplicity of codons encoding the same amino acid, or due to alternative splicing of pre-mRNA, or the presence of polymorphisms, such as single nucleotide polymorphisms (SNPs), and allelic variants. Based on the presence of the sufficient complementary sequence to the oligonucleotide, the oligonucleotide of the invention may therefore target the target nucleic acid and naturally occurring variants thereof.

In some embodiments, the naturally occurring variants have at least 95% such as at least 98% or at least 99% homology to a mammalian FUBP1 target nucleic add, such as a target nucleic acid selected form the group consisting of SEQ ID NO 1, 2, 3, 4 or 5. In some embodiments, the naturally occurring variants have at least 99% homology to the human FUBP1 target nucleic acid of SEQ ID NO: 1.

Inhibition of Expression

The term "Inhibition of expression" as used herein is to be understood as an overall term for n oligonucleotide's ability to inhibit the amount or the activity of FUBP1 in a target cell. Inhibition of activity may be determined by measuring the level of FUBP1 pre-mRNA or FUBP1 mRNA, or by measuring the level of FUBP1 or FUBP1 activity in a cell. Inhibition of expression may therefore be determined in vitro or in vivo.

Typically, inhibition of expression is determined by comparing the inhibition of activity due to the administration of an effective amount of the antisense oligonucleotide to the target cell and comparing that level to a reference level obtained from a target cell without administration of the antisense oligonucleotide (control experiment), or a known reference level (e.g. the level of expression prior to administration of the effective amount of the antisense oligonucleotide, or a predetermine or otherwise known expression level).

For example a control experiment may be an animal or person, or a target ell treated with a saline composition or a reference oligonucleotide (often a scrambled control).

The term inhibition or inhibit may also be referred as down-regulate, reduce, suppress, lessen, lower, the expression of FUBP1.

The inhibition of expression may occur e.g. by degradation of pre-mRNA or mRNA (e.g. using RNase H recruiting oligonucleotides, such as gapmers).

High Affinity Modified Nucleosides

A high affinity modified nucleoside is a modified nucleotide which, when incorporated into the oligonucleotide enhances the affinity of the oligonucleotide for its complementary target, for example as measured by the melting temperature (Tm). A high affinity modified nucleoside of the present invention preferably result in an increase in melting temperature between +0.5 to +12° C., more preferably between +1.5 to +10° C. and most preferably between +3 to +8° C. per modified nucleoside. Numerous high affinity modified nucleosides are known in the art and include for example, many 2' substituted nucleosides as well as locked nucleic acids (LNA) (see e.g. Freier & Altmann; Nucl. Acid Res., 1997, 25, 4429-4443 and Uhlmann; Curr. Opinion in Drug Development, 2000, 3(2), 293-213).

Sugar Modifications

The oligomer of the invention may comprise one or more nucleosides, which have a modified sugar moiety, i.e. a modification of the sugar moiety when compared to the ribose sugar moiety found in DNA and RNA.

Numerous nucleosides with modification of the ribose sugar moiety have been made, primarily with the aim of improving certain properties of oligonucleotides, such as affinity and/or nuclease resistance.

Such modifications include those where the ribose ring structure is modified, e.g. by replacement with a hexose ring (HNA), or a bicyclic ring, which typically have a biradicle bridge between the C2 and C4 carbons on the ribose ring (LNA), or an unlinked ribose ring which typically lacks a bond between the C2 and C3 carbons (e.g. UNA). Other sugar modified nucleosides include, for example, bicyclo-hexose nucleic acids (WO2011/017521) or tricyclic nucleic acids (WO2013/154798). Modified nucleosides also include nucleosides where the sugar moiety is replaced with a non-sugar moiety, for example in the case of peptide nucleic acids (PNA), or morpholino nucleic acids.

Sugar modifications also include modifications made via altering the substituent groups on the ribose ring to groups other than hydrogen, or the 2'—OH group naturally found in DNA and RNA nucleosides. Substituents may, for example be introduced at the 2', 3', 4' or 5' positions.

2' Sugar Modified Nucleosides

A 2' sugar modified nucleoside is a nucleoside which has a substituent other than H or —OH at the 2' position (2' substituted nucleoside) or comprises a 2' linked biradicle capable of forming a bridge between the 2' carbon and a second carbon in the ribose ring, such as LNA (2'-4' biradicle bridged) nucleosides.

Indeed, much focus has been spent on developing 2' sugar substituted nucleosides, and numerous 2' substituted nucleosides have been found to have beneficial properties when incorporated into oligonucleotides. For example, the 2' modified sugar may provide enhanced binding affinity and/or increased nuclease resistance to the oligonucleotide. Examples of 2' substituted modified nucleosides are 2'-O-alkyl-RNA, 2'-O-methyl-RNA, 2'-alkoxy-RNA, 2'-O-methoxyethyl-RNA (MOE), 2'-amino-DNA, 2'-Fluoro-RNA, and 2'-F-ANA nucleoside. For further examples, please see e.g. Freier & Altmann; Nucl. Acid Res., 1997, 25, 4429-4443 and Uhlmann; Curr. Opinion in Drug Development, 2000, 3(2), 293-213, and Deleavey and Damha, Chemistry and Biology 2012, 19, 937. Below are illustrations of some 2' substituted modified nucleosides.

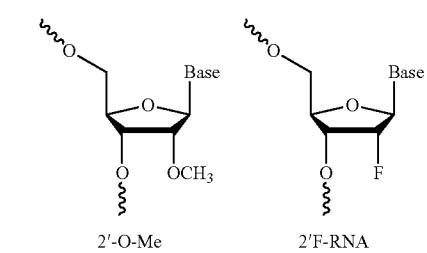

2'-O-Me                2'F-RNA

45

-continued

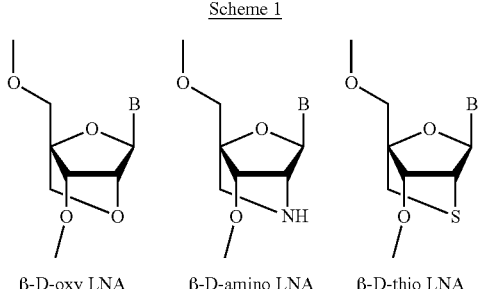

2'F-ANA

2'-O-MOE

2'-O-Allyl

2'-O-Ethylamine

In relation to the present invention 2' substituted sugar modified nucleosides does not include 2' bridged nucleosides like LNA.

Locked Nucleic Acid Nucleosides (LNA Nucleoside)

A "LNA nucleoside" is a 2'-modified nucleoside which comprises a biradical linking the C2' and C4' of the ribose sugar ring of said nucleoside (also referred to as a "2'-4' bridge"), which restricts or locks the conformation of the ribose ring. These nucleosides are also termed bridged nucleic acid or bicyclic nucleic acid (BNA) in the literature. The locking of the conformation of the ribose is associated with an enhanced affinity of hybridization (duplex stabilization) when the LNA is incorporated into an oligonucleotide for a complementary RNA or DNA molecule. This can be routinely determined by measuring the melting temperature of the oligonucleotide/complement duplex.

Non limiting, exemplary LNA nucleosides are disclosed in WO 99/014226, WO 00/66604, WO 98/039352, WO 2004/046160, WO 00/047599, WO 2007/134181, WO 2010/077578, WO 2010/036698, WO 2007/090071, WO 2009/006478, WO 2011/156202, WO 2008/154401, WO 2009/067647, WO 2008/150729, Morita et al., Bioorganic & Med. Chem. Lett. 12, 73-76, Seth et al. J. Org. Chem. 2010, Vol 75(5) pp. 1569-81, and Mitsuoka et al., Nucleic Acids Research 2009, 37(4), 1225-1238, and Wan and Seth, J. Medical Chemistry 2016, 59, 9645-9667. Further non limiting, exemplary LNA nucleosides are disclosed in Scheme 1.

Scheme 1

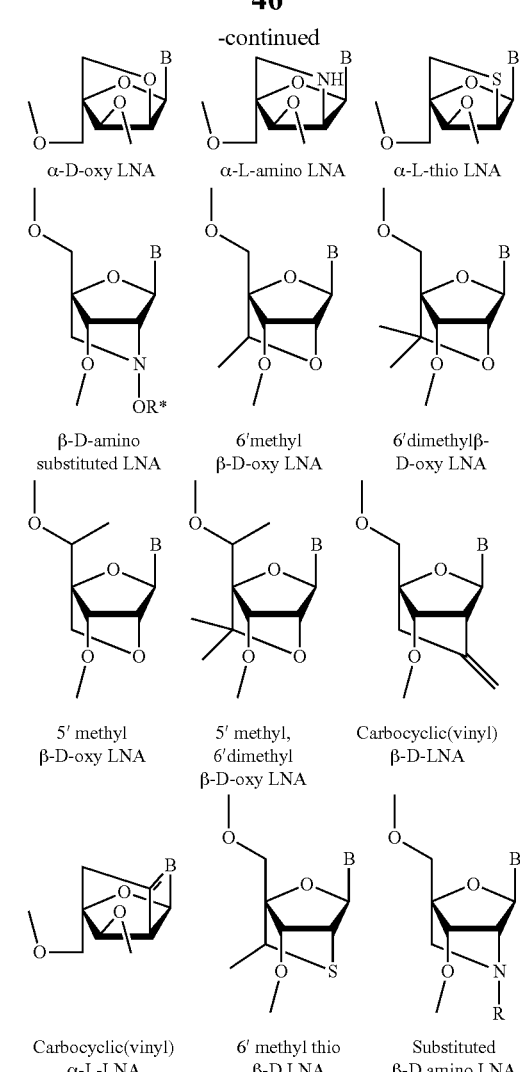

β-D-oxy LNA    β-D-amino LNA    β-D-thio LNA

46

-continued

α-D-oxy LNA    α-L-amino LNA    α-L-thio LNA

β-D-amino substituted LNA    6'methyl β-D-oxy LNA    6'dimethylβ-D-oxy LNA

5' methyl β-D-oxy LNA    5' methyl, 6'dimethyl β-D-oxy LNA    Carbocyclic(vinyl) β-D-LNA Carbocyclic(vinyl) α-L-LNA    6' methyl thio β-D LNA    Substituted β-D amino LNA Particular LNA nucleosides are beta-D-oxy-LNA, 6'-methyl-beta-D-oxy LNA such as (S)-6'-methyl-beta-D-oxy-LNA (ScET) and ENA. A particularly advantageous LNA is beta-D-oxy-LNA.

Nuclease Mediated Degradation

Nuclease mediated degradation refers to an oligonucleotide capable of mediating degradation of a complementary nucleotide sequence when forming a duplex with such a sequence.

In some embodiments, the oligonucleotide may function via nuclease mediated degradation of the target nucleic acid, where the oligonucleotides of the invention are capable of recruiting a nuclease, particularly an endonuclease, preferably endoribonuclease (RNase), such as RNase H. Examples of oligonucleotide designs which operate via nuclease mediated mechanisms are oligonucleotides which typically comprise a region of at least 5 or 6 consecutive DNA nucleosides and are flanked on one side or both sides by affinity enhancing nucleosides, for example gapmers.

RNase H Activity and Recruitment

The RNase H activity of an antisense oligonucleotide refers to its ability to recruit RNase H when in a duplex with a complementary RNA molecule. WO01/23613 provides in vitro methods for determining RNase H activity, which may be used to determine the ability to recruit RNase H. Typically an oligonucleotide is deemed capable of recruiting RNase H if it, when provided with a complementary target nucleic acid sequence, has an initial rate, as measured in pmol/l/min, of at least 5%, such as at least 10% or more than 20% of the of the initial rate determined when using a oligonucleotide having the same base sequence as the modified oligonucleotide being tested, but containing only DNA monomers with phosphorothioate linkages between all monomers in the oligonucleotide, and using the methodology provided by Example 91-95 of WO01/23613 (hereby incorporated by reference). For use in determining RHase H activity, recombinant human RNase H1 is available from Creative Biomart® (Recombinant Human RNase H1 fused with His tag expressed in *E. coli*).

Gapmer

The antisense oligonucleotide of the invention, or contiguous nucleotide sequence thereof, may be a gapmer, also termed gapmer oligonucleotide or gapmer designs. The antisense gapmers are commonly used to inhibit a target nucleic acid via RNase H mediated degradation. A gapmer oligonucleotide comprises at least three distinct structural regions a 5'-flank, a gap and a 3'-flank, F-G-F' in the '5->3' orientation. The "gap" region (G) comprises a stretch of contiguous DNA nucleotides which enable the oligonucleotide to recruit RNase H. The gap region is flanked by a 5' flanking region (F) comprising one or more sugar modified nucleosides, advantageously high affinity sugar modified nucleosides, and by a 3' flanking region (F') comprising one or more sugar modified nucleosides, advantageously high affinity sugar modified nucleosides. The one or more sugar modified nucleosides in region F and F' enhance the affinity of the oligonucleotide for the target nucleic acid (i.e. are affinity enhancing sugar modified nucleosides). In some embodiments, the one or more sugar modified nucleosides in region F and F' are 2' sugar modified nucleosides, such as high affinity 2' sugar modifications, such as independently selected from LNA and 2'-MOE.

In a gapmer design, the 5' and 3' most nucleosides of the gap region are DNA nucleosides, and are positioned adjacent to a sugar modified nucleoside of the 5' (F) or 3' (F') region respectively. The flanks may further be defined by having at least one sugar modified nucleoside at the end most distant from the gap region, i.e. at the 5' end of the 5' flank and at the 3' end of the 3' flank.

Regions F-G-F' form a contiguous nucleotide sequence. Antisense oligonucleotides of the invention, or the contiguous nucleotide sequence thereof, may comprise a gapmer region of formula F-G-F'. In some embodiments, all internucleoside linkages between the nucleosides of the gapmer region of formula F-G-F' are phosphorothioate internucleoside linkages.

The overall length of the gapmer design F-G-F' may be, for example 12 to 32 nucleosides, such as 13 to 24, such as 14 to 22 nucleosides, such as from 15 to 20 such as 16 to 18 nucleosides. In some embodiments, the overall length is 17 nucleosides. In some embodiments, the overall length is 17 nucleosides.

By way of example, the gapmer oligonucleotide of the present invention can be represented by the following formula:

$$F_{1\text{-}8}\text{-}G_{5\text{-}16}\text{-}F'_{1\text{-}8}, \text{ such as}$$

$$F_{1\text{-}8}\text{-}G_{7\text{-}16}\text{-}F'_{2\text{-}8}, \text{ or}$$

$$F_{4\text{-}8}\text{-}G_{7\text{-}12}\text{-}F'_{2\text{-}8}, \text{ or}$$

$$F_{4\text{-}6}\text{-}G_{7\text{-}11}\text{-}F_{2\text{-}6}$$

with the proviso that the overall length of the gapmer regions F-G-F' is at least 12, such as at least 14 nucleotides in length.

In an embodiment, the gapmer oligonucleotide of the present invention can be represented by the following formula:

$$F_{4\text{-}6}\text{-}G_{7\text{-}11}\text{-}F_{2\text{-}6}$$

preferably wherein the overall length of the gapmer regions F-G-F' is at least 16 nucleotides, such as 17 or 18 nucleotides.

In an aspect of the invention the antisense oligonucleotide or contiguous nucleotide sequence thereof consists of or comprises a gapmer of formula 5'-F-G-F'-3', where region F and F' independently comprise or consist of 1-8 nucleosides, of which 1-4 are 2' sugar modified and defines the 5' and 3' end of the F and F' region, and G is a region between 6 and 16 nucleosides, such as 7 to 12 nucleosides, which are capable of recruiting RNase H.

In some embodiments, all the modified nucleosides of region F and F' are beta-D-oxy LNA nucleosides. Further, region F or F', or F and F' may optionally comprise DNA nucleosides. Optionally, the flanking region F or F', or both flanking regions F and F' may comprise one or more DNA nucleosides (an alternating flank, see definition of the alternating flank for more details).

Regions F, G and F' are further defined below and can be incorporated into the F-G-F' formula.

Gapmer—Region G

Region G (gap region) of the gapmer is a region of nucleosides which enables the oligonucleotide to recruit RNaseH, such as human RNase H1, typically DNA nucleosides. RNase H is a cellular enzyme which recognizes the duplex between DNA and RNA, and enzymatically cleaves the RNA molecule. Suitably gapmers may have a gap region (G) of at least 5 or 6 contiguous DNA nucleosides, such as 5-16 contiguous DNA nucleosides, such as 6-15 contiguous DNA nucleosides, such as 7-14 contiguous DNA nucleosides, such as 8-12 contiguous DNA nucleotides, such as 8-12 contiguous DNA nucleotides in length. The gap region G may, in some embodiments consist of 6, 7, 8, 9, 10, 11, 12, 13, 14, 15 or 16 contiguous DNA nucleosides.

In some embodiments, the gap region G may consist of 12 or less contiguous DNA nucleosides, such as of 7, 8, 9, 10, or 11 contiguous DNA nucleosides, such as 9, 10 or 11 contiguous DNA nucleosides. One or more cytosine (C) DNA in the gap region may in some instances be methylated (e.g. when a DNA c is followed by a DNA g). Such residues are either annotated as 5-methyl-cytosine ($^{me}C$). In some embodiments, the gap region G may consist of 6, 7, 8, 9, 10, 11, 12, 13, 14, 15 or 16 contiguous phosphorothioate linked DNA nucleosides.

In some embodiments, all internucleoside linkages in the gap are phosphorothioate linkages.

Gapmer—Flanking Regions, F and F'

Region F is positioned immediately adjacent to the 5' DNA nucleoside, of region G. The 5' most nucleoside of region F is a sugar modified nucleoside, such as a high affinity sugar modified nucleoside, for example a 2' substituted nucleoside, such as a MOE nucleoside, or an LNA nucleoside.

Region F' is positioned immediately adjacent to the 3' DNA nucleoside of region G. The 5' most nucleoside of region F' is a sugar modified nucleoside, such as a high affinity sugar modified nucleoside, for example a 2' substituted nucleoside, such as a MOE nucleoside, or an LNA nucleoside.

Region F is 1-8 contiguous nucleotides in length, such as 2-6, such as 4-6 contiguous nucleotides in length. In some embodiments, the length of region F is 4 contiguous nucleotides. In some embodiments, the length of region F is 5 contiguous nucleotides. In some embodiments, the length of region F is 6 contiguous nucleotides.

Advantageously the 5' most nucleoside of region F is a sugar modified nucleoside. In some embodiments the two 5' most nucleosides of region F are sugar modified nucleosides. In some embodiments the 5' most nucleoside of region F is an LNA nucleoside. In some embodiments the two 5' most nucleosides of region F are LNA nucleosides.

Region F' is 1-8 contiguous nucleotides in length, such as 2-6, such as 2-5 contiguous nucleotides in length. In some embodiments, the length of region F' is 2 contiguous nucleotides. In some embodiments, the length of region F' is 3 contiguous nucleotides. In some embodiments, the length of region F' is 4 contiguous nucleotides. In some embodiments, the length of region F' is 5 contiguous nucleotides.

Advantageously, the 3' most nucleoside of region F' is a sugar modified nucleoside. In some embodiments, the two 3' most nucleosides of region F' are sugar modified nucleosides. In some embodiments, the two 3' most nucleosides of region F' are LNA nucleosides. In some embodiments the 3' most nucleoside of region F' is an LNA nucleoside.

It should be noted that when the length of region F is one, it is advantageously an LNA nucleoside. Further, it is noted that when the length of region F and/or F' is two, both nucleosides of region F and/or F' are advantageously LNA nucleosides.

In some embodiments, the sugar modified nucleosides in region F and F' consist of only one type of sugar modified nucleosides, such as only MOE or only beta-D-oxy LNA or only ScET. Such designs are also termed uniform flanks or uniform gapmer design.

In some embodiments, all the nucleosides of region F or F', or F and F' are LNA nucleosides, such as beta-D-oxy LNA nucleosides. In an alternative embodiment, all the sugar modified nucleosides of region F and F' are LNA nucleosides, such as beta-D-oxy LNA nucleosides, wherein region F or F', or both regions F and F' may comprise DNA nucleosides (an alternating flank, see definition of these for more details).

In some embodiments the 5' most and the 3' most nucleosides of region F and F' are LNA nucleosides, such as beta-D-oxy LNA nucleosides nucleosides.

In some embodiments, the internucleoside linkage between region F and region G and/or the internucleoside linkage between region F' and region G is a phosphorothioate internucleoside linkage.

In some embodiments, the internucleoside linkages between the nucleosides of region F or F', F and F' are phosphorothioate internucleoside linkages.

LNA Gapmer

An LNA gapmer is a gapmer wherein either one or both of region F and F' comprises or consists of LNA nucleosides. A beta-D-oxy gapmer is a gapmer wherein either one or both of region F and F' comprises or consists of beta-D-oxy LNA nucleosides.

In some embodiments, the LNA gapmer is of formula: $[LNA]_{1-5}$-[region G]-$[LNA]_{1-5}$, wherein region G is or comprises a region of contiguous DNA nucleosides which are capable of recruiting RNase H.

MOE Gapmers

A MOE gapmers is a gapmer wherein regions F and F' consist of MOE nucleosides. In some embodiments, the MOE gapmer is of design $[MOE]_{1-8}$-[Region G]$_{5-16}$-

$[MOE]_{1-8}$, such as $[MOE]_{2-7}$-[Region G]$_{6-14}$-$[MOE]_{2-7}$, such as $[MOE]_{3-6}$-[Region G]$_{8-12}$-$[MOE]_{3-6}$, wherein region G is as defined in the Gapmer definition. MOE gapmers with a 5-10-5 design (MOE-DNA-MOE) have been widely used in the art.

Mixed Wing Gapmer

A mixed wing gapmer is an LNA gapmer wherein one or both of region F and F' comprise a 2' substituted nucleoside, such as a 2' substituted nucleoside independently selected from the group consisting of 2'-O-alkyl-RNA units, 2'-O-methyl-RNA, 2'-amino-DNA units, 2'-fluoro-DNA units, 2'-alkoxy-RNA, MOE units, arabino nucleic acid (ANA) units and 2'-fluoro-ANA units, such as a MOE nucleoside. In some embodiments wherein at least one of region F and F', or both region F and F' comprise at least one LNA nucleoside, the remaining nucleosides of region F and F' are independently selected from the group consisting of MOE and LNA. In some embodiments wherein at least one of region F and F', or both region F and F' comprise at least two LNA nucleosides, the remaining nucleosides of region F and F' are independently selected from the group consisting of MOE and LNA. In some mixed wing embodiments, one or both of region F and F' may further comprise one or more DNA nucleosides.

Alternating Flank Gapmers

Flanking regions may comprise both LNA and DNA nucleoside and are referred to as "alternating flanks" as they comprise an alternating motif of LNA-DNA-LNA nucleosides. Gapmers comprising at least one alternating flank are referred to as "alternating flank gapmers". "Alternative flank gapmers" are thus LNA gapmer oligonucleotides, where at least one of the flanks (F or F') comprises one ore more DNA nucleotides in addition to the LNA nucleoside(s). In some embodiments at least one of region F or F', or both region F and F', comprise both LNA nucleosides and DNA nucleosides. In such embodiments, the flanking region F or F', or both F and F' comprise at least three nucleosides, wherein the 5' and 3' most nucleosides of the F and/or F' region are LNA nucleosides. Alternating flank LNA gapmers are disclosed in WO2016/127002.

An alternating flank region may comprise up to 3 contiguous DNA nucleosides, such as 1 to 2 or 1 or 2 or 3 contiguous DNA nucleosides.

The alternating flank regions can be annotated as a series of integers, representing a number of LNA nucleosides (L) followed by a number of DNA nucleosides (D), for example $[L]_{1-3}$-$[D]_{1-3}$-$[L]_{1-3}$ or $[L]_{1-2}$-$[D]_{1-2}$-$[L]_{1-2}$-$[D]_{1-2}$-$[L]_{1-2}$. In oligonucleotide designs these will often be represented as numbers such that 2-2-1 represents 5'$[L]_2$-$[D]_2$-$[L]$3', and 1-1-1-1-1 represents 5'$[L]$-$[D]$-$[L]$-$[D]$-$[L]$ 3'. The length of the flank (region F and F') in oligonucleotides with alternating flanks may be as described herein above for these regions, such as 4 to 8, such as 5 to 6 nucleosides, such as 4, 5, 6 or 7 modified nucleosides. It may be advantageous to have at least two LNA nucleosides at the 3' end of the 3' flank (F'), to confer additional exonuclease resistance.

In an embodiment, the gapmer oligonucleotide of the present invention can be represented by the following formula:

$$F_{4-6}\text{-}G_{7-11}\text{-}F_{2-6},$$

wherein F is has a design of $[L]_{1-3}$-$[D]_{1-3}$-$[L]_{1-3}$ and F' has a design of $[L]_{1-2}$-$[D]_{1-2}$-$[L]_{2-4}$, or $[L]_{2-6}$ with the proviso that the overall length of the gapmer regions F-G-F' is at least 16 nucleotides, such as 17 or 18 nucleotides in length.

Thus, the gapmer oligonucleotide of the present invention may comprise at least one alternating flank. Typically: at least the F region is an alternating flank. In some embodiments, the both the F and the F' regions are alternating flanks. In some embodiments, the F region is an alternating flank and the F' region is a uniform flank (i.e. F' consists of only one type of sugar modified nucleosides, such as only beta-D-oxy LNA).

In some embodiments, the design of region F is selected from a design of 3-2-1 (i.e. LLLDDL), 1-1 (i.e. LLLDL), 2-1-2 (LLDLL), 2-1-1 (LLDL) and 1-3-1 (i.e. LDDDL).

In some embodiments, the design of region F is 1-1-3 (i.e. LDLLL) or 1-1-2 (i.e. LDLL). In some embodiments, the design of region F is LL, LLL or LLLL.

Region D' or D" in an Oligonucleotide

The oligonucleotide of the invention may in some embodiments comprise or consist of the contiguous nucleotide sequence of the oligonucleotide which is complementary to the target nucleic acid, such as a gapmer region F-G-F', and further 5' and/or 3' nucleosides. The further 5' and/or 3' nucleosides may or may not be fully complementary to the target nucleic acid. Such further 5' and/or 3' nucleosides may be referred to as region D' and D" herein.

The addition of region D' or D" may be used for the purpose of joining the contiguous nucleotide sequence, such as the gapmer, to a conjugate moiety or another functional group. When used for joining the contiguous nucleotide sequence with a conjugate moiety is can serve as a biocleavable linker. Alternatively, it may be used to provide exonucleoase protection or for ease of synthesis or manufacture.

Region D' and D" can be attached to the 5' end of region F or the 3' end of region F', respectively to generate designs of the following formulas D'-F-G-F', F-G-F'-D" or D'-F-G-F'-D". In this instance the F-G-F' is the gapmer portion of the oligonucleotide and region D' or D" constitute a separate part of the oligonucleotide.

Region D' or D" may independently comprise or consist of 1, 2, 3, 4 or 5 additional nucleotides, which may be complementary or non-complementary to the target nucleic acid. The nucleotide adjacent to the F or F' region is not a sugar-modified nucleotide, such as a DNA or RNA or base modified versions of these. The D' or D' region may serve as a nuclease susceptible biocleavable linker (see definition of linkers). In some embodiments, the additional 5' and/or 3' end nucleotides are linked with phosphodiester linkages, and are DNA or RNA. Nucleotide based biocleavable linkers suitable for use as region D' or D" are disclosed in WO2014/076195, which include by way of example a phosphodiester linked DNA dinucleotide. The use of biocleavable linkers in poly-oligonucleotide constructs is disclosed in WO2015/113922, where they are used to link multiple antisense constructs (e.g. gapmer regions) within a single oligonucleotide.

In one embodiment, the oligonucleotide of the invention comprises ion D' and/or D" in addition to the contiguous nucleotide sequence which constitutes the gapmer.

In some embodiments, the oligonucleotide of the present invention can be represented by the following formulae:

F-G-F'; in particular $F_{1-8}$-$G_{5-16}$-$F'_{2-8}$, such as $F_{4-6}$-$G_{7-11}$-$F'_{2-13}$ D'-F-G-F', in particular $D'_{1-3}$-$F_{1-8}$-$G_{5-16}$-$F'_{2-8}$, such as $D'_{1-3}$-$F_{4-6}$-$G_{7-11}$-$F'_{2-6}$ F-G-F-D", in particular $F_{1-8}$-$G_{5-16}$-$F'_{2-8}$-$D''_{1-3}$ D'-F-G-F'-D", in particular $D'_{1-3}$-$F_{1-8}$-$G_{5-16}$-$F'_{2-8}$-$D''_{1-3}$ In some embodiments, the internucleoside linkage positioned between region D' and region F is a phosphodiester linkage. In some embodiments the internucleoside linkage positioned between region F' and region D" is a phosphodiester linkage.

Conjugate

The term conjugate as used herein refers to an oligonucleotide, which is covalently linked to a non-nucleotide moiety (conjugate moiety or region C or third region). The conjugate moiety may be covalently linked to the antisense oligonucleotide, optionally via a linker group, such as region D' or D".

Oligonucleotide conjugates and their synthesis has also been reported in comprehensive reviews by Manoharan in Antisense Drug Technology, Principles, Strategies, and Applications, S. T. Crooke, ed., Ch. 16, Marcel Dekker, Inc., 2001 and Manoharan, Antisense and Nucleic Acid Drug Development, 2002, 12, 103.

In some embodiments, the non-nucleotide moiety (conjugate moiety) is selected from the group consisting of carbohydrates (e.g. GalNAc), cell surface receptor ligands, drug substances, hormones, lipophilic substances, polymers, proteins, peptides, toxins (e.g. bacterial toxins), vitamins, viral proteins (e.g. capsids) or combinations thereof.

Exemplary conjugate moieties include those capable of binding to the asialoglycoprotein receptor (ASGPR). In particular, tri-valent N-acetylgalactosamine conjugate moieties are suitable for binding to the ASGPR, see for example WO 2014/076196, WO 2014/207232 and WO 2014/179620. Such conjugates serve to enhance uptake of the oligonucleotide to the liver.

In some embodiments, the conjugate is an antibody or an antibody fragment which has a specific affinity for a transferrin receptor, for example as disclosed in WO 2012/143379 herby incorporated by reference. In some embodiments, the non-nucleotide moiety is an antibody or antibody fragment, such as an antibody or antibody fragment that facilitates delivery across the blood-brain-barrier, in particular an antibody or antibody fragment targeting the transferrin receptor.

Linkers

A linkage or linker is a connection between two atoms that links one chemical group or segment of interest to another chemical group or segment of interest via one or more covalent bonds. Conjugate moieties can be attached to the oligonucleotide directly or through a linking moiety (e.g. linker or tether). Linkers serve to covalently connect a third region, e.g. a conjugate moiety (Region C), to a first region, e.g. an oligonucleotide or contiguous nucleotide sequence complementary to the target nucleic acid (region A).

In some embodiments, of the invention the conjugate or oligonucleotide conjugate of the invention may optionally, comprise a linker region (second region or region B and/or region Y) which is positioned between the oligonucleotide or contiguous nucleotide sequence complementary to the target nucleic acid (region A or first region) and the conjugate moiety (region C or third region).

Biocleavable linkers (Region B) comprising or consisting of a physiologically labile bond that is cleavable under conditions normally encountered or analogous to those encountered within a mammalian body. Conditions under which physiologically labile linkers undergo chemical transformation (e.g., cleavage) include chemical conditions such as pH, temperature, oxidative or reductive conditions or agents, and salt concentration found in or analogous to those encountered in mammalian cells. Mammalian intracellular conditions also include the presence of enzymatic activity normally present in a mammalian cell such as from prote-olytic enzymes or hydrolytic enzymes or nucleases. In one embodiment, the biocleavable linker is susceptible to S1 nuclease cleavage. In some embodiments, the physiologi-cally labile linker (biocleavable) comprises between 1 and 10 linked nucleosides, such as 1, 2, 3, 4, 5, 6, 7, 8, 9 or 10 linked nucleosides, such as between 2 and 6 linked nucleo-sides, such as between 2 and 5 linked nucleosides, such as between 2 and 4 linked nucleosides, where at least two consecutive linkages are biocleavable, such as phosphodi-ester linkages, such as at least 3 or 4 or 5 consecutive phosphodiester linkages. Preferably the nucleosides are DNA or RNA.

In one embodiment, the linker between the oligonucle-otide and the conjugate moiety is a physiologically labile linker composed of 2 to 5 consecutive phosphodiester linked nucleosides comprising at least two consecutive phosphodi-ester linkages at the 5' or terminal of the contiguous nucleo-tide sequence of the antisense oligonucleotide.

In some embodiments, the physiologically labile linker comprises or consists of a DNA dinucleotide with a sequence selected from the group consisting of AA, AT, AC, AG, TA, TT, TC, TG, CA, CT, CC, CG, GA, GT, GC, or GG, where there is a phosphodiester linkage between the two DNA nucleosides and at least one further phosphodiester at the 5' or 3' end of the dinucleotide linking either the oligonucleotide of the nucleic acid molecule to the dinucle-otide or the conjugate moiety to the dinucleotide. For example, the linker may by a CA dinucleotide. In some embodiments, the physiologically labile linker comprises or consists of a DNA trinucleotide of sequence AAA, AAT, AAC, AAG, ATA, ATT, ATC, ATG, ACA, ACT, ACC, ACG, AGA, AGT, AGC, AGG, TAA, TAT, TAC, TAG, TTA, TTT, TTC, TAG, TCA, TCT, TCC, TCG, TGA, TGT, TGC, TGG, CAA, CAT, CAC, CAG, CTA, CTG, CTC, CTT, CCA, CCT, CCC, CCG, CGA, CGT, CGC, CGG, GAA, GAT, GAC, CAG, GTA, GTT, GTC, GTG, GCA, GCT, GCC, GCG, GGA, GGT, GGC, or GGG, where there are phosphodiester linkages between the DNA nucleosides and potentially a further phosphodiester at the 5' or 3' end of the trinucleotide. Phosphodiester containing biocleavable linkers are described in more detail in WO 2014/076195 (hereby incor-porated by reference). In a conjugate compound with a biocleavable linker at least about 50% of the conjugate moiety is cleaved from the oligonucleotide, such as at least about 60% cleaved, such as at least about 70% cleaved, such as at least about 80% cleaved, such as at least about 85% cleaved, such as at least about 90% cleaved, such as at least about 95% of the conjugate moiety is cleaved from the oligonucleotide cleaved when compared against a standard.

Region Y refers to linkers that are not necessarily bio-cleavable but primarily serve to covalently connect a con-jugate moiety (region C or third region), to an oligonucle-otide (region A or first region). The region Y linkers may comprise a chain structure or an oligomer of repeating units such as ethylene glycol, amino acid units or amino alkyl groups.

The oligonucleotide conjugates of the present invention can be constructed of the following regional elements A-C, A-B-C, A-B-Y-C, A-Y-B-C or A-Y-C. In some embodi-ments, the linker (region Y) is an amino alkyl, such as a C2-C36 amino alkyl group, including, for example C6 to C12 amino alkyl groups. In some embodiments, the linker (region Y) is a C6 amino alkyl group.

Pharmaceutically Acceptable Salts

The term "pharmaceutically acceptable salts" refers to those salts which retain the biological effectiveness and properties of the free bases or free acids, which are not biologically or otherwise undesirable. The salts are formed with inorganic adds such as hydrochloric acid, hydrobromic acid, sulfuric acid, nitric acid, phosphoric acid, particularly hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, man-delic acid, methanesulfonic acid, ethanesulfonic acid, p-toluenesulfonic acid, salicylic acid, N-acetylcystein. In addition, these salts may be prepared form addition of an inorganic base or an organic base to the free acid. Salts derived from an inorganic base include, but are not limited to, the sodium, potassium, lithium, ammonium, calcium, magnesium salts. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylam-ine, triethylamine, tripropylamine, ethanolamine, lysine, arginine, N-ethylpiperidine, piperidine, polyamine resins. The compounds of the present invention can also be present in the form of zwitterions. Particularly preferred pharma-ceutically acceptable salts of compounds of formula (I) are the salts of hydrochloric acid, hydrobromic acid, sulfuric acid, phosphoric acid and methanesulfonic acid.

Treatment

The terms "treatment". "treating", 'treats' or the like as used herein generally means obtaining a desired pharmaco-logical and/or physiological effect. This effect is therapeutic in terms of partially or completely curing a disease and/or adverse effect attributed to the disease. The term "treatment" as used herein covers any treatment of a disease in a subject and includes: (a) inhibiting the disease; or (b) ameliorating (i.e. relieving) the disease, i.e. causing regression of the disease. A compound that ameliorates and/or inhibits a HBV infection is a compound that treats a HBV infection. Pref-erably, the term "treatment" as used herein relates to medical intervention of an already manifested disorder, like the treatment of an already defined and manifested HBV infec-tion or cancer.

Prevention

Herein the term "preventing", "prevention" or "prevents" relates to a prophylactic treatment, i.e. to a measure or procedure the purpose of which is to prevent, rather than to cure a disease. Prevention means that a desired pharmaco-logical and/or physiological effect is obtained that is pro-phylactic in terms of completely or partially preventing a disease or symptom thereof. Accordingly, herein "prevent-ing a HBV infection" includes preventing a HBV infection from occurring in a subject, and preventing the occurrence of symptoms of a HBV infection. In the present invention in particular the prevention of HBV infection in children from HBV infected mothers are contemplated. Also contemplated is the prevention of an acute HBV infection turning into a chronic HBV infection.

Patient

For the purposes of the present invention, the "subject" or "patient" may be a vertebrate. In context of the present invention, the term "subject" includes both humans and other animals, particularly mammals, and other organisms. Thus, the herein provided means and methods are applicable to both human therapy and veterinary applications. Accord-ingly, herein the subject may be an animal such as a mouse, rat, hamster, rabbit, guinea pig, ferret, cat, dog, chicken, sheep, bovine species, horse, camel, or primate. Preferably, the subject is a mammal. More preferably, the subject is human. In some embodiments, the patient is suffering from a disease as referred to herein, such as HBV infection or cancer. In some embodiments, the patient is susceptible to said disease.

DETAILED DESCRIPTION OF THE INVENTION

One aspect of the present invention is an enhanced antisense oligonucleotide targeting FUBP1, or a conjugate thereof for use in the treatment and/or prevention of a disease selected from the group consisting of HBV infection, such as chronic HBV infection and proliferative diseases such as cancer, in particular hepatocellular carcinoma.

An embodiment of the invention is an antisense oligonucleotide of the invention or conjugate thereof, which is capable of reducing HBV DNA, such as cccDNA, and HBV RNA transcripts, such as pgRNA, in an infected cell, such as an HBV infected cell.

In a further embodiment, the antisense oligonucleotide of the invention or conjugate thereof is capable of reducing HBsAg and/or HBeAg in vivo in an HBV infected individual.

Another aspect of the present invention is the use of the antisense oligonucleotides of the invention or the conjugate thereof in the treatment and/or prevention of Hepatitis B virus (HBV) infection, in particular a chronic HBV infection or in the treatment of cancer where FUBP1 is over-expressed.

The Antisense Oligonucleotide of the Invention

The enhanced antisense oligonucleotides of the invention or conjugates thereof are potentially excellent FUBP1 inhibitors since they can target the FUBP1 transcript and may promote its degradation either via RNase H cleavage.

One aspect of the present invention is an enhanced antisense oligonucleotide or conjugates thereof for use in treatment and/or prevention of HBV infection, or in the treatment of cancer.

The present section describes enhanced antisense oligonucleotides or conjugates thereof suitable for use in treatment and/or prevention of HBV infection, or in the treatment of cancer.

The antisense oligonucleotides of the present invention or conjugates thereof are capable of inhibiting expression of FUBP1 in vitro and in vivo. The inhibition is achieved by hybridizing an antisense oligonucleotide to a target nucleic acid encoding FUBP1 or which is involved in the regulation of FUBP1. The target nucleic acid may be a mammalian FUBP1 sequence, such as a sequence selected from the group consisting of SEQ ID NO: 1, 2, 3, 4 and/or 5.

The oligonucleotide of the invention is thus an antisense oligonucleotide, which targets FUBP1

In some embodiments, the antisense oligonucleotide of the invention or conjugates thereof is capable of modulating the expression of the target by inhibiting or down-regulating it. Preferably, such modulation produces an inhibition of expression of at least 20% compared to the normal expression level of the target, more preferably at least 30%, at least 40%, at least 50%, at least 60%, at least 70%, at least 80%, or at least 90% inhibition compared to the normal expression level of the target. In some embodiments, the antisense oligonucleotide of the invention or conjugates thereof may be capable of inhibiting expression levels of FUBP1 mRNA by at least 50% or 60% in vitro using 25 μM in PXB-PHH cells. In some embodiments, the antisense oligonucleotide of the invention or conjugates thereof may be capable of inhibiting expression levels of FUBP1 protein by at least 50% in vitro using 25 μM in PXB-PHH cells, this range of target reduction is advantageous in terms of selecting antisense oligonucleotides with good correlation to the cccDNA reduction. Suitably, the examples provide assays, which may be used to measure FUBP1 RNA inhibition (e.g. Example 1 or 2). The target inhibition is triggered by the hybridization between a contiguous nucleotide sequence of the antisense oligonucleotide and the target nucleic acid. In some embodiments, the antisense oligonucleotide of the invention comprises mismatches between the antisense oligonucleotide and the target nucleic acid. Despite mismatches hybridization to the target nucleic acid may still be sufficient to show a desired inhibition of FUBP1 expression. Reduced binding affinity resulting from mismatches may advantageously be compensated by increased number of nucleotides in the oligonucleotide and/or an increased number of modified nucleosides capable of increasing the binding affinity to the target, such as 2' sugar modified nucleosides, including LNA, present within the antisense oligonucleotide sequence.

An aspect of the present invention relates to an enhanced antisense oligonucleotide of 12 to 30, such as 12 to 22, such as 16 to 20 nucleotides in length, which comprises a contiguous nucleotide sequence of at least 12 nucleotides in length, such as 14, 15, 16, or 17 nucleotides in length, with at least 90% complementarity, such as 100% complementarity, a target sequence from nucleotides 16184-16205, such as a target sequence selected from 16184-16200, 16186-16203, 16188-16205 and 16189-16205 of SEQ ID NO: 1. In particular, antisense oligonucleotides which are capable of inhibiting the expression of FUBP1, i.e. are capable of reducing a FUBP1 nucleic acid such as FUBP1 mRNA are considered part of the present invention.

In some embodiments, the antisense oligonucleotide of the present invention comprises a contiguous nucleotide sequence of 12 to 22 nucleotides, such as of 15 to 20 nucleotides, with at least 90% complementarity, such as fully complementary, to the target nucleic acid of SEQ ID NO: 10.

In some embodiments, antisense oligonucleotide comprises a contiguous nucleotide sequence of 15 to 18 nucleotides, such as of 17 or 18 nucleotides, with at least 90% complementarity, such as fully complementary, to the target nucleic acid of SEQ ID NO: 11.

In some embodiments, antisense oligonucleotide comprises a contiguous nucleotide sequence of 15 to 18 nucleotides, such as of 17 or 18 nucleotides, with at least 90% complementarity, such as fully complementary, to the target nucleic acid of SEQ ID NO: 18.

In some embodiments, the antisense oligonucleotide comprises a contiguous nucleotide sequence of 15 to 22 nucleotides, such as of 15 to 18 nucleotides, such as of 17 or 18>nucleotides with at least 90% complementarity, such as fully complementary, to the target nucleic acid selected from the following regions of SEQ ID NO: 1: 16184-16205, 16184-16200, 16186-16203, 16188-16205 and 16189-16205 of SEQ ID NO: 1. Moreover, it may comprise a contiguous nucleotide sequence of 15 to 22 nucleotides, such as of 15 to 18 nucleotides, such as of 17 or 18 nucleotides with at least 90% complementarity, such as fully complementary, to the target nucleic acid selected from the following region of SEQ ID NO: 1: 30536-30553.

In some embodiments, the antisense oligonucleotide comprises a contiguous sequence of 12 to 30 nucleotides in length, which is at least 90% complementary, such as at least 91%, such as at least 92%, such as at least 93%, such as at least 94%, such as at least 95%, such as at least 96%, such as at least 97%, such as at least 9% or 100% complementary with a region of the target nucleic acid or a target sequence.

It is advantageous if the antisense oligonucleotide of the invention, or contiguous nucleotide sequence thereof is fully complementary (100% complementary) to a region of the target nucleic acid, or in some embodiments may comprise one or two mismatches between the oligonucleotide and the target nucleic acid.

In some embodiments, the antisense oligonucleotide sequence is 100% complementary to a corresponding target nucleic acid of SEQ ID NO: 1.

In some embodiments, the antisense oligonucleotide or the contiguous nucleotide sequence of the invention is at least 95% complementarity, such as fully (or 100%) complementary, to the target nucleic acid of SEQ ID NO: 1 and SEQ ID NO: 4.

In some embodiments, the antisense oligonucleotide comprises contiguous nucleotide sequence of 15 to 22 nucleotides in length with at least 90% complementary, such as 100% complementarity, to a corresponding target sequence present in SEQ ID NO: 1, wherein the target sequence is selected from nucleotides 16184-16205, 16184-16200, 16186-16203, 16188-16205, 16189-16205 and 30536-30553 of SEQ ID NO: 1.

In some embodiments, the contiguous nucleotide sequence of the antisense oligonucleotide is at least 90% complementary, advantageously 100% complementary, to a target site sequence of SEQ ID NO: 10.

In some embodiments, the contiguous nucleotide sequence of the antisense oligonucleotide is at least 90% complementary, advantageously 100% complementary, to a target site sequence of SEQ ID NO: 11.

In some embodiments, the contiguous nucleotide sequence of the antisense oligonucleotide is at least 90% complementary, advantageously 100% complementary, to a target site sequence of SEQ ID NO: 15.

In some embodiments, the contiguous nucleotide sequence of the antisense oligonucleotide is at least 90% complementary, advantageously 100% complementary, to a target site sequence of SEQ ID NO: 19.

In some embodiments, the contiguous nucleotide sequence comprises a sequence of nucleobases selected from the group consisting of SEQ ID NO: 6, 7, 8, 9 and 18, or at least 14 contiguous nucleotides thereof, such as 17 or 18 contiguous nucleotides thereof.

In some embodiments, the antisense oligonucleotide of the invention or contiguous nucleotide sequence thereof, comprises or consists of 10 to 30 nucleotides in length, such as from 12 to 25, such as 11 to 22, such as from 12 to 20, such as from 14 to 18 or 16 to 18 contiguous nucleotides in length.

In some embodiments, the antisense oligonucleotide or contiguous nucleotide sequence thereof comprises or consists of 22 or less nucleotides, such as 20 or less, or 18 or less nucleotides. For example, antisense oligonucleotide or contiguous nucleotide sequence thereof may comprise 14, 15, 16 or 17 nucleotides. It is to be understood that any range given herein includes the range endpoints. Accordingly, if an oligonucleotide is said to include from 10 to 30 nucleotides, both 10 and 30 are included.

The invention provides antisense oligonucleotides according to the invention, such as antisense oligonucleotides 12-24 nucleotides in length, such as 12-18 nucleotides in length, wherein the antisense oligonucleotide comprises a contiguous nucleotide sequence comprising at least 12, such as at least 13, such as at least 14, such as at least 15 or at least 16 contiguous nucleotides present in SEQ ID NO: 6.

The invention provides antisense oligonucleotides according to the invention, such as antisense oligonucleotides 12-24 nucleotides in length, such as 12-18 nucleotides in length, wherein the antisense oligonucleotide comprises a contiguous nucleotide sequence comprising at least 12, such as at least 13, such as at least 14, such as at least 15 or at least 16 contiguous nucleotides present in SEQ ID NO: 7

The invention provides antisense oligonucleotides according to the invention, such as antisense oligonucleotides 12-24 nucleotides in length, such as 12-18 nucleotides in length, wherein the antisense oligonucleotide comprises a contiguous nucleotide sequence comprising at least 12, such as at least 13, such as at least 14, such as at least 15 or at least 16 contiguous nucleotides present in SEQ ID NO: 8.

The invention provides antisense oligonucleotides according to the invention, such as antisense oligonucleotides 12-24 nucleotides in length, such as 12-18 nucleotides in length, wherein the antisense oligonucleotide comprises a contiguous nucleotide sequence comprising at least 12, such as at least 13, such as at least 14, such as at least 15 or at least contiguous nucleotides present in SEQ ID NO: 9.

The invention provides antisense oligonucleotides according to the invention, such as antisense oligonucleotides 12-24 nucleotides in length, such as 12-18 nucleotides in length, wherein the antisense oligonucleotide comprises a contiguous nucleotide sequence comprising at least 12, such as at least 13, such as at least 14, such as at least 15, at least 16, at least 17 or 18 contiguous nucleotides present in SEQ ID NO: 18.

In some embodiments, the contiguous nucleotide sequence comprises or consists of 12, 13, 14, 15, 16, 17, 18, 19, 20, 21 or 22 contiguous nucleotides in length, such as 16, 17 or 18 contiguous nucleotides.

In some embodiments, the antisense oligonucleotide or contiguous nucleotide sequence thereof comprises or consists of a sequence selected from SEQ ID NO: 6, 7, 8, 9 and 18.

In advantageous embodiments, the antisense oligonucleotide comprises one or more sugar modified nucleosides, such as one or more 2' sugar modified nucleosides, such as one or more 2' sugar modified nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides. It is advantageous if one or more of the modified nucleoside(s) is a locked nucleic acid (LNA).

In some embodiments, the contiguous nucleotide sequence comprises LNA nucleoside In some embodiments, the contiguous nucleotide sequence comprises LNA nucleosides and DNA nucleosides.

In some embodiments, the contiguous nucleotide sequence comprises 2'-O-methoxyethyl (2'MOE) nucleosides.

In some embodiments, the contiguous nucleotide sequence comprises 2'-O-methoxyethyl (2'MOE) nucleosides and DNA nucleosides.

Advantageously, the 3' most nucleoside of the antisense oligonucleotide; or contiguous nucleotide sequence thereof is a 2' sugar modified nucleoside.

Advantageously, the antisense oligonucleotide comprises at least one modified internucleoside linkage, such as phosphorothioate or phosphorodithioate.

In some embodiments, the at least one internucleoside linkage in the contiguous nucleotide sequence is a phosphorothioate internucleoside linkages.

In some embodiments, at least one internucleoside linkage in the contiguous nucleotide sequence is a phosphorodithioate internucleoside linkages.

In some embodiments, at least one internucleoside linkage in the contiguous nucleotide sequence is a phosphodiester internucleoside linkages.

In some embodiments, all the internucleoside linkages within the contiguous nucleotide sequence are phosphorothioate internucleoside linkages.

In some embodiments, at least 75% the internucleoside linkages within the antisense oligonucleotide, or contiguous nucleotide sequence thereof, are phosphorothioate internucleoside linkages.

In some embodiments, all the internucleoside linkages within the antisense oligonucleotide, or contiguous nucleotide sequence thereof, are phosphorothioate internucleoside linkages.

In an advantageous embodiment of the invention the antisense oligonucleotide of the invention is capable of In some embodiments of the invention, the LNA gapmer is an alternating flank LNA gapmer. In some embodiments, the alternating flank LNA gapmer comprises at least one alternating flank (such as flank F). In some embodiments, the alternating flank LNA gapmer comprises one alternating flank (such as flank F) and one uniform flank (such as flank F'). In some embodiments, the alternating flank LNA gapmer comprises two alternating flanks. For example, the LNA gapmer may have a design selected from the following designs: 3-2-1-9-2, 3-1-1-10-2, 2-1-2-10-3, 2-1-1-11-3, 2-1-1-10-1-1-2, 2-1-1-10-4, 1-3-1-7-1-1-3, and 3-2-1-9-3. Alternatively, the LNA gapmer may have the following design: 1-1-3-9-1-1-2.

Table 6 lists preferred designs for each motif sequence.

The invention provides the following oligonucleotide compound (Table 6):

TABLE 6 list of oligonucleotide motif sequences of the invention (indicated by SEQ ID NO), designs of these, as well as specific oligonucleotide compounds of the invention (indicated by CMP ID NO) designed based on the motif sequence.

| SEQ ID NO | Motif sequence | position on SEQ ID NO: 1 Start | end | Design | CMP ID NO | Oligonucleotide Compound |
|---|---|---|---|---|---|---|
| 6 | CTTATGCTTTTTATGGT | 16189 | 16205 | 3-2-1-9-2 | 6_1 | CTTatGcttttatgGT |
| 6 | CTTATGCTTTTTATGGT | 16189 | 16205 | 3-1-1-10-2 | 6_2 | CTTaTgcttttatgGT |
| 7 | CTTATGCTTTTTATGGTT | 16188 | 16205 | 2-1-2-10-3 | 7_1 | CTtATgcttttatgGTT |
| 7 | CTTATGCTTTTTATGGTT | 16188 | 16205 | 2-1-1-11-3 | 7_2 | CTtAtgcttttatgGTT |
| 7 | CTTATGCTTTTTATGGTT | 16188 | 16205 | 2-1-1-10-1-1-2 | 7_3 | CTtAtgcttttatGgTT |
| 7 | CTTATGCTTTTTATGGTT | 16188 | 16205 | 2-1-1-10-4 | 7_4 | CTtAtgcttttatGGTT |
| 8 | GCTTTTTATGGTTTCAC | 16184 | 16200 | 1-3-1-7-1-1-3 | 8_1 | GcttTttatggtTtCAC |
| 9 | TATGCTTTTTATGGTTTC | 16186 | 16203 | 3-2-1-9-3 | 9_1 | TATgcTttttatggtTTC |
| 18 | ACCAATTTTCATTTCTAC | 30536 | 30553 | 1-1-3-9-1-1-2 | 18_1 | AcCAattttcatttCtAC | recruiting RNase H, such as RNase H1. In some embodiments, the antisense oligonucleotide of the invention, or the contiguous nucleotide sequence thereof is a gapmer.

In some embodiments, the antisense oligonucleotide, or contiguous nucleotide sequence thereof, consists or comprises a gapmer of formula 5'-F-G-F'-3'.

In some embodiments, region G consists of 6-16 DNA nucleosides, such as 7 to 12 DNA nucleosides. In some embodiments, region F comprises 4 to 6 nucleosides and/or region F' comprises 2 to 6 nucleosides.

In some embodiments, region F and F each comprise at least one LNA nucleoside.

In some embodiments of the oligonucleotide of the present invention, all LNA nucleosides are beta-D-oxy LNA nucleosides.

In some embodiments, the oligonucleotide of the present invention is a LNA gapmer with uniform flanks.

The heading "Oligonucleotide compound" in the table represents specific designs of a motif sequence. Capital letters are beta-D-oxy LNA nucleosides, lowercase letters are DNA nucleosides, all LNA C are 5-methyl cytosine, all internucleoside linkages are phosphorothioate internucleoside linkages. The heading "Designs" refers to the gapmer design, F-G-F'. In gapmers with alternating flank designs the flanks of the oligonucleotide are annotated as a series of integers, representing a number of beta-D-oxy LNA nucleosides (L) followed by a number of DNA nucleosides (D). For example, a flank with a 2-2-1 motif represents LLDDL. Both flanks have a beta-D-oxy LNA nucleoside at the 5' and 3' terminal. The gap region (G), which is constituted of a number of DNA nucleosides is located between the flanks.

For some embodiments of the invention, the oligonucleotide is selected from the group of oligonucleotide compounds with CMP ID NO: 6_1, 6_2, 7_1, 7_2, 7_3, 7_4; 8_1 and 9_1 (see Table 6). For example, the compound may be the compound with CMP ID NO: 7_3.

In an alternative embodiment, the oligonucleotide is oligonucleotide the compound with CMP ID NO: 18_1 (see Table 6).

In all instances, the F-G-F' design may further include region D' and/or D" as described in the "Definitions" section under "Region D' or D" in an oligonucleotide". In some embodiments, the oligonucleotide of the invention has 1, 2 or 3 phosphodiester linked nucleoside units, such as DNA units, at the 5' or 3' end, such as at the 5' end, of the gapmer region. In some embodiments, the oligonucleotide of the invention consists of two 5' phosphodiester linked DNA nucleosides followed by a F-G-F' gapmer region as defined above. Oligonucleotides that contain phosphodiester linked DNA units at the 5' or 3' end are suitable for conjugation and may further comprise a conjugate moiety as described herein. For delivery to the liver ASGPR targeting moieties are particular advantageous as conjugate moieties, see the Conjugate section for further details.

Conjugates

Since HBV infection primarily affects the hepatocytes in the liver it is advantageous to conjugate the enhanced antisense oligonucleotide of the invention to a conjugate moiety that will increase the delivery of the antisense oligonucleotide to the liver compared to the unconjugated antisense oligonucleotide. In one embodiment, liver targeting moieties are selected from moieties comprising cholesterol or other lipids or conjugate moieties capable of binding to the asialoglycoprotein receptor (ASGPR).

In some embodiments, the invention provides a conjugate comprising an antisense oligonucleotide of the invention covalently attached to a conjugate moiety.

The asialoglycoprotein receptor (ASGPR) conjugate moiety comprises one or more carbohydrate moieties capable of binding to the asialoglycoprotein receptor (ASPGR targeting moieties) with affinity equal to or greater than that of galactose. The affinities of numerous galactose derivatives for the asialoglycoprotein receptor have been studied (see for example: Jobst, S. T. and Drickamer, K. JB. C. 1996, 271, 6686) or are readily determined using methods typical in the art.

In one embodiment, the conjugate moiety comprises at least one asialoglycoprotein receptor-targeting moiety selected from group consisting of galactose, galactosamine, N-formyl-galactosamine, N-acetylgalactosamine, N-propionyl-galactosamine, N-n-butanoyl-galactosamine and N-isobutanoylgalactosamine. Advantageously the asialoglycoprotein receptor-targeting moiety is N-acetylgalactosamine (GalNAc).

To generate the ASGPR conjugate moiety the ASPGR targeting moieties (preferably GalNAc) can be attached to a conjugate scaffold. Generally, the ASPGR targeting moieties can be at the same end of the scaffold. In one embodiment, the conjugate moiety consists of two to four terminal GalNAc moieties linked to a spacer, which links each GalNAc moiety to a brancher molecule that can be conjugated to the antisense oligonucleotide.

In a further embodiment, the conjugate moiety is monovalent, di-valent, tri-valent or tetra-valent with respect to asialoglycoprotein receptor-targeting moieties. Advantageously the asialoglycoprotein receptor-targeting moiety comprises N-acetylgalactosamine (GalNAc) moieties.

GalNAc conjugate moieties can include, for example, those described in WO 2014/179620 and WO 2016/055601 and PCT/EP2017/059080 (hereby incorporated by reference as well as small peptides with GalNAc moieties attached such as Tyr-Glu-Glu-(aminohexyl GalNAc)3 (YEE(ahGalNAc)3; a glycotripeptide that binds to asialoglycoprotein receptor on hepatocytes, see, e.g., Duff, et al., Methods Enzymol, 2000, 313, 297); lysine-based galactose clusters (e.g., L3G4; Biessen, et al., Cardovasc. Med., 1999, 214); and cholane-based galactose clusters (e.g., carbohydrate recognition motif for asialoglycoprotein receptor).

The ASGPR conjugate moiety, in particular a trivalent GalNAc conjugate moiety, may be attached to the 3'- or 5'-end of the oligonucleotide using methods known in the art. In one embodiment, the ASGPR conjugate moiety is linked to the 5'-end of the oligonucleotide.

Figure 2:
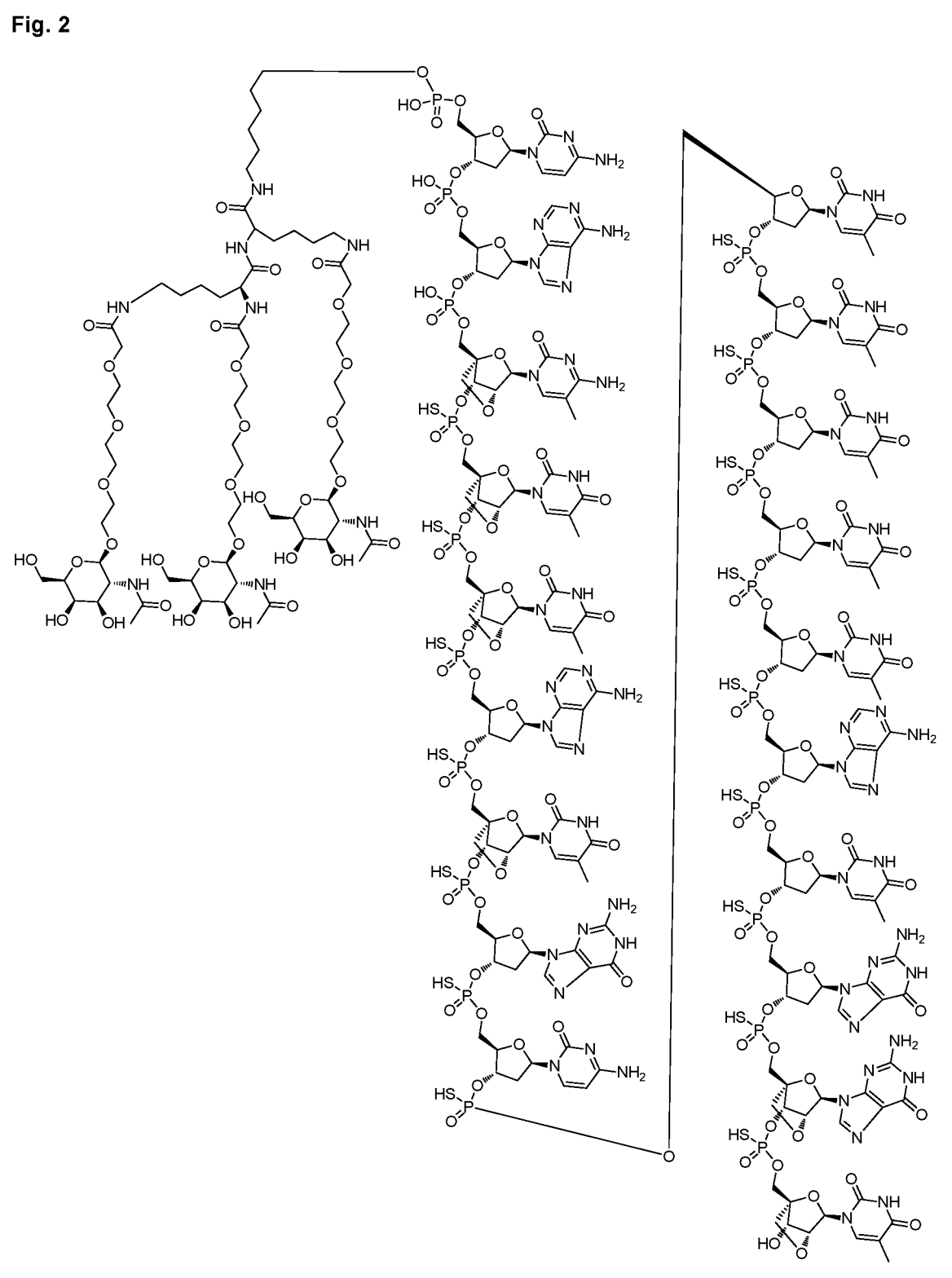
Figure 2A:
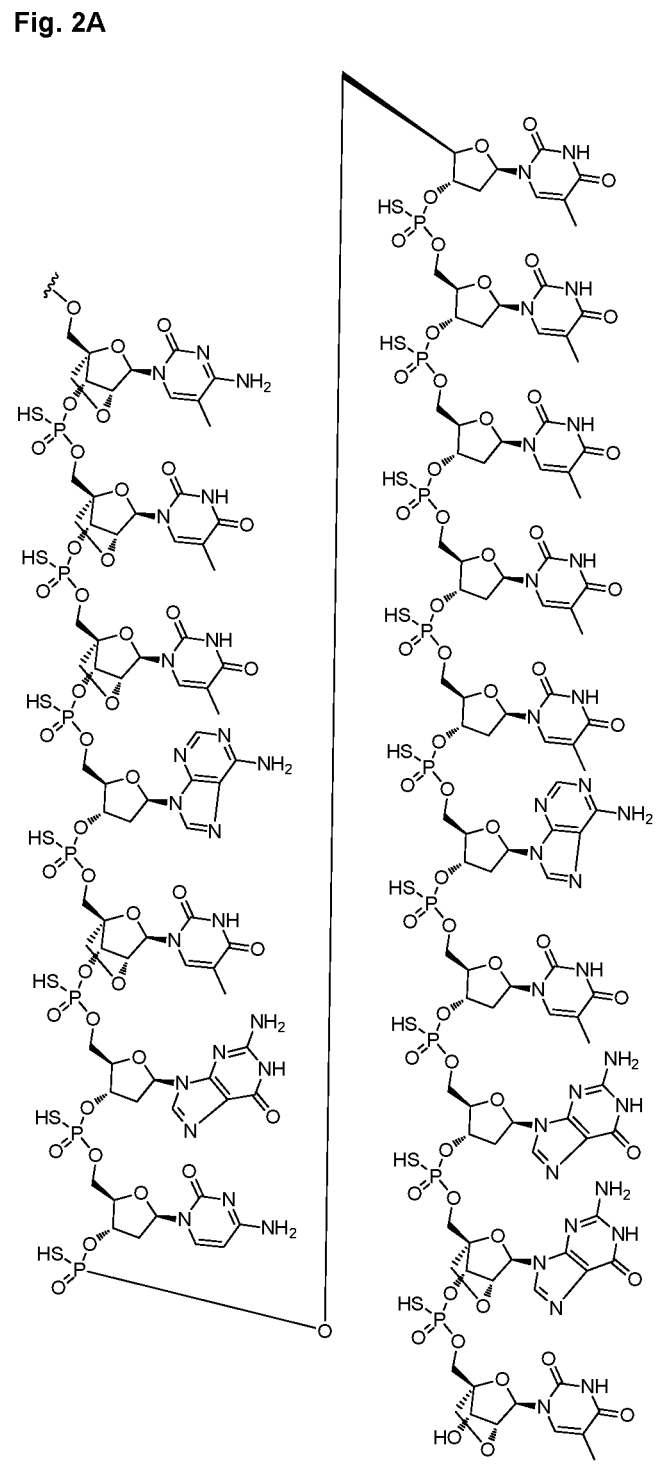
Figure 9:
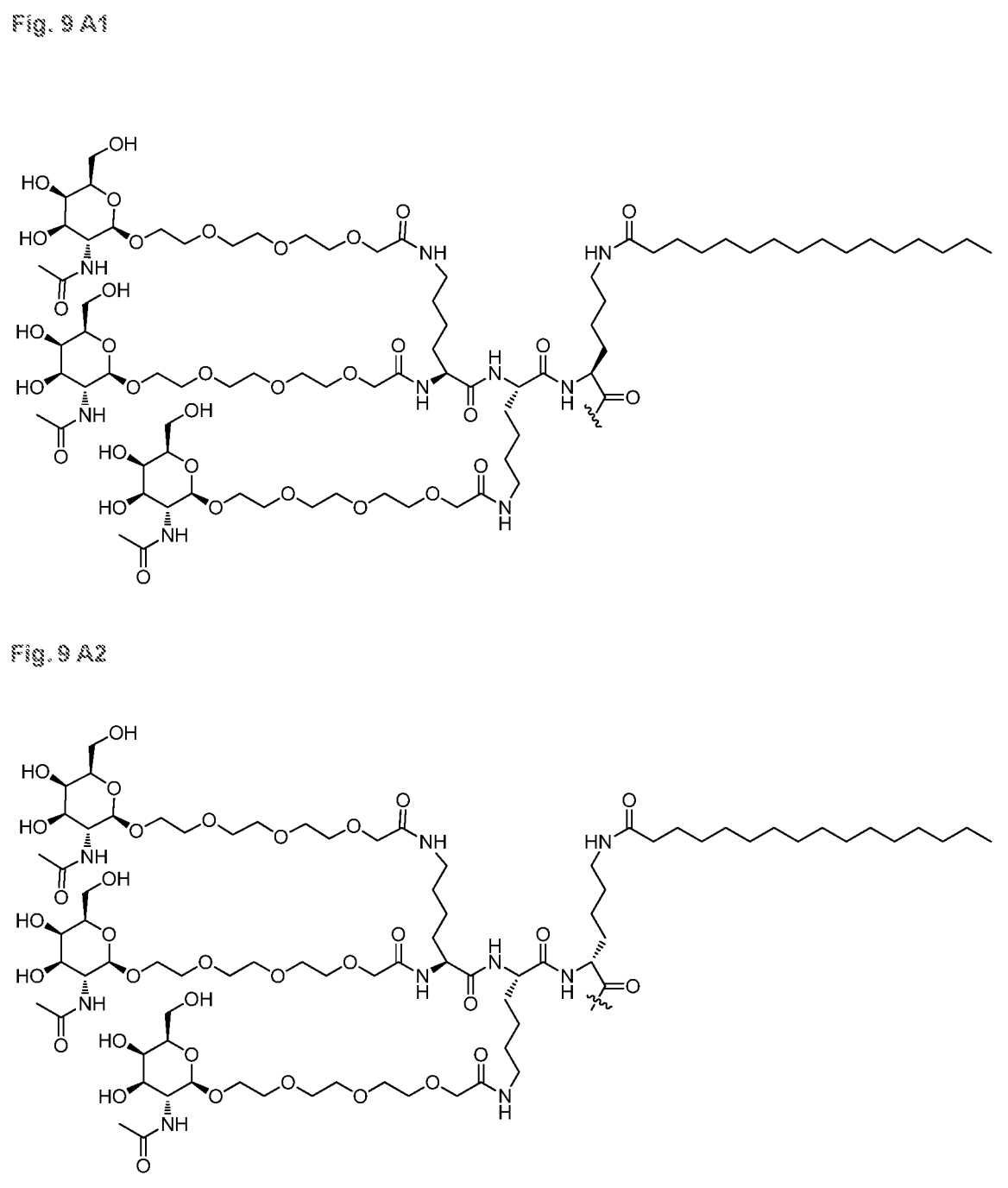
Figure 9:
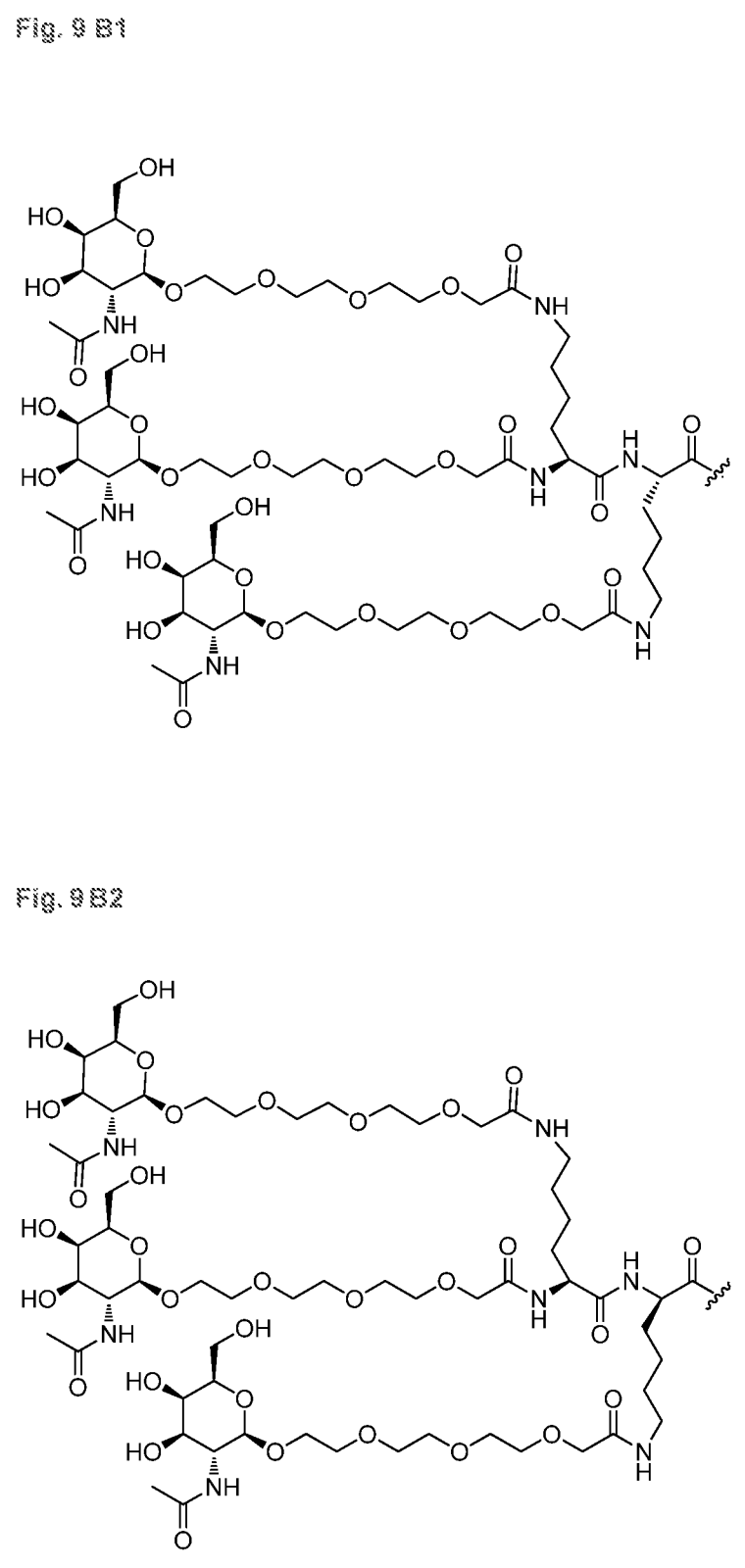
Figure 9:
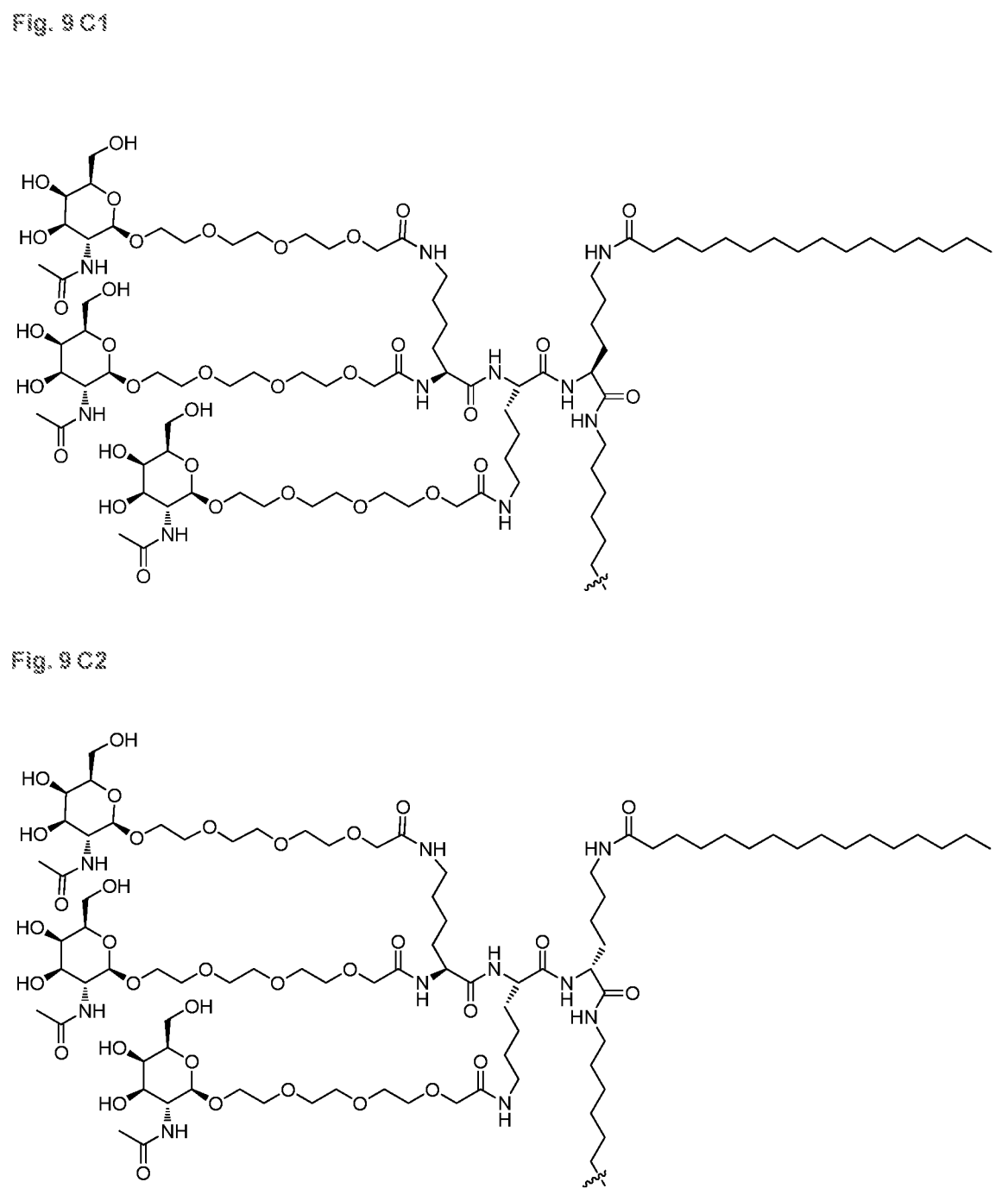
Figure 9:
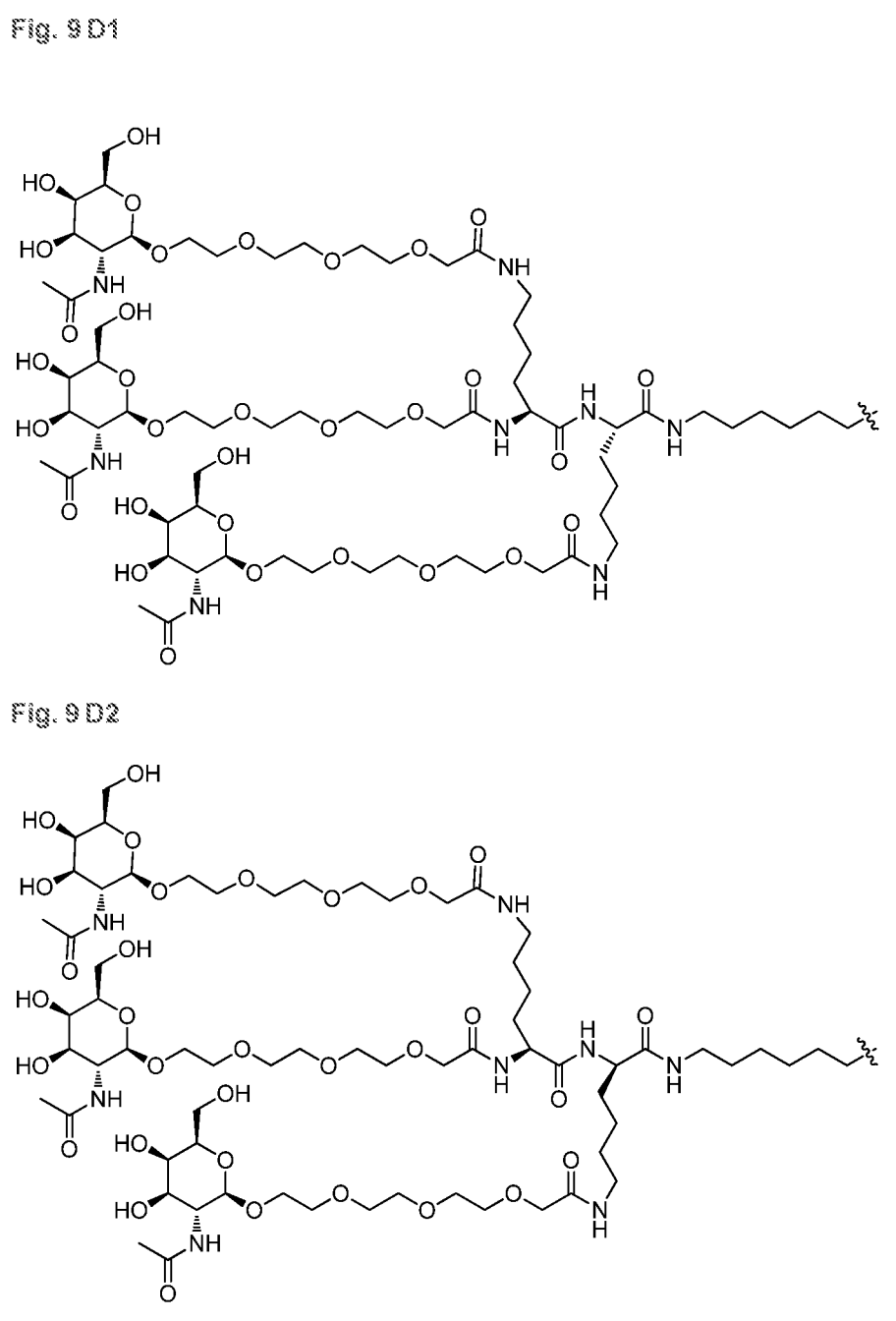
Figures 9E1, 9F1:
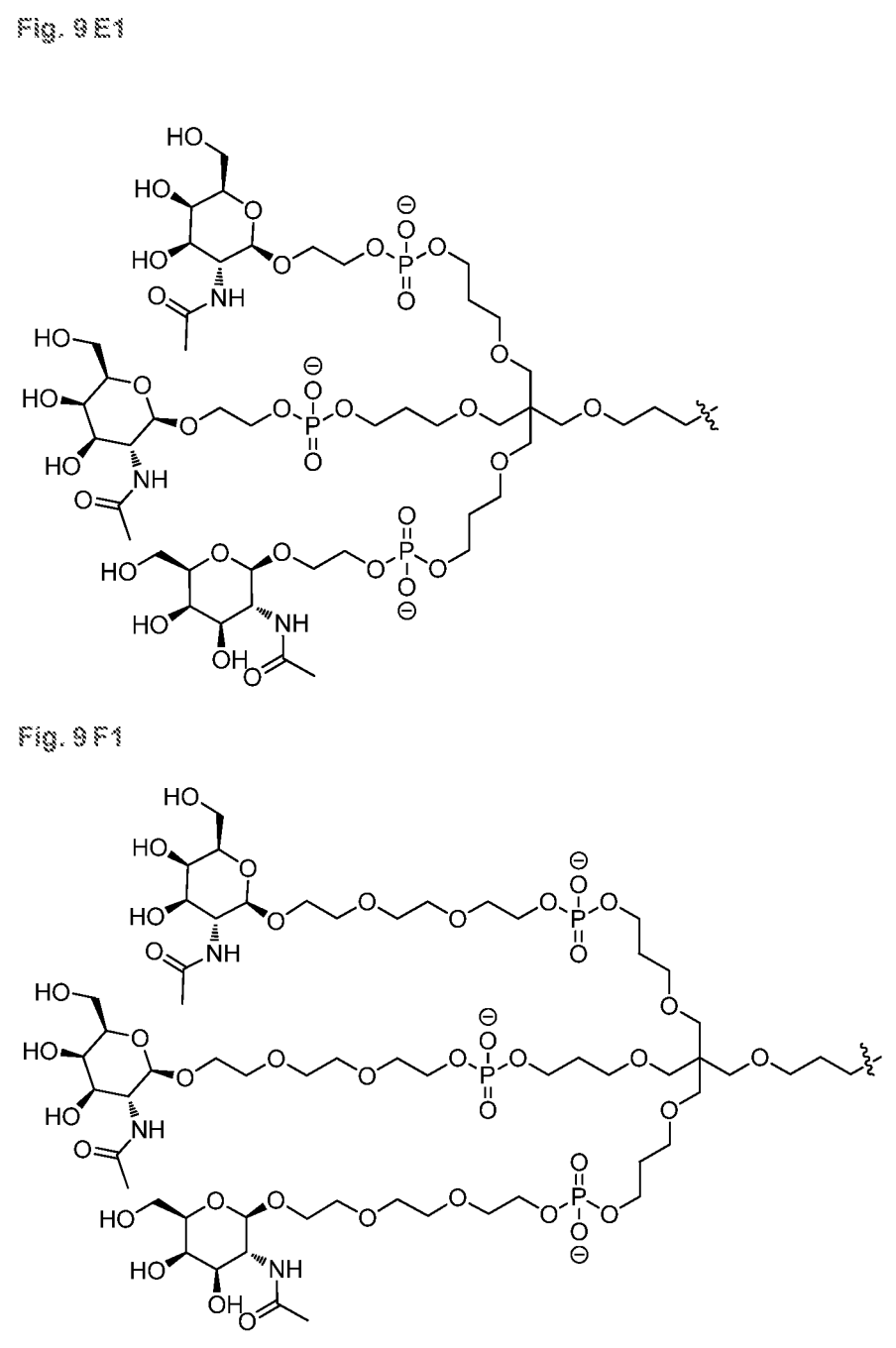
Figure 9:
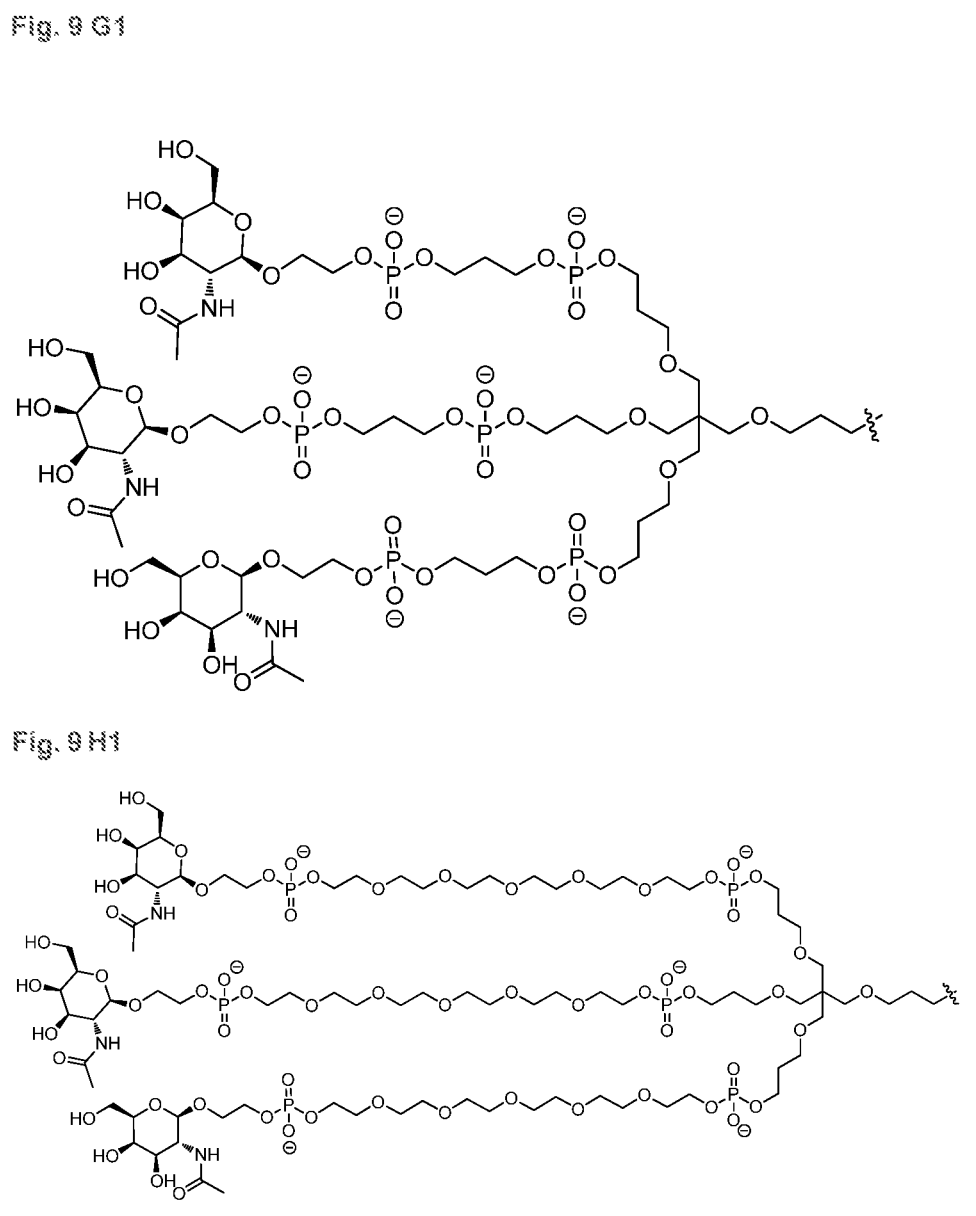
Figure 9:
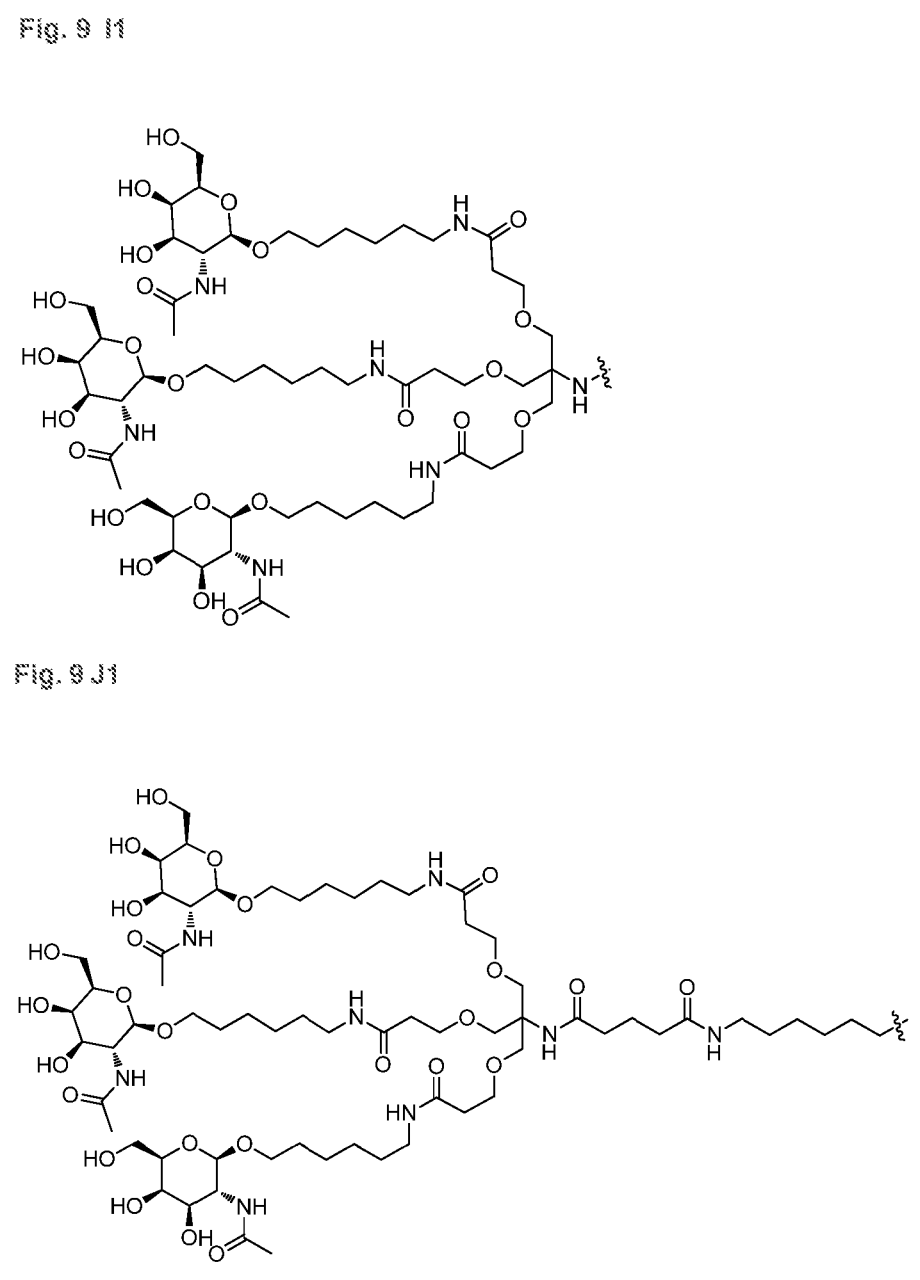
Figure 9:
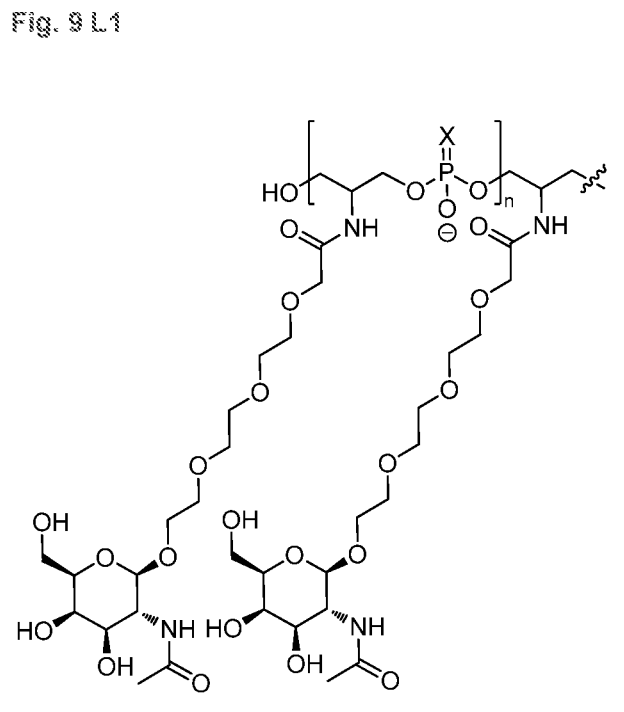
Figure 9:
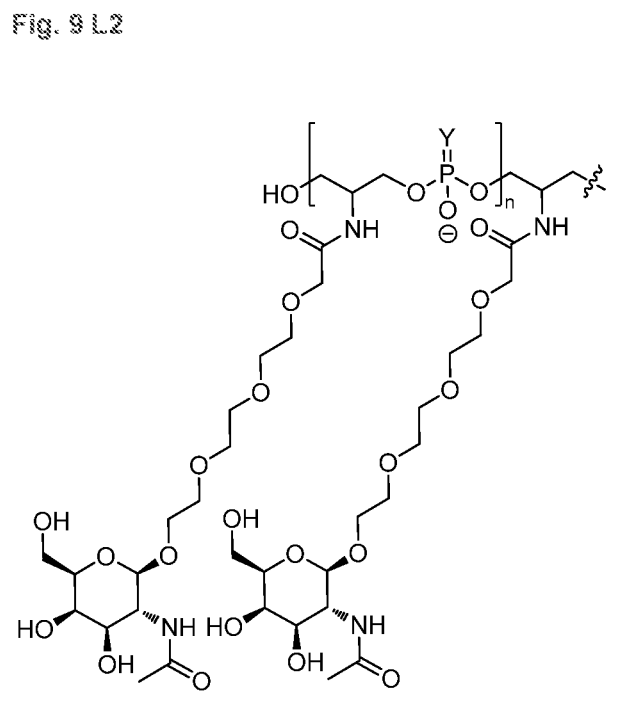

In one embodiment, the conjugate moiety is a tri-valent N-acetylgalactosamine (GalNAc), such as those shown in FIG. 9A1, 9A2; 9C1, 9C2, 9D1, 9D2, 9E1, 9F1, 9G1, 9H1, 9I1, 9J1, 9L1 and 9L2, or the conjugate moiety is a mixture of 9A1 and 9A2; a mixture of 9C1 and 9C2 or a mixture of 9D1 and 9D2, in particular a tri-valent Nacetylgalactosamine (GalNAc), as shown in FIG. 9D1 or 9D2 or a mixture thereof.

In some embodiments, the conjugate is selected from the group consisting of $5'-GN2-C6_0C0a_0 \ ^mC_sT_sT_sa_st_sG_sc_st_st_st_st_sa_st_sg_sG_sT,$ $5'-GN2-C6_0C0a_0 \ ^mC_sT_sT_sa_sT_sg_sc_st_st_st_st_sa_st_sg_sG_sT,$ $5'-GN2-C6_0C0a_0 \ ^mC_sT_st_sa_sT_sg_sc_st_st_st_st_sa_st_sg_sG_sT_sT,$ $5'-GN2-C6_0C0a_0 \ ^mC_sT_st_sA_st_sg_sc_st_st_st_st_sa_st_sg_sG_sT_sT,$ $5'-GN2-C6_0C0a_0 \ ^mC_sT_st_sA_st_sg_sc_st_st_st_st_sa_st_sG_sg_sT_sT,$ $5'-GN2-C6_0C0a_0 \ ^mC_sT_st_sA_st_sg_sc_st_st_st_st_sa_st_sG_sG_sT_sT,$ $5'-GN2-C6_0C0a_0 \ G_sC_st_st_sT_st_st_sa_st_sg_sg_st_sT_st_s^mC_sA_s^mC, \ and$ $5'-GN2-C6_0C0a_0 \ T_sA_sT_sg_sc_sT_st_st_st_sa_st_sg_sg_st_sT_sT_s^mC,$ $5'-GN2-C6_0C0a_0 \ A_sc_s^mC_sA_sA_st_st_st_sc_sa_st_st_s^mC_stA_s^mC$ wherein a capital letter represents a beta-D-oxy LNA nucleoside, a lower case letter represents a DNA nucleoside, wherein each LNA cytosine is 5-methyl cytosine, and wherein subscript s represents a phosphorothioate internucleoside linkage, and a subscript o represents a phosphodiester internucleoside linkage, and GN2-C6 is tri-valent N-acetylgalactosamine (GalNAc) as shown in FIG. 9D, such as a tri-valent N-acetylgalactosamine (GalNAc) as shown in FIG. 9D-1 or FIG. 9D2, or a mixture of both, preferably bound via a phosphodiester linkage at the 5' end of the oligonucleotide. Chemical drawings representing some of the molecules are shown in FIGS. 1 to 8 and 8.1.

In some embodiments, the conjugate is the conjugate as shown in FIG. 1.

In some embodiments, the conjugate is the conjugate as shown in FIG. 2.

Figure 3:
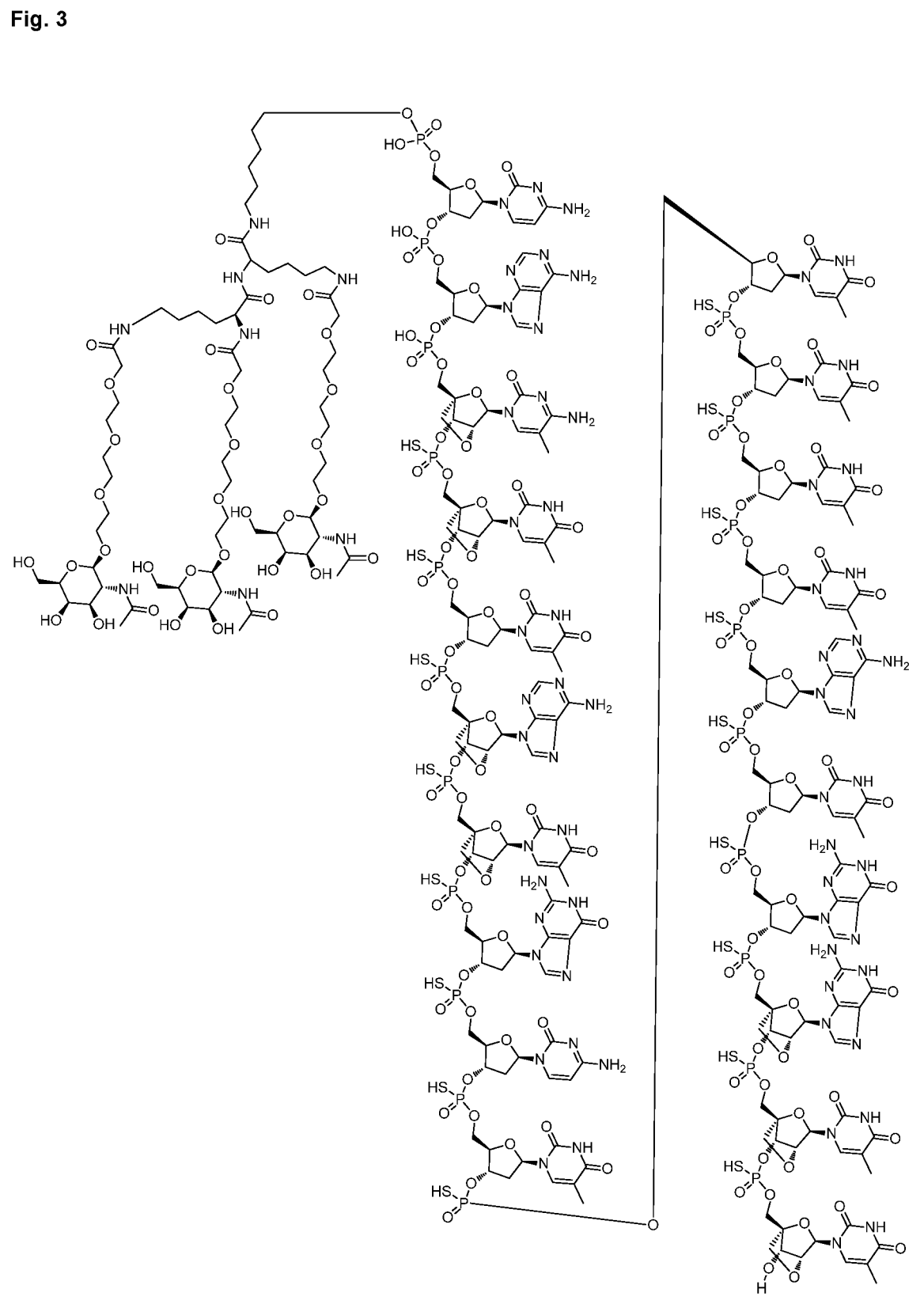
Figure 3A:
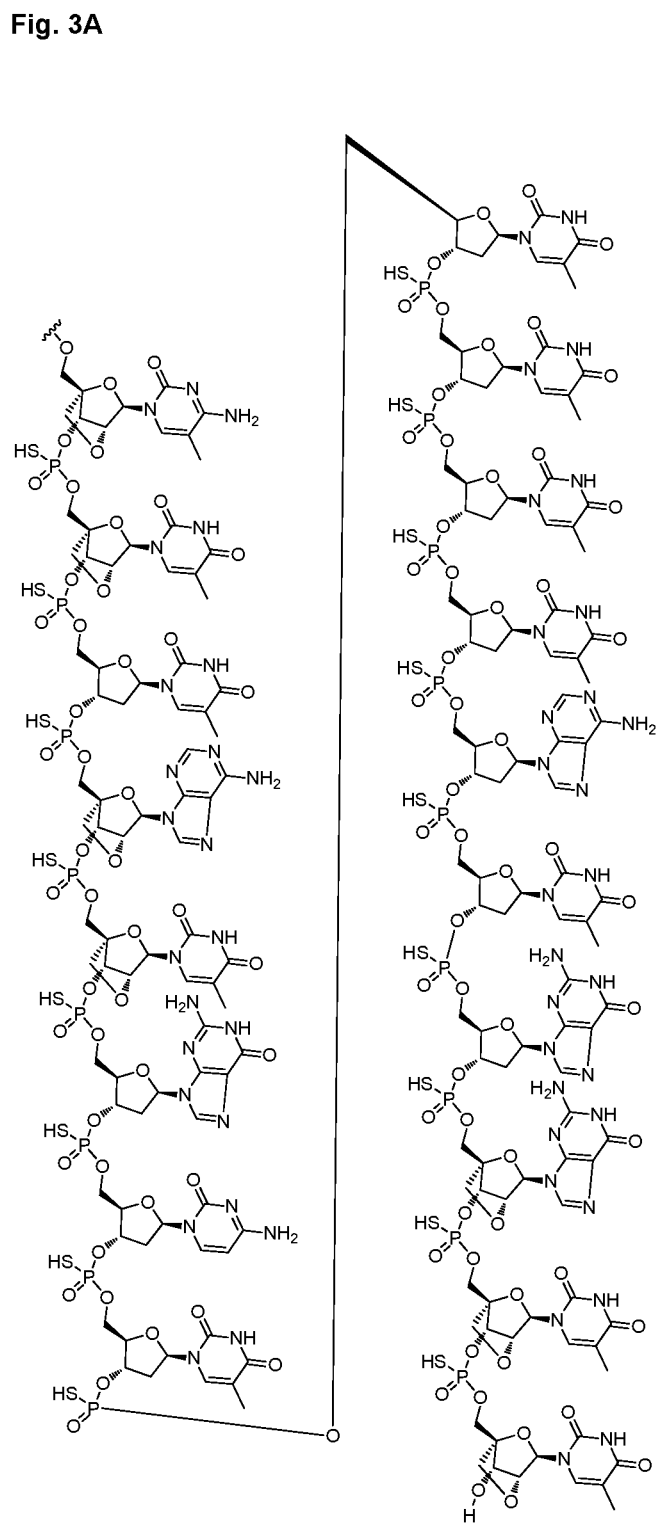

In some embodiments, the conjugate is the conjugate as shown in FIG. 3,

In some embodiments the conjugate is the conjugate as shown in FIG. 4.

Figure 5:
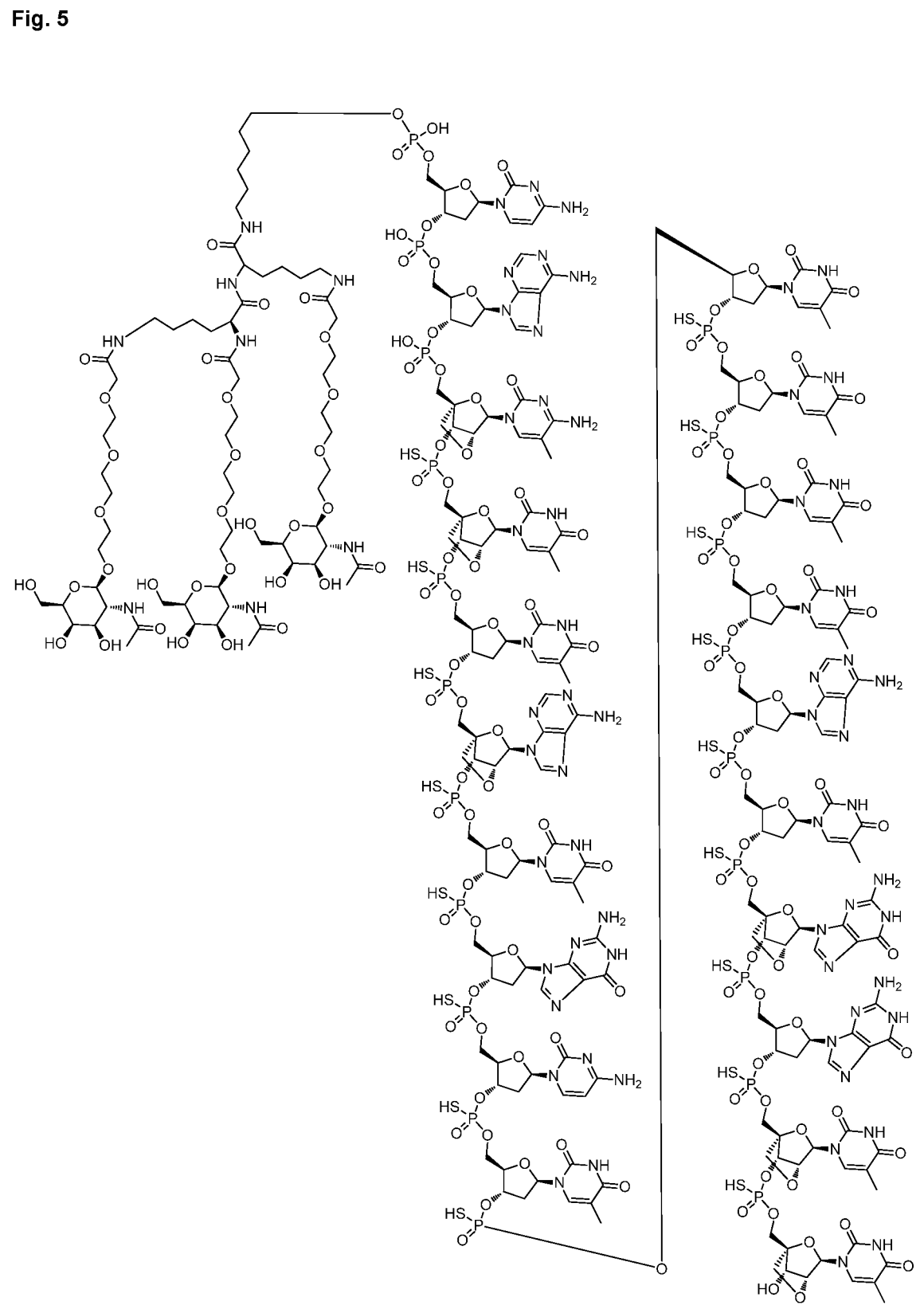
Figure 5A:
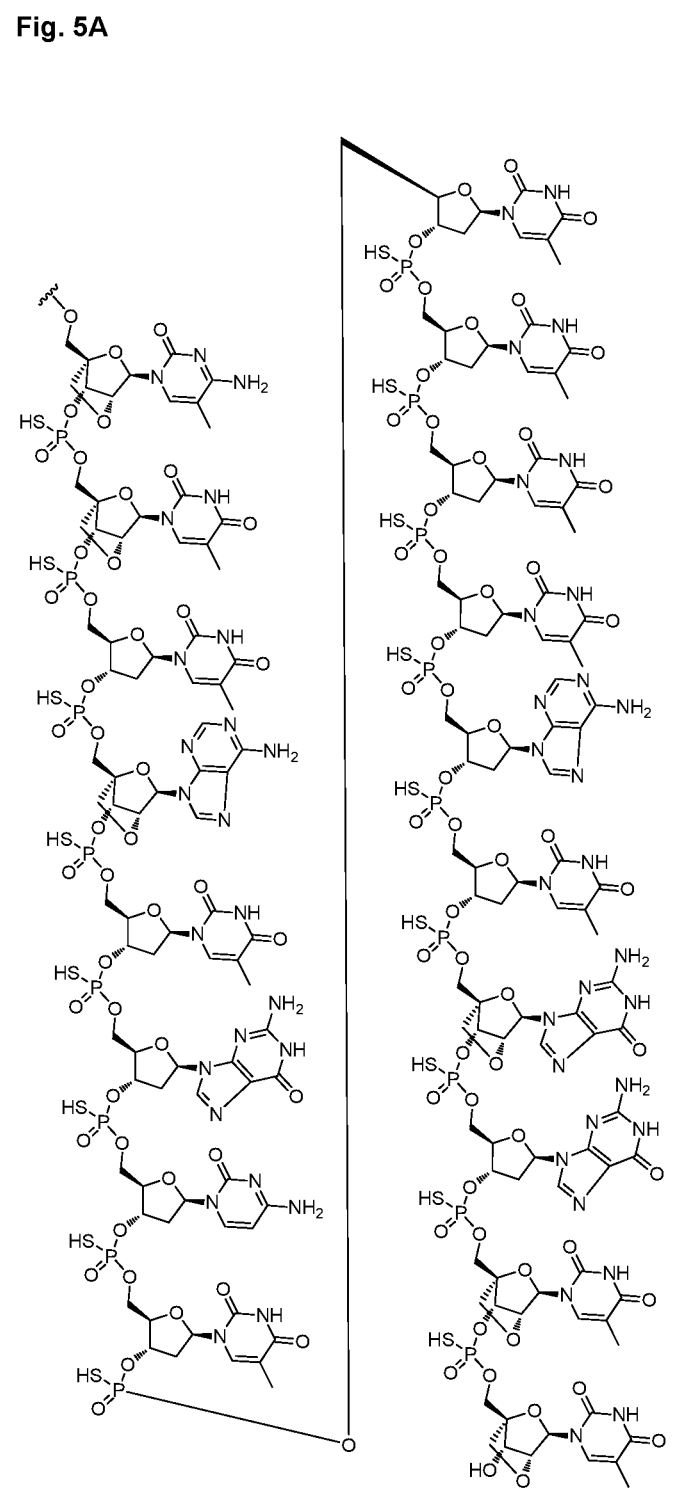

In some embodiments, the conjugate is the conjugate as shown in FIG. 5.

Figure 6:
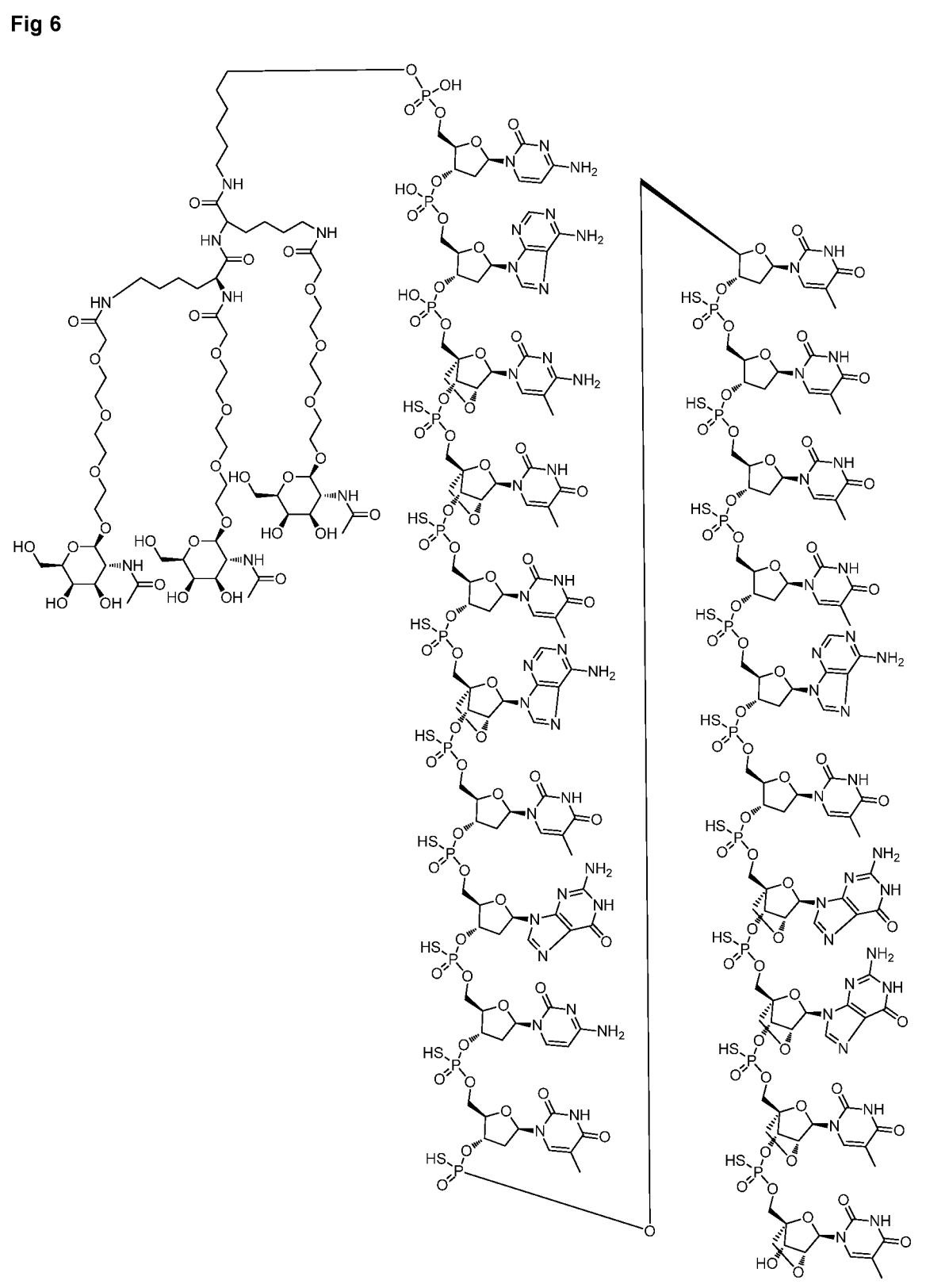
Figure 6A:
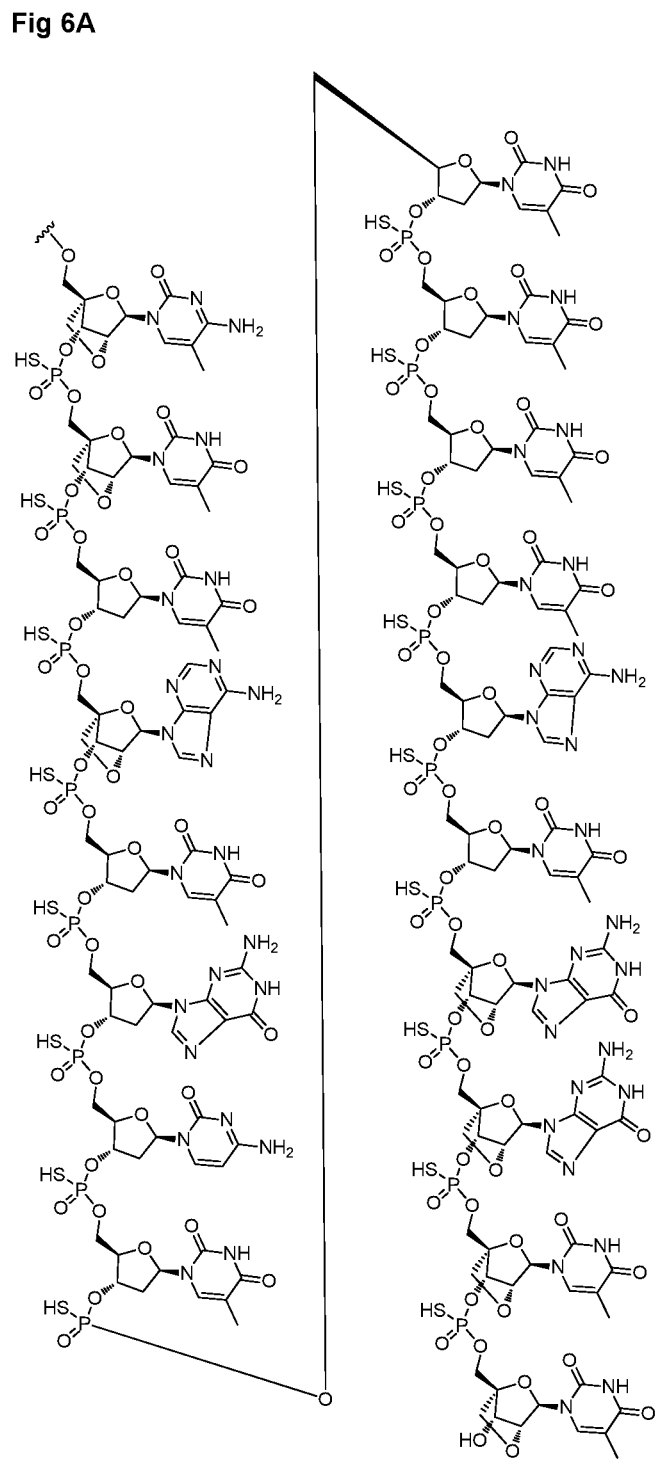

In some embodiments, the conjugate is the conjugate as shown in FIG. 6.

Figure 7:
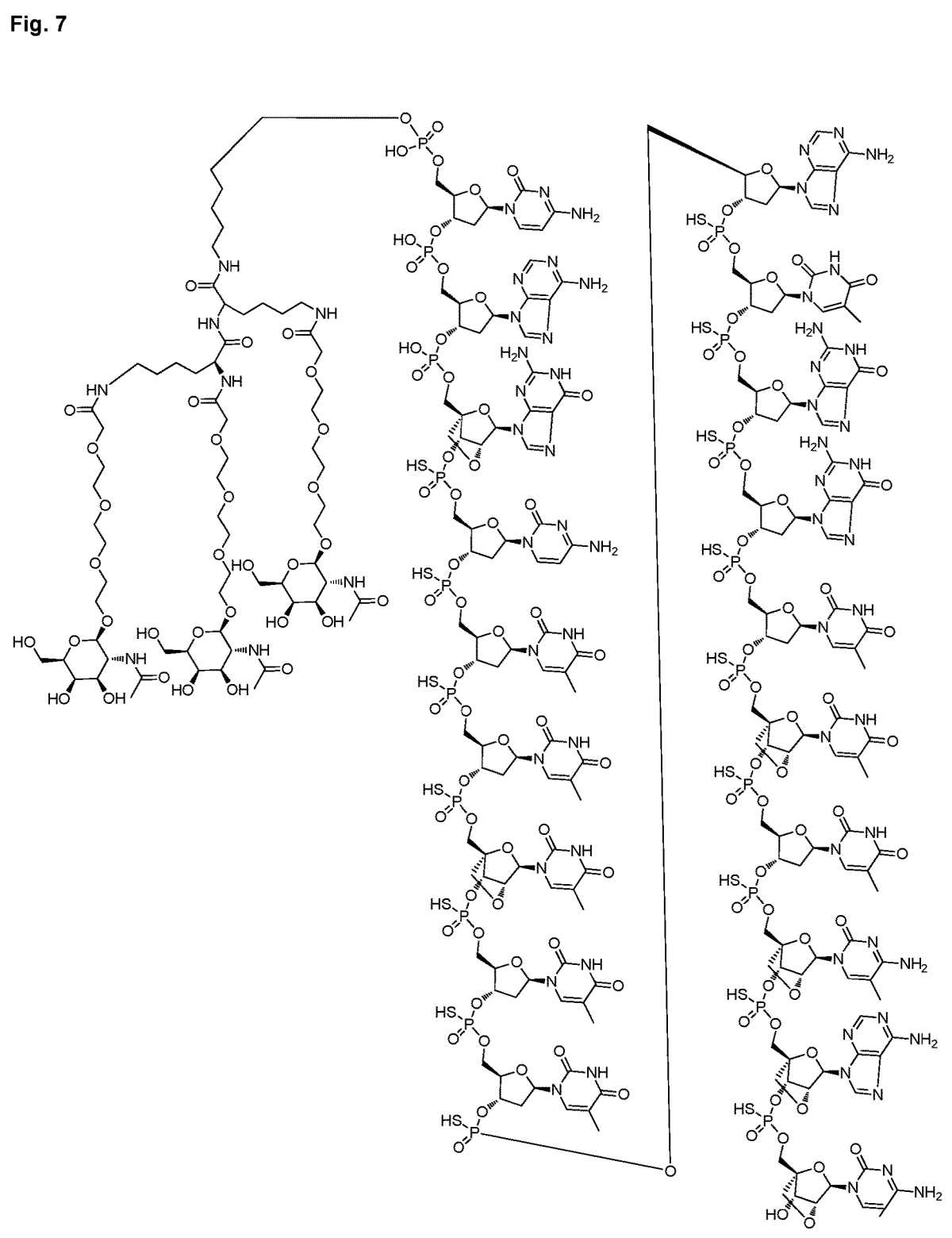
Figure 7A:
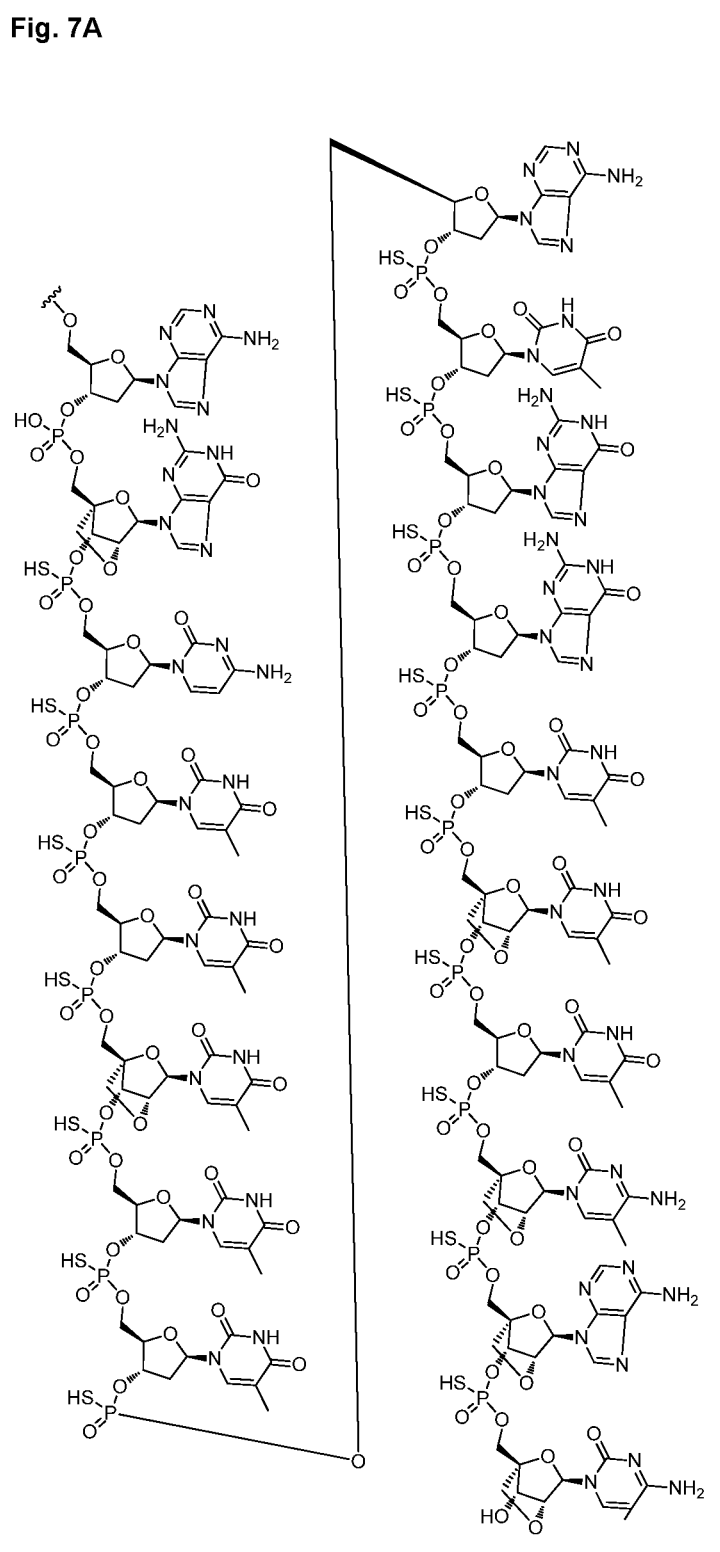

In some embodiments, the conjugate is the conjugate as shown in FIG. 7.

Figure 8:
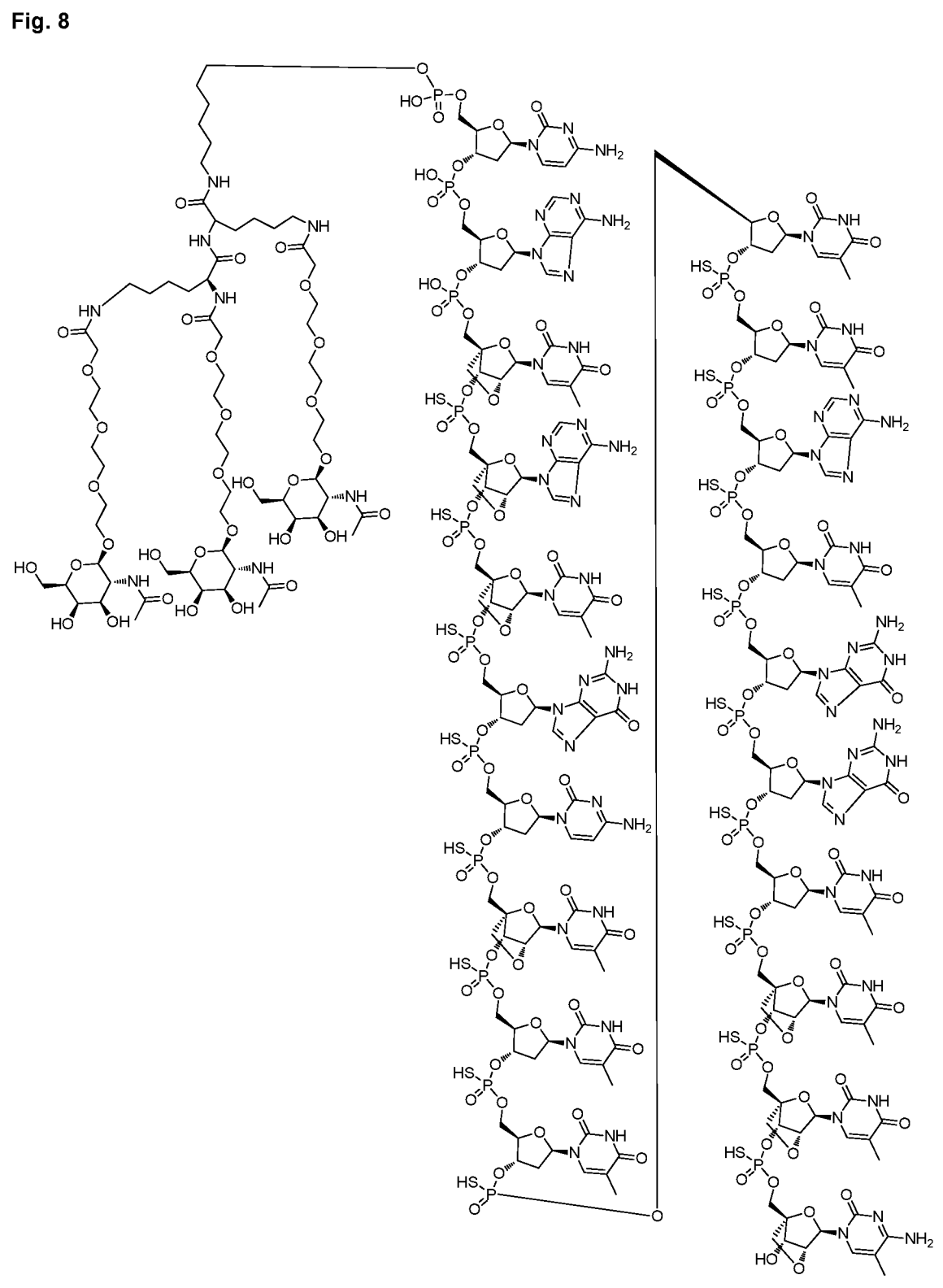
Figure 8A:
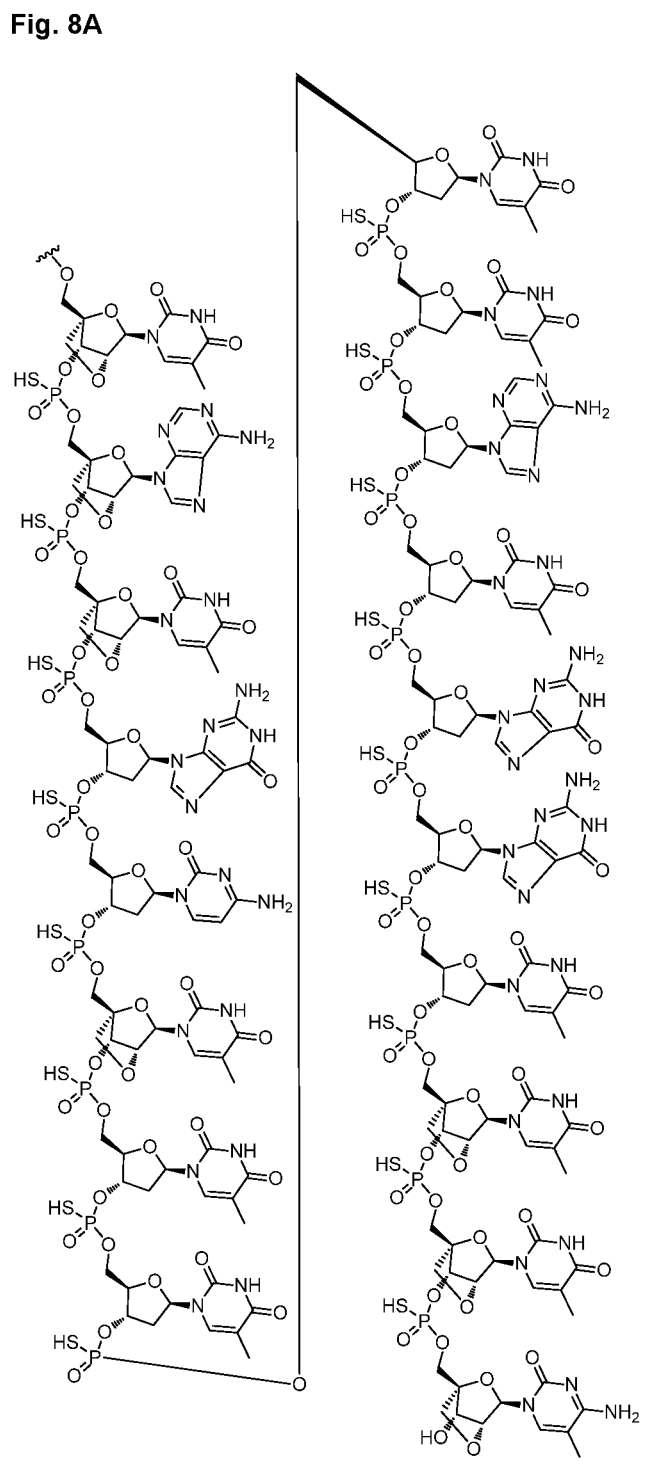
Figure 8:
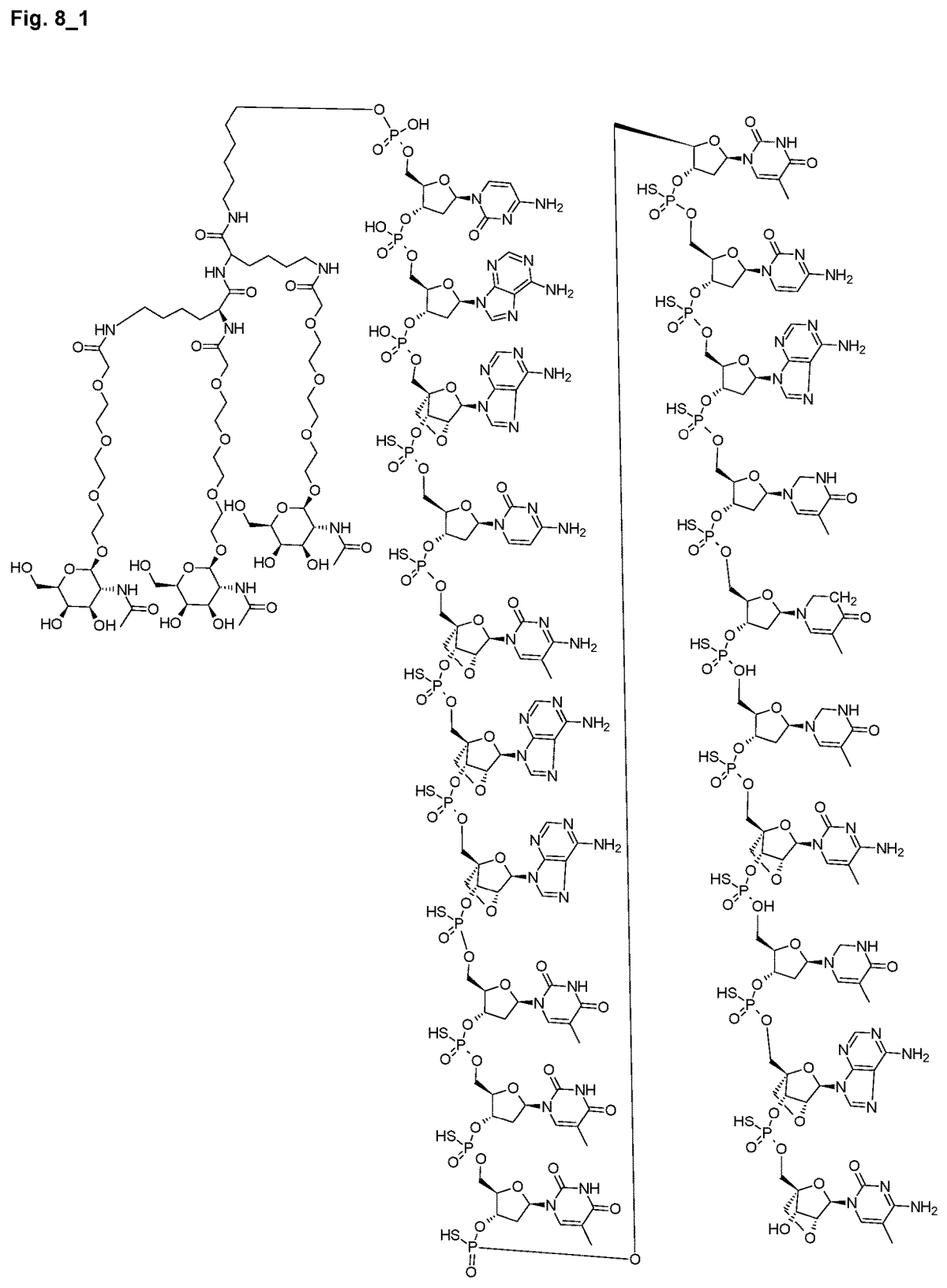
Figure 8:
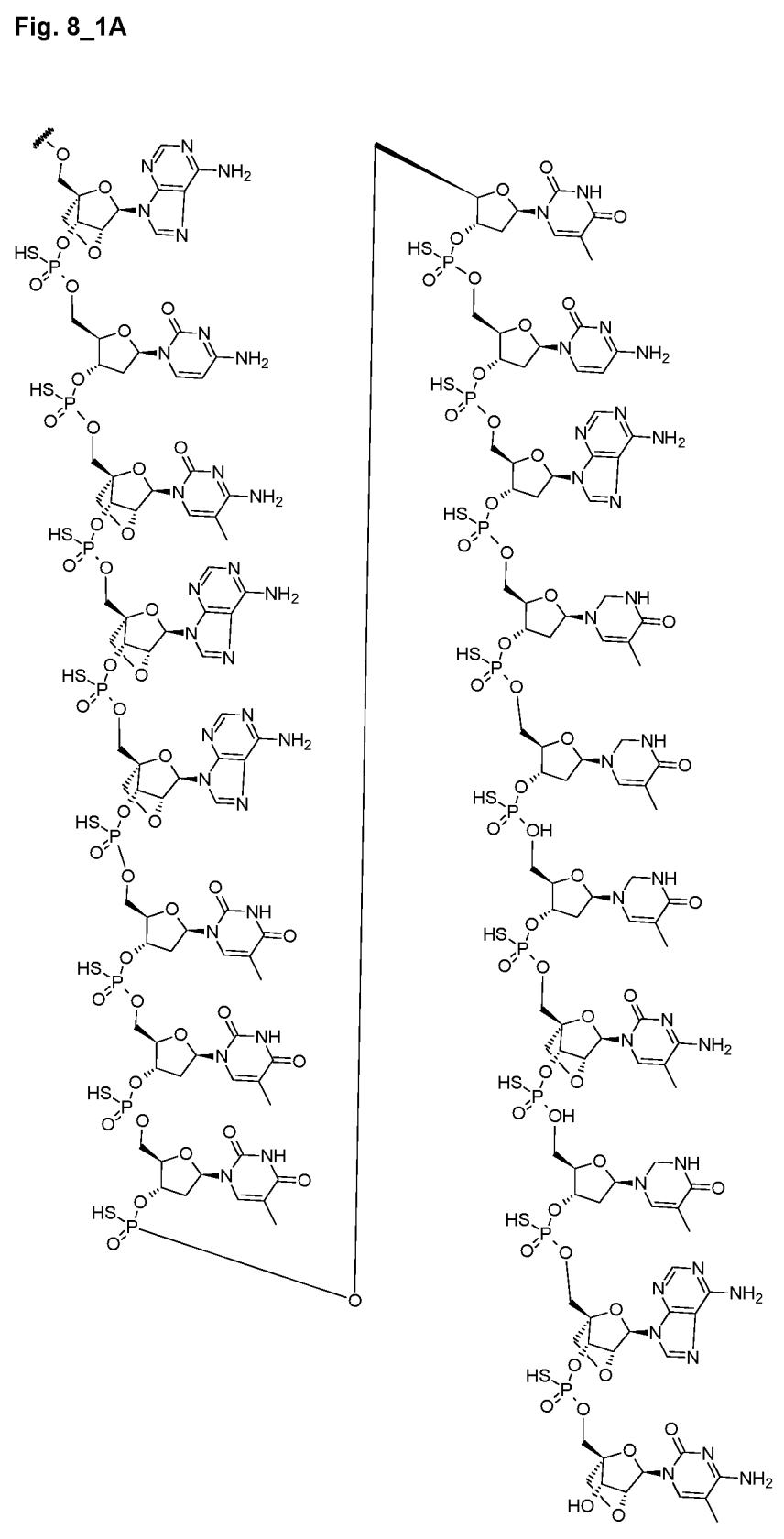

In some embodiments, the conjugate is the conjugate as shown in FIG. 8.

In some embodiments, the conjugate is the conjugate as shown in FIG. 8.1.

The compounds illustrated in FIGS. 1-8, and 8.1 are shown in the protonated form—the S atom on the phosphorothioate linkage is protonated—it will be understood that the presence of the proton will depend on the acidity of the environment of the molecule, and the presence of an alternative cation (e.g. when the oligonucleotide is in salt form). Protonated phosphorothioates exist in tautomeric forms.

Pharmaceutically Acceptable Salts

The compounds according to the present invention may exist in the form of their pharmaceutically acceptable salts. The term "pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Acid-addition salts include for example those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and, quaternary ammonium hydroxides, such as for example, tetramethyl ammonium hydroxide. The chemical modification of a pharmaceutical compound into a salt is a technique well known to pharmaceutical chemists in order to obtain improved physical and chemical stability, hygroscopicity, flowability and solubility of compounds. It is for example described in Bastin, Organic Process Research & Development 2000, 4, 427-435 or in Ansel, In: Pharmaceutical Dosage Forms and Drug Delivery Systems, 6th ed. (1995), pp. 196 and 1456-1457. For example, the pharmaceutically acceptable salt of the compounds provided herein may be a sodium salt.

In a further aspect, the invention provides a pharmaceutically acceptable salt of the antisense oligonucleotide or a conjugate thereof, such as a pharmaceutically acceptable sodium salt, ammonium salt or potassium salt.

Method of Manufacture

In a further aspect, the invention provides methods for manufacturing the oligonucleotides of the invention comprising reacting nucleotide units and thereby forming covalently linked contiguous nucleotide units comprised in the oligonucleotide. Preferably, the method uses phophoramidite chemistry (see for example Caruthers et al, 1987, Methods in Enzymology vol. 154, pages 287-313). In a further embodiment, the method further comprises reacting the contiguous nucleotide sequence with a conjugating moiety (ligand) to covalently attach the conjugate moiety to the oligonucleotide. In a further aspect, a method is provided for manufacturing the composition of the invention, comprising mixing the oligonucleotide or conjugated oligonucleotide of the invention with a pharmaceutically acceptable diluent, solvent, carrier, salt and/or adjuvant.

Pharmaceutical Composition

In a further aspect, the invention provides pharmaceutical compositions comprising any of the aforementioned oligonucleotides and/or oligonucleotide conjugates or salts thereof and a pharmaceutically acceptable diluent, carrier, salt and/or adjuvant. A pharmaceutically acceptable diluent includes phosphate-buffered saline (PBS) and pharmaceutically acceptable salts include, but are not limited to, sodium, ammonium and potassium salts. In some embodiments the pharmaceutically acceptable diluent is sterile phosphate buffered saline. Alternatively, the diluent may be water or a sodium chloride solution. In some embodiments, the oligonucleotide is used in the pharmaceutically acceptable diluent at a concentration of 50-300 μM solution.

Suitable formulations for use in the present invention are found in Remington's Pharmaceutical Sciences, Mack Publishing Company, Philadelphia, Pa., 17th ed., 1985. For a brief review of methods for drug delivery, see, e.g., Langer (Science 249:1527-1533, 1990). WO 2007/031091 provides further suitable and preferred examples of pharmaceutically acceptable diluents, carriers and adjuvants (hereby incorporated by reference). Suitable dosages, formulations, administration routes, compositions, dosage forms, combinations with other therapeutic agents, pro-drug formulations are also provided in WO2007/031091.

In some embodiments, the antisense oligonucleotide of the invention or conjugate thereof, or pharmaceutically acceptable salt thereof is in a solid form, such as a powder, such as a lyophilized powder.

In some embodiments, the antisense oligonucleotide of the invention or conjugate thereof may be mixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the preparations typically will be between 3 and 11, more preferably between 5 and 9 or between 6 and 8, and most preferably between 7 and 8, such as 7 to 7.5. The resulting compositions in solid form may be packaged in multiple single dose units, each containing a fixed amount of the above-mentioned agent or agents, such as in a sealed package of tablets or capsules. The composition in solid form can also be packaged in a container for a flexible quantity, such as in a squeezable tube designed for a topically applicable cream or ointment.

In some embodiments, the antisense oligonucleotide of the invention or conjugate thereof is a prodrug. In particular, with respect to antisense oligonucleotide conjugates the conjugate moiety is cleaved off the oligonucleotide once the prodrug is delivered to the site of action, e.g. the target cell.

Applications

The enhanced antisense oligonucleotides of the invention thereof may be utilized as research reagents for, for example, diagnostics, therapeutics and prophylaxis.

In research, such antisense oligonucleotides may be used to specifically modulate the synthesis of FUBP1 protein in cells (e.g. in vitro cell cultures) and experimental animals thereby facilitating functional analysis of the target or an appraisal of its usefulness as a target for therapeutic intervention. Typically, the target modulation is achieved by degrading or inhibiting the mRNA producing the protein, thereby prevent protein formation or by degrading or inhibiting a modulator of the gene or mRNA producing the protein.

If employing the antisense oligonucleotides of the invention in research or diagnostics the target nucleic acid may be a cDNA or a synthetic nucleic acid derived from DNA or RNA.

Also encompassed by the present invention is an in vivo or in vitro method for modulating FUBP1 expression in a target cell, which is expressing FUBP1, said method comprising administering an antisense oligonucleotide, a conjugate thereof or pharmaceutical composition of the invention in an effective amount to said cell.

In some embodiments, the target cell, is a mammalian cell in particular a human cell. The target cell may be an in vitro cell culture or an in vivo cell forming part of a tissue in a mammal. In preferred embodiments, the target cell is present in in the liver. The target cell may be a hepatocyte.

One aspect of the present invention is related the antisense oligonucleotides, conjugate thereof or pharmaceutical compositions of the invention for use as a medicament.

In an aspect of the invention the antisense oligonucleotides, conjugate thereof or pharmaceutical composition of the invention is capable of reducing the cccDNA level in the infected cells and therefore inhibiting HBV infection. In particular, the antisense oligonucleotide or conjugate thereof is capable of affecting one or more of the following parameters i) reducing cccDNA and/or ii) reducing pgRNA and/or iii) reducing HBV DNA and/or iv) reducing HBV viral antigens in an infected cell.

For example, the antisense oligonucleotide or conjugate thereof that inhibits HBV infection may reduce i) the cccDNA levels in an infected cell by at least 40% such as 50%, 60%, 70%, 80%, or 90% reduction compared to controls; or ii) the level of pgRNA by at least 40% such as 50%, 60%, 70%, 80%, or 90% reduction compared to controls. The controls may be untreated cells or animals, or cells or animals treated with an appropriate control.

Inhibition of HBV infection may be measured in vitro using HBV infected primary human hepatocytes or in vivo using humanized hepatocytes PXB mouse model (available at PhoenixBio, see also Kakuni et al 2014 Int. J. Mol. Sci. 15:58-74). Inhibition of secretion of HBsAg and/or HBeAg may be measured by ELISA, e.g. by using the CLIA ELISA Kit (Autobio Diagnostic) according to the manufacturers' instructions. Reduction of intracellular cccDNA or HBV mRNA and pgRNA may be measured by qPCR, e.g. as described in the Materials and Methods section. Further methods for evaluating whether a test compound inhibits HBV infection are measuring secretion of HBV DNA by qPCR e.g. as described in WO 2015/173208 or using Northern Blot; in-situ hybridization, or immuno-fluorescence.

Due to the reduction of FUBP1 level the antisense oligonucleotide, conjugate thereof or pharmaceutical compositions of the present invention can be used to inhibit development of or in the treatment of HBV infection. In particular, the destabilization and reduction of the cccDNA, the antisense oligonucleotide, conjugate thereof or pharmaceutical compositions of the present invention more efficiently inhibits development of or treats a chronic HBV infection as compared to a compound that only reduces secretion of HBsAg.

Accordingly, one aspect of the present invention is related to use of the antisense oligonucleotide, conjugate thereof or pharmaceutical compositions of the invention to reduce cccDNA and/or pgRNA in an HBV infected individual.

A further aspect of the invention relates to the use of the antisense oligonucleotide, conjugate thereof or pharmaceutical compositions of the invention to inhibit development of or treat a chronic HBV infection.

A further aspect of the invention relates to the use of the antisense oligonucleotide, conjugate thereof or pharmaceutical compositions of the invention to reduce the infectiousness of a HBV infected person. In a particular aspect of the invention, the antisense oligonucleotide, conjugate thereof or pharmaceutical compositions of the invention inhibits development of a chronic HBV infection.

The subject to be treated with the antisense oligonucleotide, conjugate thereof or pharmaceutical compositions of the invention (or which prophylactically receives antisense oligonucleotides, conjugates thereof or pharmaceutical compositions of the present invention) is preferably a human, more preferably a human patient who is HBsAg positive and/or HBeAg positive, even more preferably a human patient that is HBsAg positive and HBeAg positive.

Accordingly, the present invention relates to a method of treating a HBV infection, wherein the method comprises administering an effective amount of the antisense oligonucleotide, conjugate thereof or pharmaceutical compositions of the invention. The present invention further relates to a method of preventing liver cirrhosis and hepatocellular carcinoma caused by a chronic HBV infection.

The invention also provides for the use of an antisense oligonucleotide, conjugate thereof or a pharmaceutical composition of the invention for the manufacture of a medicament, in particular a medicament for use in the treatment of HBV infection or chronic HBV infection or reduction of the infectiousness of a HBV infected person. In preferred embodiments, the medicament is manufactured in a dosage form for subcutaneous administration.

The invention also provides for the use of an antisense oligonucleotide, conjugate thereof, the pharmaceutical composition of the invention for the manufacture of a medicament wherein the medicament is in a dosage form for intravenous administration.

Combination Therapy

In some embodiments, the enhanced antisense oligonucleotide, conjugate thereof or the pharmaceutical composition of the invention is for use in a combination treatment with another therapeutic agent. The therapeutic agent can for example be the standard of care for the diseases or disorders described above.

By way of example, the antisense oligonucleotide, conjugate thereof or the pharmaceutical composition may be used in combination with other actives, such as oligonucleotide-based antivirals—such as sequence specific oligonucleotide-based antivirals—acting either through antisense (including other LNA oligomers), siRNAs (such as ARC520), aptamers, morpholinos or any other antiviral, nucleotide sequence-dependent mode of action.

By way of further example, the antisense oligonucleotide, conjugate thereof or the pharmaceutical composition may be used in combination with other actives, such as immune stimulatory antiviral compounds, such as interferon (e.g. pegylated interferon alpha), TLR7 agonists (e.g. GS-9620), or therapeutic vaccines.

By way of further example, the antisense oligonucleotide, conjugate thereof or the pharmaceutical composition may be used in combination with other actives, such as small molecules, with antiviral activity. These other actives could be, for example, nucleoside/nucleotide inhibitors (eg entecavir or tenofovir disoproxil fumarate), encapsidation inhibitors, entry inhibitors (e.g. Myrcludex B).

In certain embodiments, the additional therapeutic agent may be an HBV agent, a Hepatitis C virus (HCV) agent, a chemotherapeutic agent, an antibiotic, an analgesic, a non-steroidal anti-inflammatory (NSAID) agent, an antifungal agent, an antiparasitic agent, an anti-nausea agent, an anti-diarrheal agent, or an immunosuppressant agent.

In particular, related embodiments, the additional HBV agent may be interferon alpha-2b, interferon alpha-2a, and interferon alphacon-1 (pegylated and unpegylated), ribavirin; an HBV RNA replication inhibitor; a second antisense oligomer; an HBV therapeutic vaccine; an HBV prophylactic vaccine; lamivudine (3TC); entecavir (ETV); tenofovir diisoproxil fumarate (TDF); telbivudine (LdT); adefovir; or an HBV antibody therapy (monoclonal or polyclonal).

In other particular related embodiments, the additional HCV agent may be interferon alpha-2b, interferon alpha-2a, and interferon alphacon-1 (pegylated and unpegylated); ribavirin; pegasys; an HCV RNA replication inhibitor (e.g., ViroPharma's VP50406 series); an HCV antisense agent; an HCV therapeutic vaccine; an HCV protease inhibitor; an HCV helicase inhibitor; or an HCV monoclonal or polyclonal antibody therapy.

Administration

The enhanced antisense oligonucleotide, conjugate thereof, or pharmaceutical composition of the invention is formulated, dosed, and administered in a fashion consistent with good medical practice. Factors for consideration in this context include the particular mammal being treated, the clinical condition of the individual patient, the site of delivery of the agent, the method of administration, the scheduling of administration, the age and sex of the patients and other factors known to medical practitioners. Herein, an "effective amount" (also known as "(therapeutically) effective dose") means the amount of a compound that will elicit the biological or medical response of a subject that is being sought by a medical doctor or other clinician. The "effective amount" of an oligonucleotide, conjugate compound or pharmaceutical composition of the invention, will be governed by such considerations, and is the minimum amount necessary to inhibit HBsAg and/or HBeAg. For example, such amount may be below the amount that is toxic to the cells of the recipient, or to the mammal as a whole.

In some embodiments, the antisense oligonucleotide, conjugate thereof or pharmaceutical composition of the invention is administered at a dose of 0.1-15 mg/kg, such as from 0.2-10 mg/kg, such as from 0.25-5 mg/kg. The administration can be once a week, every second week, every third week or even once a month.

The antisense oligonucleotides, conjugates thereof or pharmaceutical compositions of the present invention may be administered topical (such as, to the skin, inhalation, ophthalmic or otic) or enteral (such as, orally or through the gastrointestinal tract) or parenteral (such as, intravenous, subcutaneous, or intra-muscular).

In a preferred embodiment, the antisense oligonucleotide, conjugate thereof or pharmaceutical compositions of the present invention are administered by a parenteral route including intravenous, intraarterial, subcutaneous, intraperitoneal or intramuscular injection or infusion. In one embodiment, the active oligonucleotide or oligonucleotide conjugate is administered intravenously. With GalNAc conjugated compounds it may be advantageous to administer subcutaneously in order to delay saturation of the ASGP receptor.

Embodiments of the Invention

The following embodiments of the present invention may be used in combination with any other embodiments described herein. The definitions and explanations provided herein above, in particular in the sections "SUMMARY OF INVENTION", "DEFINITIONS" and DETAILED DESCRIPTION OF THE INVENTION" apply mutatis mutandis to the following.

1. An antisense oligonucleotide which comprises a contiguous nucleotide sequence, which is at least 90% complementary, such as fully complementary to a FUBP1 nucleic acid, wherein the antisense oligonucleotide is capable of inhibiting the expression of FUBP1, such as human FUBP1, in a cell.

2. The antisense oligonucleotide of embodiment 1, wherein
   a) the contiguous nucleotide sequence is at least 90% complementary, such as fully complementary to a region within exon 14 of human FUBP1 (see Table 3), or
   b) the contiguous nucleotide sequence is at least 90% complementary, such as fully complementary to a region within exon 20 of human FUBP1 (see Table 3).

3. The antisense oligonucleotide of embodiments 1 and 2, wherein
   a) the contiguous nucleotide sequence is fully complementary to a region from nucleotides 16184 to 16205 of the human FUBP1 pre-mRNA as shown in in SEQ ID NO: 1, such as to a region selected from a region from nucleotides 16184 to 16200, from nucleotides 16186 to 16203, from nucleotides 16188 to 16205, and from nucleotides 16189 to 16205 of SEQ ID NO: 1, or
   b) the contiguous nucleotide sequence is fully complementary to a region from nucleotides 30536-30553 of the human FUBP1 pre-mRNA as shown in in SEQ ID NO: 1

4. The antisense oligonucleotide of any one of embodiments 1 to 3, wherein a) the contiguous nucleotide sequence is fully complementary to SEQ ID NO 10 and/or SEQ ID NO: 11 or b) the contiguous nucleotide sequence is fully complementary to SEQ ID NO: 19.

5. The antisense oligonucleotide of any one of embodiments 1 to 4, wherein the antisense oligonucleotide is 12-30 nucleotides in length, such as 12 to 22 nucleotides in length, such as 16 to 20 nucleotides in length.

6. The antisense oligonucleotide of any one of embodiments 1 to 4, wherein the contiguous nucleotide sequence is a contiguous sequence of at least 12 nucleotides, such as of 14, 15, 16, 17 or 18 nucleotides.

7. The antisense oligonucleotide of embodiment 6, wherein the contiguous nucleotide sequence is a contiguous sequence of 17 or 18 nucleotides.

8. The antisense oligonucleotide of any one of embodiments 1 to 7, wherein the contiguous nucleotide sequence is 100% identical to a sequence selected from the group consisting of SEQ ID NOs: 6, 7, 8, 9 and 18, or at least 15 contiguous nucleotides thereof.

9. The antisense oligonucleotide of any one of embodiments 1 to 8, comprising one or more modified nucleosides in the contiguous nucleotide sequence.

10. The antisense oligonucleotide of embodiment 9, wherein the one or more modified nucleosides in the contiguous nucleotide sequence are 2' sugar modified nucleosides.

11. The antisense oligonucleotide of embodiment 10, wherein the one or more 2' sugar modified nucleosides are independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA and LNA nucleosides.

12. The antisense oligonucleotide of any one of embodiments 9 to 11, wherein the one or more modified nucleosides are LNA nucleosides, such as oxy-LNA with the following 2'-4' bridge —O—CH$_2$—.

13. The antisense oligonucleotide of embodiment 12, wherein the one or more modified nucleosides are beta-D-oxy-LNA.

14. The antisense oligonucleotide of any one of embodiments 1 to 13, wherein at least one internucleoside linkage in the contiguous nucleotide sequence is a phosphorothioate internucleoside linkage.

15. The antisense oligonucleotide of any one of embodiments 1 to 14, wherein at least one internucleoside linkage in the contiguous nucleotide sequence is a phosphorodithioate internucleoside linkage.

16. The antisense oligonucleotide of any one of embodiments 1 to 15, wherein at least one internucleoside linkage in the contiguous nucleotide sequence is a phosphodiester internucleoside linkage.

17. The antisense oligonucleotide of embodiment 16, wherein all the internucleoside linkages within the contiguous nucleotide sequence are phosphorothioate internucleoside linkages.

18. The antisense oligonucleotide of any one of embodiments 1 to 17, wherein the antisense oligonucleotide is an antisense oligonucleotide which is capable of recruiting RNase H, such as RNase H1.

19. The antisense oligonucleotide of embodiment 18, wherein the antisense oligonucleotide, or contiguous nucleotide sequence thereof, consists of or comprises a gapmer of formula 5'-F-G-F'-3'.

20. The antisense oligonucleotide according to embodiment 19, wherein region G has a length of 16 DNA nucleosides, such as 7 to 12 DNA nucleosides, such as 7 to 11 DNA nucleosides 21. The antisense oligonucleotide according to any one of embodiments 18 to 20, wherein region F and F' each comprise at least one LNA nucleoside, for example wherein region F and F' each comprise at least one LNA nucleoside.

22. The antisense oligonucleotide according to any one of embodiments 18 to 21, wherein region F has a length of 1 to 8 DNA nucleosides, such as 4 to 6 DNA nucleosides.

23. The antisense oligonucleotide according to any one of embodiments 18 to 22, wherein region F' has a length of 1 to 8 DNA nucleosides, such as 2 to 6 DNA nucleosides.

24. The antisense oligonucleotide according to any one of embodiments 18 to 23, wherein the antisense oligonucleotide, or contiguous nucleotide sequence thereof, consists or comprises a gapmer of formula $F_{4-6}$-$G_{7-11}$-$F'_{2-6}$, and preferably, wherein the gapmer comprises at least one alternating flank.

25. The antisense oligonucleotide according to any one of embodiments 1 to 24, wherein the antisense oligonucleotide is selected from the group of antisense oligonucleotides consisting of

```
                                    (SEQ ID NO: 6)
CTTatGctttttatgGT, (SEQ ID NO: 6)
CTTaTgctttttatgGT, (SEQ ID NO: 7)
CTtATgctttttatgGTT, (SEQ ID NO: 7)
CTtAtgctttttatgGTT,
```

```
-continued
                                    (SEQ ID NO: 7)
CTtAtgctttttatGgTT, (SEQ ID NO: 7)
CTtAtgctttttatGGTT, (SEQ ID NO: 8)
GcttTttatggtTtCAC, (SEQ ID NO: 9)
TATgcTttttatggtTTC, and (SEQ ID NO: 18)
AcCAAttttcatttCtAC
``` wherein capital letters are beta-D-oxy LNA nucleosides, lowercase letters are DNA nucleosides, all LNA C are 5-methyl cytosine, all internucleoside linkages are phosphorothioate internucleoside linkages.

26. A conjugate comprising the antisense oligonucleotide according to any one of embodiments 1 to 25, and at least one conjugate moiety covalently attached to said antisense oligonucleotide 27. The conjugate of embodiment 27, wherein the conjugate moiety comprises at least one asialoglycoprotein receptor-targeting moiety selected from the group consisting of galactose, galactosamine, N-formyl-galactosamine, N-acetylgalactosamine, N-propionyl-galactosamine, N-n-butanoyl-galactosamine and N-isobutanoylgalactosamine.

28. The conjugate compound of embodiment 27, wherein the asialoglycoprotein receptor-targeting moiety is N-acetylgalactosamine (GalNAc).

29. The conjugate compound of embodiment 27 or 28, wherein the conjugate moiety is mono-valent, di-valent, tri-valent or tetra-valent with respect to asialoglycoprotein receptor-targeting moieties.

30. The conjugate compound of embodiment 29, wherein the conjugate moiety consists of two to four terminal GalNAc moieties and a spacer linking each GalNAc moiety to a brancher molecule that can be conjugated to the antisense compound.

31. The conjugate compound of embodiment 30, wherein the spacer is a PEG spacer.

32. The conjugate compound of any one of embodiments 26 to 31, wherein the conjugate moiety is tri-valent N-acetylgalactosamine (GalNAc) moiety.

33. The conjugate compound of any one of embodiments 26 to 32, wherein the conjugate moiety is selected from one of the trivalent GalNAc moieties in FIG. 9A1, 9A2; 9C1, 9C2, 9D1, 9D2, 9E1, 9F1, 9G1, 9H1, 9I1, 9J1, 9L1 and 9L2.

34. The conjugate compound of embodiment 33, wherein the conjugate moiety is the trivalent GalNAc moiety in FIG. 9D1, or 9D2 or a mixture thereof 35. The conjugate compound of any one of embodiments 26 to 34, comprising a linker which is positioned between the antisense oligonucleotide and the conjugate moiety.

36. The conjugate compound of embodiment 35, wherein the linker comprises or consists of 2 to 5 consecutive phosphodiester linked nucleosides, such as 2 consecutive phosphodiester linked nucleosides, such as phosphodiester linked nucleosides ca.

37. The conjugate according to any one of embodiments 26 to 36, wherein the conjugate is selected from the group consisting of 5'-GN2-C$_6$$_0$c$_0$a$_0$ $^m$C$_s$T$_s$T$_s$a$_s$t$_s$G$_s$c$_s$t$_s$t$_s$t$_s$t$_s$a$_s$t$_s$g$_s$G$_s$T, 5'-GN2-C$_6$$_0$c$_0$a$_0$ $^m$C$_s$T$_s$T$_s$a$_s$T$_s$g$_s$c$_s$t$_s$t$_s$t$_s$t$_s$a$_s$t$_s$g$_s$G$_s$T, 5'-GN2-C$_6$$_0$c$_0$a$_0$ $^m$C$_s$T$_s$t$_s$a$_s$T$_s$g$_s$c$_s$t$_s$t$_s$t$_s$t$_s$a$_s$t$_s$g$_s$G$_s$T$_s$T, 5'-GN2-C$_6$$_0$c$_0$a$_0$ $^m$C$_s$T$_s$t$_s$A$_s$t$_s$g$_s$c$_s$t$_s$t$_s$t$_s$t$_s$a$_s$t$_s$g$_s$G$_s$T$_s$T, 5'-GN2-C$_6$$_0$c$_0$a$_0$ $^m$C$_s$T$_s$t$_s$A$_s$t$_s$g$_s$c$_s$t$_s$t$_s$t$_s$t$_s$a$_s$t$_s$G$_s$g$_s$T$_s$T, 5'-GN2-C$_6$$_0$c$_0$a$_0$ $^m$C$_s$T$_s$t$_s$A$_s$t$_s$g$_s$c$_s$t$_s$t$_s$t$_s$t$_s$a$_s$t$_s$G$_s$G$_s$T$_s$T, 5'-GN2-C$_6$$_0$c$_0$a$_0$ G$_s$C$_s$t$_s$t$_s$T$_s$t$_s$t$_s$a$_s$t$_s$g$_s$g$_s$t$_s$T$_s$t$_s$$^m$C$_s$A$_s$$^m$C, 5'-GN2-C$_6$$_0$c$_0$a$_0$ T$_s$A$_s$T$_s$g$_s$c$_s$T$_s$t$_s$t$_s$t$_s$a$_s$t$_s$g$_s$g$_s$t$_s$T$_s$T$_s$$^m$C,  and 5'-GN2-C$_6$$_0$c$_0$a$_0$ A$_s$c$_s$$^m$C$_s$A$_s$A$_s$t$_s$t$_s$t$_s$c$_s$a$_s$t$_s$t$_s$$^m$C$_s$tA$_s$$^m$C preferably, wherein a capital letter represents a beta-D-oxy LNA nucleoside, a lower case letter represents a DNA nucleoside, wherein each LNA cytosine is 5-methyl cytosine, and mc is 5-methyl cytosine DNA, and wherein subscript s represents a phosphorothioate internucleoside linkage, and a subscript o represents a phosphodiester internucleoside linkage, and GN2-C6 is a tri-valent N-acetylgalactosamine (GalNAc) as shown in FIG. 9D, such as a tri-valent N-acetylgalactosamine (GalNAc) as shown in FIG. 9D-1 or FIG. 9D2, or a mixture of both, preferably bound via a phosphodiester linkage at the 5' end of the oligonucleotide.

38. A conjugate as shown in FIG. 1.

39. A conjugate as shown in FIG. 2.

40. A conjugate as shown in FIG. 3.

41. A conjugate as shown in FIG. 4.

42. A conjugate as shown in FIG. 5.

43. A conjugate as shown in FIG. 6.

44. A conjugate as shown in FIG. 7.

45. A conjugate as shown in FIG. 8.

46. A conjugate as shown in FIG. 8.1.

47. A pharmaceutically acceptable salt of the oligonucleotide of any one of embodiments 1 to 25, or the conjugate according to any one of embodiments 26 to 46.

48. A pharmaceutical composition comprising the antisense oligonucleotide of any one of embodiments 1 to 25, the conjugate of any one of embodiments 26 to 46, or the pharmaceutically acceptable salt of embodiment 48, and a pharmaceutically acceptable diluent, solvent, carrier, salt and/or adjuvant.

49. An in vivo or in vitro method for modulating FUBP1 expression in a target cell which is expressing FUBP1, said method comprising administering the antisense oligonucleotide of any one of embodiments 1 to 25, the conjugate of any one of embodiments 26 to 46, the pharmaceutically acceptable salt of embodiment 48, or the pharmaceutical composition of embodiment 48 in an effective amount to said cell.

50. A method for treating or preventing a disease comprising administering a therapeutically or prophylactically effective amount of the antisense oligonucleotide of any one of embodiments 1 to 25, the conjugate of any one of embodiments 26 to 46, the pharmaceutically acceptable salt of embodiment 47, or the pharmaceutical composition of embodiment 48 to a subject suffering from or susceptible to the disease, wherein the disease is hepatitis B virus (HBV) infection and/or cancer.

51. The antisense oligonucleotide of any one of embodiments 1 to 25, the conjugate of any one of embodiments 26 to 46, the pharmaceutically acceptable salt of embodiment 47, or the pharmaceutical composition of embodiment 48 for use in medicine.

52. The antisense oligonucleotide of any one of embodiments 1 to 25, the conjugate of any one of embodiments 26 to 46, the pharmaceutically acceptable salt of embodiment 47, or the pharmaceutical composition of embodiment 48 for use in the treatment or prevention of hepatitis B virus (HBV) infection and/or cancer.

53. Use of antisense oligonucleotide of any one of embodiments 1 to 25, the conjugate of any one of embodiments 26 to 46, the pharmaceutically acceptable salt of embodiment 47, or the pharmaceutical composition of embodiment 48, for the preparation of a medicament for treatment or prevention of a hepatitis B virus (HBV) infection and/or cancer.

54. The method of embodiment 50, the antisense oligonucleotide, conjugate, pharmaceutical composition, or the pharmaceutically acceptable salt for use of embodiment 52, or the use of embodiment 53, wherein the disease is hepatitis B virus (HBV) infection, such as chronic HBV infection.

55. The method of embodiment 50, the antisense oligonucleotide, conjugate, pharmaceutical composition, or the pharmaceutically acceptable salt for use of embodiment 52, or the use of embodiment 53, wherein the disease is cancer, such as hepatocellular carcinoma.

56. The antisense oligonucleotide according to any one of embodiments 1 to 25, the conjugate of any one of embodiments 26 to 33 and 45, the pharmaceutically acceptable salt of embodiment 47, or the pharmaceutical composition of embodiment 48, the use of embodiment 53, or the method of embodiments 54 and 54, wherein the antisense oligonucleotide is AcCAAttttcatttCtAC (SEQ ID NO: 18).

57. The antisense oligonucleotide according to any one of embodiments 1 to 25, the conjugate of any one of embodiments 26 to 33 and 42, the pharmaceutically acceptable salt of embodiment 47, or the pharmaceutical composition of embodiment 48, the use of embodiment 53, or the method of embodiments 54 and 54, wherein the antisense oligonucleotide is CTtAtgcttttatGgTT (SEQ ID NO: 7).

EXAMPLES

Introduction

Overexpression of and mutations in FUBP1 has been known to be associated with cancers for many years. In particular, strong overexpression of FUBP1 in human hepatocellular carcinoma (HCC) supports tumor growth and correlates with poor patient prognosis.

HBV cccDNA in infected hepatocytes is responsible for persistent chronic infection and reactivation, being the template for all viral subgenomic transcripts and pre-genomic RNA (pgRNA) to ensure both newly synthesized viral progeny and cccDNA pool replenishment via intracellular nucleocapsid recycling.

In WO 2019/193165, it was shown that FUBP1 is associated with cccDNA stability. This knowledge allows for the opportunity to destabilize cccDNA in HBV infected subjects which in turn opens the opportunity for a complete cure of chronically infected HBV patients.

In the present study, more than 2000 antisense oligonucleotides targeting human FUBP1 were screened. In this screening, compounds were identified which are particularly potent and effective to target human FUBP1. Specifically, nine alternating flank gapmer LNA oligonucleotides were identified which target a region within exon 14 of human FUBP1 and which conferred a strong down-regulation of human FUBP1 in vitro. Furthermore, one alternating flank gapmer LNA oligonucleotide was identified which targets a region within exon 20 of human FUBP1 and which conferred a strong down-regulation of human FUBP1 as well. An overview on the identified nine compounds is provided in Table 6 above.

The target sequence of the identified compounds overlaps with the target sequence of CMP ID NO 53_1 and 54_1 as disclosed in WO 2019/193165. These two compounds inhibit FUBP1 in HeLa cells to around ~'70% at 5 µM. However, the nine identified compounds are clearly more efficacious, as they inhibit FUBP1 in HeLa cells down to about ~25% to 35% at 3.3 µM or to ~27% at 5 µM (CMP ID NO: 18_1. In addition, they are more efficious in targeting FUBP1 in HeLa cells than CMP ID NO 50_1, which is the best compound of WO 2019/193165 (see Example 1).

An overview on the prior art compounds 35_1, 50_1, 53_1, 54_1, 78_1 and 79_1 of WO 2019/193165 is provided in Table 7 below. The compounds are gapmers with uniform flanks. CMP ID NO: 50_1 was the best compound in PHH cells, CMP ID NO: 35_1 was the best compound in HeLa cells. CMP ID NO 53_1 and 54_1 are the closest compounds for CMP ID Nos: 6_1, 6_2, 7_1, 7_2, 7_3, 7_4; 8_1 and 9_1. CMP ID NO 78_1 and 79_1 are the closest compounds for CMP ID NO: 18_1.

ered Saline (PBS), [Sigma cat. no 14190-094] followed by addition of 0.25% Trypsin-EDTA solution (Sigma, T3924), 2-3 minutes incubation at 37° C., and trituration before cell seeding.

For experimental use, 2500 cells per well were seeded in 96 well plates (Nunc cat no 167008) in 190 µL growth media. ASO dissolved in PBS was added approximately 24 hours after the cells were seeded to reach final custom concentrations. Cells were incubated or 3 days without any media change.

After incubation, cells were harvested by removal of media followed by addition of 125 µL RLT Lysis buffer (Qiagen 79216) and 125 µL 70% ethanol. RNA was purified according to the manufacturer's instruction (Qiagen RNeasy 96 kit) and eluted in a final volume of 200 µL DNase/RNase free Water (Gibco).

The RNA was heat shocked for 40 seconds at 90° C. to melt RNA:LNA duplexes, moved directly to ice and spun down before use. For one-step qPCR reaction qPCR-mix (qScript™ XLE 1-step RT-qPCR TOUGHMIX®Low ROX from QauntaBio, cat. no 95134-500) was mixed with two IDT probes (final concentration 1×) to generate the master-mix. Taqman probes were acquired from IDT: FUBP1: Hs.PT.58.26883775 (primer-probe ratio 2, FAM) or ThermoFisher Scientific: GUSB: 4326320E. Mastermix (6 µL) and RNA (4 µL, 1-2 ng/µL) were then mixed in a qPCR plate (MICROAMP®optical 384 well, 4309849). After sealing, the plate was given a quick spin, 1000 g for 1 minute at RT, and transferred to a Viia™ 7 system (Applied Biosystems, Thermo), and the following PCR conditions used: 50° C. for 15 minutes; 95° C. for 3 minutes; 40 cycles of: 95° C. for 5 sec followed by a temperature decrease of 1.6° C./sec

TABLE 7 list of control oligonucleotide compounds (as disclosed in WO 2019/193165)

| SEQ ID NO | Motif sequence | position on SEQ ID NO: 1 | | | CMP ID NO | Oligonucleotide Compound |
| --- | --- | --- | --- | --- | --- | --- |
| | | Start | end | Design | | |
| 22 | CCCATAACCATAGTCAT | 9142 | 9157 | 3-12-2 | 35_1 | CCCataaccatagtcAT |
| 12 | CCATTTCTTCCTATTACAA | 14783 | 14801 | 3-14-2 | 50_1 | CCAtttcttcctattacAA |
| 13 | GCTTTTTATGGTTTCACC | 16183 | 16200 | 1-15-2 | 53_1 | Gctttttatggtttcacc |
| 14 | ATGCTTTTTATGGTTTCACC | 16183 | 16202 | 1-17-2 | 54_1 | Atgctttttatggtttcacc |
| 20 | atattaacctcctatcagt | 30511 | 30530 | 1-15-3 | 78_1 | Atattaacctcctatcagt |
| 21 | aatattaacctcctatcag | 30512 | 30531 | 3-13-3 | 79_1 | AATattaacctcctatCAG |

For Compounds: Capital letters represent LNA nucleosides (beta-D-oxy LNA nucleosides were used), all LNA cytosines are 5-methyl cytosine, lower case letters represent DNA nucleosides. All internucleoside linkages are phosphorothioate internucleoside linkages.

Example 1: Testing In Vitro Efficacy of Antisense Oligonucleotides Targeting Human FUBP1 mRNA in Hela Cells Antisense oligonucleotides targeting FUBP1 were tested for their ability to reduce FUBP1 mRNA expression in human Hela cells acquired from ECACC (Catalog No. 93021013), Hela cells were grown in cell culturing media (EMEM [Sigma, cat. no M2279], supplemented with 10% Fetal Bovine Serum [Sigma, cat. no F7524], 2 mM Glutamine [Sigma, G7513], 0.1 mM NEAA [Sigma, M7145] and 0.025 mg/ml Gentamicin [Sigma, cat. no G1397]). Cells were trypsinized every 5 days, by washing with Phosphate Bufffollowed by 60° C. for 45 sec. The data was analyzed using the QuantStudio™ Real_time PCR Software.

The qPCR data was captured and raw data quality control done in Quantstudio7 software.

The data were then imported into E-Workbook where a BioBook template was used to capture and analyze the data. The data were analyzed using the following steps:

1. Quantity calculated by the delta delta Ct method (Quantity=2^(−Ct)*1000000000)

2. Quantity normalized to the calculated quantity for the housekeeping gene assay run in the same well. Relative Target Quantity=QUANTITY_target/QUANTITY_housekeeping 3. The RNA knockdown was calculated for each well by division with the mean of all PBS-treated wells on the same plate. Normalised Target Quantity=(Relative Target Quantity/[mean] Relative Target Quantity] _pbs_wells)*100

4. The final data are shown as a percentage of untreated (PBS) wells.

5. For concentration-response experiments, a curve was fitted from the RNA knockdown values (step 3-4) for each compound [either 8 or 10 concentrations, depending on the dilution model]. Curves are fitted using a 4 Parameter Sigmoidal Dose-Response Model in Biobook.

The relative FUBP1 mRNA expression levels are shown in Table 8 as % of control, i.e. the lower the value the larger the inhibition. Further, the results are shown in FIG. 11.

TABLE 8

In vitro efficacy of anti-FUBP1 compounds in Hela cells. FUBP1 mRNA levels are normalized to GUSB and shown as % of control.

| CMP ID NO | FUBP1 Residual mRNA level, % of ctrl | |
| | 3.3 µM | 5 µM |
| --- | --- | --- |
| 6_1 | 34 | nd |
| 6_2 | 26 | nd |
| 7_1 | 29 | nd |
| 7_2 | 29 | nd |
| 7_3 | 34 | nd |
| 7_4 | 26 | nd |
| 8_1 | nd | 15 |
| 9_1 | 33 | nd |
| 18_1 | nd | 27.8 |
| 17_1** | 54 | 34 |
| 16_1** | 59 | 32 |
| 50_1* | nd | 62 |
| 53_1* | nd | 70 |
| 54_1* | nd | 78 |
| 78_1* | nd | 68.4*** |
| 79_1* | nd | 51.4*** |

*Control compounds,
nd: not determined
**CMP ID NO: 17_1 is as follows: ATgctTtttatggtttCA (SEQ ID NO: 17), CMP ID NO: 16_1 is as follows: TTAtgcttttttatggTTT (SEQ ID NO: 16), wherein capital letters are beta-D-oxy LNA nucleosides, lowercase letters are DNA nucleosides, all LNA C are 5-methyl cytosine, all internucleoside linkages are phosphorothioate internucleoside linkages. CMP ID NO: 17 targets nt 16185 to 16202 of SEQ ID NO: 1. CMP ID NO: 16 targets nt 16187 of 16204 of SEQ ID NO: 1.
***Data are from WO 2019/193165
Experiments with the control compounds were carried out separately

Example 2: Testing In Vitro Efficacy of Antisense Oligonucleotides Targeting Human FUBP1 mRNA in Primary Human Hepatocytes (PXB-PHH)

Fresh primary human hepatocytes (PXB-PHH) harvested from humanized mice (uPA/SCID mice)—herein called PHH—were obtained from PhoenixBio Co., Ltd (Japan) in 96-well format and cultured in modified hepatocyte clonal growth medium (dHCGM). dHCGM is a DMEM medium containing 100 U/ml Penicillin, 100 µg/ml Streptomycin, 20 mM Hepes, 44 mM NaHCO$_3$, 15 µg/ml L-proline, 0.25 µg/ml Insulin, 50 nM Dexamethazone, 5 ng/ml EGF, 0.1 mM Asc-2P, 2% DMSO and 10% FBS (Ishida et al., 2015).

Cells were cultured at 37° C., in a humidified atmosphere with 5% CO$_2$. Culture medium eras replaced 2 times per week until harvest.

Non-infected cells received a single treatment at 5 µM and were harvested 7 days later. In all treatments cells were dosed with oligonucleotide compounds in a final volume of 120 µl/well of dHCGM Medium. The experiments for RNA measurement were performed in biological duplicated.

Afterwards a real-time PCR for FUBP1 RNA was carried out. Total mRNA was extracted from the cells using a MagNA Pure robot and the MagNA Pure 96 Cellular RNA Large Volume Kit (Roche, #05467535001) according to the manufacturers protocol. The mRNA expression levels were quantified in technical duplicates by qPCR using a Quant-Studio 12K Flex (Applied Biosystems), the TaqMan RNA-to-CT 1-Step Kit (Applied Biosystems, #4392938), and human GusB endogenous control (Applied Biosystems, #Hs00939627_m1). The mRNA expression was analyzed using the comparative cycle threshold 2-ΔΔCt method normalized to the reference gene GusB and to non-treated cells. TaqMan primers used for GusB RNA and FUBP1 RNA quantification are listed in the table below:

TABLE 9

Primers for GusB RNA and FUBP1 RNA quantification

| Parameter | Source |
| --- | --- |
| FUBP1 | ThermoFisher - Assay ID: Hs00900762_m1 |
| GusB | ThermoFisher - Assay ID: Hs00939627_m1 |

The relative FUBP1 mRNA expression levels of 8 compounds (CMP ID Nos: 6_1, 6_2, 7_1, 7_2, 7_3, 7_4; 8_1 and 9_1. CMP ID NO 78_1 and 79_1) in PXB-PHH cells are shown in Table 10 as % of control, i.e. the lower the value the larger the inhibition. The FUBP1 mRNA expression levels of CMP ID NO: 18_1) in PXB-PHH cells is analyzed in Example 3.

TABLE 10

In vitro efficacy of anti-FUBP1 compounds in PXB-PHH cells. FUBP1 mRNA levels are normalized to GUSB and shown as % of control.

| SEQ ID NO | CMP ID NO | Rel. mRNA level PXB-PHH at 25 µM | SD | Rel. mRNA PXB-PHH at 5 µM | SD |
| --- | --- | --- | --- | --- | --- |
| 6 | 6_1 | 37 | 3 | 46 | 4 |
| 6 | 6_2 | 33 | 4 | 45 | 4 |
| 7 | 7_1 | 31 | 1 | 52 | 15 |
| 7 | 7_2 | 21 | 1 | 43 | 2 |
| 7 | 7_3 | 33 | 1 | 49 | 5 |
| 7 | 7_4 | 26 | 0 | 41 | 0 |
| 8 | 8_1 | 33 | 1 | 59 | 5 |
| 9 | 9_1 | 22 | 2 | 60 | 38 |

Conclusions Drawn from Examples 1 and 2

The data in Examples 1 and 2 show that targeting FUBP1 with an LNA ASO as shown in Table 6 leads to an efficient reduction of FUBP1.

Example 3: Further Analysis of CMP IDs NO: 7_1 and 18_1

In the following, additional experiments with two of the nine identified compounds are described: CMP IDs NO: 7_3 and 18_1. In these experiments, the two compounds were compared to two prior compounds which gave the best results in WO 2019/193165.

Materials and Methods

Primary Human Hepatocytes (PXB-PHH)

Fresh primary human hepatocytes (PXB-PHH) were cultivated as described in Example 2, except that 24-well format was used.

ASOs Sequences and Compounds

Table 11 provides an overview on the compounds tested in Example 3:

TABLE 11

Human FUBP1 sequences targeted by the ASOs

| Description | Sequence | CMP ID |
|---|---|---|
| Compound according to invention | 5'-CTTATGCTTTTTATGGTT-3' (SEQ ID NO: 7) | 7_3* |
| Control compound (best prior art compound in HeLa cells) | 5'-CCCATAACCATAGTCAT-3' (SEQ ID NO: 22) | 35_1** |
| Compound according to invention | 5'-ACCAATTTTCATTTCTAC-3' (SEQ ID NO: 18) | 18_1* |
| Control compound (best prior art compound in PHH cells) | 5'-CCATTTCTTCCTATTACAA-3' (SEQ ID NO: 12) | 50_1** |

*see Table 6, compounds according to the inventon
**see Table 7: control compounds as disclosed in WO 2019/193165

HBV Infection and Oligonucleotide Treatment

Upon arrival, PHH were infected with an MOI 110 using chronic patient-derived purified inoculum (genotype C) by incubating the PHH cells with HBV in 4% (v/v) PEG in PHH medium for 16 hours. The cells were then washed three times with PBS and cultured in a humidified atmosphere with 5% $CO_2$ in fresh PHH medium. Four days post-infection the cells were treated with FUBP1 LNAs (see Table 11) at a final concentration of 10 μM in duplicate or with PBS as no drug control (NDC). On the day of the treatment, the old medium was removed from the cells and replaced by 400 μl/well of fresh PHH medium. Per well, 100 μL of each FUBP1 LNA at 50 μM or PBS as NDC were added to the 400 μL PHH medium. The same treatment was repeated 3 times on days 4, 11 and 18 post-infection. Cell culture medium was changed with fresh one every three days on days 7, 14 and 21 post-infection.

Real-Time PCR Intracellular HBV pgRNA and FUBP1 mRNA

Following cell viability determination the cells were washed with PBS once. Total RNA was extracted from the cells using a MagNA Pure robot and the MagNA Pure 96 Cellular RNA Large Volume Kit (Roche, #05467535001) according to the manufacturer's protocol. The FUBP1 mRNA and the viral pgRNA expression levels were quantified in technical duplicates by qPCR using a QuantStudio 12K Flex (Applied Biosystems), the TaqMan RNA-to-CT 1-Step Kit (Applied Biosystems, #4392938), and human GusB endogenous control (Applied Biosystems, #Hs00939627_m1) have been used. The FUBP1 mRNA and the viral pgRNA relative expressions were analyzed using the comparative cycle threshold 2-ΔΔCt method normalized to the reference gene GusB and non-treated cells. TaqMan primers used for GusB RNA, FUBP1 RNA and HBV pgRNA quantifications are listed in Table 12.

TABLE 12

TaqMan primers used for GusB gene, FUBP1 RNA and HBV pgRNA quantifications

| Parameter | Source |
|---|---|
| FUBP1 | ThermoFisher - Assay ID: Hs00900762_m1 |
| HBV pgRNA | custom: AILJKX5 |
| GusB | ThermoFisher - Assay ID: Hs00939627_m1 |

Results

The relative FUBP1 mRNA expression levels of the tested compounds are shown in Table 13 and FIG. 12. As can be derived from the table and FIG. 13, both compounds of the invention (CMP ID NO: 7_3 and 18_1) reduce target mRNA expression by about 80% compared to the NDC. Their effect on the FUBP1 mRNA level is much stronger than the effect of the prior art compounds (CMP ID NO: 50_1 and 35_1).

TABLE 13

In vitro efficacy of anti-FUBP1 compounds in PXB-PHH cells. FUBP1 mRNA levels are normalized to GUSB and shown as % of control.

| CMP ID 7_3 | | Best naked Prio Art in HeLa CMP ID 35_1 | | CMP ID 18_1 | | Best naked Prio Art in PHH CMP ID 50_1 | |
|---|---|---|---|---|---|---|---|
| Residual Expression Rel to NDC (=100) | SD | Residual Expression Rel to NDC (=100) | SD | Residual Expression Rel to NDC (=100) | SD | Residual Expression Rel to NDC (=100) | SD |
| 23 | 4 | 46 | 5 | 22 | 0 | 38 | 3 |

Table 14 shows the pgRNA in HBV infected infected PHH cells treated with different concentrations of antisense compounds. As can be derived from the table, the down-regulation was related to the concentration of antisense compounds. At a concentration of 10 µM, the lowest pgRNA level was observed for CMP ID NO: 7_3. Moreover, the highest pgRNA level was observed for the prior art compound with CMP ID NO: 35_1. CMP ID NO: 18_1 down-regulated HBV pgRNA in a similar manner as prior art compound CMP ID NO: 50_1.

-continued

| Material | Vendor | Catalog No. |
|---|---|---|
| MagNaPure LC RNA Isolation Tissue buffer | Roche Applied Science | 03604721001 |

Liver samples were received frozen in 2 ml round bottom Eppendorf tubes and homogenized in MagNa pure buffer (Roche) on a TissueLyser II (Qiagen) for 2×1.5 minutes after addition of a 5 mm homogenization bead. After complete

TABLE 14

In vitro efficacy of anti-FUBP1 compounds in HBV infected PXB-PHH cells: pgRNA. pgRNA levels are normalized to untreated cells (NDC) and are shown shown as % of control.

| Concentration (µM) | CMP ID NO: 7_3 Residual Expression Rel to NDC (=100) | SD | N | CMP ID NO: 35_1 Residual Expression Rel to NDC (=100) | SD | N | CMP ID NO: 18_1 Residual Expression Rel to NDC (=100) | SD | N | CMP ID NO: 50_1 Residual Expression Rel to NDC (=100) | SD | N |
|---|---|---|---|---|---|---|---|---|---|---|---|---|
| 10 | 34 | 21 | 2 | 62 | 15 | 2 | 54 | 1 | 2 | 52 | 3 | 2 |
| 2 | 65 | 11 | 2 | 68 | 21 | 2 | 88 | 6 | 2 | 97 | 13 | 2 |
| 4 | 88 | 23 | 2 | 95 | 1 | 2 | 84 | 19 | 2 | 81 | 14 | 2 |
| 0.08 | 113 | 8 | 2 | 117 | 15 | 2 | 87 | 17 | 2 | 99 | 12 | 2 |

The cells were also tested at a concentration of 2 µM once per week for three weeks. At 2 µM, CMP ID NO: 73 showed the best FUBP1 mRNA KD with 50% reduction of mRNA expression. Thus, the effect depends on the concentration (since 80% reduction was observed at 2 µM). Moreover, CMP ID NO: 18_1 showed a similar effect on target mRNA expression level compared to the prior art oligos (at 2 µM).

Example 4: FUBP1 ASO in Vivo PK/PD

The in vivo liver PK/PD correlation of the oligonucleotides with CMP ID Nos: 7_3 and 18_1 conjugated to a GalNAc moiety via a phosphodiester linked DNA dinucleotide was assessed in a single-dose mouse study using C57BL/6 mice (for the structure of the conjugates, see e.g. FIGS. 5 and 8.1). The mice were dosed 3 mg/kg subcutasample homogenization, the homogenate was left for 30 minutes at room temperature (RT) to complete the tissue lysis. All steps of the homogenization process were carried out in a flow hood due to the buffer thiocyanate salt and mercaptoethanol contents. After lysis, the homogenates were centrifuged for 3 minutes at 17.000 g.

Homogenates were diluted to approx. 20 mg tissue per 400 µL to avoid overloading the MagNa pure instrument. 350 µL of the homogenate was used for RNA extraction on a MagNA pure 96 instrument for subsequent qPCR analysis. The remaining aliquot of the homogenate was used for hELISA analysis Hybridization ELISA The following oligos and (all-LNA phospho-diester) ELISA probes were used for the hELISA analysis, all designed, synthesized and qualified at Roche Innovation Center Copenhagen A/S.

| Conjugate | Biotinylated capture probe | Digoxigenin-conjugated detection probe |
|---|---|---|
| Conjugate of CMP ID NO 18_1 | 5'-bio-GTAGAAA-3' | 5'-GAAAATTGG-dig-3' |
| Conjugate of CMP ID NO 7_3 | 5'-bio-AACCATAAAA-3' | 5'-AGCATAAG-dig-3' | neously and terminated at different time points. Fubp1 mRNA knockdown, compound exposure and PKPD was measured as described below Materials and Methods Tissue Sample Processing

| Material | Vendor | Catalog No. |
|---|---|---|
| Eppendorf 2 ml tubes | Eppendorf | 0030 123.344 |
| Tungsten carbide beads 5 mm | Qiagen | 69989 |

| Materials | Vendor | Catalog No. |
|---|---|---|
| Polypropylene 96-well plate with round bottom (dilution plate) | Thermo Scientific | 267334 |
| Roche StreptaWell High Bind, 96-well plate clear | Roche Applied Science | 11989685001 |
| Substrate (AP) Blue Phos Substrate | KPL | 50-88-00 |
| Anti-Digoxigenin-AP, Fab fragments | Roche Applied Science | 11093274910 |

| Buffers | Comments |
|---|---|
| 5 x SSCT buffer, pH 7.0 | 750 mM NaCl, and 75 mM sodium citrate, containing 0.05% (v/v) Tween-20 |

-continued

| 2 x SSCT buffer, pH 7.0 | 300 mM NaCl, and 30 mM sodium citrate, containing 0.05% (v/v) Tween-20 |
|---|---|
| PBST, pH 7.2 | Phosphate buffered saline, containing 0.05% (v/v) Tween-20 |
| Conjugate of CMP ID NO 18__1 Capture - detection solution | A solution of capture probe 5 nM and detection probe 5 nM in 5xSSCT buffer |
| Conjugate of CMP ID NO 7__3 Capture - detection solution | A solution of capture probe 35 nM and detection probe 35 nM in 5xSSCT buffer |

Before hELISA analysis, the homogenates were brought to RT and vortexed before use. The samples were diluted at least 10-fold in 5×SSCT buffer.

Appropriate standards matching sample matrix and dilution factor were run on every plate and prepared in parallel with the samples using the relevant oligo (from a quality and identity checked formulation). The standard for each compound was spiked in to a sample pool from un-dosed samples. The spike-in concentrations were made so they were within ~10 fold of the sample oligo content.

Samples and standards were added to a dilution plate in the desired setup, and dilution series were made. 300 μL sample/standard plus capture-detection solution was added to the first wells and 150 μL capture-detection solution in the remaining wells.

A two-fold dilution series of standards and samples was made by transferring 150 μL liquid sequentially. 2-4 wells were kept for blanks (capture-detection solution only). A two-fold sample dilution series of at least 6 wells is recommended for optimal results.

The samples in the dilution plate were incubated for 30 minutes at RT. 100 μL of liquid was transferred from the dilution plate to a streptavidin plate. The plate was incubated for 1 hour at RT with gentle agitation (plate shaker). The wells were aspirated and washed three times with 300 μL of 2×SSCT buffer.

100 μL anti-DIG-AP diluted 1:4000 in PBST (made on the same day) were added to each well and incubated for 1 hour at RT under gentle agitation. The wells were aspirated and washed three times with 300 μL of 2×SSCT buffer.

100 μL of substrate (AP) solution (freshly prepared) were added to each well. The intensity of the color was measured spectrophotometrically at 615 nm after a 30-minute incubation with gentle agitation.

Raw data were exported from the readers (Gen5 2.0 software) to excel format and further analysed in excel. Standard curves were generated using GraphPad Prism 8 software and a logistic 4PL regression model.

Data points were reported as the mean value of the technical replicates.

RNA Purification

All samples were purified using the MagNA Pure 96 Instrument (Roche) using the manufacturer's protocol.

| Material | Material | Catalog No. |
|---|---|---|
| MagNaPure LC RNA Isolation Tissue buffer | Roche | No. 03 604 721 001 |
| MagNa Pure 96 Cellular RNA Large Volume Kit (elution buffer) | Roche | 05467535001 |
| MagNA Pure 96 Processing Cartridge | Roche | 06241603001 |
| Sealing foil | Roche | 5435307001 |

350 μL of the tissue homogenate was transferred to a MagNaPure 96 Processing Cartridge. Remaining lysate was stored for later analysis of oligonucleotide exposure analysis. RNA was purified using the MagNa Pure 96 with the kit Cellular RNA Large Volume Kit, and using the protocol "RNA Tissue FF Standard LV 3.1". RNA was eluted in 50 μL elution buffer (from kit, 05467535001).

The RNA concentration and A260/280 ration of ~2.0 of all samples was determined using an Eon Microplate Spectrophotometer (BioTek Instruments). Based on these concentrations, samples were normalized to 25 ng/μL by dilution in DNase/RNase free water and further diluted down to a working concentration of 2.5 ng/μl.

The samples were then used as input for c ne-step qPCR analysis. The essay details are show below.

qPCR Analysis qPCR was run as a one-step qPCR format using the following materials:

| Material | Vendor | Catalog No. | Comments |
|---|---|---|---|
| RNA dilution plate | Thermo Scientific | #AB0900 | — |
| qScript ™ XLT One-Step RT-qPCR ToughMix ®, Low ROX ™ | Quanta Bioscience | 95134-500 | Assay buffer |
| Fubp1 probe/primer sets | IDT | Mm.PT.58.7603777, Dye Quencher Mod. 6-FAM/ZEN/IBFQ (Primer to Probe ratio 3, 5) Mm.PT.58.11399179, Dye Quencher Mod. 6-FAM/ZEN/IBFQ (Primer to Probe ratio 3, 5) | Mouse Fubp1 assays |
| Control probe/primer sets | Thermo (__m1) IDT (rest) | Mm 01197698__m1, Dye Quencher Mod. VIC-MGB__PL Mm.PT.58.43894205 Dye Quencher Mod. HEX/ZEN/IBFQ (Primer to Probe ratio 2) Mm.PT.5821577577 Dye Quencher Mod. HEX/ZEN/IBFQ (Primer to Probe ratio 2) Mm.PT.39a.22214839 Dye Quencher Mod. | Housekeeping control assays (mouse Gusb, RpIp0, Rps29, Tbp respectively) |

-continued

| Material | Vendor | Catalog No. | Comments |
|---|---|---|---|
| | | HEX/ZEN/IBFQ (Primer to Probe ratio 2) | |
| MicroAmp Optical 384-well plate | Applied Biosystems | 4309849 | qPCR plate |
| Quantstudio v.1.3 | Applied Biosystems | — | Software for qPCR analysis. |
| MicroAmp Optical Adhesive Film | Applied Biosystems | 4311971 | — |

Preparation of RNA for qPCR Analysis

The reaction was kept cool for all steps of this protocol to avoid unwanted RT enzyme activity. The diluted RNA was then heat shocked for 40 seconds at 90° C. to dissociate RNA:ASO duplexes and placed on ice. Prior to analyses the RNA samples were spun to the bottom of the wells.

A standard curve was run on each plate and used for quantification and amplification efficiency measurement. 4 uL of a 10 ng/uL PBS sample was used as input in a 10 uL reaction. A 2-fold dilution series was prepared in RNase free water, to form a 7-point standard curve.

2 separate mouse Fubp1 assays and 4 control assays were run in duplex reactions with two technical replicates for each animal.

For the qPCR the following steps were followed:

For each qPCR well, a stock mastermix was prepared containing 5 μL ALT One-Step mix, 0.5 μL Probe mix1 (20×), 0.5 μL Probe mix2 (20×). From the stock mastermix, 6 μL was added to each well in a 384-well plate (MicroAmp Optical 384-well plate-Applied Biosystems 4309849).

From the RNA dilution plate, 4 μL of diluted RNA (2.5 ng/uL) was added to each well of master mix. Plates were then sealed and vortexed. The plates were then centrifuged at high speed for 3 minutes. The qPCR reactions were kept cold until transferring to the qPCR instrument (Life Technology Viia7; software: QuantStudio v. 1.3) set to run the following program: 15 minutes at 50° C. and then 3 minutes at 95° C., with a set temperature change rate to 1.9° C./s. This was followed by 40 cycles of 95° C. for 5 seconds and 60° C. for 45 seconds with a set temperature change rate to 1.6° C./s.

All samples were analyzed in the same run limiting technical variability to a minimum.

qPCR Data Processing qPCR data were reviewed in the Quantstudio software (Applied Biosystems). Based on irregularities in the amplification curve possible outlier wells were identified and removed. Following this review of each plate, an export file was generated with quantities calculated from the ct-values of each sample based on the standard curves for each qPCR assay and analysed using Excel.

In general, the standard curves were of high quality with efficiencies between the recommended 95-105%, indicating high performing assays.

Four different HK genes (Gusb, Rplp0, Rps29, and Tbp) were assayed and a geometric mean of these used for normalization. The stability of the HK genes was assessed before inclusion using the method published by Vandesompele et al. (Vandesompele et al., 2002). By using four HK genes the pairwise HK gene variation is below the recommended threshold of 0.15 for all tissues.

The "% remaining Fubp1" was calculated as follows: Quantities from each of the Fubp1 qPCR assays were normalized to the geometric mean of the HK assays and further divided by the mean of the untreated group to give a % mRNA remaining. A mean of the two % Fubp1 mRNA remaining results was used as a final readout.

PKPD Plotting and Calculations

Figure 13:
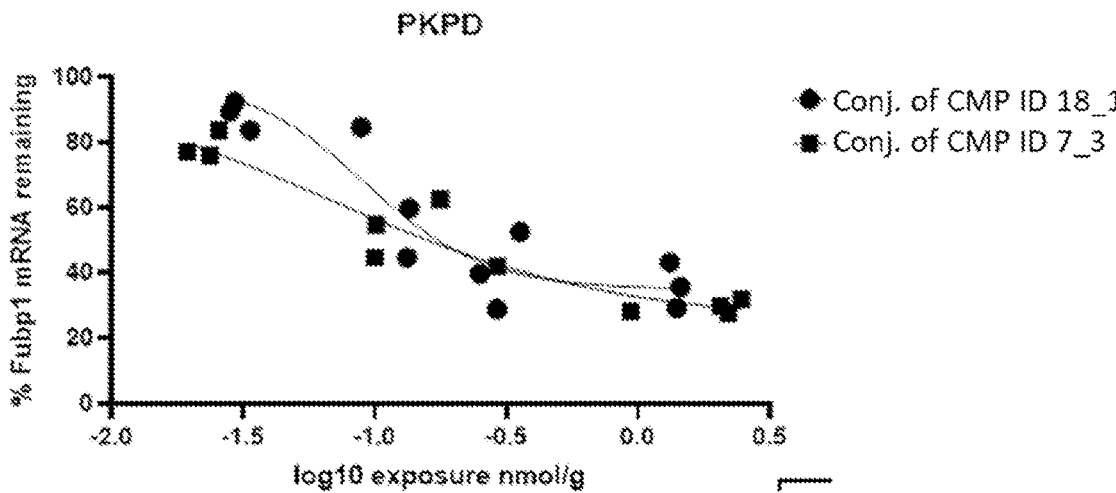
FIG. 13: Assessment of in vivo liver PK/PD correlation of the oligonucleotides with CMP ID Nos: 7_3 and 18_1 conjugated to a GalNAc moiety via a phosphodiester linked DNA dinucleotide was assessed in a single-dose mouse study (Conj.=Conjugate, see Example 4 for more details).

Liver tissue exposure values were calculated as nmol compound per g tissue (nmol/g). They were further log 10-transformed and plotted against the % Fubp1 mRNA remaining (FIG. 13). GraphPad Prism 8 was used to fit a non-linear regression curve (4PL regression model, constrained at top=100). The best-fit estimated PKPD IC50 was calculated by the software (Regression IC50: Conjugate of CMP ID 18_1: 0.092 nmol/g; Conjugate of CMP ID 7_3: 0.068 nmol/g).

Results: Both tested conjugates have a good PK profile. The Conjugate of CMP ID 7 is slightly superior to the Conjugate of CMP ID 18_1 in term of early onset on target KD.

The invention claimed is:

1. An antisense oligonucleotide selected from the group of antisense oligonucleotides consisting of (SEQ ID NO: 7)
        CTtAtgctttttatGgTT, and (SEQ ID NO: 18)
        AcCAAttttcatttCtAC, wherein capital letters are beta-D-oxy LNA nucleosides, lowercase letters are DNA nucleosides, all LNA C are 5-methyl cytosine, and all internucleoside linkages are phosphorothioate internucleoside linkages.

2. A conjugate comprising the antisense oligonucleotide of claim 1, and at least one conjugate moiety covalently attached to said antisense oligonucleotide.

3. The conjugate of claim 2, wherein the at least one conjugate moiety is capable of binding to an asialoglyco-protein receptor.

4. The conjugate of claim 2, wherein the conjugate moiety is selected from one of the-trivalent GalNAc moieties in FIG. 9 as follows:

185                                                          186

A1

A2

-continued

B1

B2

-continued

C1

C2

-continued

D1

D2

-continued

E1

F1

195                                          196

G1

H1

I1

J1

-continued

L1 L2

5. The conjugate of claim 4, wherein the conjugate moiety is the trivalent GalNAc moiety in FIG. 9D1, or 9D2 or a mixture thereof as follows:

D1

201                                                     202

-continued

D2

6. A conjugate of claim 2, comprising a linker positioned between the antisense oligonucleotide and the conjugate moiety.

7. The conjugate of claim 6, wherein the linker comprises 2 to 5 consecutive phosphodiester linked nucleosides.

8. A conjugate as shown in FIG. 8 or FIG. 8.1 as follows:

9. A pharmaceutically acceptable salt of the oligonucleotide of claim 1.

10. A pharmaceutical composition comprising the antisense oligonucleotide of claim 1, and a pharmaceutically acceptable diluent, solvent, carrier, salt and/or adjuvant.

11. A method for modulating FUBP1 expression in a target cell which is expressing FUBP1, the method comprising administering the antisense oligonucleotide of claim 1 in an effective amount to the cell.

12. A method for treating a disease comprising administering a therapeutically or prophylactically effective amount of the antisense oligonucleotide of claim 1 to a subject suffering from or susceptible to the disease, wherein the disease is hepatitis B virus (HBV) infection and/hepatocellular cancer.

13. An antiviral or antitumor medicine comprising the antisense oligonucleotide of claim 1.

14. A method of treating hepatitis B virus (HBV) infection and/or hepatocellular cancer, comprising the antisense oligonucleotide of claim 1.

15. A medicament, comprising the antisense oligonucleotide of claim 1, for the treatment of a hepatitis B virus (HBV) infection and/or hepatocellular cancer.

16. The method of claim 12, wherein the disease is a hepatitis B virus (HBV) infection.

17. The method of claim 12, wherein the disease is hepatocellular cancer.

18. A method for treating a disease comprising administering a therapeutically or prophylactically effective amount of the antisense oligonucleotide of claim 1 to a subject suffering from or susceptible to the disease, wherein the disease is a chronic HBV infection.

19. A method for treating a disease comprising administering a therapeutically or prophylactically effective amount of the antisense oligonucleotide of claim 1 to a subject suffering from or susceptible to the disease, wherein the disease is a hepatocellular carcinoma.

\* \* \* \* \*